United States Patent
St. Geme, III

(10) Patent No.: US 7,033,799 B2
(45) Date of Patent: Apr. 25, 2006

(54) HAEMOPHILUS ADHERENCE AND PENETRATION PROTEINS

(75) Inventor: Joseph W. St. Geme, III, St. Louis, MO (US)

(73) Assignee: Washington University, St. Louis, MS (US)

( * ) Notice: Subject to any disclaimer, the term of this patent is extended or adjusted under 35 U.S.C. 154(b) by 20 days.

(21) Appl. No.: 10/687,046

(22) Filed: Oct. 15, 2003

(65) Prior Publication Data

US 2004/0157241 A1    Aug. 12, 2004

Related U.S. Application Data

(60) Division of application No. 10/080,505, filed on Feb. 22, 2002, now Pat. No. 6,676,948, which is a continuation-in-part of application No. 08/296,791, filed on Aug. 25, 1994, now Pat. No. 6,245,337, and a continuation-in-part of application No. 09/839,996, filed on Apr. 20, 2001, now Pat. No. 6,642,371, which is a division of application No. 08/296,791.

(51) Int. Cl.
*C12P 21/04* (2006.01)

(52) U.S. Cl. ............ 435/71.1; 536/23.7; 536/24.1; 536/24.32; 435/320.1; 435/69.1; 435/69.3; 435/252.3

(58) Field of Classification Search ........... 536/23.7, 536/24.1, 24.32; 435/320.1, 69.1, 69.3, 71.1, 435/252.3
See application file for complete search history.

(56) References Cited

FOREIGN PATENT DOCUMENTS

| WO | WO96/05858 | * | 2/1996 |
| WO | WO96/33276 | * | 10/1996 |

OTHER PUBLICATIONS

St.Geme et al. Molecul. Microbiol. 1994. 14(2): 217-233.*
Fleischmann et al. Science. 1995. 269(5223): 496-512.*
Mikayama et al. (Nov. 1993. Proc.Natl.Acad.Sci. USA, vol. 90 : 10056-10060).*
Rudinger et al. (Jun. 1976. Peptide Hormones. Biol. Council. pp. 5-7).*
David Zuhn. Jun. 14, 2005. PTO Board: Disclosure of Sequence Enables at least 5% of Natural Variance. Patently-O: Patent Law Blog.*

* cited by examiner

*Primary Examiner*—Jennifer E. Graser
(74) *Attorney, Agent, or Firm*—Dorsey & Whitney LLP; Richard F. Trecartin

(57) ABSTRACT

Haemophilus adhesion and penetration proteins, nucleic acids, vaccines and monoclonal antibodies are provided.

7 Claims, 45 Drawing Sheets

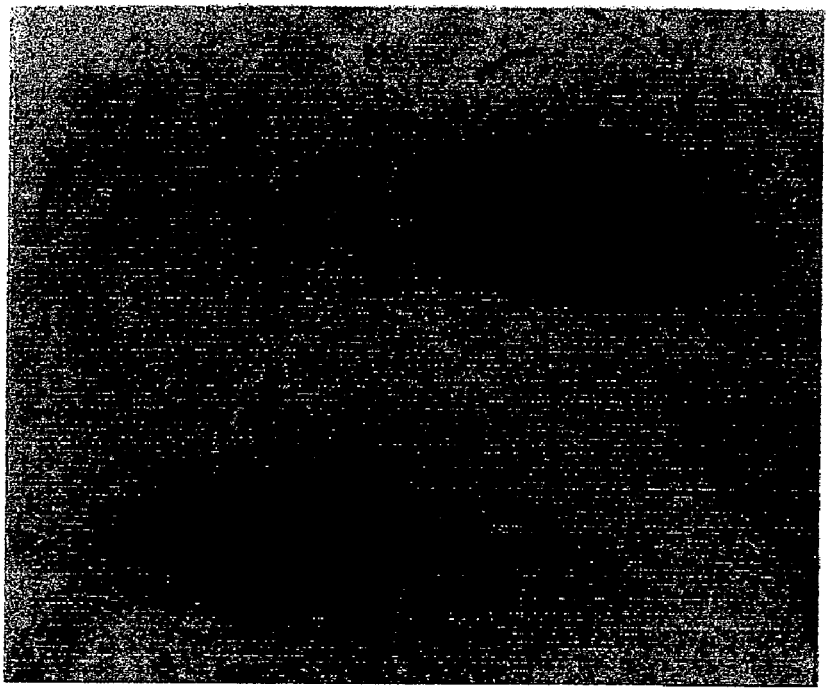
FIG._1B
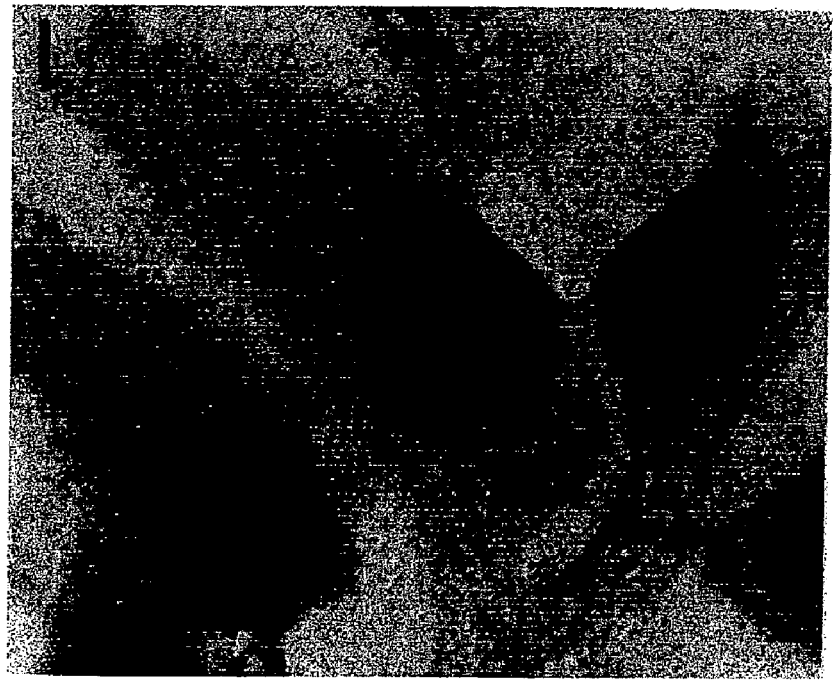
FIG._1A

FIG._2B
FIG._2A

FIG._2D
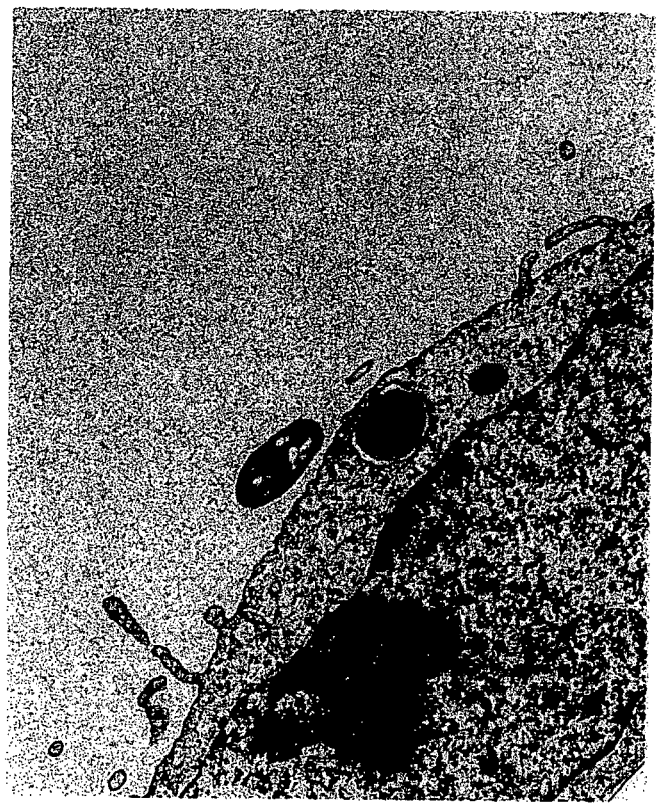
FIG._2C

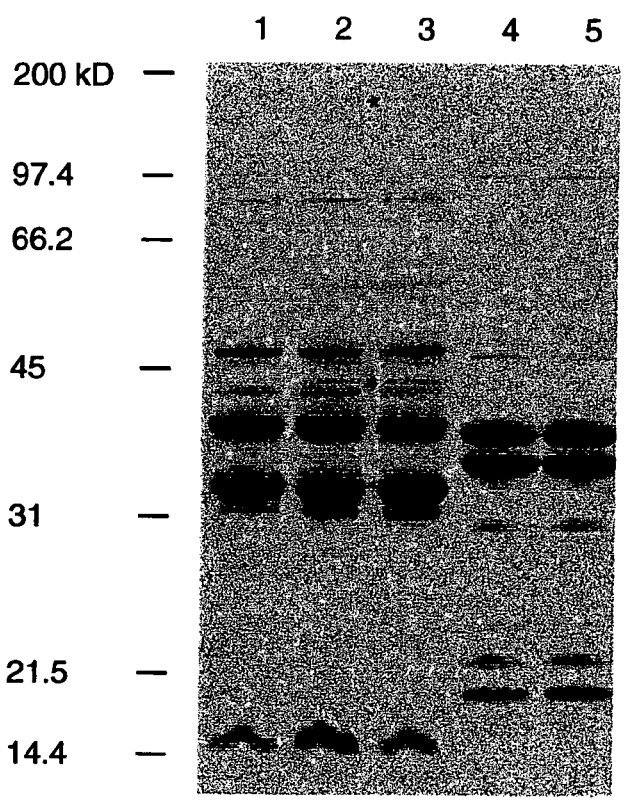
FIG._3
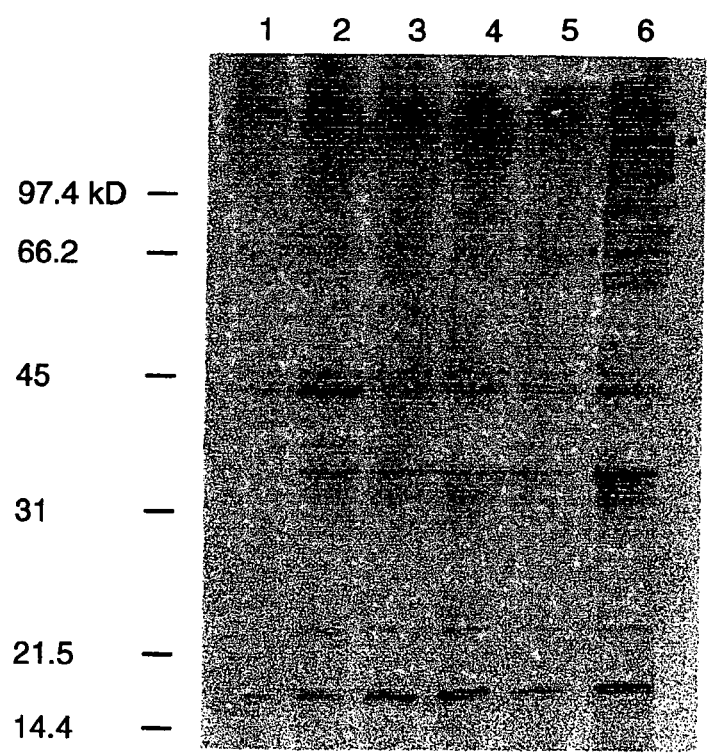
FIG._5

```
          10                     30                     50                     70                     90
TCAATAGTCGTTGTTAACTAGTATTTTTAATACGAAAAAATTACTTAATAAATAAACATTATGAAAAAAACTGTATTTCGTCTTAATTTT
       ‾‾‾‾‾‾                                        ‾‾‾‾‾‾                    ┌─────────────────────┐
        -35                                           -10                      │ M  K  K  T  V  F  R  L  N  F │

110                    130                    150                    170
TTAACCGCTTGCATTTCATTAGGGATAGTATCGCAAGCGTGGCTGTCACACTTATTTTTGGGATTGATTACCAATATATTCGTGATTTT
│ L  T  A  C  I  S  L  G  I  V  S  Q  A  W  A │ G  H  T  Y  F  G  I  D  Y  Q  Y  Y  R  D  F
└──────────────────────────────────────────────┘

190                    210                    230                    250                    270
GCCCGAGAATAAAGGGAAGTTCACAGTTGGGGCTCAAAATATTAAGGTTTATAACAAGGGCAATAGTTGGCACACATCAATGACAAAA
  A  E  N  K  G  K  F  T  V  G  A  Q  N  I  K  V  Y  N  K  Q  G  Q  L  V  G  T  S  M  T  K 290                    310                    330                    350
GCCCCGATGATTGATTTTCTGTAGTGTTCACGGCGTGGCAGCCTTGGTTGAAATCAATATTGTGAGCGTGGCACATAACGTA
  A  P  M  I  D  F  S  V  V  S  R  N  G  V  A  A  L  V  E  N  Q  Y  I  V  S  V  A  H  N  V 370                    390                    410                    430                    450
GGATATACAGATGTTGATTTTGGTGCAGAGGGAAACAACCCCGATCAACATCGTTTTACTTATAGATTGTAAAACGAAATAACTACAAA
  G  Y  T  D  V  D  F  G  A  E  G  N  N  P  D  Q  H  R  F  T  Y  K  I  V  K  R  N  N  Y  K 470                    490                    510                    530
AAAGATAATTACATCCTTATGAGGACGATTACCACGATTACATAAATTCGTTACAGAAGCGGCTCCAATTGATATGACTTCG
  K  D  N  L  H  P  Y  E  D  D  Y  H  N  P  R  L  H  K  F  V  T  E  A  A  P  I  D  M  T  S 550                    570                    590                    610                    630
AATATGAATGGCAGTACTTATTCAGATAGAACAAAAATATCCAGAACGTGTTCGTATCGGCTCTGGACGGCAGTTTTGGCGAAATGATCAA
  N  M  N  G  S  T  Y  S  D  R  T  K  Y  P  E  R  V  R  I  G  S  G  R  Q  F  W  R  N  D  Q 650                    670                    690                    710
GACAAAGGCGACCAAGTTGCCGGTGCAATATCATTATCTGACAGCTGGCAATACACACAATCAGCGTGGAGCAGGTAATGGATATTCGTAT
  D  K  G  D  Q  V  A  G  A  Y  H  Y  L  T  A  G  N  T  H  N  Q  R  G  A  G  N  G  Y  S  Y
```

FIG._6A

```
              730                      750                       770                        790                          810
TTGGGAGGCGATGTTCGTAAAGCGGGAGAATATGGTCCATTACCGAGTTGCAGGCTCAAAGGGGGACAGTGGTTCTCCGATGTTTATTTAT
 L  G  G  D  V  R  K  A  G  E  Y  G  P  L  P  I  A  G  S  K  G  D  S  G  S  P  M  F  I  Y
              830                      850                       870                        890
GATGCTGAAAAACAAAAATGGTTAATTAATGGGGATATTACGGGAAGGCAACCCTTTTGAAGGCAAAGAAAATGGTTTCAATTGGTTCGC
 D  A  E  K  Q  K  W  L  I  N  G  I  L  R  E  G  N  P  F  E  G  K  E  N  G  F  Q  L  V  R
              910                      930                       950                        970                          990
AAATCTTATTTTGATGAAATTTTCGAAAGAGATTTACATACATCACTTTACACCCGAGCTGGTAATGGAGTGTACACAATTAGTGGAAAT
 K  S  Y  F  D  E  I  F  E  R  D  L  H  T  S  L  Y  T  R  A  G  N  G  V  Y  T  I  S  G  N
              1010                     1030                      1050                       1070
GATAATGGTCAGGGGTCTATAACTCAGAAATCAGGAATACCATCAGAAATTAAAATTACGTTAGCAAATATGAGTTTACCTTTGAAAGAG
 D  N  G  Q  G  S  I  T  Q  K  S  G  I  P  S  E  I  K  I  T  L  A  N  M  S  L  P  L  K  E
              1090                     1110                      1130                       1150                         1170
AAGGATAAAGTTCATAATCCTAGATATGACGGACCTAATATTTATTCTCCACGTTTAAACAATGGAGAAACGCTATATTTTATGGATCAA
 K  D  K  V  H  N  P  R  Y  D  G  P  N  I  Y  S  P  R  L  N  N  G  E  T  L  Y  F  M  D  Q
              1190                     1210                      1230                       1250
AAACAAGGATCATTAATCTTCGCATCTGACATTAACCAAGGGGCGGTCTTTATTTGAGGTAATTTTACAGTATCTCCAAATTCT
 K  Q  G  S  L  I  F  A  S  D  I  N  Q  G  A  G  G  L  Y  F  E  G  N  F  T  V  S  P  N  S
              1270                     1290                      1310                       1330                         1350
AACCAAACTTGGCAAGGAGCTGGCATACATGTAAGTGAAAATAGCACCGTTACTTGGAAAGTAAATGGCGTGGAACATGATCGACTTTCT
 N  Q  T  W  Q  G  A  G  I  H  V  S  E  N  S  T  V  T  W  K  V  N  G  V  E  H  D  R  L  S
              1370                     1390                      1410                       1430
AAAATTGGTAAAGGAACATTGCACGTTCAAGCCAAAGGGGAAAATAAAGGTTCGATCAGCGTAGGCGATGGTAAAGTCATTTTGGAGCAG
 K  I  G  K  G  T  L  H  V  Q  A  K  G  E  N  K  G  S  I  S  V  G  D  G  K  V  I  L  E  Q
```

FIG.-6B

```
        1450                   1470                    1490                    1510                   1530
CAGGCAGACGATCAAGGCAACAAACAAGCCTTTAGTGAAATTGGCTTGGTTAGCGGCAGAGGGACTGTTCAATTAAACGATGATAAACAA
 Q   A   D   D   Q   G   N   K   Q   A   F   S   E   I   G   L   V   S   G   R   G   T   V   Q   L   N   D   D   K   Q
              1550                    1570                    1590                    1610
TTTGATACCGATAAATTTTATTTCGGCTTTCGTGGTGGTCGCTTAGATCTTAACGGGCATTCATTAACCTTAAACGTATCCAAAATACG
 F   D   T   D   K   F   Y   F   G   F   R   G   G   R   L   D   L   N   G   H   S   L   T   F   K   R   I   Q   N   T
        1630                    1650                    1670                    1690                   1710
GACGAGGGGGCAATGATTGTGAACCATAATACAACTCAAGCCGCTAATGTCACTATTACTGGGAACAGAAAGCATTGTTCTACCTAATGGA
 D   E   G   A   M   I   V   N   H   N   T   Q   A   A   N   V   T   I   T   G   N   E   S   I   V   L   P   N   G
              1730                    1750                    1770                    1790
AATAATATTAATAACTGATTACAGAAAAGAAATTGCCTACAACGGTTGGTTTGGCGAAACAGATAAAAATAACACAATGGGCGATTA
 N   N   I   N   K   L   D   Y   R   K   E   I   A   Y   N   G   W   F   G   E   T   D   K   N   K   H   N   G   R   L
        1810                    1830                    1850                    1870                   1890
AACCTTATTATAAACCAACCACAGAAGATCGTACTTTGCTACTTTCAGGTGGTACAAATTTAAAAGGCGATATTACCCAAACAAAAGGT
 K   L   I   Y   K   P   T   T   E   D   R   T   L   L   S   G   G   T   N   L   K   G   D   I   T   Q   T   K   G
              1910                    1930                    1950                    1970
AAACTATTTTTCAGCGGTAGACCGGTAGACCGCCACCGCCTACAATCATTTAAATAACGTTGGTCAGAAATGGAAGTATACCACAAGGCGAA
 K   L   F   F   S   G   R   P   T   P   H   A   Y   N   H   L   N   K   R   W   S   E   M   E   G   I   P   Q   G   E
        1990                    2010                    2030                    2050                   2070
ATTGTGTGGGATCACGATTGGATCAACGTACAATTGGATCAACGTACAATTTAAAGCTGAAAACTTCCAAATTTAAAGGCGGTGGTTTCTCGCAATGTT
 I   V   W   D   H   D   W   I   N   R   T   F   K   A   E   N   F   Q   I   K   G   G   S   A   V   V   S   R   N   V
              2090                    2110                    2130                    2150
TCTTCAATTGAGGGAAATTGGACAGTCAGCAATAATGCCAAATCAACAAATACCATTTGCACGCGT
 S   S   I   E   G   N   W   T   V   S   N   N   A   N   A   T   F   G   V   V   P   N   Q   Q   N   T   I   C   T   R

FIG._6C
```

```
                                      2190                        2210                          2230                      2250
     2170
TCAGATTGGACAGGATTAACGACTTGTCAAAAAGTGGATTAACCGATACAAAAGTTATTAATTCTATACCAAAAACACAAATCAATGGC
 S  D  W  T  G  L  T  T  C  Q  K  V  D  L  T  D  T  K  V  I  N  S  I  P  K  T  Q  I  N  G 2270                        2290                          2310                      2330
TCTATTAATTTAACTGATAATGCAACGGCGAATGTTAAAGGTTTAGCAAAACTTAATGGCAATGTCACTTTAACAAATCACAGCCAATTT
 S  I  N  L  T  D  N  A  T  A  N  V  K  G  L  A  K  L  N  G  N  V  T  L  T  N  H  S  Q  F 2350                        2370                          2390                      2410                      2430
ACATTAAGCAACAATGCCACCCAAATAGGCAATATTCGACTTTCCGACAATTCAACTGCAACGGTGGATAATGCAAACTTGAACGGTAAT
 T  L  S  N  N  A  T  Q  I  G  N  I  R  L  S  D  N  S  T  A  T  V  D  N  A  N  L  N  G  N 2450                        2470                          2490                      2510
GTGCATTTAACGGATTCAGCTCAATTTTCTTTAAAAAACAGCCATTTTCGCACCCAAATTCAGGGAGACAAAGGCACAACAGTGACGTTG
 V  H  L  T  D  S  A  Q  F  S  L  K  N  S  H  F  S  H  Q  I  Q  G  D  K  G  T  T  V  T  L 2530                        2550                          2570                      2590                      2610
GAAAATGCGACTTGGACAATGCCTAGCGATACTACATTGCAGAATTTAACGCTAAATAACAGTACGATCACGTTAAATTCAGCTTATTCA
 E  N  A  T  W  T  M  P  S  D  T  T  L  Q  N  L  T  L  N  N  S  T  I  T  L  N  S  A  Y  S 2630                        2650                          2670                      2690
GCTAGCTCAAACAATACGCCACGTTGCCGTTCATTAGAGACGGAAACGCCAACATCGGCAGAACATCGTTCAACACATTGACAGTA
 A  S  S  N  N  T  P  R  R  R  S  L  E  T  E  T  T  P  T  S  A  E  H  R  F  N  T  L  T  V 2710                        2730                          2750                      2770                      2790
AATGGTAAATTGAGTGGGCAAGGCACATTCCAATTTACTTCATCTTTATTTGGCTATAAAAGCGATAAAATTAAATTATCCAATGACGCT
 N  G  K  L  S  G  Q  G  T  F  Q  F  T  S  S  L  F  G  Y  K  S  D  K  L  K  L  S  N  D  A 2810                        2830                          2850                      2870
GAGGGCGATTACATATTATCTGTTCGCAACAGGCAATAACTTTGGTTGAAAGCAAAGATAATCAA
 E  G  D  Y  I  L  S  V  R  N  T  G  K  E  P  E  T  L  E  Q  L  T  L  V  E  S  K  D  N  Q
```

FIG._6D

```
            2890                     2910                     2930                     2950                     2970
CCGTTATCAGATAAGCTCAAATTTACTTTAGAAAATGACCACGTTGATGCAGGTGCATTACGTTATAAATTAGTGAAGAATGATGGCGAA
 P  L  S  D  K  L  K  F  T  L  E  N  D  H  V  D  A  G  A  L  R  Y  K  L  V  K  N  D  G  E 2990                     3010                     3030                     3050
TTCCGCTTGCATAACCCCATAAAAGAGCAGGAATTGCACAATGATTTAGTAAGAGCAAGCAGAACGAACATTAGAAGCCAAACAA
 F  R  L  H  N  P  I  K  E  Q  E  L  H  N  D  L  V  R  A  E  Q  A  E  R  T  L  E  A  K  Q 3070                     3090                     3110                     3130                     3150
GTTGAACCGACTGCTAAAACACAAACAGGTGAGCCAAAAGTGCGTAGCAGAAGAGCAGCGAGAGCAGCGTTTCCTGATACCCTGCTGAT
 V  E  P  T  A  K  T  Q  T  G  E  P  P  K  V  R  S  R  R  A  A  R  A  A  F  P  D  T  L  P  D 3170                     3190                     3210                     3230
CAAAGCCTGTTAAACGCATTAGAAGCCAAACAAGCTGAAACTCAAAAAGTAAGGCAAAACACAAAAAGTGCGGTCA
 Q  S  L  L  N  A  L  E  A  K  Q  A  E  L  T  A  E  T  Q  K  S  K  A  K  T  K  K  V  R  S 3250                     3270                     3290                     3310                     3330
AAAAGAGCAGTGTTTTCTGATCCCCTGCTTGATCAAAGCCTGTTCGCATTAGAAGCCGCACTTGAGGTTATTGATGCCCCACAGCAATCG
 K  R  A  V  F  S  D  P  L  L  D  Q  S  L  F  A  L  E  A  A  L  E  V  I  D  A  P  Q  Q  S 3350                     3370                     3390                     3410
GAAAAAGATCGTCTAGCTCAAGAAGAAGCGGAAAAACAAAGACTTGATCAGCCGTTATTCAAATAGTGCGTTATCAGAA
 E  K  D  R  L  A  Q  E  E  A  E  K  Q  R  K  Q  K  D  L  I  S  R  Y  S  N  S  A  L  S  E 3430                     3450                     3470                     3490                     3510
TTATCTGCAACAGTAAATAGTATGCTTTCTGTTCAAGATGAATTAGATCGTCTTTTTGTAGATCAAGCACAATCTGCCGTGTGGACAAAT
 L  S  A  T  V  N  S  M  L  S  V  Q  D  E  L  D  R  L  F  V  D  Q  A  Q  S  A  V  W  T  N 3530                     3550                     3570                     3590
ATCGCACAGGATAAAAGACGCTATGATTCTGATGCGTTCCGTGCTTATCAGCAGCAGAAAACGAACTTACGTCAGATTGGGGTGCAAAAA
 I  A  Q  D  K  R  R  Y  D  S  D  A  F  R  A  Y  Q  Q  Q  K  T  N  L  R  Q  I  G  V  Q  K

FIG._6E
```

```
        3610                3630                3650                3670                3690
GCCTTAGCTAATGGACGAATTGGGGCGCAGTTTTCTCGCATAGCCGTTCAGATAATACCTTTGATGAACAGGTTAAAAATCACGCGACATTA
 A  L  A  N  G  R  I  G  A  V  F  S  H  S  R  S  D  N  T  F  D  E  Q  V  K  N  H  A  T  L 3710                3730                3750                3770
ACGATGATGTCGGGTTTTGCCCAATATCAATGGGGCGATTTACAATTGGTGTAAACGTGGGAACGGAATCAGTGCGAGTAAAATGGCT
 T  M  M  S  G  F  A  Q  Y  Q  W  G  D  L  Q  F  G  V  N  V  G  T  G  I  S  A  S  K  M  A 3790                3810                3830                3850                3870
GAAGAACAAAGCCGAAAAATTCATCGAAAAGCGATAAATTATGGCGTGAATGCAAGTTATCAGTTCCGTTTAGGCAATTGGGCATTCAG
 E  E  Q  S  R  K  I  H  R  K  A  I  N  Y  G  V  N  A  S  Y  Q  F  R  L  G  Q  L  G  I  Q 3890                3910                3930                3950
CCTTATTTTGGAGTTAATCGCTATTTTATTGAACGTGAAAATTATCAATCTGAGGAAGTGAAAACGCCTAGCCTTGCATTTAAT
 P  Y  F  G  V  N  R  Y  F  F  I  E  R  E  N  Y  Q  S  E  E  V  R  V  K  T  P  S  L  A  F  N 3970                3990                4010                4030                4050
CGCTATAATGCTGGCATTCGAGTTGATTATACATTTACTCCGACAGATAATATCAGCGTTAAGCCTTATTTCTTCGTCAATTATGTTGAT
 R  Y  N  A  G  I  R  V  D  Y  T  F  T  P  T  D  N  I  S  V  K  P  Y  F  F  V  N  Y  V  D 4070                4090                4110                4130
GTTTCAAACGCTAACGTACAAACCACGGTAAATCTCACGGTGTTGCAACAACCATTTGGACGTTATTGGCAAAAAGAAGTGGGATTAAAG
 V  S  N  A  N  V  Q  T  T  V  N  L  T  V  L  Q  Q  P  F  G  R  Y  W  Q  K  E  V  G  L  K 4150                4170                4190                4210                4230
GCAGAAATTTTACATTTCCAACTTTCCGCTTTTATCTCAAAATCTCAAGGTTCACAACTCGGCAAAATGTGGCGTGAAATTG
 A  E  I  L  H  F  Q  I  S  A  F  I  S  K  S  Q  G  S  Q  L  G  K  Q  Q  N  V  G  V  K  L 4250                4270                4290                4310
GGCTATCGTTGGTAAAAATCAACATAATTTATCGTTTATTGATAAACAAGGTGGTCAGATCCCACCTTTTTTATTCCAATAAT
 G  Y  R  W  *

FIG._6F
```

```
              1
Hap           MKKTVFRLNF  LTACISLGIV  SQAWAGHTYF  GIDYQYYRDF  AENKGKFTVG
HK368IGA      MLNKKFKLNF  IALTVAYALT  PYTEAALVRD  DVDYQIFRDF  AENKGKFSVG
HK393IGA      MLNKKFKLNF  IALTVAYALT  PYTEAALVRD  DVDYQIFRDF  AENKGKFSVG
HK715IGA      MLNKKFKLNF  IALTVAYALT  PYTEAALVRD  DVDYQIFRDF  AENKGKFSVG
HK61IGA       MLNKKFKLNF  IALTVAYALT  PYTEAALVRD  DVDYQIFRDF  AENKGKFSVG
Consensus     M----F-LNF  ---------   ----A-----  --DYQ---RDF AENKG-F-VG 51                                                      100
Hap           AQNIKVYNKQ  GQLVGTSMTK  A.PMIDFSVV  SRNG.VAALV  ENQYIVSVAH
HK368IGA      ATNVLVRDKN  NKDLGTALPN  GIPMIDFSVV  DVDKRIATLI  NPQYVVGVKH
HK393IGA      ATNVEVRDKN  NRPLGNVLPN  GIPMIDFSVV  DVDKRIATLV  NPQYVVGVKH
HK715IGA      ATNVEVRDKN  NHSLGNVLPN  GIPMIDFSVV  DVDKRIATLI  NPQYVVGVKH
HK61IGA       ATNVEVRDKK  NQSLGSALPN  GIPMIDFSVV  DVDKRIATLV  NPQYVVGVKH
Consensus     A-N--V--K-  -----G----  --PMIDFSVV  ------A-L-  --QY-V-V-H 101                                                     150
Hap           .....NVGY   TDVDFGAEGN  NPDQHR....  LHKFVTEAAP  .. FTYKIVKR
HK368IGA      VSNGVSELHF  GNLNGNMNNG  NAKAHRDVSS  LDKFVTEVAP  EENRYFSVEK
HK393IGA      VSNGVSELHF  GNLNGNMNNG  NAKAHRDVSS  LDKFVTEVAP  EENRYYTVEK
HK715IGA      VSNGVSELHF  GNLNGNMNNG  NDKSHRDVSS  LDKFVTEVAP  EENRYFSVEK
HK61IGA       VSNGVSELHF  GNLNGNMNNG  NAKSHRDVSS  LDKFVTEVAP  EENRYYTVEK
Consensus     ----------  ----------  N---HR----  L-KFVTE-AP  ----Y--V--

151                                                     200
Hap           NNY.......  IDM.TSNMNG  STYSDRTKYP
HK368IGA      NEYPTKLNGK  TVTTEDQ.TQ  KRREDYYMPR  IEASTASSDA  GTYNDQNKYP
HK393IGA      NEYPTKLNGK  AVTTEDQ.AQ  KRREDYYMPR  IEASTDSSDA  GTYNNKDKYP
HK715IGA      NEYPTKLNGK  AVTTEDQ.TQ  KRREDYYMPR  IEASTASSDA  GTYNDQNKYP
HK61IGA       NNFPTENVTS  FTTKEEQDAQ  KRREDYYMPR  IEASTANNNK  GEYNNSDKYP
Consensus     N---------  ----------  ----DY---PR I---T-----  --Y----KYP
```

FIG._7A

```
                201                                                                              250
Hap        ERVRIGSGRQ  F.........  ..........  .....WRNDQ  DKGDQVAGAY
HK368IGA   AFVRLGSSGSQ FIYKKGDNYS  LIL.......N NH....EVGG  NNLKLVGDAY
HK393IGA   YFVRLGSSGTQ FIYENGTRYE  LWL.......G KEGQKSDAGG  YNLKLVGNAY
HK715IGA   AFVRLGSGSQ  FIYKKGDNYS  LIL.......N NH....EVGG  NNLKLVGDAY
HK61IGA    AFVRLGSGSQ  FIYKKGSRYQ  LILTEKDKQG  NLLRNWDVGG  DNLELVGNAY
Consensus  --VR-GSG-Q  F---------  ----------  ----------  ----V--AY 251                                                                              300
Hap        HYLTAGNTHN  ORGAGNGYSY  LGG......D  VRKAGEYGPL  PIAGSKGDSG
HK368IGA   TYGIAGTPYK  VNHENNGLIG  FGNSKEEHSD  PKGILSQDPL  TNYAVLGDSG
HK393IGA   TYGIAGTPYE  VNHENDGLIG  FGNSNNEYIN  PKEILSKKPL  TNYAVLGDSG
HK715IGA   TYGIAGTPYK  VNHENNGLIG  FGNSKEEHSD  PKGILSQDPL  TNYAVLGDSG
HK61IGA    TYGIAGTPYK  VNHENNGLIG  FGNSKEEHSD  PKGILSQDPL  TNYAVLGDSG
Consensus  -Y--AG----  ------G---  ----G-----  ------PL--  -----GDSG 301                                                                              350
Hap        SPMFIYDAEK  QKWLINGILR  EGNPFEGKEN  GFQLVRKSYF  D.EIFERDLH
HK368IGA   SPLFVYDREK  GKWLFLGSYD  FWAGYN....  .....KKSWQ  EWNIYKSQFT
HK393IGA   SPLFVYDREK  GKWLFLGSYD  YWAGYN....  .....KKSWQ  EWNIYKPEFA
HK715IGA   SPLFVYDREK  GKWLFLGSYD  FWAGYN....  .....KKSWQ  EWNIYKPEFA
HK61IGA    SPLFVYDREK  GKWLFLGSYD  FWAGYN....  .....KKSWQ  EWNIYKHEFA
Consensus  SP-F-YD-EK  -KWL--G---  ----------  ------KS--  ----I----

351                                                                              400
Hap        TSLYTRAGNG  VYTISGNDNG  QGSITQKSGI  PSEIKITLAN  MSLPLKEKDK
HK368IGA   KDVLNKDSAG  SLIGSKTDYS  WSSNGKTSTI  TGGEK.....S LNVDLAD...
HK393IGA   EKIYEOYSAG  SLIGSKTDYS  WSSNGKTSTI  TGGEK.....S LNVDLAD...
HK715IGA   KTVLDKDTAG  SLTGSNTQYN  WNPTGKTSVI  SNGSE.....S LNVDLFD...
HK61IGA    EKIYQQYSAG  SLTGSNTQYT  WQATGSTSTI  TGGGE.....P LSVDLTD...
Consensus  ----------  ----S-----  ----------  ------S-I- -----L----
```

FIG. 7B

```
              401
Hap           VHNPRYDGPN IYSPRLNNGE TLYFMDQKQG SLIFASDINQ GAGGLYFEGN
HK368IGA      ........GKD. .....KPNHGK SVTFEG...SG TLTLNNNIDQ GAGGLFFEGD
HK393IGA      ........GKD. .....KPNHGK SVTFEG...SG TLTLNNNIDQ GAGGLFFEGD
HK715IGA      ........SSQD TDSKKNNHGK SVTLRG...SG TLTLNNNIDQ GAGGLFFEGD
HK61IGA       ........GKD. .....KPNHGK SITLRG...SG TLTLNNHHDQ GAGGLFFEGD
Consensus     ------------ -----N-G-- ---------G -L-------I-Q -GAGGL-FEG-
                                                                    450

451
Hap           FTVSPNSNQ. TWQGAGIHVS ENSTVTWKVN GVEHDRLSKI GKGTLHVQAK
HK368IGA      YEVKGTSDNT TWKGAGVSVA EGKTVTWKVH NPQYDRLAKI GKGTLIVEGT
HK393IGA      YEVKGTSDNT TWKGAGVSVA EGKTVTWKVH NPQYDRLAKI GKGTLIVEGT
HK715IGA      YEVKGTSDST TWKGAGVSVA DGKTVTWKVH NPKSDRLAKI GKGTLIVEGK
HK61IGA       YEVKGTSDST TWKGAGVSVA DGKTVTWKVH NPKYDRLAKI GKGTLVVEGK
Consensus     --V----S--- TW-GAG---V- ---TVTWKV- ---DRL--KI GKGTL-V---
                                                                    500

501
Hap           GENKGSISVG DGKVILEQQA DDQGNKQAFS EIGLVSGRGT VQLNDDKQFD
HK368IGA      GDNKGSLKVG DGTVILKQQT NGSGQ.HAFA SVGIVSGRST LVLNDDKQVD
HK393IGA      GDNKGSLKVG DGTVILKQQT NGSGQ.HAFA SVGIVSGRST LVLNDDKQVD
HK715IGA      GENKGSLKVG DGTVILKQQA DANNKVKAFS QVGIVSGRST VVLNDDKQVD
HK61IGA       GKNEGLLKVG DGTVILKQKA DANNKVQAFS QVGIVSGRST LVLNDDKQVD
Consensus     G-N-G---VG DG-VIL-Q-- ------AF- ------- --G-VSGR-T --LNDDKQ-D
                                                                    550

551
Hap           TDKFYTGFRG GRLDLNGHSL TFKKRIQNTDE GAMIVNHNTT QAANVTITGN
HK368IGA      PNSIYFGFRG GRLDLNGNSL TFDHIRNIDD GARLVNHNMT NASNITITGE
HK393IGA      PNSIYFGFRG GRLDLNGNSL TFDHIRNIDE GARLVNHSTS KHSTVTITGD
HK715IGA      PNSIYFGFRG GRLDANGNNL TFEHIRNIDD GARLVNHNTS KTSTVTITGE
HK61IGA       PNSIYFGFRG GRLDLNGNSL TFDHIRNIDD GARVVNHNMT NTSNITITGE
Consensus     ----YFGFRG GRLD-NG--L TF---I-N-D- GA---VNH--- ----TITG-
                                                                    600
```

*FIG. 7C*

```
           601                                                                      650
Hap        ESIVLPNG..  ..........  ..........  ..........  ..........  ..........
HK368IGA   SLITDPNTIT  PYNIDAPDED  NPYAFRRIKD  GGQLYLNLEN  YTYYALRKGA
HK393IGA   NLITDPNNVS  IYYVKPLEDD  NPYAIRQIKY  GYQLYFNEEN  RTYYALKKDA
HK715IGA   SLITDPNTIT  PYNIDAPDED  NPYAFRRIKD  GGQLYLNLEN  YTYYALRKGA
HK61IGA    SLITNPNTIT  SYNIEAQDDD  HPLRIRSIPY  R.QLYFNQDN  RSYYTLKKGA
Consensus  --I---PN--- ---------- ---------- ---------- ----------

651                                                                      700
Hap        ..........  ..........  ..........  ..........  ..........
HK368IGA   STRSELPKNS  GESNENWLYM  GKTSDEAKRN  VMNHINNERM  NGFNGYFGEE
HK393IGA   SIRSEFPQNR  GESNNSWLYM  GTEKADAQKN  AMNHINNERM  NGFNGYFGEE
HK715IGA   STRSELPKNS  GESNENWLYM  GKTSDEAKRN  VMNHINNERM  NGFNGYFGEE
HK61IGA    STRSELPQNS  GESNENWLYM  GRTSDEAKRN  VMNHINNERM  NGFNGYFGEE
Consensus  ---------- ---------- ---------- ---N------ ----NG-FGE- 701                                                                      750
Hap        D.KNKHNGRL  NLIYKPTTED  RTLLLSGGTN  LKGDITQTKG  KLFFSGRPTP
HK368IGA   EGK..NNGNL  NVTFKGKSEQ  NRFLLTGGTN  LNGDLTVEKG  TLFLSGRPTP
HK393IGA   EGK..NNGNL  NVTFKGKSEQ  NRFLLTGGTN  LNGDLNVQQG  TLFLSGRPTP
HK715IGA   EGK..NNGNL  NVTFKGKSEQ  NRFLLTGGTN  LNGDLKVEKG  TLFLSGRPTP
HK61IGA    ETKATQNGKL  NVTFNGKSDQ  NRFLLTGGTN  LNGDLNVEKG  TLFLSGRPTP
Consensus  --K---NG-L  N--------- ---LL-GGTN  L-GD------G  -LF-SGRPTP 751                                                                      800
Hap        HAYNHLNKRW  SEMEG..IPQ  GEIVWDHDWI  NRTFKAENFQ  IKGGSAVVS.
HK368IGA   HARDIAGISS  TKKDPHFAEN  NEVVVEDDWI  NRNFKATTMN  VTGNASLYSG
HK393IGA   HARDIAGISS  TKKDSHFSEN  NEVVVEDDWI  NRNFKATNIN  VTNNATLYSG
HK715IGA   HARDIAGISS  TKKDQHFAEN  NEVVVEDDWI  NFNERATNIN  VTNNATLYSG
HK61IGA    HARDIAGISS  TKKDPHFTEN  NEVVVEDDWI  NRNFKATTMN  VTGNASLYSG
Consensus  HA-------- ---------- --E-V----DWI  NR-FKA---- -------S-
```

FIG._7D

```
           801
Hap        RNVSSIEGNW TVSNNANATF GVVPNQQNTI CTRSDWTGLT TCQKVDLTDT
HK368IGA   RNVANITSNI TASNKAQVHI GY..KTGDTV CVRSDYTGYV TCTTDKLSD.
HK393IGA   RNVESITSNI TASNNAKVHI GY..KAGDTV CVRSDYTGYV TCTTDKLSD.
HK715IGA   RNVANITSNI TASDNAKVHI GY..KAGDTV CVRSDYTGYV TCTTDKLSD.
HK61IGA    RNVANITSNI TASNNAQVHI GY..KTGDTV CVRSDYTGYV TCHNSNLSE.
Consensus  RNV---I--N- T-S--A---- G-------T- C-RSD-TG-- TC----L---
                                                  *            *
           851                                                850
Hap        KVINSIPKTQ INGSINLTDN ATANVKGLAK LNGNVTLTNH SQFTLSNNAT
HK368IGA   KALNSFNPTN LRGNVNLTES A......... .......... ..........
HK393IGA   KALNSFNPTN LRGNVNLTES A......... .......... ..........
HK715IGA   KALNSFNATN VSGNVNLSGN A......... .......... ..........
HK61IGA    KALNSFNPTN LRGNVNLTEN A......... .......... ..........
Consensus  K--NS---T- --G--NL--- A--------- ---------- ----------
                                                              900
           901
Hap        QIGNIRLSDN STATVDNANL NGNVHLTDSA QFSLKNSHFS HQIQGDRGTT
HK368IGA   .......... .NFVLGKANL FGTIQSRGNS QVRLT..... ..........
HK393IGA   .......... .NFVLGKANL FGTIQSRGNS QVRLT..... ..........
HK715IGA   .......... .NFVLGKANL FGTISGTGNS QVRLT..... ..........
HK61IGA    .......... .SFTLGKANL FGTIQSIGTS QVNLK..... ..........
Consensus  ---------- -----ANL -G-------- Q---L----- ----------
                                                              950
           951
Hap        VTLENATWTM PSDTTLQNLT LNNSTITLNS AYSASSNNTP RRRSLETETT
HK368IGA   ...ENSHWHL TGNSDVHQLD LANGHIHLNS ADNSNNVTK. ..........
HK393IGA   ...ENSHWHL TGNSDVHQLD LANGHIHLNS ADNSNNVTK. ..........
HK715IGA   ...ENSHWHL TGDSNVNQLN LDKGHIHLNA QNDANKVTT. ..........
HK61IGA    ...ENSHWHL TGNSNVNQLN LTNGHIHLNA QNDANKVTT. ..........
Consensus  ---EN--W-- ---------- L-----I-LN- ---L----- ----------
                                                             1000
```

FIG. 7E

```
              1001                                                              1050
Hap           PTSAEHRFNT  LTVNGKLSGQ  GTFQFTSSLF  GYKSDKLKLS  NDAEGDYILS
HK368IGA      ........YNT LTVNS.LSGN  GSFYYLTDLS  NKQGDKVVVT  KSATGNFTLQ
HK393IGA      ........YNT LTVNS.LSGN  GSFYYLTDLS  NKQGDKVVVT  KSATGNFTLQ
HK715IGA      ........YNT LTVNS.LSGN  GSFYYLTDLS  NKQGDKVVVT  KSATGNFTLQ
HK61IGA       ........YNT LTVNS.LSGN  GSFYYWVDFT  NNKSNKVVVN  KSATGNFTLQ
Consensus     --------NT  LTVN---LSG- G-F-------  ------K---  --A-G----L-

1051                                                             1100
Hap           VRNTGKEPET  LEQLTIVESK  DNQPLSDKLK  FTLENDHVDA  GALRYKLVKN
HK368IGA      VADKTGEPNH  .NELTLFDAS  KAQR..DHLN  VSLVGNTVDL  GAWKYKLRNV
HK393IGA      VADKTGEPNH  .NELTLFDAS  KAQR..DHLN  VSLVGNTVDL  GAWKYKLRNV
HK715IGA      VADKTGEPTK  .NELTLFDAS  NATR..NNLN  VSLVGNTVDL  GAWKYKLRNV
HK61IGA       VADKTGEPNH  .NELTLFDAS  NATR..NNLE  VTLANGSVDR  GAWKYKLRNV
Consensus     V-----EP--  ---LTL----  ----------  --L-----VD- GA--YKL---

1101                                                             1150
Hap           DGEFRLHNPI  KEQELHNDLV  ..........  ..........  NNEEIARVDE
HK368IGA      NGRYDLYNP.  .EVEKRNQTV  DTTNITTPNN  IQADVPSVPS  NNEEIARVDE
HK393IGA      NGRYDLYNP.  .EVEKRNQTV  DTTNITTPNN  IQADVPSVPS  NNEEIARVDE
HK715IGA      NGRYDLYNP.  .EVEKRNQTV  DTTNITTPNN  IQADVPSVPS  NNEEIARV.E
HK61IGA       NGRYDLYNP.  .EVEKRNQTV  DTTNITTPND  IQADAPSAQS  NNEEIARV.E
Consensus     -G----L-NP- -E-E---N--V ----------  ----------  ----------

1151                                                             1200
Hap           APVPPPAPAT  ..........  ..........  ..........  ..........
HK368IGA      APVPPPAPAT  ..........  ..........  ..........  ..........
HK393IGA      TPVPPPAPAT  ..........  ..........  ..........  ..........
HK715IGA      TPVPPPAPAT  ESAIASEQPE  TRPAETAQPA  MEETNTANST  ETAPKSDTAT
HK61IGA       TPVPPPAPAT  ..........  ..........  ..........  ..........
Consensus     ----------  ----------  ----------  ----------  ----------
```

*FIG._7F*

```
                                                                  1250
Hap          ..........  ..........  RAEQAERTLE  AKQVEPT...  ..........
HK368IGA     ..........  PSETTETVAE  NSKQESKTVE  KNEQDATETT  AQNREVAKEA
HK393IGA     ..........  PSETTETVAE  NSKQESKTVE  KNEQDATETT  AQNREVAKEA
HK715IGA     ..........  PSETTETVAE  NSKQESKTVE  KNEQDATETT  AQNGEVAEEA
HK61IGA      QTENPNSESV  PSETTEKVAE  NPPQENETVA  KNEQEATEPT  PQNGEVAKED
Consensus    ----------  ----------  -----Q---T  ---T------  ----------

1300
Hap          .....AKTQT  GE........  ..........  ..........  ..........
HK368IGA     KSNVKANTQT  NEVAQSGSET  KETQTTETK.  ..........  ....ETATVE
HK393IGA     KSNVKANTQT  NEVAQSGSET  KETQTTETK.  ..........  ....ETATVE
HK715IGA     KPNVKANTQT  NEVAQSGSET  EETQTTEIK.  ..........  ....ETAKVE
HK61IGA      QPTVEANTQT  NEATQSEGKT  EETQTAETKS  EPTESVTVSE  NQPEKTVSQS
Consensus    -----A-TQT  -E--------  ----------  ----------  ----------

1350
Hap          ..........  ..........  ..........  ..........  ..........
HK368IGA     KEEK......  ..........  ..........  ..........  KEEK......
HK393IGA     KEEEKAKVEKE  EKAKVEKDEI  ..........  SPKQAKPAPK  EVSTDTKVEE
HK715IGA     TEDKVVVEKE  EKAKVETEET  ..........  PPKQAEPAPE  EVPTDTNAEE
HK61IGA      ----------  ----------  ----------  ----------  ----------
Consensus    ----------  ----------  ----------  ----------  ----------

1400
Hap          ..........  ..........  ..........  ..........  ..........
HK368IGA     ..........  ..........  ..........  ..........  ..........
HK393IGA     TQVQAQPQTQ  STTVAAAEAT  SPNSKPAEET  .QPSEKTNAE  PVTPVVSKNQ
HK715IGA     A..QALQQTQ  PTTVAAAETT  SPNSKPAEET  QQPSEKTNAE  PVTPVVS...
HK61IGA      ----------  ----------  ----------  ----------  ----------
Consensus    ----------  ----------  ----------  ----------  ----------
```

FIG._7G

```
                1401                                              1450
Hap             ........  ........  ........  ....PKVRS  RRAARAAFPD  TLP.......
HK368IGA        ........  ........  ....AKVETE  KTQEVPKVTS  QVSPKQEQSE  T.........
HK393IGA        ........  ........  ....AKVETE  KTQEVPKVTS  QVSPKQEQSE  T.........
HK71SIGA        TENTTDQPTE  REKTAKVETE  KTQEPPQVAS  QASPKQEQSE  T.........
HK61IGA         .ENTATQPTE  TEETAKVEKE  KTQEVPQVAS  QESPKQEQPA  AKPQAQTKPQ
Consensus       ----------  ----------  ---------  ----P-V-S  ----------  ---------

1451                                              1500
Hap             ........  ........  ........  ........  ........  .........
HK368IGA        ........  ........  ........  ........  ........  .........V
HK393IGA        ........  ........  ........  ........  ........  .........V
HK71SIGA        ........  ........  ........  ........  ........  .........V
HK61IGA         AEPARENVLT  TKNVGEPQPQ  AQPQTQSTAV  PTTGETAANS  KPAAKPQAQA
Consensus       ----------  ----------  ----------  ----------  ----------

1501                                              1550
Hap             .......D  QSLLNALEA.  ....KQAEL  TAETQKSKAK  TKK.......
HK368IGA        QPQAEPAREN  DPTVNIKEP.  ....QSQTNT  TADTEQPAKE  TSSNVE....
HK393IGA        QPQAEPAREN  DPTVNIKEP.  ....QSQTNT  TADTEQPAKE  TSSNVE....
HK71SIGA        QPQAVLESEN  VPTVNNAEEV  QAQLQTQTSA  TVSTKQPAPE  NSINTG....
HK61IGA         KPQTEPAREN  VSTVNTKEP.  ....QSQTSA  TVSTEQPAKE  TSSNVEQPAP
Consensus       ----------  ----N--E--  -------Q--  ----T--T--  ----------

1551                                              1600
Hap             ........  ........  ........  .V  RSKRAVFSDP  LLDQSL....
HK368IGA        ........  ........  ....QPVT  ESTTVNTGNS  VVEN......
HK393IGA        ........  ........  ....QPVT  ESTTVNTGNS  VVEN......
HK71SIGA        ....SAT  AITETAEKSD  KPQTETAAST  EDASQHKANT  VADNSVANNS
HK61IGA         ENSINTGSAT  TMTETAEKSD  KPQMET..VT  ENDRQPEANT  VADNSVANNS
Consensus       ----------  ----------  ----------  ----------  ----------
```

FIG._7H

```
            1601                                                                      1650
Hap         ...........  ...........  ...........  .F ALEAALEVID APQQSEKDRL AQEEAEKQRK
HK368IGA    ...........  ...........  ...........  PENTTPATTQ PTVNSESSN.  .KPK.NRHRR
HK393IGA    ...........  ...........  ...........  PENTTPATTQ PTVNSESSN.  .KPK.NRHRR
HK715IGA    ESSEPKSRRR  RSISQPQETS  ...........  AEETTAASTD ETTIADNSKR SKPN.RRSRR
HK61IGA     ESSESKSRRR  RSVSQPKETS  ...........  AEETTVASTQ ETTVDNSVST PKPRSRRTRR
Consensus   ----------  ----------  ----------  ---------- ---------- -----R----

1651                                                                      1700
Hap         ...........  ...........  ...........  ...........  ....QKDLI SRYSNSALSE
HK368IGA    SVRSVPHNVE  PATTSSND..   ...........  ...........  RSTVALCDLT STNTNAVLSD
HK393IGA    SVRSVPHNVE  PATTSSND..   ...........  ...........  RSTVALCDLT STNTNAVLSD
HK715IGA    SVRS.....E  PTVTNGSD..   ...........  ...........  RSTVALRDLT STNTNAVISD
HK61IGA     SVQTNSYEPV  ELPTENAENA  ENVQSGNNVA  ...........  NSQPALRNLT SKNTNAVLSN
Consensus   ----------  ----------  ----------  ----------  ------L---  S---N----S-

1701                                                                      1750
Hap         LSA.....TV  NSMLSVQDEL  DRL.FVDQAQ  SAVWTNIAQD KRRYDSDAFR
HK368IGA    ARAKAQFVAL  NVGKAVSQHI  SQLEMNNEGQ  YNVWVSNTSM NKNYSSSQYR
HK393IGA    ARAKAQFVAL  NVGKAVSQHI  SQLEMNNEGQ  YNVWVSNTSM NKNYSSSQYR
HK715IGA    AMAKAQFVAL  NVGKAVSQHI  SQLEMNNEGQ  YNVWVSNTSM NENYSSSQYR
HK61IGA     AMAKAQFVAL  NVGKAVSQHI  SQLEMNNEGQ  YNVWISNTSM NKNYSSEQYR
Consensus   ------A---  N-------I  ---L------Q  --VW------ --Y-S---R 1751                                                                      1800
Hap         AYQQQKTNLR  QIGVQKALAN  GRIGAVFSHS  RSDNTFDEQV KNHATLTMMS
HK368IGA    RFSSKSTQTQ  LGWDQTISNN  VQLGGVFTYV  RNSNNFDKAT SKN.TLAQVN
HK393IGA    RFSSKSTQTQ  LGWDQTISNN  VQLGGVFTYV  RNSNNFDKAT SKN.TLAQVN
HK715IGA    RFSSKSTQTQ  LGWDQTISNN  VQLGGVFTYV  RNSNNFDKAS SKN.TLAQVN
HK61IGA     RFSSKSTQTQ  LGWDQTISNN  VQLGGVFTYV  RNSNNFDKAS SKN.TLAQVN
Consensus   ------T---  ---Q------N  ---G-VF---  R---N-FD---  ----TL----
```

FIG._71

```
              1801                                                                    1850
Hap           GFAQYQWGDL QF..GVNVGT GISASKMAEE QSRKIHRKAI NYGVNASYQF
HK368IGA      FYSKY.YADN HWYLGIDLGY GKFQSKLQTN HNAKFARHTA QFGLTAGKAF
HK393IGA      FYSKY.YADN HWYLGIDLGY GKFQSKLQTN HNAKFARHTA QFGLTAGKAF
HK715IGA      FYSKY.YADN HWYLGIDLGY GKFQSNLKTN HNAKFARHTA QFGLTAGKAF
HK61IGA       FYSKY.YADN HWYLGIDLGY GKFQSNLQTN NNAKFARHTA QIGLTAGKAF
Consensus     -----Y---- ----G----G- G-----S--- ---K---R-- --G---A---F 1851                                                                    1900
Hap           RLGQLGIQPY FGVNRYFIER ENYQSEEVRV KTPSLAFNRY NAGIRVDYTF
HK368IGA      NLGNFGITPI VGVRYSYLSN ADFALDQARI KVNPISVKTA FAQVDLSYTY
HK393IGA      NLGNFGITPI VGVRYSYLSN ADFALDQARI KVNPISVKTA FAQVDLSYTY
HK715IGA      NLGNFGITPI VGVRYSYLSN ANFALAKDRI KVNPISVKTA FAQVDLSYTY
HK61IGA       NLGNFAVKPT VGVRYSYLSN ADFALAQDRI KVNPISVKTA FAQVDLSYTY
Consensus     -LG-----P- -GV------- ------R--- K--------- -A-----YT- 1901                                                                    1950
Hap           TPTDNISVKP YFFVNYVDVS NANVQTTVNL TVLQQPFGRY WQKEVGLKAE
HK368IGA      .HLGEFSVTP ILSARY.DAN QGSGKINVNG YDFAYNVENQ QQYNAGLKLK
HK393IGA      .HLGEFSVTP ILSARY.DAN QGSGKINVNG YDFAYNVENQ QQYNAGLKLK
HK715IGA      .HLGEFSVTP ILSARY.DTN QGSGKINVNQ YDFAYNVENQ QQYNAGLKLK
HK61IGA       .HLGEFSITP ILSARY.DAN QGNGKINVSV YDFAYNVENQ QQYNAGLKLK
Consensus     ------S--P -----Y-D-- --------V- --------- -Q---GLK--

1951                                    1982
Hap           ILHFQISAFI SKSQGSQLGK QQNVGVKLGY RW
HK368IGA      YENVKLSLIG GLTKAKQAEK QKTAELKLSF SF
HK393IGA      YENVKLSLIG GLTKAKQAEK QKTAELKLSF SF
HK715IGA      YENVKLSLIG GLTKAKQAEK QKTAEVKLSF SF
HK61IGA       YENVKLSLIG GLTKAKQAEK QKTAEVKLSF SF
Consensus     -------S-- -------Q--K Q-----KL-- --
```

FIG._7J

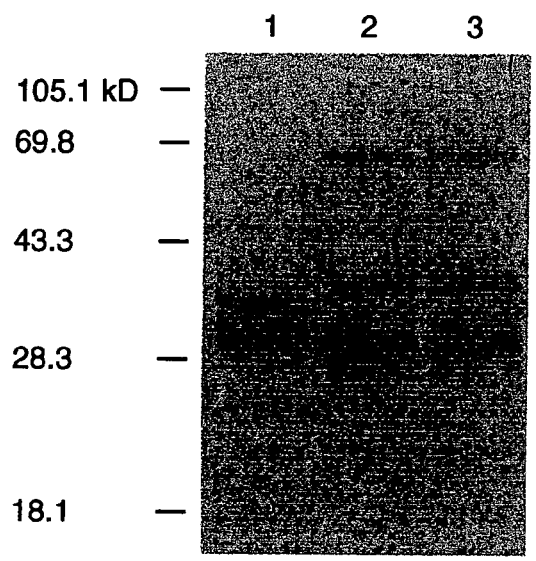
FIG._8
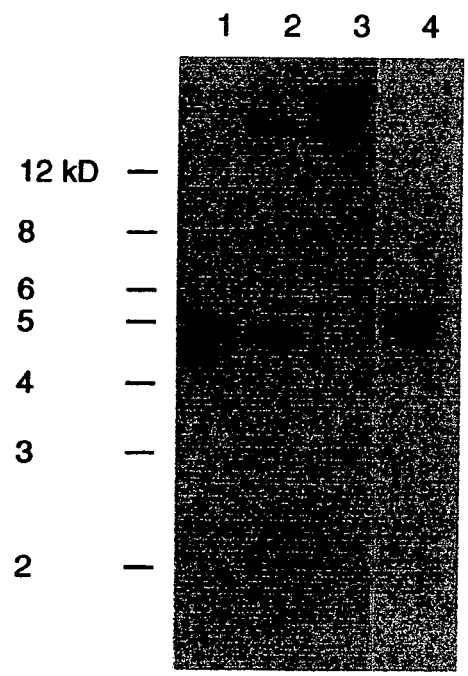
FIG._9A
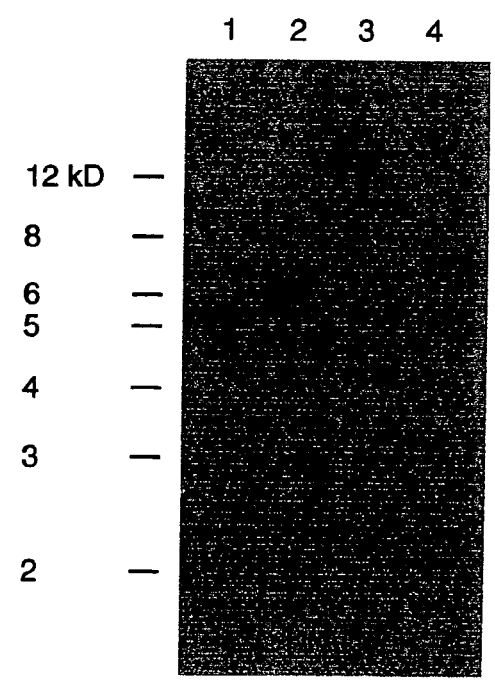
FIG._9B

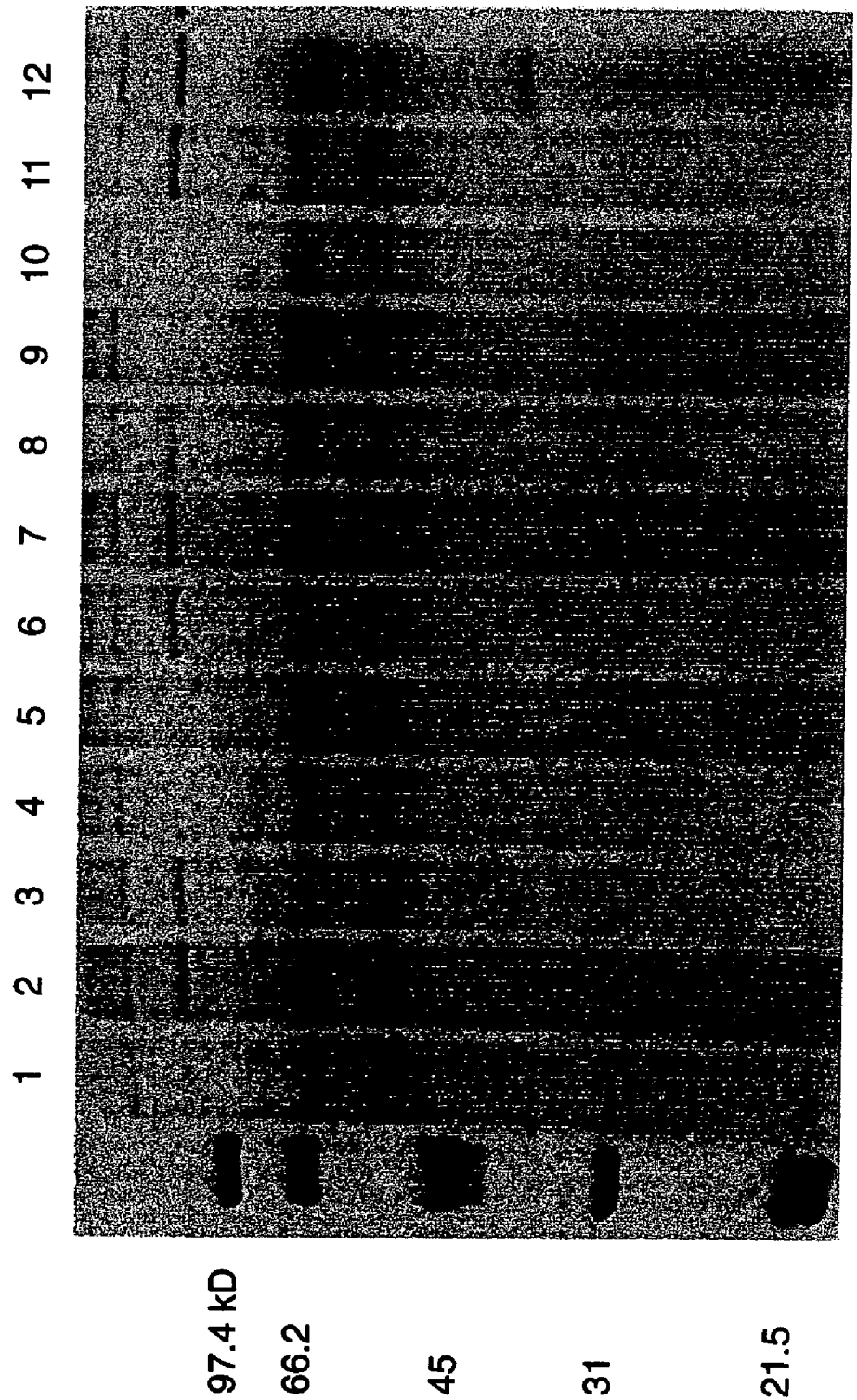
FIG._10

```
              1                                                   50
HapN187    (1) MKKTVFRLNFLTACISLGIVSQAWAGHTYFGIDYQYYRDFAENKGKFTVG
HapTN106   (1) MKKTVFRLNFLTACISLGIVSQAWAGHTYFGIDYQYYRDFAENKGKFTVG
Hap860295  (1) MKKTVFRLNFLTACISLGIVSQAWAGHTYFGIDYQYYRDFAENKGKFSVG
Consensus  (1) MKKTVFRLNFLTACISLGIVSQAWAGHTYFGIDYQYYRDFAENKGKF VG 51                                                 100
HapN187   (51) AQNIKVYNKQGQLVGTSMTKAPMIDFSVVSRNGVAALVENQYIVSVAHNV
HapTN106  (51) AQDIDIYNKKGEMIGTMMKGVPMPDLSSMVRGGYSTLISEQHLISVAHNV
Hap860295 (51) AKNIEVYNKEGTLVGTSMTKAPMIDFSVVSRNGVAALVGDQYIVSVAHNG
Consensus (51) A  I YNK G  GT M  PM D S  RG     L  Q   SVAHN 101                                                150
HapN187  (101) GYTDVDFGAEGNNPDQHRFTYKIVKRNNYKKDNLHPYEDDYHNPRLHKFV
HapTN106 (101) GYDVVDFGMEGENPDQHRFKYKVVKRYNYKSG--DRQYNDYQHPRLEKFV
Hap860295(101) GYNSVDFGAEGPNPDQHRFTQIVKRNNYKPGKDNPYHGDYHMPRLHKFV
Consensus(101) GY  VDFG EG NPDQHRF Y  VKR NYK       DY   PRL KFV 151                                                200
HapN187  (151) TEAAPIDMTSNMNGSTYSDRTKYPERVRIGSGRQFWRNDQDK--GDQ---
HapTN106 (141) TETAPIEMVSYMDGNHYKNFNQYPLRVRVGSGHQWWKDDNNKTIGD----
Hap860295(151) TDAEPAKMTDNMNGKNYADLSKYPDRVRIGTGEQWWRDDEEQKQGSKSSW
Consensus(151) T   P  M   M G  Y      YP RVR G G QWW  D        G 201                                                250
                                                          *
HapN187  (196) VAGAYHYLTAGNTHNQRGAGNGYSYLGGDVRKAGEYGPLBIAGSKGDSGS
HapTN106 (195) LAYGGSWLIGGNTFEDGPAGNGTLELNGRVQNPNKYGPLPTAGSFGDSGS
Hap860295(201) LADAYLWRIAGNTHSQSGAGNGTVNLSGDITKPNNYGPLPTGVSFGDSGS
Consensus(201)  A        GNT     AGNG    L  G        YGPLP  S GDSGS 251                                                300
HapN187  (246) PMFIYDAEKQKWLINGILREGNPFEGKENGFQLVRKSYFDE-IFERDIHT
HapTN106 (245) PMFIYDKEVKKWLLNGVLREGNHYAAVGNSYQITRKDYFQG-ILNQDITA
Hap860295(251) PMFIYDATKQKWLINGVLQTGNPFSGAGNGFQLIRKNWEYDNVFVEDLPI
Consensus(251) PMFIYD   KWL NG L    GNP     N   Q RK  F         D 301                                                350
HapN187  (295) SLYTRAGNGVYTISGNDNG-----QGSITQKSGIPSEIKITLANMSLPLK
HapTN106 (294) NFWDTNAEYRFNIGSDHNGRVATIKSTLPKKAIQPERIVGLYDNSQLHDA
Hap860295(301) TFLEPRSNGHYSFTSNNNG-----TGTVTQTNEKVSMPQFKVRTVQLFNE
Consensus(301)                  NG                                 L 351                                                400
HapN187  (340) -EKDKVHNPRYDGP--NLYSPRLNNGETLYFMDQKQGSLIFASDINQGAG
HapTN106 (344) RDKNGDESPSYKGP--NPWSPALHHGKSIYFGDQGTGTLTIENNINQGAG
Hap860295(346) ALKEKDKEPVYAAGGVNAYKPRLNNGKNIYFGDRGTGTLTIENNINQGAG
Consensus(351)          K  P Y   N    P L  G     YF D  G L     INQGAG
```

*FIG._11A*

```
              401                                               450
HapN187   (387) GLYFEGNFTVSPNSN-QTWQGAGIHVSENSTVTWKVNGVEHDRLSKIGKG
HapTN106  (392) GLYFEGNFVVKGNQNNITWQGAGVSVGEESTVEWQVHNPEGDRLSKIGLG
Hap860295 (396) GLYFEGNFTVSSENN-ATWQGAGVHVGEDSTVTWKVNGVEHDRLSKIGKG
Consensus (401) GLYFEGNF V  N   TWQGAG V  STV W V   E DRLSKIG G 451                                               500
HapN187   (436) TLHVQAKGENKGSISVGDGKVILEQQADDQGNKQAFSEIGLVSGRGTVQL
HapTN106  (442) TLLVNGKGKNLGSLSVGNGLVVLDQQADESGQKQAFKEVGIVSGRATVQL
Hap860295 (445) TLHIQAKGENLGSISVGKGKVILDQQADENNQKQAFKEVGIVSGRATVQL
Consensus (451) TL   KG N GS SVG G V L QQAD   KQAF E G VSGR TVQL 501                                               550
HapN187   (486) NDDKQFDTDKFYFGFRGGRLDLNGHSLTFKRIQNTDEGAMIVNHNTTQAA
HapTN106  (492) NSADQVDPNNIYFGFRGGRLDLNGHSLTFERIQNTDEGAMIVNHNASQTA
Hap860295 (495) NSADQVDPNNIYFGFRGGRLDLNGHSLTFKRIQNTDEGAMIVNHNTTQVA
Consensus (501) N  Q D    YFGFRGGRLDLNGHSLTF RIQNTDEGAMIVNHN Q A 551                                               600
HapN187   (536) NVTITGNESIVLP-NGNNINKLDYRKEIAYNGWFGETDKNKHNGRLNLIY
HapTN106  (542) NITITGNATINS-----DSKQLTNKKDIAFNGWFGEQDKAKTNGRLNVNY
Hap860295 (545) NITITGNESITAPSNKNNINKLDYSKEIAYNGWFGETDENKHNGRLNLIY
Consensus (551) N TITGN  I          L   K IA NGWFGE D K NGRLN  Y 601                                               650
HapN187   (585) KPTTEDRTLLLSGGTNLKGDITQTKGKLFFSGRPTPHAYNHLNKRWSEME
HapTN106  (587) QPVNAENHLLLSGGTNLNGNITQNGGTLVFSGRPTPHAYNHLRRDLSNME
Hap860295 (595) KPTTEDRTLLLSGGTNLKGNITQEGGTLVFSGRPTPHAYNHLNK--PNEL
Consensus (601)  P      LLLSGGTNL G ITQ  G L FSGRPTPHAYNHL 651                                               700
HapN187   (635) GIPQGEIVWDHDWINRTFKAENFQIKGGSAVVSRNVSSIEGNWTVSNNAN
HapTN106  (637) GIPQGEIVWDHDWINRTFKAENFQIKGGSAVVSRNVSSIEGNWTVSNNAN
Hap860295 (643) GRPQGEVVIDDDWETRTFKAENFQIKGGSAVVSRNVSSIEGNWTVSNNAN
Consensus (651) G PQGE V D DWI RTFKAENFQIKGGSAVVSRNVSSIEGNWTVSNNAN 701                                               750
HapN187   (685) ATFGVVPNQQNTICTRSDWTGLTTCQKVDLTDTKVINSIPKTQINGSINL
HapTN106  (687) ATFGVVPNQQNTICTRSDWTGLTTCKTVDLTDKKVINSIPTTQINGSINL
Hap860295 (693) AAFGVVPNQQNTICTRSDWTGLTTCKTVDLTDTKVINSIPTTQINGSINL
Consensus (701) A FGVVPNQQNTICTRSDWTGLTTC  VDLTD KVINSIP TQINGSINL 751                                               800
HapN187   (735) TDNATANVKGLAKLNGNVTLTNHSQFTLSNNATQTGNIRLSDNSTATVDN
HapTN106  (737) TDNATVNIHGLAKLNGNVTLIDHSQFTLSNNATQTGNIKLSNHANATVDN
Hap860295 (743) TDNATVNIHGLAKLNGVVTLINHSQFTLSNNATQTGNIQLSNHANATVDN
Consensus (751) TDNAT N  GLAKLNGNVTL  HSQFTLSNNATQTGNI LS    ATVDN
```

FIG._11B

```
                    801                                              850
HapN187     (785)  ANLNGNVHLTDSAQFSLKNSHFSHQIQGDKGTTVTLENATWTMPSDTTLQ
HapTN106    (787)  ANLNGNVNLMDSAQFSLKNSHFSHQIQGGEDTTVMLENATWTMPSDTTLQ
Hap860295   (793)  ANLNGNVHLTDSAQFSLKNSHFSHQIQGDKDTTVTLENATWTMPSDATLQ
Consensus   (801)  ANLNGNV L DSAQFSLKNSHFSHQIQG   TTV LENATWTMPSD TLQ 851                                              900
HapN187     (835)  NLTLNNSTITLNSAYSASSNNTPRRRRRSLETETTPTSAEHRFNTLTVNG
HapTN106    (837)  NLTLNNSTYTLNSAYSAISNNAPRRRRRSLETETTPTSAEHRFNTLTVNG
Hap860295   (843)  NLTLNNSTYTLNSAYSASSNNAPR-HRRSLETETTPTSAEHRFNTLTVNG
Consensus   (851)  NLTLNNST TLNSAYSA SNN PR  RRSLETETTPTSAEHRFNTLTVNG 901                                              950
HapN187     (885)  KLSGQGTFQFTSSLFGYKSDKLKLSNDAEGDYILSVRNTGKEPETLEQLT
HapTN106    (887)  KLSGQGTFQFTSSLFGYKSDKLKLSNDAEGDYTLSVRNTGKEPVTFGQLT
Hap860295   (892)  KLSGQGTFQFTSSLFGYKSDKLKLSNDAEGDYTLSVRNTGKEPEALEQLT
Consensus   (901)  KLSGQGTFQFTSSLFGYKSDKLKLSNDAEGDY LSVRNTGKEP   QLT 951                                             1000
HapN187     (935)  LVESKDNQPLSDKLKFTLENDHVDAGALRYKLVKNDGEFRLHNPIKEQEL
HapTN106    (937)  LVESKDNKPLSDKLTFTLENDHVDAGALRYKLVKNDGEFRLHNPIKEQEL
Hap860295   (942)  LVESKDNKPLSDKLKFTLENDHVDAGALRYKLVKNNGEFRLHNPIKEQEL
Consensus   (951)  LVESKDN PLSDKL FTLENDHVDAGALRYKLVKN GEFRLHNPIKEQEL 1001                                             1050
HapN187     (985)  HNDLVRAEQAERTLEAKQVEPTAKTQTGEPKVRSRAARAAPPDTLPDQS
HapTN106    (987)  RSDLVRAEQAERTLEAKQVEQTAKTQTSKARVRSR---RAVFSDPLPAQS
Hap860295   (992)  RNDLVRAEQAERTLEAKQVEQTAETQTSNARVRSK---RAVFSDTLPDQS
Consensus  (1001)    DLVRAEQAERTLEAKQVE TA TQT    VRS   RA F D LP QS 1051                                             1100
HapN187    (1035)  LLNALEAKQAELTAETQKSKAKTKKVRSKRAV--FSDPLLDQS------
HapTN106   (1034)  LLKALEAKQA-LTTETQTS--KAKKVRSKRAAREFSDTLPDQ-------
Hap860295  (1039)  QLDVLQAEQVEPTAEKQKN--KAKKVRSKRAV--FSDTLPDSQLDVLQA
Consensus  (1051)   L  LAQ   TE Q   K KKVRSKRA   FSD L DQ 1101                                             1150
HapN187    (1076)  -------------------------------IFALEAALEVIDAQQ
HapTN106   (1073)  --------------------------------ILQAALEVIDAQQ
Hap860295  (1085)  EQVEPTAEKQKNKAKKVRSKRAAREFSDTPLDLSRLKVLEVKLEVINAQQ
Consensus  (1101)                                      L   LEVI A Q 1151                                             1200
HapN187    (1091)  QSEKDRLAQEEAEK-QRKQKDLISRYSNSALSELSATVNSMLSVQDELDR
HapTN106   (1086)  QVKKEPQTQEEEEKRQRKQKELISRYSNSALSELSATVNSMLSVQDELDR
Hap860295  (1135)  QVKKEPQDQ---EK-QRKQKDLISRYSNSALSELSATVNSMLSVQDELDR
Consensus  (1151)  Q  K  Q   EK QRKQK LISRYSNSALSELSATVNSMLSVQDELDR
```

*FIG._11C*

```
                 1201                                              1250
HapN187    (1140) LFVDQAQSAVWTNIAQDKRRYDSDAFRAYQQKTNLRQIGVQKALANGRIG
HapTN106   (1136) LFVDQAQSAVWTNIAQDKRRYDSDAFRAYQQKTNLRQIGVQKALDNGRIG
Hap860295  (1181) LFVDQAQSAVWTNIAQDKRRYDSDAFRAYQQKTNLRQIGVQKALANGRIG
Consensus  (1201) LFVDQAQSAVWTNIAQDKRRYDSDAFRAYQQKTNLRQIGVQKAL NGRIG 1251                                              1300
HapN187    (1190) AVFSHSRSDNTFDEQVKNHATLTMMSGFAQYQWGDLQFGVNVGTGISASK
HapTN106   (1186) AVFSHSRSDNTFDEQVKNHATLAMMSGFAQYQWGDLQFGVNVGAGISASK
Hap860295  (1231) AVFSHSRSDNTFDEQVKNHATLTMMSGFAQYQWGDLQFGVNVGTGISASK
Consensus  (1251) AVFSHSRSDNTFDEQVKNHATL MMSGFAQYQWGDLQFGVNVG GISASK 1301                                              1350
HapN187    (1240) MAEEQSRKIHRKAINYGVNASYQFRLGQLGIQPYFGVNRYFIERENYQSE
HapTN106   (1236) MAEEQSRKIHRKAINYGVNASYQFRLGQLGIQPYIGVNRYFIERENYQSE
Hap860295  (1281) MAEEQSRKIHRKAINYGVNASYQFRLGQLGIQPYFGVNRYFIERENYQSE
Consensus  (1301) MAEEQSRKIHRKAINYGVNASYQFRLGQLGIQPY GVNRYFIERENYQSE 1351                                              1400
HapN187    (1290) EVRVKTPSLAFNRYNAGIRVDYTFTPTDNISVKPYFFVNYVDVSNANVQT
HapTN106   (1286) EVKVQTPSLVFNRYNAGIRVDYTFTPTDNISIKPYFFVNYVDVSNANVQT
Hap860295  (1331) EVKVKTPSLAFNRYNAGIRVDYTFTPTDNISVKPYFFVNYVDVSNANVQT
Consensus  (1351) EV V TPSL FNRYNAGIRVDYTFTPTDNIS KPYFFVNYVDVSNANVQT 1401                                              1450
HapN187    (1340) TVNLTVLQQPFGRYWQKEVGLKAEILHFQISAFISKSQGSQLGKQQNVGV
HapTN106   (1336) TVNRTMLQQSFGRYWQKEVGLKAEILHFQLSAFISKSQGSQLGKQQNVGV
Hap860295  (1381) TVNSTVLQQPFGRYWQKEVGLKAEILHFQISAFISKSQGSQLGKQQNVGV
Consensus  (1401) TVN T LQQ FGRYWQKEVGLKAEILHFQ SAFISKSQGSQLGKQQNVGV 1451
HapN187    (1390) KLYGRW
HapTN106   (1386) KLYGRW
Hap860295  (1431) KLYGRW
Consensus  (1451) KLYGRW
```

FIG._11D

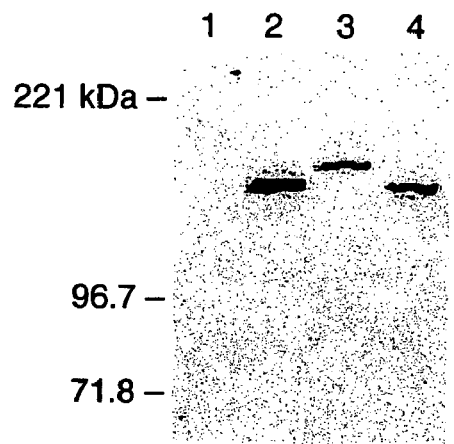
FIG._12A
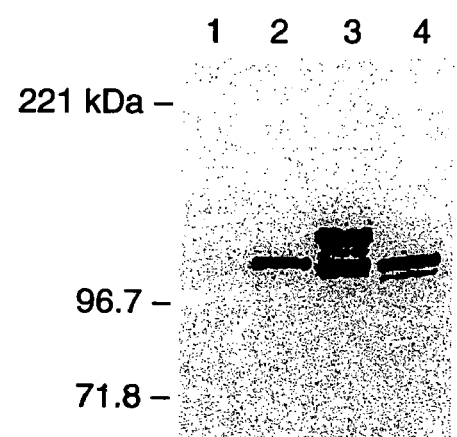
FIG._12B
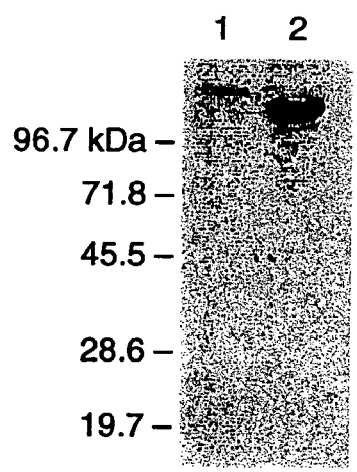
FIG._14

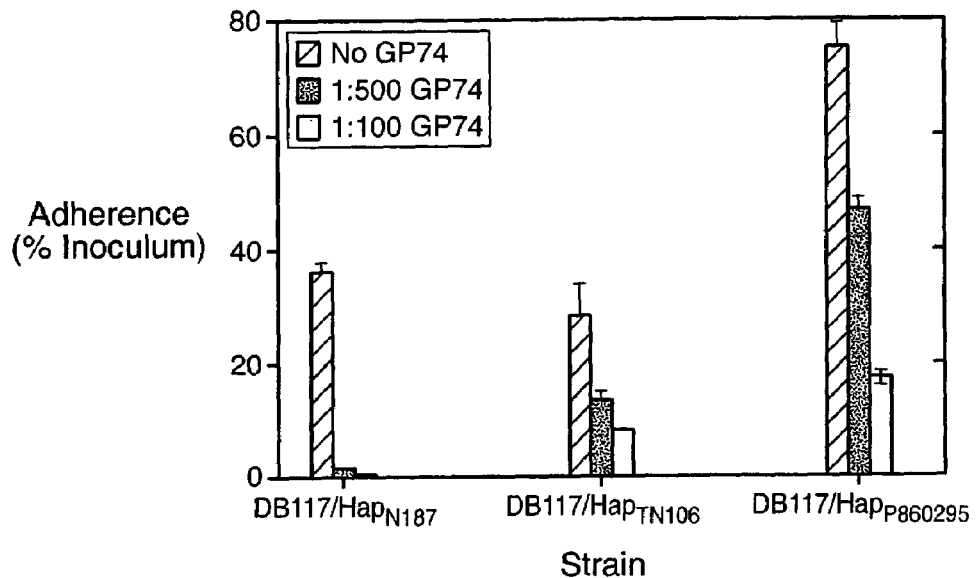
FIG._13
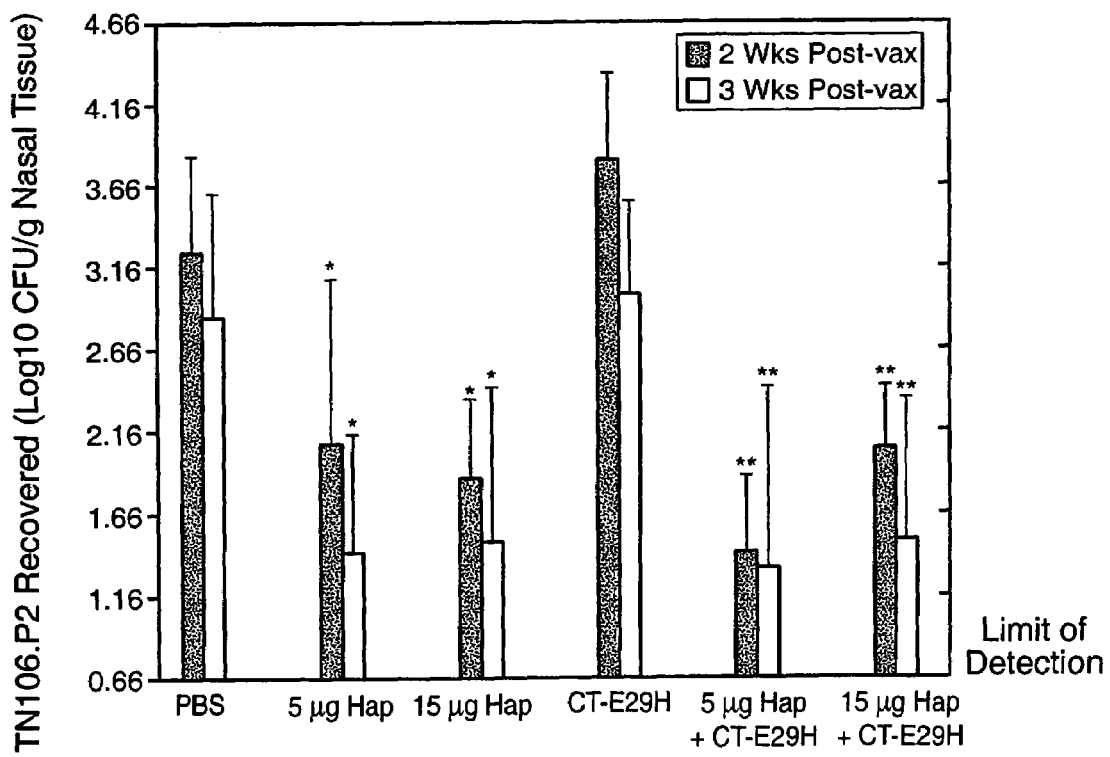
FIG._15

Nucleotide sequence for NTHi strain 11 hap gene (start codon to stop codon):

```
   1 ATGAAAAAAA CTGTATTTCG TCTTAATTTT TTAACCGCTT GCATTTCATT
  51 AGGGATAGTA TCGCAAGCGT GGGCAGGTCA TACTTATTTT GGGATTGACT
 101 ACCAATATTA TCGTGATTTT GCCGAGAATG AAGGCAAGTT TGCAGTTGGG
 151 GCTAAAAATA TTGATGTTTA TAACAAAGAA GGGCAATTAG TTGGCACATC
 201 AATGACAAAA GCCCCGATGA TTGATTTCTC AGTCGTTTCC AGAAATGGAG
 251 TTGCTGCCTT AGTAGGCGAT CAGTATATTG TGAGTGTGGC ACATAATGTA
 301 GGCTATACCA ATGTGGATTT TGGTGCTGAA GGACAAAATC CTGATCAACA
 351 TCGTTTTACT TATAAAATTG TGAAACGGAA TAATTATAAT CACGATGCGA
 401 AGCACCGCTA TCTAGATGAC TACCATAATC ACGTTTACA TAAATTTGTA
 451 ACGGATGCGG CACCAATTGA TATGACTTCA CATATGGATG CAATAAGTA
 501 TGCAAATAAG GAAAAATATC CTGAACGAGT ACGCGTCGGA TCTGGAGATC
 551 AGTATTGGGA TGACGATCAA ACAACAGAA CTTATTTATC TGACGGATAT
 601 AATTATTTAA CAGGTGGGAA TACATATAAT CAAAGCGGTA GAGGTGATGG
 651 ATATTCATAT GTGAGAGGTG ATATTCGCAA AGTTGGCGAT TATGGTCCAT
 701 TACCGATTGC AAGTTCATTC GGGGACAGTG GATCTCCAAT GTTTATTTAT
 751 GATGCTGAAA CACAAAAATG gcTAATTAAT GGAGTATTGC GGGAGGGGCA
 801 ACCTTATACA GGCGAATTCG ATGGATTTCA ATTAGCCCGT AAATCTTTCC
 851 TTGATGAAAT TATACGCAAA GATCAACCAA ATGGTTTTTT AACCCCTAAG
 901 GGGAATGGCG TTTATACCAT TTCTAAAAGT GACGATGGGA TAGGAGTTGT
 951 TACTTCGAAA ATTGGAAAAC CTCGTGAAAT ACCTTTAGCG AACAACAAAT
1001 TAAAAATAGA AGATAAAGAT ACTGTCTATA ATAACAGATA TAATGGTCCT
1051 AATATTTATT CTCCTCAATT AAACAATGGC AAGAATATTT ATTTTGGAGA
1101 TGAAGAATTA GGATCCATAA CTTTAACGAC TGATATCGAT CAAGGTGCAG
1151 GCGGTTTGTA TTTTGAGGGG GATTTTATAG TTTCGCCTAC CAAAAATGAA
1201 ACGTGGAAAG GTGCGGGCAT TCATGTCAGT GAAATTAGTA CCGTTACTTG
1251 GAAAGTAAAC GGCGTGGAAA ATGATCGACT TTCTAAAATC GGTAAAGGAA
1301 CATTACACGT TAAAGCCAAA GGGGAAAATA AAGGTTCGAT CAGCGTAGGC
1351 GATGGTAAAG TCATTTTGGA GCAGCAGGCA GACGATCAAG CAACAAACA
1401 AGCCTTTAGT GAAATTGGCT TGGTTAGCGG CAGAGGGACT GTTCAATTAA
1451 ACGATGATAA ACAATTTGAT ACCGATAAAT TTTATTTCGG CTTTCGTGGT
1501 GGTCGCTTAG ATCTTAACGG ACATTCATTA ACCTTTAAAC GTATCCAAAA
1551 TACGGACGAG GGGGCGATGA TTGTGAACCA TAATACAACT CAAGTCGCTA
1601 ATATTACTAT TACTGGGAAC GAAAGTATTA CTGCTCCATC TAATAAAAAT
1651 AATATTAATA AACTTGATTA CAGCAAAGAA ATTGCCTACA ACGGCTGGTT
1701 TNGCGAAACA GATAAAATA AACATAATGG ACGATTAAAC CTTATTTATA
1751 AACCAACCAC AGAAGATCGT ACTTTGCTAC TTTCAGGCGG CACAAACTTA
1801 AAAGGCGATA TTACTCAAAC AAAAGGTAAA CTATTTTTCA GCGGTAGACC
1851 GACACCCCAC GCCTACAATC ATTTAGACAA ACGTTGGTCA GAAATGGAAG
1901 GTATCCCACA AGGCGAAATT GTGTGGGATT ACGATTGGAT TAACCGCACA
1951 TTTAAAGCTG AAAACTTCCA AATTAAAGGC GGAAGTGCGG TGGTTTCTCG
2001 CAATGTTTCT TCAATTGAGG GAAATTGGAC AGTCAGCAAT AATGCAAATG
```

FIG._16A

```
2051  CCACATTTGG TGTTGTGCCA AATCAGCAAA ATACCATTTG CACGCGTTCA
2101  GATTGGACAG GATTAACGAC TTGTAAAACA GTTAATTTAA CCGATAAAAA
2151  AGTTATTGAT TCCATACCGA CAACACAAAT TAATGGTTCT ATTAATTTAA
2201  CTGATAATGC AACAGTGAAT ATTAATGGTT TAGCAAAACT TAATGGTAAT
2251  GTCACTTTAA TAAATCATAG CCAATTTACA TTGAGCAACA ATGCCACCCA
2301  AATAGGCAAT ATCAAACTTT CAAATCACGC AAATGCAAGG GTAAATAATG
2351  CCACTTTAAT GGGCGATGTG AATTTAGCGG ATACTAGCCG TTTTACATTA
2401  AGCAATCAAG CAACACAGAT TGGCACAATC AGTCTTCATC AGCAAGCTCA
2451  AGCAACAGTG GATAATGCAA ACTTGAACGG TAATGTGCAT TTAACGGATT
2501  CTGCCAGATT TTCTTTAAAA AACAGTCATT TTTCGCACCA AATTCAGGGC
2551  GACAAGACA  CAACAGTGAC GTTGGAAAAT GCGACTTGGA CAATGCCTAG
2601  CGATACTACA TTGCAGAATT TAACGCTAAA TAATAGTACT GTTACGTTAA
2651  ATTCAGCTTA TTCAGCTAGC TCAAATAATG CGCCACGTCG CCgCCGTTCA
2701  TTAGAGACGG AAACAACGCC AACATCGGCA GAACATCGTT TCAACACATT
2751  GACAGTAAAT GGTAAATTGA GCGGCAAGG  CACATTCCAA TTTACTCCAT
2801  CTTTATTTGG CTATGAAAGC GATAAATTAA AATTATCCAA TGACGCTGAG
2851  GGCGATTACA CATTATCTGT TCGCAACACA GGCAAAGAAC CCGTGACCCT
2901  TGAGCAATTA ACTTTGGTTG AAAGCAAAGA TAATAAACCG TTATCAGACA
2951  AACTCAAATT TACTTTAGAA AATGACCACG TTGATGCAGG TGCATTACGT
3001  TATAAATTAG TGAAGAATAA GGGCGAATTC CGCTTGCATA ACCCAATAAA
3051  AGAGCAGGAA TTGCGCTCTG ATTTAGTAAG AGCAGAGCAA GCAGAACGAA
3101  CATTAGAAGC CAAACAAGTT GAACAGACTG CTGAAACACA AACAAGTAAT
3151  GCAAGAGTGC GGTCAAGAAG AGCGGTGTTG TCTGATACCC CGTCTGCTCA
3201  AAGCCTGTTA AACGCATTAG AAGTCAAACA AGCTGAACCG AATGCTAAAA
3251  CACAAAAAAG TAAGGCAAAA ACAAAAAAAG CGCGGTCAAA AAGAGCATTG
3301  AGAGAAGCGT TTTCTGATAC CCCGCCTGAT CTAAGCCAGT TAAACGTATT
3351  AGAAGCCGCA CTTAAGGTTA TTAATGCCCA ACCGCAAACA GAAAAAGAAC
3401  GTCAAGCTCA AGAGGAAGAA GCGAAAAGAC AACGCaAACA AAAAGACTTG
3451  ATCAGCCGTT ACTCAAATAG TGCGTTATCG GAGTTGTCTG CAACAGTAAA
3501  TAGTATGCTT TCCGTTCAAG ATGAATTGGA TCGTCTTTTT GTAGATCAAG
3551  CACAATCTGC CCTGTGGACA AATATCGCAC AGGATAAAAG ACGCTATGAT
3601  TCTGATGCGT TCCGTGCTTA TCAGCAGAAA ACGAACTTGC GTCAAATTGG
3651  GGTGCAAAAA GCCTTAGATA ATGGACGAAT TGGGGCGGTT TTCTCGCATA
3701  GCCGTTCAGA TAATACCTTT GACGAACAGG TTAAAAATCA CGCGACATTA
3751  ACGATGATGT CGGGTTTTGC CCAATATCAA TGGGCGATT  TACAATTTGG
3801  TGTAAACGTG GGCGCGGGAA TTAGTGCGAG TAAAATGGCT GAAGAACAAA
3851  GCCGAAAAAT TCATCGAAAA GCGATAAATT ATGGTGTGAA TGCAAGTTAT
3901  CAGTTCCGTT TAGGGCAATT GGGTATTCAG CCTTATTTGG GTGTTAATCG
3951  ATATTTTATT GAACGTGAAA ATTATCAATC TGAAGAAGTG AAAGTGCAAA
4001  CACCGAGCCT TGCATTTAAT CGCTATAATG CTGGCATTCG AGTTGATTAT
4051  ACATTTACCC CGACAGATAA TATCAGCGTT AAGCCTTATT TCTTTGTCAA
4101  TTATGTTGAT GTTTCAAACG CTAACGTACA AACCACTGTA AATAGCACGA
4151  TGTTGCAACA ATCATTTGGG CGTTATTGGC AAAAAGAAGT GGGATTAAAG
4201  GCAGAAATTT TACATTTCCA ACTTTCCGCT TTTATCTCAA AATCTCAAGG
4251  TTCACAACTC GGTAAACAGC AAAATGTGGG CGTGAAATTG GGCTATCGTT
4301  GGTAA
```

FIG._16B

Amino acid sequence for NTHi strain 11 Hap protein (first amino acid to last amino acid):

```
   1  MKKTVFRLNF  LTACISLGIV  SQAWAGHTYF  GIDYQYYRDF  AENEGKFAVG
  51  AKNIDVYNKE  GQLVGTSMTK  APMIDFSVVS  RNGVAALVGD  QYIVSVAHNV
 101  GYTNVDFGAE  GQNPDQHRFT  YKIVKRNNYN  HDAKHRYLDD  YHNPRLHKFV
 151  TDAAPIDMTS  HMDGNKYANK  EKYPERVRVG  SGDQYWDDDQ  NNRTYLSDGY
 201  NYLTGGNTYN  QSGRGDGYSY  VRGDIRKVGD  YGPLPIASSF  GDSGSPMFIY
 251  DAETQKWLIN  GVLREGQPYT  GEFDGFQLAR  KSFLDEIIRK  DQPNGFLTPK
 301  GNGVYTISKS  DDGIGVVTSK  IGKPREIPLA  NNKLKIEDKD  TVYNNRYNGP
 351  NIYSPQLNNG  KNIYFGDEEL  GSITLTTDID  QGAGGLYFEG  DFIVSPTKNE
 401  TWKGAGIHVS  EISTVTWKVN  GVENDRLSKI  GKGTLHVKAK  GENKGSISVG
 451  DGKVILEQQA  DDQGNKQAFS  EIGLVSGRGT  VQLNDDKQFD  TDKFYFGFRG
 501  GRLDLNGHSL  TFKRIQNTDE  GAMIVNHNTT  QVANITITGN  ESITAPSNKN
 551  NINKLDYSKE  IAYNGWFXET  DKNKHNGRLN  LIYKPTTEDR  TLLLSGGTNL
 601  KGDITQTKGK  LFFSGRPTPH  AYNHLDKRWS  EMEGIPQGEI  VWDYDWINRT
 651  FKAENFQIKG  GSAVVSRNVS  SIEGNWTVSN  NANATFGVVP  NQQNTICTRS
 701  DWTGLTTCKT  VNLTDKKVID  SIPTTQINGS  INLTDNATVN  INGLAKLNGN
 751  VTLINHSQFT  LSNNATQIGN  IKLSNHANAR  VNNATLMGDV  NLADTSRFTL
 801  SNQATQIGTI  SLHQQAQATV  DNANLNGNVH  LTDSARFSLK  NSHFSHQIQG
 851  DKDTTVTLEN  ATWTMPSDTT  LQNLTLNNST  VTLNSAYSAS  SNNAPRRRRS
 901  LETETTPTSA  EHRFNTLTVN  GKLSGQGTFQ  FTPSLFGYES  DKLKLSNDAE
 951  GDYTLSVRNT  GKEPVTLEQL  TLVESKDNKP  LSDKLKFTLE  NDHVDAGALR
1001  YKLVKNKGEF  RLHNPIKEQE  LRSDLVRAEQ  AERTLEAKQV  EQTAETQTSN
1051  ARVRSRRAVL  SDTPSAQSLL  NALEVKQAEP  NAKTQKSKAK  TKKARSKRAL
1101  REAFSDTPPD  LSQLNVLEAA  LKVINAQPQT  EKERQAQEEE  AKRQRKQKDL
1151  ISRYSNSALS  ELSATVNSML  SVQDELDRLF  VDQAQSALWT  NIAQDKRRYD
1201  SDAFRAYQQK  TNLRQIGVQK  ALDNGRIGAV  FSHSRSDNTF  DEQVKNHATL
1251  TMMSGFAQYQ  WGDLQFGVNV  GAGISASKMA  EEQSRKIHRK  AINYGVNASY
1301  QFRLGQLGIQ  PYLGVNRYFI  ERENYQSEEV  KVQTPSLAFN  RYNAGIRVDY
1351  TFTPTDNISV  KPYFFVNYVD  VSNANVQTTV  NSTMLQQSFG  RYWQKEVGLK
1401  AEILHFQLSA  FISKSQGSQL  GKQQNVGVKL  GYRW
```

FIG._17

Nucleotide sequence for NTHi strain TN106 hap gene (start codon begins at position 422, stop codon begins at position 4595):

```
   1 TGGCGGCGGA CAAATTATTG CGACGGGTAC ACCAGAACAA GTTGCTAAAG
  51 TAAAAAGTTC CCACACCGCT CGCTTCCTTA AACCGATTTT AGAAAAACCT
 101 TAGAAAAAAT GACCGCACTT TCAGAGAAAA CTCACATAAA GTGCGGTTAT
 151 TTTATTAGTG ATATTGTTTT AATTTTAGTT ATCTGTATAA ATTACATACA
 201 ATATTAATCC ATCGCAAGAT TAGATTACCC ACTAAGTATT AAGCAAAAAC
 251 CTAGAAATTT TGGCTTAATT ACTATATAGT TTTACTCATT TATTTTCTTT
 301 TGTGCCTTTT AGTTCATTTT TTTAGCTGAA ATCCCTTAGA AAATCACCGC
 351 ACTTTTATTG TTCAATAGTC GTTAACCAC GTATTTTTA ATACGAAAAA
 401 TTACTTAATT AAATAAACAT TATGAAAAAA ACTGTATTTC GTCTGAATTT
 451 TTTAACCGCT TGCATTTCAT TAGGGATAGT ATCGCAAGCG TGGGCAGGTC
 501 ATACTTATTT TGGGATTGAC TACCAATATT ATCGTGATTT TGCCGAGAAT
 551 AAAGGGAAGT TTACAGTTGG GGCTCAAGAT ATTGATATCT ACAATAAAAA
 601 AGGGGAAATG ATAGGTACGA TGATGAAAGG TGTGCCTATG CCTGATTTAT
 651 CTTCCATGGT TCGTGGTGGT TATTCAACAT TGATAAGTGA GCAGCATTTA
 701 ATTAGCGTCG CACATAATGT AGGGTATGAT GTCGTTGATT TGGTATGGA
 751 GGGGGAAAAT CCAGACCAAC ATCGTTTTAA GTATAAAGTT GTTAAACGAT
 801 ATAATTATAA GAGCGGTGAT AGACAATATA ATGATTATCA ACATCCAAGA
 851 TTAGAGAAAT TTGTAACGGA AACTGCACCT ATTGAAATGG TTTCATATAT
 901 GGATGGTAAT CATTACAAAA ATTTTAATCA ATATCCTTTG CGAGTTAGAG
 951 TTGGAAGTGG GCATCAATGG TGGAAAGACG ATAATAATAA AACCATTGGA
1001 GACTTAGCCT ATGGAGGTTC ATGGTTAATA GGTGGAAATA CCTTTGAAGA
1051 TGGACCAGCT GGTAACGGTA CATTAGAATT AAATGGGCGA GTACAAAATC
1101 CTAATAAATA TGGTCCACTA CCTACGGCAG GTTCATTCGG GGATAGTGGT
1151 TCTCCAATGT TTATTTATGA TAAGGAAGTT AAGAAATGGT TATTAAATGG
1201 CGTGTTACGT GAAGGAAATC CTTATGCTGC AGTAGGAAAC AGCTATCAAA
1251 TTACACGAAA AGATTATTTT CAAGGTATTC TTAATCAAGA CATTACAGCT
1301 AATTTTTGGG ATACTAATGC TGAATATAGA TTTAATATAG GGAGTGACCA
1351 CAATGGAAGA GTGGCAACAA TCAAAAGTAC ATTACCTAAA AAAGCTATTC
1401 AGCCTGAACG AATAGTGGGT CTTTATGATA ATAGCCAACT TCATGATGCT
1451 AGAGATAAAA ATGGCGATGA ATCTCCCTCT TATAAAGGTC CTAATCCATG
1501 GTCGCCAGCA TTACATCATG GAAAAGTAT TTACTTTGGC GATCAAGGAA
1551 CAGGAACTTT AACAATTGAA ATAATATAA ATCAAGGTGC AGGTGGATTG
1601 TATTTTGAAG GTAATTTTGT TGTAAAAGGC AATCAAAATA ATATAACTTG
1651 GCAAGGTGCA GGCGTTTCTG TTGGAGAAGA AAGTACTGTT GAATGGCAGG
1701 TGCATAATCC AGAAGGCGAT CGCTTATCCA AAATTGGGCT GGGAACCTTA
1751 CTTGTTAATG GTAAAGGGAA AAACTTAGGA AGCCTGAGTG TCGGTAACGG
1801 TTTGGTTGTG TTAGATCAAC AAGCAGATGA ATCAGGTCAA AAACAAGCCT
1851 TAAAGAAGT TGGCATTGTA AGTGGTAGAG CTACCGTTCA ACTAAATAGT
1901 GCAGATCAAG TTGATCCTAA CAATATTTAT TTCGGCTTTC GTGGTGGTCG
1951 CTTAGATCTT AATGGGCATT CATTAACCTT TGAACGTATC CAAAATACGG
2001 ATGAAGGCGC GATGATTGTG AACCACAACG CTTCTCAAAC CGCAAATATT
```

FIG._18A

```
2051  ACGATTACAG GCAACGCAAC TATTAATTCA GATAGCAAAC AACTTACTAA
2101  TAAAAAGAT ATTGCATTTA ACGGCTGGTT TGGTGAGCAA GATAAAGCTA
2151  AAACAAATGG TCGTTTAAAT GTGAATTATC AACCAGTTAA TGCAGAAAAT
2201  CATTTGTTGC TTTCTGGGGG GACAAATTTA AACGGCAATA TCACGCAAAA
2251  TGGTGGTACG TTAGTTTTTA GTGGTCGTCC AACGCCTCAT GCTTACAATC
2301  ATTTAAGAAG AGACTTGTCT AACATGGAAG GTATCCCACA AGGCGAAATT
2351  GTGTGGGATC ACGATTGGAT CAACCGCACA TTTAAAGCTG AAAACTTCCA
2401  AATTAAAGGC GGAAGTGCGG TGGTTTCTCG CAATGTTTCT TCAATTGAGG
2451  GAAATTGGAC AGTCAGCAAT AATGCAAATG CCACATTTGG TGTTGTGCCA
2501  AATCAGCAAA ATACCATTTG CACGCGTTCA GATTGGACAG GATTAACGAC
2551  TTGTAAAACA GTTGATTTAA CCGATAAAAA AGTTATTAAT TCCATACCGA
2601  CAACACAAAT TAATGGTTCT ATTAATTTAA CTGATAATGC AACAGTGAAT
2651  ATTCATGGTT TAGCAAAACT TAATGGTAAT GTCACTTTAA TAGATCACAG
2701  CCAATTTACA TTGAGCAACA ATGCCACCCA AACAGGCAAT ATCAAACTTT
2751  CAAATCACGC AAATGCAACG GTGGACAATG CAAATTTGAA CGGTAATGTG
2801  AATTTAATGG ATTCTGCTCA ATTTCTTTA AAAACAGCC ATTTTCGCA
2851  CCAAATCCAA GGTGGGGAAG ACACAACAGT GATGTTGAA AATGCGACTT
2901  GGACAATGCC TAGCGATACC ACATTGCAGA ATTTAACGCT AAATAATAGT
2951  ACTGTTACGT TAAATTCAGC TTATTCAGCT ATCTCAAATA ATGCGCCACG
3001  CCGTCGCCGC CGTTCATTAG AGACGGAAAC AACGCCAACA TCGGCAGAAC
3051  ATCGTTTCAA CACATTGACA GTAAATGGTA AATTGAGCGG GCAAGGCACA
3101  TTCCAATTTA CTTCATCTTT ATTTGGCTAT AAAAGCGATA AATTAAAATT
3151  ATCCAATGAC GCTGAGGGCG ATTACACATT ATCTGTTCGC AACACAGGCA
3201  AAGAACCCGT GACCTTTGGG CAATTAACTT TGGTTGAAAG CAAAGATAAT
3251  AAACCGTTAT CAGACAAACT CACATTCACG TTAGAAAATG ACCACGTTGA
3301  TGCAGGTGCA TTACGTTATA AATTAGTGAA GAATGATGGC GAATTCCGCT
3351  TACATAACCC AATAAAAGAG CAGGAATTGC GCTCTGATTT AGTAAGAGCA
3401  GAGCAAGCAG AACGAACATT AGAAGCAAA CAAGTTGAAC AGACTGCTAA
3451  AACACAAACA AGTAAGGCAA GAGTGCGGTC AAGAAGAGCG GTGTTTTCTG
3501  ATCCCCTGCC TGCTCAAAGC CTGTTAAAAG CATTAGAAGC CAAACAAGCT
3551  CTGACTACTG AAACACAAAC AAGTAAGGCA AAAAAAGTGC GGTCAAAAAG
3601  AGCTGCGAGA GAGTTTTCTG ATACCCTGCC TGATCAAATA TTACAAGCCG
3651  CACTTGAGGT TATTGATGCC CAACAGCAAG TGAAAAAAGA ACCTCAAACT
3701  CAAGAGGAAG AAGAGAAAAG ACAACGCAAA CAAAAAGAAT TGATCAGCCG
3751  TTACTCAAAT AGTGCGTTAT CGGAGTTGTC TGCGACAGTA AATAGTATGC
3801  TTTCCGTTCA AGATGAATTG GATCGTCTTT TTGTAGATCA AGCACAATCT
3851  GCCGTGTGGA CAAATATCGC ACAGGATAAA AGACGCTATG ATTCTGATGC
3901  GTTCCGTGCT TATCAGCAGA AAACGAACTT GCGTCAAATT GGGGTGCAAA
3951  AAGCCTTAGA TAATGGACGA ATTGGGGCGG TTTTCTCGCA TAGCCGTTCA
4001  GATAATACCT TGACGAACA GGTTAAAAAT CACGCGACAT TAGCGATGAT
4051  GTCGGGTTTT GCCCAATATC AATGGGGCGA TTTACAATTT GGTGTAAACG
4101  TGGGTGCGGG AATTAGTGCG AGTAAAATGG CTGAAGAACA AAGCCGAAAA
4151  ATTCATCGAA AAGCGATAAA TTATGGTGTG AATGCAAGTT ATCAGTTCCG
4201  TTTAGGGCAA TTGGGTATTC AGCCTTATTT GGGTGTTAAT CGATATTTTA
```

*FIG. 18B*

```
4251  TTGAACGTGA AAATTATCAA TCTGAAGAAG TGAAAGTGCA AACACCGAGC
4301  CTTGTATTTA ATCGCTATAA TGCTGGCATT CGAGTTGATT ATACATTTAC
4351  CCCGACAGAT AATATCAGCA TTAAGCCTTA TTTCTTCGTC AATTATGTTG
4401  ATGTTTCAAA CGCTAACGTA CAAACCACTG TAAATCGCAC GATGTTGCAA
4451  CAATCATTTG GCGTTATTG GCAAAAAGAA GTGGGATTAA AGGCAGAAAT
4501  TTTACATTTC CAACTTTCCG CTTTTATCTC AAAATCTCAA GGTTCACAAC
4551  TCGGCAAACA GCAAATGTGG GCGTGAAAT TGGGGTATCG TTGGTAAAAA
4601  TCAAC
```

FIG._18C

Amino acid sequence for NTHi strain TN106 Hap protein (first amino acid to last amino acid):

```
   1  MKKTVFRLNF LTACISLGIV SQAWAGHTYF GIDYQYYRDF AENKGKFTVG
  51  AQDIDIYNKK GEMIGTMMKG VPMPDLSSMV RGGYSTLISE QHLISVAHNV
 101  GYDVVDFGME GENPDQHRFK YKVVKRYNYK SGDRQYNDYQ HPRLEKFVTE
 151  TAPIEMVSYM DGNHYKNFNQ YPLRVRVGSG HQWWKDDNNK TIGDLAYGGS
 201  WLIGGNTFED GPAGNGTLEL NGRVQNPNKY GPLPTAGSFG DSGSPMFIYD
 251  KEVKKWLLNG VLREGNPYAA VGNSYQITRK DYFQGILNQD ITANFWDTNA
 301  EYRFNIGSDH NGRVATIKST LPKKAIQPER IVGLYDNSQL HDARDKNGDE
 351  SPSYKGPNPW SPALHHGKSI YFGDQGTGTL TIENNINQGA GGLYFEGNFV
 401  VKGNQNNITW QGAGVSVGEE STVEWQVHNP EGDRLSKIGL GTLLVNGKGK
 451  NLGSLSVGNG LVVLDQQADE SGQKQAFKEV GIVSGRATVQ LNSADQVDPN
 501  NIYFGFRGGR LDLNGHSLTF ERIQNTDEGA MIVNHNASQT ANITITGNAT
 551  INSDSKQLTN KKDIAFNGWF GEQDKAKTNG RLNVNYQPVN AENHLLLSGG
 601  TNLNGNITQN GGTLVFSGRP TPHAYNHLRR DLSNMEGIPQ GEIVWDHDWI
 651  NRTFKAENFQ IKGGSAVVSR NVSSIEGNWT VSNNANATFG VVPNQQNTIC
 701  TRSDWTGLTT CKTVDLTDKK VINSIPTTQI NGSINLTDNA TVNIHGLAKL
 751  NGNVTLIDHS QFTLSNNATQ TGNIKLSNHA NATVDNANLN GNVNLMDSAQ
 801  FSLKNSHFSH QIQGGEDTTV MLENATWTMP SDTTLQNLTL NNSTVTLNSA
 851  YSAISNNAPR RRRSLETET TPTSAEHRFN TLTVNGKLSG QGTFQFTSSL
 901  FGYKSDKLKL SNDAEGDYTL SVRNTGKEPV TFGQLTLVES KDNKPLSDKL
 951  TFTLENDHVD AGALRYKLVK NDGEFRLHNP IKEQELRSDL VRAEQAERTL
1001  EAKQVEQTAK TQTSKARVRS RRAVFSDPLP AQSLLKALEA KQALTTETQT
1051  SKAKKVRSKR AAREFSDTLP DQILQAALEV IDAQQQVKKE PQTQEEEEKR
1101  QRKQKELISR YSNSALSELS ATVNSMLSVQ DELDRLFVDQ AQSAVWTNIA
1151  QDKRRYDSDA FRAYQQKTNL RQIGVQKALD NGRIGAVFSH SRSDNTFDEQ
1201  VKNHATLAMM SGFAQYQWGD LQFGVNVGAG ISASKMAEEQ SRKIHRKAIN
1251  YGVNASYQFR LGQLGIQPYL GVNRYFIERE NYQSEEVKVQ TPSLVFNRYN
1301  AGIRVDYTFT PTDNISIKPY FFVNYVDVSN ANVQTTVNRT MLQQSFGRYW
1351  QKEVGLKAEI LHFQLSAFIS KSQGSQLGKQ QNVGVKLGYR W
```

FIG._19

Nucleotide sequence for NTHi strain 860295 hap gene (start codon begins at position 430, stop codon begins at position 4738):

```
   1  GGAGGCAGTG GTGGCGGACA AATTATTGCG ACGGGTACGC CAGAACAAGT
  51  TGCCAAAGTA GAAAGTTCCC ACACCGCCCG CTTCCTTAAA CCGATTTTAG
 101  AAAAACCTTA GAAAAAATGA CCGCACTTTC AGAGAAAACT CACATAAAGT
 151  GCGGTTATTT TATTAGTGAT ATTGTTTTAA TTTTAGTTAT CTGTATAAAT
 201  TACATATAAT ATTAATCCAT CGCAAGATAA GATTACCCAC TAAGTATTAA
 251  GCAAAAACCT AGAAATTTTG GCTTAATTAC TATATAGTTT TACTGCTTTA
 301  TTTTCTTTTG TGCCTTTTAG TTCGTTTTTT TAGCTGAAAT CCCTTAGAAA
 351  ATCACCGCAC TTTTATTGTT CAATAGTCGT TTAACCACGT ATTTTTAAT
 401  ACGAAAAATT ACTTAATTAA ATAAACATTA TGAAAAAAAC TGTATTTCGT
 451  CTGAACTTTT TAACCGCTTG CATTTCATTA GGGATAGTAT CGCAAGCGTG
 501  GGCAGGTCAC ACTTATTTTG GGATTGACTA CCAATATTAT CGTGATTTTG
 551  CTGAGAATAA AGGGAAGTTT TCAGTTGGGG CTAAAAATAT TGAGGTTTAT
 601  AACAAAGAGG GGACTTTAGT TGGCACATCA ATGACAAAAG CCCCGATGAT
 651  TGATTTTTCT GTGGTGTCGC GAAATGGGGT GGCGGCATTA GTAGGCGATC
 701  AGTATATTGT GAGTGTGGCA CATAACGGTG GATATAATAG CGTTGATTTT
 751  GGAGCAGAAG GTCCAAATCC CGATCAGCAT CGTTTTACTT ATCAAATTGT
 801  AAAAAGAAAT AATTATAAGC AGGCAAAGA TAACCCTTAT CATGGTGACT
 851  ATCACATGCC TCGTTTGCAC AAATTTGTCA CTGACGCTGA ACCAGCAAAG
 901  ATGACAGACA ATATGAATGG AAAGAACTAC GCTGATTTAA GTAAATATCC
 951  TGATCGTGTG CGTATTGGTA CAGGTGAACA ATGGTGGAGG ACTGATGAAG
1001  AACAAAAGCA AGGAAGTAAG AGTTCATGGC TTGCTGATGC TTATCTGTGG
1051  AGAATAGCAG GTAACACACA TTCACAAAGT GGAGCGGGCA ACGGCACGGT
1101  AAACTTAAGT GGAGATATCA CAAAACCAAA TAACTATGGA CCTCTTCCTA
1151  CGGGTGTTTC GTTTGGAGAT AGTGGTTCTC CAATGTTTAT TTATGATGCA
1201  ATAAAACAAA AATGGCTTAT TAATGGCGTA TTGCAAACTG GTAACCCTTT
1251  CTCGGGAGCT GGAAATGGAT TCCAATTAAT TAGAAAAAAT TGGTTTTATG
1301  ATAATGTCTT TGTAGAAGAT TTGCCTATAA CATTTTTAGA GCCAAGAAGT
1351  AACGGTCATT ATTCATTTAC TTCAAATAAT AATGGAACTG GTACGGTTAC
1401  TCAAACGAAT GAAAAGTGA GTATGCCTCA ATTTAAAGTC AGAACGGTTC
1451  AGTTATTTAA TGAAGCATTA AAAGAAAAAG ATAAAGAACC TGTTTATGCT
1501  GCAGGTGGTG TAAATGCTTA TAAACCAAGA CTAAATAATG GTAAAAATAT
1551  TTACTTTGGC GATCGAGGAA CAGGAACTTT AACAATTGAA AATAATATAA
1601  ATCAAGGTGC TGGTGGTTTG TATTTGAGG GTAACTTTAC GGTATCTTCA
1651  GAAAATAATG CAACTTGGCA AGGTGCTGGA GTGCATGTAG GTGAAGACAG
1701  TACTGTTACT TGGAAAGTAA ACGGCGTGGA ACATGATCGC CTTTCTAAAA
1751  TTGGTAAAGG AACGTTGCAT ATTCAAGCAA AAGGTGAAAA CTTAGGCTCA
1801  ATTAGCGTAG GTGACGGCAA AGTCATTTTA GATCAACAAG CCGATGAGAA
1851  CAACCAAAAA CAAGCCTTTA AGAAGTTGG CATTGTAAGT GGTAGAGCTA
1901  CCGTTCAACT AAATAGTGCA GATCAAGTTG ATCCTAACAA TATTTATTTC
1951  GGATTCGTG GTGGTCGCTT AGATCTTAAC GGACATTCAT TAACCTTTAA
2001  ACGTATCCAA AATACGGACG AGGGCGCGAT GATTGTGAAC CATAATACAA
```

FIG. 20A

```
2051  CTCAAGTCGC TAATATTACT ATTACTGGGA ACGAAAGTAT TACTGCTCCA
2101  TCTAATAAAA ATAATATTAA TAAACTTGAT TACAGCAAAG AAATTGCTTA
2151  CAACGGTTGG TTTGGCGAAA CAGATGAAAA TAAACACAAT GGAAGATTAA
2201  ACCTTATTTA TAAACCAACC ACAGAAGATC GTACTTTGCT ACTTTCAGGT
2251  GGAACAAATT TAAAAGGCAA TATTACTCAG GAAGGCGGCA CTTTAGTGTT
2301  TAGTGGTCGC CCAACTCCAC ACGCTTACAA TCATTTAAAT CGCCCAAACG
2351  AGCTTGGGCG ACCTCAAGGC GAAGTGGTTA TTGATGACGA TTGGATCACC
2401  CGCACATTTA AAGCTGAAAA CTTCCAAATT AAAGGCGGAA GTGCGGTGGT
2451  TTCTCGCAAT GTTTCTTCAA TTGAGGGAAA TTGGACAGTC AGCAATAATG
2501  CAAATGCCGC ATTTGGTGTT GTGCCAAATC AGCAAAATAC CATTTGCACG
2551  CGTTCAGATT GGACAGGATT AACGACTTGT AAAACTGTGG ATTTAACCGA
2601  TACAAAAGTT ATTAATTCCA TACCGACAAC ACAAATTAAT GGCTCTATTA
2651  ATTTAACTGA TAATGCAACA GTGAATATTC ATGGTTTAGC AAAACTTAAT
2701  GGTAATGTCA CTTTAATAAA TCATAGCCAA TTTACATTGA GCAACAATGC
2751  CACCCAAACA GGCAATATCC AACTTTCAAA TCACGCAAAT GCAACGGTGG
2801  ACAATGCAAA TTTGAACGGT AATGTGCATT TAACGGATTC TGCTCAATTT
2851  TCTTTAAAAA ACAGCCATTT TTCGCACCAA ATTCAGGGCG ACAAAGACAC
2901  AACAGTGACG TTGGAAAATG CGACTTGGAC AATGCCTAGC GATGCCACAT
2951  TGCAGAATTT AACGCTAAAT AATAGTACTG TTACGTTAAA TTCAGCTTAT
3001  TCAGCTAGCT CAAATAATGC GCCACGTCAC CGCCGTTCAT TAGAGACGGA
3051  AACAACGCCA ACATCGGCAG AACATCGTTT CAACACATTG ACAGTAAATG
3101  GTAAATTGAG CGGGCAAGGC ACATTCCAAT TTACTTCATC TTTATTTGGC
3151  TATAAAAGCG ATAAATTAAA ATTATCCAAT GACGCTGAGG GCGATTACAC
3201  ATTATCTGTT CGCAACACAG GCAAAGAACC CGAAGCCCTT GAGCAATTAA
3251  CTTTGGTTGA AAGCAAAGAT AATAAACCGT TATCAGACAA ACTCAAATTT
3301  ACTTTAGAAA ATGACCACGT TGATGCAGGT GCATTACGTT ATAAATTAGT
3351  GAAGAATAAT GGCGAATTCC GCTTGCATAA CCCAATAAAA GAGCAGGAAT
3401  TGCGCAATGA TTTAGTAAGA GCAGAGCAAG CAGAACGAAC ATTAGAAGCC
3451  AAACAAGTTG AACAGACTGC TGAAACACAA ACAAGTAATG CAAGAGTGCG
3501  GTCAAAAAGA GCGGTGTTTT CTGATACCCT GCCTGATCAA AGCCAGTTAG
3551  ACGTATTACA AGCCGAACAA GTTGAACCGA CTGCTGAAAA ACAAAAAAAT
3601  AAGGCAAAAA AAGTGCGGTC AAAAAGAGCG GTGTTTTCTG ATACCCTGCC
3651  TGATCAAAGC CAGTTAGACG TATTACAAGC CGAACAAGTT GAACCGACTG
3701  CTGAAAAACA AAAAAATAAG GCAAAAAAAG TGCGGTCAAA AAGAGCCGCG
3751  AGAGAGTTTT CTGATACCCC GCTTGATCTA AGCCGGTTAA AGGTATTAGA
3801  AGTCAAACTT GAGGTTATTA ATGCCCAACA GCAAGTGAAA AAAGAACCTC
3851  AAGATCAAGA GAAACAACGC AAACAAAAAG ACTTGATCAG CCGTTATTCA
3901  AATAGTGCGT TATCAGAATT ATCTGCAACA GTAAATAGTA TGCTTTCTGT
3951  TCAAGATGAA TTAGATCGTC TTTTTGTAGA TCAAGCACAA TCTGCCGTGT
4001  GGACAAATAT CGCACAGGAT AAAAGACGCT ATGATTCTGA TGCGTTCCGT
4051  GCTTATCAGC AGAAAACGAA CTTACGTCAA ATTGGGGTGC AAAAAGCCTT
4101  AGCTAATGGA CGAATTGGGG CAGTTTTCTC GCATAGCCGT TCAGATAATA
4151  CTTTTGATGA ACAGGTTAAA AATCACGCGA CATTAACGAT GATGTCGGGT
4201  TTGCCCAAT ATCAATGGGG CGATTTACAA TTTGGTGTAA ACGTGGGAAC
```

FIG._20B

```
4251  GGGAATCAGT GCGAGTAAAA TGGCTGAAGA ACAAAGCCGA AAAATTCATC
4301  GAAAAGCGAT AAATTATGGC GTGAATGCAA GTTATCAGTT CCGTTTAGGG
4351  CAATTGGGCA TTCAGCCTTA TTTTGGAGTT AATCGCTATT TTATTGAACG
4401  TGAAAATTAT CAATCTGAGG AAGTGAAAGT GAAAACGCCT AGCCTTGCAT
4451  TTAATCGCTA TAATGCTGGC ATTCGAGTTG ATTATACATT TACTCCGACA
4501  GATAATATCA GCGTTAAGCC TTATTTCTTC GTCAATTATG TTGATGTTTC
4551  AAACGCTAAC GTACAAACCA CGGTAAATAG CACGGTGTTG CAACAACCAT
4601  TTGGACGTTA TTGGCAAAAA GAAGTGGGAT TAAAAGCGGA AATTTTACAT
4651  TTCCAACTTT CTGCTTTTAT TTCTAAATCT CAAGGTTCGC AACTCGGCAA
4701  ACAGCAAAAT GTGGGCGTGA ATTGGGGTA TCGTTGGTAA AAATCAACAT
4751  AATTGTATCG TTTATTGATA AACAAGGTGG GGCAGATCCC ACCTTTTTTA
4801  TTTCAATAAT GGAACTTTAT TTAATTAAGA GCATCTAAGT AGCACCCCAT
4851  ATAGGGGATT AATTAAGAGG ATTTAATAAT GAATTTAACT AAACTTTTAC
4901  CAGCATTTGC TGCTGCAGTC GTATTATCTG CTTGTGCAAA GGATGCACCT
4951  GAAATGACAA AATCATCTGC GCAAATAGCT GAAATGCAAA CACTTCCAAC
5001  AATCACTGAT AAAACAGTTG TATATTCCTG CAATAAACAA ACTGTAACTG
5051  CCGTGTATCA ATTGAAAAC CAAGAACCAG TTGCTGCAAT GGTAAGTGTG
5101  GGCGATGGCA TTATTGCGAA AGATTTTACT CGTGATAAAT CACAAAATGA
5151  CTTTACAAGT TTCGTTTCTG GGGATTATGT TTGGAATGTA GATAGTGGCT
5201  TAACGTTAGA TAAATTTGAT TCTGTTGTGC CTGTCAATTT AATTC
```

FIG._20C

Amino acid sequence for NTHi strain 860295 Hap protein (first amino acid to last amino acid):

```
   1  MKKTVFRLNF  LTACISLGIV  SQAWAGHTYF  GIDYQYYRDF  AENKGKFSVG
  51  AKNIEVYNKE  GTLVGTSMTK  APMIDFSVVS  RNGVAALVGD  QYIVSVAHNG
 101  GYNSVDFGAE  GPNPDQHRFT  YQIVKRNNYK  PGKDNPYHGD  YHMPRLHKFV
 151  TDAEPAKMTD  NMNGKNYADL  SKYPDRVRIG  TGEQWWRTDE  EQKQGSKSSW
 201  LADAYLWRIA  GNTHSQSGAG  NGTVNLSGDI  TKPNNYGPLP  TGVSFGDSGS
 251  PMFIYDAIKQ  KWLINGVLQT  GNPFSGAGNG  FQLIRKNWFY  DNVFVEDLPI
 301  TFLEPRSNGH  YSFTSNNNGT  GTVTQTNEKV  SMPQFKVRTV  QLFNEALKEK
 351  DKEPVYAAGG  VNAYKPRLNN  GKNIYFGDRG  TGTLTIENNI  NQGAGGLYFE
 401  GNFTVSSENN  ATWQGAGVHV  GEDSTVTWKV  NGVEHDRLSK  IGKGTLHIQA
 451  KGENLGSISV  GDGKVILDQQ  ADENNQKQAF  KEVGIVSGRA  TVQLNSADQV
 501  DPNNIYFGFR  GGRLDLNGHS  LTFKRIQNTD  EGAMIVNHNT  TQVANITITG
 551  NESITAPSNK  NNINKLDYSK  EIAYNGWFGE  TDENKHNGRL  NLIYKPTTED
 601  RTLLLSGGTN  LKGNITQEGG  TLVFSGRPTP  HAYNHLNRPN  ELGRPQGEVV
 651  IDDDWITRTF  KAENFQIKGG  SAVVSRNVSS  IEGNWTVSNN  ANAAFGVVPN
 701  QQNTICTRSD  WTGLTTCKTV  DLTDTKVINS  IPTTQINGSI  NLTDNATVNI
 751  HGLAKLNGNV  TLINHSQFTL  SNNATQTGNI  QLSNHANATV  DNANLNGNVH
 801  LTDSAQFSLK  NSHFSHQIQG  DKDTTVTLEN  ATWTMPSDAT  LQNLTLNNST
 851  VTLNSAYSAS  SNNAPRHRRS  LETETTPTSA  EHRFNTLTVN  GKLSGQGTFQ
 901  FTSSLFGYKS  DKLKLSNDAE  GDYTLSVRNT  GKEPEALEQL  TLVESKDNKP
 951  LSDKLKFTLE  NDHVDAGALR  YKLVKNNGEF  RLHNPIKEQE  LRNDLVRAEQ
1001  AERTLEAKQV  EQTAETQTSN  ARVRSKRAVF  SDTLPDQSQL  DVLQAEQVEP
1051  TAEKQKNKAK  KVRSKRAVFS  DTLPDQSQLD  VLQAEQVEPT  AEKQKNKAKK
1101  VRSKRAAREF  SDTPLDLSRL  KVLEVKLEVI  NAQQQVKKEP  QDQEKQRKQK
1151  DLISRYSNSA  LSELSATVNS  MLSVQDELDR  LFVDQAQSAV  WTNIAQDKRR
1201  YDSDAFRAYQ  QKTNLRQIGV  QKALANGRIG  AVFSHSRSDN  TFDEQVKNHA
1251  TLTMMSGFAQ  YQWGDLQFGV  NVGTGISASK  MAEEQSRKIH  RKAINYGVNA
1301  SYQFRLGQLG  IQPYFGVNRY  FIERENYQSE  EVKVKTPSLA  FNRYNAGIRV
1351  DYTFTPTDNI  SVKPYFFVNY  VDVSNANVQT  TVNSTVLQQP  FGRYWQKEVG
1401  LKAEILHFQL  SAFISKSQGS  QLGKQQNVGV  KLGYRW
```

FIG._21

Nucleotide sequence for NTHi strain 3219B hap gene (start codon begins at position 388, stop codon begins at position 4561):

```
   1  CCTGAAGACG TTGCTCAAGT TAAAGGCTCT CACACAGCCC GATTCCTTAA
  51  ACCGATTTTA GAAAAACCTT AGAAAAAATG ACCGCACTTT CAGAGAAAAC
 101  TCACATAAAG TGCGGTTATT TTATTAGTGA TATTGTTTTA ATTATTTGTA
 151  TAAATTACAT ACAATATTAA TCCATCGAAA AATAAGATTA CCCACTAAGT
 201  ATTAAGCCAA AACCTAGAAA TTTTGGCTTA ATTACTATAT AATTTTACTC
 251  CTTTATTTTC TTTTGTGCCT TTAGTTAGT TCGTTTTTA GCTGAAATCC
 301  CTCAGAAAAT CACCGCACTT TTATTGTTCA ATAGTCGTTT AACCACGTAT
 351  TTTTTAATAC GAAAAATTAC TTAATTAAAT AAACATTATG AAAAAAACTG
 401  TATTTCGTCT TAATTTTCTA ACCGCTTGTA TTTCATTAGG GATAGTATCG
 451  CAAGCGTGGG CAGGTCACAC TTATTTTGGG ATTGACTACC AATATTATCG
 501  TGATTTTGCC GAGAATAAAG GGAAGTTTAC AGTTGGGGCT CAAGATATTG
 551  ATATCTACAA TAAAAAGGG GAAATGATAG GTACGATGAT GAAAGGTGTG
 601  CCTATGCCTG ATTTATCTTC CATGGTTCGT GGTGGTTATT CAACATTGAT
 651  AAGTGAGCAG CATTTAATTA GCGTCGCACA TAATGTAGGG TATGATGTCG
 701  TTGATTTTGG TATGGAGGGG GAAAATCCAG ACCAACATCG TTTTAAGTAT
 751  AAAGTTGTTA AACGATATAA TTATAAGAGC GGTGATAGAC AATATAATGA
 801  TTATCAACAT CCAAGATTAG AGAAATTTGT AACGGAAACT GCACCTATTG
 851  AAATGGTTTC ATATATGGAT GGTAATCATT ACAAAAATTT TAATCAATAT
 901  CCTTTGCGAG TTAGAGTTGG AAGTGGGCAT CAATGGTGGA AAGACGATAA
 951  TAATAAAACC ATTGGAGACT TAGCCTATGG AGGTTCATGG TTAATAGGTG
1001  GAAATACCTT TGAAGATGGA CCAGCTGGTA ACGGTACATT AGAATTAAAT
1051  GGGCGAGTAC AAAATCCTAA TAAATATGGT CCACTACCTA CGGCAGGTTC
1101  ATTCGGGGAT AGTGGTTCTC CAATGTTTAT TTATGATAAG GAAGTTAAGA
1151  AATGGTTATT AAATGGCGTG TTACGTGAAG GAAATCCTTA TGCTGCAGTA
1201  GGAAACAGCT ATCAAATTAC ACGAAAAGAT TATTTTCAAG GTATTCTTAA
1251  TCAAGACATT ACAGCTAATT TTTGGGATAC TAATGCTGAA TATAGATTTA
1301  ATATAGGGAG TGACCACAAT GGAAGAGTGG CAACAATCAA AAGTACATTA
1351  CCTAAAAAAG CTATTCAGCC TGAACGAATA GTGGGTCTTT ATGATAATAG
1401  CCAACTTCAT GATGCTAGAG ATAAAAATGG CGATGAATCT CCCTCTTATA
1451  AAGGTCCTAA TCCATGGTCG CCAGCATTAC ATCATGGGAA AAGTATTTAC
1501  TTTGGCGATC AAGGAACAGG AACTTTAACA ATTGAAAATA ATATAAATCA
1551  AGGTGCAGGT GGATTGTATT TTGAAGGTAA TTTTGTTGTA AAAGGCAATC
1601  AAAATAATAT AACTTGGCAA GGTGCAGGCG TTTCTGTTGG AGAAGAAAGT
1651  ACTGTTGAAT GGCAGGTGCA TAATCCAGAA GGCGATCGCT TATCCAAAAT
1701  TGGGCTGGGA ACCTTACTTG TTAATGGTAA AGGGAAAAAC TTAGGAAGCC
1751  TGAGTGTCGG TAACGGTTTG GTTGTGTTAG ATCAACAAGC AGATGAATCA
1801  GGTCAAAAAC AAGCCTTTAA AGAAGTTGGC ATTGTAAGTG GTAGAGCTAC
1851  CGTTCAACTA AATAGTGCAG ATCAAGTTGA TCCTAACAAT ATTTATTTCG
1901  GCTTTCGTGG TGGTCGCTTA GATCTTAATG GCATTCATT AACCTTTGAA
1951  CGTATCCAAA ATACGGATGA AGGCGCGATG ATTGTGAACC ACAACGCTTC
2001  TCAAACCGCA AATATTACGA TTACAGGCAA CGCAACTATT AATTCAGATA
```

FIG._22A

```
2051  GCAAACAACT TACTAATAAA AAAGATATTG CATTTAACGG CTGGTTTGGT
2101  GAGCAAGATA AAGCTAAAAC AAATGGTCGT TTAAATGTGA ATTATCAACC
2151  AGTTAATGCA GAAAATCATT TGTTGCTTTC TGGGGGGACA AATTTAAACG
2201  GCAATATCAC GCAAAATGGT GGTACGTTAG TTTTTAGTGG TCGTCCAACG
2251  CCTCATGCTT ACAATCATTT AAGAAGAGAC TTGTCTAACA TGGAAGGTAT
2301  CCCACAAGGC GAAATTGTGT GGGATCACGA TTGGATCAAC CGCACATTTA
2351  AAGCTGAAAA CTTCCAAATT AAAGGCGGAA GTGCGGTGGT TTCTCGCAAT
2401  GTTTCTTCAA TTGAGGGAAA TTGGACAGTC AGCAATAATG CAAATGCCAC
2451  ATTTGGTGTT GTGCCAAATC AGCAAAATAC CATTTGCACG CGTTCAGATT
2501  GGACAGGATT AACGACTTGT AAAACAGTTG ATTTAACCGA TAAAAAAGTT
2551  ATTAATTCCA TACCGACAAC ACAAATTAAT GGTTCTATTA ATTTAACTGA
2601  TAATGCAACA GTGAATATTC ATGGTTTAGC AAAACTTAAT GGTAATGTCA
2651  CTTTAATAGA TCACAGCCAA TTTACATTGA GCAACAATGC CACCCAAGCA
2701  GGCAATATCA AACTTTCAAA TCACGCAAAT GCAACGGTGG ACAATGCAAA
2751  TTTGAACGGT AATGTGAATT TAATGGATTC TGCTCAATTT TCTTTAAAAA
2801  ACAGCCATTT TTCGCACCAA ATCCAAGGTG GGGAAGACAC AACAGTGATG
2851  TTGGAAAATG CGACTTGGAC AATGCCTAGC GATACCACAT TGCAGAATTT
2901  AACGCTAAAT AATAGTACTG TTACGTTAAA TTCAGCTTAT TCAGCTATCT
2951  CAAATAATGC GCCACGCCGT CGCCGCCGTT CATTAGAGAC GGAAACAACG
3001  CCAACATCGG CAGAACATCG TTTCAACACA TTGACAGTAA ATGGTAAATT
3051  GAGCGGGCAA GGCACATTCC AATTTACTTC ATCTTTATTT GGCTATAAAA
3101  GCGATAAATT AAAATTATCC AATGACGCTG AGGGCGATTA CACATTATCT
3151  GTTCGCAACA CAGGCAAAGA ACCCGTGACC TTTGGGCAAT TAACTTTGGT
3201  TGAAAGCAAA GATAATAAAC CGTTATCAGA CAAACTCACA TTCACGTTAG
3251  AAAATGACCA CGTTGATGCA GGTGCATTAC GTTATAAATT AGTGAAGAAT
3301  GATGGCGAAT TCCGCTTACA TAACCCAATA AAAGAGCAGG AATTGCGCTC
3351  TGATTTAGTA AGAGCAGAGC AAGCAGAACG AACATTAGAA GCCAAACAAG
3401  TTGAACAGAC TGCTAAAACA CAAACAAGTA AGGCAAGAGT GCGGTCAAGA
3451  AGAGCGGTGT TTTCTGATCC CCTGCCTGCT CAAAGCCTGT TAAACGCATT
3501  AGAAGCCAAA CAAGCTCTGA CTACTGAAAC ACAAACAAGT AAGGCAAAAA
3551  AAGTGCGGTC AAAAAGAGCT GCGAGAGAGT TTTCTGATAC CCTGCCTGAT
3601  CAAATATTAC AAGCCGCACT TGAGGTTATT GATGCCCAAC AGCAAGTGAA
3651  AAAAGAACCT CAAACTCAAG AGGAAGAAGA GAAAGACAA CGCAAACAAA
3701  AAGAATTGAT CAGCCGTTAC TCAAATAGTG CGTTATCGGA GTTGTCTGCG
3751  ACAGTAAATA GTATGCTTTC CGTTCAAGAT GAATTGGATC GTCTTTTTGT
3801  AGATCAAGCA CAATCTGCCG TGTGGACAAA TATCGCACAG GATAAAAGAC
3851  GCTATGATTC TGATGCGTTC CGTGCTTATC AGCAGAAAAC GAACTTGCGT
3901  CAAATTGGGG TGCAAAAAGC CTTAGATAAT GGACGAATTG GGGCGGTTTT
3951  CTCGCATAGC CGTTCAGATA ATACCTTTGA CGAACAGGTT AAAAATCACG
4001  CGACATTAGC GATGATGTCT GGTTTTGCCC AATATCAATG GGCGATTTA
4051  CAATTTGGTG TAAACGTGGG TGCGGGAATT AGTGCGAGTA AAATGGCTGA
4101  AGAACAAAGC CGAAAAATTC ATCGAAAAGC GATAAATTAT GGTGTGAATG
4151  CAAGTTATCA GTTCCGTTTA GGGCAATTGG GTATTCAGCC TTATTTGGGT
4201  GTTAATCGAT ATTTTATTGA ACGTGAAAAT TATCAATCTG AAGAAGTGAA
```

FIG._22B

```
4251 AGTGCAAACA CCGAGCCTTG TATTTAATCG CTATAATGCT GGCATTCGAG
4301 TTGATTATAC ATTTACCCCG ACAGATAATA TCAGCATTAA GCCTTATTTC
4351 TTCGTCAATT ATGTTGATGT TCAAACGCT AACGTACAAA CCACTGTAAA
4401 TCGCACGATG TTGCAACAAT CATTTGGGCG TTATTGGCAA AAAGAAGTGG
4451 GATTAAAGGC AGAAATTTTA CATTTCCAAC TTTCCGCTTT TATCTCAAAA
4501 TCTCAAGGTT CACAACTCGG CAAACAGCAA ATGTGGGCG TGAAATTGGG
4551 GTATCGTTGG TAAAAATCAA CATAATTTTA TCGTTTATTG ATAAACAAGG
4601 TGGGGCAGAT CAAATCCTAC CTTTTTTATT CCAATAATGG AACTTTATTT
4651 TATTAAAGGT ATCTAAGTAG CACCCTATAT AGGGATTAAT TAAGAGGATT
4701 TAATAATGAA TTTAACTAAA ATTTTACCCA CATTTGCTGC TGTAGTCGTA
4751 TTATCTGCTT GTGCAAAGGA TGCACCTGAA ATGACAAAAT CATCTGCGCA
4801 AATAGCTGAA ATGCAAACAC TT
```

FIG._22C

Amino acid sequence for NTHi strain 3219B Hap protein (first amino acid to last amino acid):

```
   1 MKKTVFRLNF LTACISLGIV SQAWAGHTYF GIDYQYYRDF AENKGKFTVG
  51 AQDIDIYNKK GEMIGTMMKG VPMPDLSSMV RGGYSTLISE QHLISVAHNV
 101 GYDVVDFGME GENPDQHRFK YKVVKRYNYK SGDRQYNDYQ HPRLEKFVTE
 151 TAPIEMVSYM DGNHYKNFNQ YPLRVRVSG HQWWKDDNNK TIGDLAYGGS
 201 WLIGGNTFED GPAGNGTLEL NGRVQNPNKY GPLPTAGSFG DSGSPMFIYD
 251 KEVKKWLLNG VLREGNPYAA VGNSYQITRK DYFQGILNQD ITANFWDTNA
 301 EYRFNIGSDH NGRVATIKST LPKKAIQPER IVGLYDNSQL HDARDKNGDE
 351 SPSYKGPNPW SPALHHGKSI YFGDQGTGTL TIENNINQGA GGLYFEGNFV
 401 VKGNQNNITW QGAGVSVGEE STVEWQVHNP EGDRLSKIGL GTLLVNGKGK
 451 NLGSLSVGNG LVVLDQQADE SGQKQAFKEV GIVSGRATVQ LNSADQVDPN
 501 NIYFGFRGGR LDLNGHSLTF ERIQNTDEGA MIVNHNASQT ANITITGNAT
 551 INSDSKQLTN KKDIAFNGWF GEQDKAKTNG RLNVNYQPVN AENHLLLSGG
 601 TNLNGNITQN GGTLVFSGRP TPHAYNHLRR DLSNMEGIPQ GEIVWDHDWI
 651 NRTFKAENFQ IKGGSAVVSR NVSSIEGNWT VSNNANATFG VVPNQQNTIC
 701 TRSDWTGLTT CKTVDLTDKK VINSIPTTQI NGSINLTDNA TVNIHGLAKL
 751 NGNVTLIDHS QFTLSNNATQ AGNIKLSNHA NATVDNANLN GNVNLMDSAQ
 801 FSLKNSHFSH QIQGGEDTTV MLENATWTMP SDTTLQNLTL NNSTVTLNSA
 851 YSAISNNAPR RRRRSLETET TPTSAEHRFN TLTVNGKLSG QGTFQFTSSL
 901 FGYKSDKLKL SNDAEGDYTL SVRNTGKEPV TFGQLTLVES KDNKPLSDKL
 951 TFTLENDHVD AGALRYKLVK NDGEFRLHNP IKEQELRSDL VRAEQAERTL
1001 EAKQVEQTAK TQTSKARVRS RRAVFSDPLP AQSLLNALEA KQALTTETQT
1051 SKAKKVRSKR AAREFSDTLP DQILQAALEV IDAQQQVKKE PQTQEEEEKR
1101 QRKQKELISR YSNSALSELS ATVNSMLSVQ DELDRLFVDQ AQSAVWTNIA
1151 QDKRRYDSDA FRAYQQKTNL RQIGVQKALD NGRIGAVFSH SRSDNTFDEQ
1201 VKNHATLAMM SGFAQYQWGD LQFGVNVGAG ISASKMAEEQ SRKIHRKAIN
1251 YGVNASYQFR LGQLGIQPYL GVNRYFIERE NYQSEEVKVQ TPSLVFNRYN
1301 AGIRVDYTFT PTDNISIKPY FFVNYVDVSN ANVQTTVNRT MLQQSFGRYW
1351 QKEVGLKAEI LHFQLSAFIS KSQGSQLGKQ QNVGVKLGYR W
```

FIG._23

Nucleotide sequence for NTHi strain 1396B *hap* gene (start codon begins at position 313, stop codon begins at position 4546):

```
   1  TGACCGCACT TTCAGAGAAA ACTCACATAA AGTGCGGTTA TTTTATTAGT
  51  GATATTGTTT TAATTTTAGT TATCTGTATA AATTACATAC AATATTAATC
 101  CATCGCAAGA TAAGATTACC CACTAAGTAT TAAGCAAAAA CCTAGAAATT
 151  TTGGCTTAAT TACTATATAG TTTTACTCAT TTATTTTCTT TTGTGCCTTT
 201  TAGTTCGTTT TTTTAGCTGA AATCCCTTAG AAAATCACCG CACTTTTATT
 251  GTTCAATAGT CGTTAACCA CGTATTTTTT AATACGAAAA ATTACTTAAT
 301  TAAATAAACA TTATGAAAAA AACTGTATTT CGTCTGAATT TTTTAACCGC
 351  TTGCATTTCA TTAGGGATAG TATCGCAAGC GTGGGCAGGT CATACTTATT
 401  TTGGGATTGA CTACCAATAT TATCGTGATT TGCCGAGAA TAAAGGGAAG
 451  TTCACAGTTG GGGCTAAAAA TATTGAGGTT ACAATAAAA ATGGAAATTT
 501  AGTTGGCACA TCAATGACAA AAGCCCCAAT GATTGATTTT TCCGTGGTGT
 551  CGCGAAATGG GGTGGCGGCA TTGGTGGGCG ATCAGTATAT TGTGAGTGTG
 601  GCACATAATG TAGGCTATAC CAATGTGGAT TTTGGTGCTG AAGGACAAAA
 651  TCCTGATCAA CATCGTTTTA CTTATAAAAT TGTGAAACGG AATAATTATA
 701  AAAACGATCA AACGCATCCT TATGAGAAAG ACTACCACAA CCCACGCTTA
 751  CATAAATTTG TTACGGAAGC CACCCCAATC GATATGACTT CTGATATGAA
 801  CGGCAACAAA TATACAGATA GGACGAAATA TCCCGAACGC GTGCGTATCG
 851  GCTCCGGGTG GCAGTTTTGG CGAAACGATC AAAACAACGG CGACCAAGTT
 901  GCCGGCGCAT ATCATTACCT GACAGCAGGC AATACACACA ACCAAGGCGG
 951  AGCAGGGGGC GGCTGGTCAA GTCTGAGCGG CGATGTGCGC CAAGCGGGCA
1001  ATTACGGCCC CATTCCTATT GCAGGCTCAA GCGGCGACAG CGGTTCGCCT
1051  ATGTTTATTT ATGATGCGGA AAAACAAAAA TGGTTGATTA ACGGCGTATT
1101  GAGGACCGGC AACCCTTGGG CGGGGACAGA GAATACATTC CAACTGGTAC
1151  GCAAGTCTTT TTTTGATGAA ATCCTTGAAA AAGATTGCG TACATCGTTT
1201  TATAGCCCAT CGGGCAATGG TGCATACACC ATTACAGACA AAGGCGACGG
1251  CAGCGGCATT GTCAAACAAC AAACAGGAAG ACCATCTGAA GTCCGCATCG
1301  GTTTAAAAGA CGACAAATTA CCTGCCGAAG GTAAAGACGA TGTTTACCAA
1351  TACCAAGGTC CAAATATATA CCTGCCTCGT TTGAATAACG GTGGAAACCT
1401  GTATTTCGGA GATCAAAAAA ACGGCACTGT TACCTTATCA ACCAACATCA
1451  ACCAAGGTGC GGGCGGTTTG TATTTTGAGG GTAACTTTAC GGTATCTTCA
1501  GAAAATAATG CAACTTGGCA AGGTGCTGGA GTGCATGTAG GTGAAGACAG
1551  TACTGTTACT TGGAAAGTAA ATGGTGTTGA AAATGATCGC CTTTCTAAAA
1601  TCGGCAAAGG CACATTGCAC GTTAAAGCCA AGGGGAAAA TAAAGGTTCG
1651  ATCAGCGTAG GCGATGGTAA AGTCATTTTG GAGCAGCAGG CAGACGATCA
1701  AGGCAACAAA CAAGCCTTTA GTGAAATTGG CTTGGTTAGT GGCAGAGGTA
1751  CGGTTCAGTT AAACGATGAC AAGCAATTTA ATACTGATAA ATTTATTTC
1801  GGCTTCCGTG GTGGTCGCTT AGATCTTAAT GGGCATTCAT TAACCTTTAA
1851  ACGTATCCAA AATACGGATG AGGGAGCAAC GATTGTTAAT CACAATGCCA
1901  CAACAGAATC TACAGTGACC ATTACTGGCA GCGATACCAT TAATGACAAC
1951  ACTGGCGATT TAACCAATAA ACGTGATATT GCTTTTAATG GTTGGTTTGG
2001  TGATAAAGAT GATACTAAAA ATACTGGACG TTTGAATGTT ACTTACAATC
```

FIG._24A

```
2051  CGCTTAACAA AGATAATCAC TTCCTTCTAT CAGGTGGAAC AAATTTAAAA
2101  GGCAATATTA CTCAAGACGG TGGCACTTTA GTGTTAGTG GTCGCCCAAC
2151  ACCACACGCA TACAATCATT TAAATCGCCT AAACGAGCTT GGGCGACCTA
2201  AGGGCGAAGT GGTTATTGAT GACGATTGGA TCAACCGTAC ATTTAAAGCT
2251  GAAAACTTCC AAATTAAAGG CGGAAGTACG GTGGTTTCTC GCAATGTTTC
2301  TTCAATTGAA GGAAATTGGA CAATCAGCAA TAACGCCAAC GCGACATTTG
2351  GTGTTGTGCC AAATCAACAA AATACCATTT GCACGCGTTC AGATTGGACA
2401  GGATTAACGA CTTGTAAAAC AGTTAATTTA ACCGATAAAA AAGTTATTGA
2451  TTCCATACCG ACAACACAAA TTAATGGCTC TATTAATTTA ACTAATAATG
2501  CAACAGTGAA TATTCATGGT TTAGCAAAAC TTAATGGTAA TGTCACTTTA
2551  ATAAATCATA GCCAATTTAC ATTGAGCAAC AATGCCACCC AAACAGGCAA
2601  TATCCAACTT TCAAATCACG CAAATGCAAC GGTGGATAAT GCAAACTTGA
2651  ACGGTAATGT GCATTTAACG GATTCTGCTC AATTTTCTTT AAAAAACAGC
2701  CATTTTTCGC ACCAAATTCA GGGCGACAAA GACACAACAG TGACGTTGGA
2751  AAATGCGACT TGGACAATGC CTAGCGATAC TACATTGCAG AATTTAACGC
2801  TAAATAATAG TACTGTTACG TTAAATTCAG CTTATTCAGC TAGCTCAAAT
2851  AATGCGCCAC GTCACCGCCG TTCATTAGAG ACGGAAACAA CGCCAACATC
2901  GGAAGAACAT CGTTTCAACA CATTGACAGT AAATGGTAAA TTGAGCGGGC
2951  AAGGCACATT CCAATTTACT TCATCTTTAT TTGGCTATAA AAGCGATAAA
3001  ATAAAATTAT CTAATGACGC TGAAGGCGAT TACACATTAG CTGTTCGCGA
3051  CACAGGCAAA GAACCTGTGA CCCTTGAGCA ATTAACTTTA ATTGAAGGCT
3101  TGGATAATCA ACCCTTGCCA GATAAGCTAA AAATTACTTT AAAAAATAAA
3151  CACGTTGATG CGGGTGCATG GCGTTATGAA TTAGTGAAGA AAAACGGCGA
3201  ATTCCGCTTG CATAATCCAA TAAAAGAGCA GGAATTGCGC AATGATTTAG
3251  TAAAAGCAGA GCAAGTAGAA CGAGCATTAG AAGCAAAACA AGCTGAACTG
3301  ACTACTAAAA AACAAAAAAC TGAGGCTAAA GTGCGGTCAA AAAGAGCGGC
3351  GTTTTCTGAT ACCCCGCCTG ATCAAAGCCA GTTAAACGCA TTACAAGCCG
3401  AACTCGAGAC GATTAATGCC CAACAGCAAG TGGCACAAGC GGTGCAAAAT
3451  CAGAAAGTAA CTGCACTTAA CCAAAAGAAC GAGCAAGTTA AAACCACTCA
3501  AGATAAAGCA AATTTAGTCT TGGCAACTGC ATTGGTGGAA AAAGAAACCG
3551  CTCAGATTGA TTTTGCTAAT GCAAAATTAG CTCAGTTGAA TTTAACACAA
3601  CAACTAGAAA AAGCCTTAGC AGTGGCTGAG CAAGCAGAAA AAGAGCGTAA
3651  AGCTCAAGAG CAAGCGAAAA GACAACGCAA ACAAAAAGAC TTGATCAGCC
3701  GTTATTCAAA TAGTGCGTTA TCAGAATTAT CTGCAACAGT AAATAGTATG
3751  CTTTCCGTTC AAGATGAATT AGATCGTCTT TTTGTAGATC AAGCTCAATC
3801  TGCGGTGTGG ACAAATATCT CACAGGATAA AAGACGTTAT GATTCTGATG
3851  CGTTCCGTGC TTATCAGCAG AAAACGAACT TGCGTCAAAT TGGGGTGCAA
3901  AAAGCCTTAG CTAACGGACG AATTGGGGCA GTTTTCTCGC ATAGCCGTTC
3951  AGATAATACT TTTGATGAAC AGGTTAAAAA TCACGCAACA TTAACGATGA
4001  TGTCGGGTTT TGCCCAATAT CAATGGGGTG ATTTACAATT TGGTGTAAAC
4051  GTGGGAACGG AATTAGTGCC GAGTAAAATG GCTGAAGAAC AAAGCCGAAA
4101  AATTCATCGA AAAGCGATAA ATTATGGCGT GAATGCAAGT TATTCGTTCC
4151  ATTTAGGGCA ATTGGGTATT CAGCCTTATT TGGAGTTAA TCGCTATTTT
4201  ATTGAACGTA AAAATTATCA ATCTGAGGAA GTGAAAGTGC AAACACCGAG
```

FIG. 24B

```
4251  CCTTGCATTT  AATCGCTATA  ATGCTGGAGT  ACGGGTCGAT  TATACGTTTA
4301  CCCCGACAGA  GAATATCAGC  GTTAAGCCTT  ATTTCTTCGT  CAATTATGTT
4351  GATGTTTCAA  ACGCTAACGT  ACAAACCACT  GTAAATCGCG  CGGTGTTGCA
4401  ACAACCATTT  GGACGTTATT  GGCAAAAAGA  AGTGGGATTA  AAAGCGGAAA
4451  TTTTACATTT  CCAACTTTCT  GCTTTTATTT  CTAAATCTCA  AGGTTCGCAA
4501  CTCGGTAAAC  AGCGAAATAT  GGGCGTGAAA  TTAGGATATC  GTTGGTAAAA
4551  ATCAACATAA  TTTTATTCTA  ATAATGGAAC  TTTATTTAAT  TAAAAGTATC
4601  TAAGTAGCAC  CCTATAGGGG  ATTAATTAAG  AGGATTTAAT  AATGAATTTA
4651  ACTAAAATTT  TACCCGCATT  TGCTGCTGCA  GTCGTATTAT  CTGCTTGTGC
4701  AAAGGATGCA  CCTGAAATGA  CAAAATCATC  TGCGCAAATA  GCTGAAATGC
4751  AAACACTTCC  AACAATCACT  GATAAAACAG  TTGTATATTC  TTGCAATAAA
4801  CAAACTGTGA  CTGCAGTGTA  TCAATTTG
```

FIG._24C

Amino acid sequence for NTHi strain 1396B Hap protein (first amino acid to last amino acid):

```
   1  MKKTVFRLNF  LTACISLGIV  SQAWAGHTYF  GIDYQYYRDF  AENKGKFTVG
  51  AKNIEVYNKN  GNLVGTSMTK  APMIDFSVVS  RNGVAALVGD  QYIVSVAHNV
 101  GYTNVDFGAE  GQNPDQHRFT  YKIVKRNNYK  NDQTHPYEKD  YHNPRLHKFV
 151  TEATPIDMTS  DMNGNKYTDR  TKYPERVRIG  SGWQFWRNDQ  NNGDQVAGAY
 201  HYLTAGNTHN  QGGAGGGWSS  LSGDVRQAGN  YGPIPIAGSS  GDSGSPMFIY
 251  DAEKQKWLIN  GVLRTGNPWA  GTENTFQLVR  KSFFDEILEK  DLRTSFYSPS
 301  GNGAYTITDK  GDGSGIVKQQ  TGRPSEVRIG  LKDDKLPAEG  KDDVYQYQGP
 351  NIYLPRLNNG  GNLYFGDQKN  GTVTLSTNIN  QGAGGLYFEG  NFTVSSENNA
 401  TWQGAGVHVG  EDSTVTWKVN  GVENDRLSKI  GKGTLHVKAK  GENKGSISVG
 451  DGKVILEQQA  DDQGNKQAFS  EIGLVSGRGT  VQLNDDKQFN  TDKFYFGFRG
 501  GRLDLNGHSL  TFKRIQNTDE  GATIVNHNAT  TESTVTITGS  DTINDNTGDL
 551  TNKRDIAFNG  WFGDKDDTKN  TGRLNVTYNP  LNKDNHFLLS  GGTNLKGNIT
 601  QDGGTLVFSG  RPTPHAYNHL  NRLNELGRPK  GEVVIDDDWI  NRTFKAENFQ
 651  IKGGSTVVSR  NVSSIEGNWT  ISNNANATFG  VVPNQQNTIC  TRSDWTGLTT
 701  CKTVNLTDKK  VIDSIPTTQI  NGSINLTNNA  TVNIHGLAKL  NGNVTLINHS
 751  QFTLSNNATQ  TGNIQLSNHA  NATVDNANLN  GNVHLTDSAQ  FSLKNSHFSH
 801  QIQGDKDTTV  TLENATWTMP  SDTTLQNLTL  NNSTVTLNSA  YSASSNNAPR
 851  HRRSLETETT  PTSEEHRFNT  LTVNGKLSGQ  GTFQFTSSLF  GYKSDKIKLS
 901  NDAEGDYTLA  VRDTGKEPVT  LEQLTLIEGL  DNQPLPDKLK  ITLKNKHVDA
 951  GAWRYELVKK  NGEFRLHNPI  KEQELRNDLV  KAEQVERALE  AKQAELTTKK
1001  QKTEAKVRSK  RAAFSDTPPD  QSQLNALQAE  LETINAQQQV  AQAVQNQKVT
1051  ALNQKNEQVK  TTQDKANLVL  ATALVEKETA  QIDFANAKLA  QLNLTQQLEK
1101  ALAVAEQAEK  ERKAQEQAKR  QRKQKDLISR  YSNSALSELS  ATVNSMLSVQ
1151  DELDRLFVDQ  AQSAVWTNIS  QDKRRYDSDA  FRAYQQKTNL  RQIGVQKALA
1201  NGRIGAVFSH  SRSDNTFDEQ  VKNHATLTMM  SGFAQYQWGD  LQFGVNVGTG
1251  ISASKMAEEQ  SRKIHRKAIN  YGVNASYSFH  LGQLGIQPYF  GVNRYFIERK
1301  NYQSEEVKVQ  TPSLAFNRYN  AGVRVDYTFT  PTENISVKPY  FFVNYVDVSN
1351  ANVQTTVNRA  VLQQPFGRYW  QKEVGLKAEI  LHFQLSAFIS  KSQGSQLGKQ
1401  RNMGVKLGYR  W
```

FIG._25

SEQUENCE LISTING

```
<160> NUMBER OF SEQ ID NOS: 58

<210> SEQ ID NO 1
<211> LENGTH: 4319
<212> TYPE: DNA
<213> ORGANISM: Haemophilus influenzae
<220> FEATURE:
<221> NAME/KEY: CDS
<222> LOCATION: (60)..(4241)
<223> OTHER INFORMATION:

<400> SEQUENCE: 1
tcaatagtcg tttaactagt attttttaat acgaaaaatt acttaattaa ataaacatt        59 atg aaa aaa act gta ttt cgt ctt aat ttt tta acc gct tgc att tca       107
Met Lys Lys Thr Val Phe Arg Leu Asn Phe Leu Thr Ala Cys Ile Ser
1               5                   10                  15 tta ggg ata gta tcg caa gcg tgg gct ggt cac act tat ttt ggg att       155
Leu Gly Ile Val Ser Gln Ala Trp Ala Gly His Thr Tyr Phe Gly Ile
            20                  25                  30 gat tac caa tat tat cgt gat ttt gcc gag aat aaa ggg aag ttc aca       203
Asp Tyr Gln Tyr Tyr Arg Asp Phe Ala Glu Asn Lys Gly Lys Phe Thr
        35                  40                  45 gtt ggg gct caa aat att aag gtt tat aac aaa caa ggg caa tta gtt       251
Val Gly Ala Gln Asn Ile Lys Val Tyr Asn Lys Gln Gly Gln Leu Val
    50                  55                  60 ggc aca tca atg aca aaa gcc ccg atg att gat ttt tct gta gtg tca       299
Gly Thr Ser Met Thr Lys Ala Pro Met Ile Asp Phe Ser Val Val Ser
65                  70                  75                  80 cgt aac ggc gtg gca gcc ttg gtt gaa aat caa tat att gtg agc gtg       347
Arg Asn Gly Val Ala Ala Leu Val Glu Asn Gln Tyr Ile Val Ser Val
                85                  90                  95 gca cat aac gta gga tat aca gat gtt gat ttt ggt gca gag gga aac       395
Ala His Asn Val Gly Tyr Thr Asp Val Asp Phe Gly Ala Glu Gly Asn
            100                 105                 110 aac ccc gat caa cat cgt ttt act tat aag att gta aaa cga aat aac       443
Asn Pro Asp Gln His Arg Phe Thr Tyr Lys Ile Val Lys Arg Asn Asn
        115                 120                 125
```

```
tac aaa aaa gat aat tta cat cct tat gag gac gat tac cat aat cca     491
Tyr Lys Lys Asp Asn Leu His Pro Tyr Glu Asp Asp Tyr His Asn Pro
    130                 135                 140 cga tta cat aaa ttc gtt aca gaa gcg gct cca att gat atg act tcg     539
Arg Leu His Lys Phe Val Thr Glu Ala Ala Pro Ile Asp Met Thr Ser
145                 150                 155                 160 aat atg aat ggc agt act tat tca gat aga aca aaa tat cca gaa cgt     587
Asn Met Asn Gly Ser Thr Tyr Ser Asp Arg Thr Lys Tyr Pro Glu Arg
                165                 170                 175 gtt cgt atc ggc tct gga cgg cag ttt tgg cga aat gat caa gac aaa     635
Val Arg Ile Gly Ser Gly Arg Gln Phe Trp Arg Asn Asp Gln Asp Lys
            180                 185                 190 ggc gac caa gtt gcc ggt gca tat cat tat ctg aca gct ggc aat aca     683
Gly Asp Gln Val Ala Gly Ala Tyr His Tyr Leu Thr Ala Gly Asn Thr
        195                 200                 205 cac aat cag cgt gga gca ggt aat gga tat tcg tat ttg gga ggc gat     731
His Asn Gln Arg Gly Ala Gly Asn Gly Tyr Ser Tyr Leu Gly Gly Asp
    210                 215                 220 gtt cgt aaa gcg gga gaa tat ggt cca tta ccg att gca ggc tca aag     779
Val Arg Lys Ala Gly Glu Tyr Gly Pro Leu Pro Ile Ala Gly Ser Lys
225                 230                 235                 240 ggg gac agt ggt tct ccg atg ttt att tat gat gct gaa aaa caa aaa     827
Gly Asp Ser Gly Ser Pro Met Phe Ile Tyr Asp Ala Glu Lys Gln Lys
                245                 250                 255 tgg tta att aat ggg ata tta cgg gaa ggc aac cct ttt gaa ggc aaa     875
Trp Leu Ile Asn Gly Ile Leu Arg Glu Gly Asn Pro Phe Glu Gly Lys
            260                 265                 270 gaa aat ggg ttt caa ttg gtt cgc aaa tct tat ttt gat gaa att ttc     923
Glu Asn Gly Phe Gln Leu Val Arg Lys Ser Tyr Phe Asp Glu Ile Phe
        275                 280                 285 gaa aga gat tta cat aca tca ctt tac acc cga gct ggt aat gga gtg     971
Glu Arg Asp Leu His Thr Ser Leu Tyr Thr Arg Ala Gly Asn Gly Val
    290                 295                 300 tac aca att agt gga aat gat aat ggt cag ggg tct ata act cag aaa    1019
Tyr Thr Ile Ser Gly Asn Asp Asn Gly Gln Gly Ser Ile Thr Gln Lys
305                 310                 315                 320 tca gga ata cca tca gaa att aaa att acg tta gca aat atg agt tta    1067
Ser Gly Ile Pro Ser Glu Ile Lys Ile Thr Leu Ala Asn Met Ser Leu
                325                 330                 335 cct ttg aaa gag aag gat aaa gtt cat aat cct aga tat gac gga cct    1115
Pro Leu Lys Glu Lys Asp Lys Val His Asn Pro Arg Tyr Asp Gly Pro
            340                 345                 350 aat att tat tct cca cgt tta aac aat gga gaa acg cta tat ttt atg    1163
Asn Ile Tyr Ser Pro Arg Leu Asn Asn Gly Glu Thr Leu Tyr Phe Met
        355                 360                 365 gat caa aaa caa gga tca tta atc ttc gca tct gac att aac caa ggg    1211
Asp Gln Lys Gln Gly Ser Leu Ile Phe Ala Ser Asp Ile Asn Gln Gly
    370                 375                 380 gcg ggt ggt ctt tat ttt gag ggt aat ttt aca gta tct cca aat tct    1259
Ala Gly Gly Leu Tyr Phe Glu Gly Asn Phe Thr Val Ser Pro Asn Ser
385                 390                 395                 400 aac caa act tgg caa gga gct ggc ata cat gta agt gaa aat agc acc    1307
Asn Gln Thr Trp Gln Gly Ala Gly Ile His Val Ser Glu Asn Ser Thr
                405                 410                 415 gtt act tgg aaa gta aat ggc gtg gaa cat gat cga ctt tct aaa att    1355
Val Thr Trp Lys Val Asn Gly Val Glu His Asp Arg Leu Ser Lys Ile
            420                 425                 430 ggt aaa gga aca ttg cac gtt caa gcc aaa ggg gaa aat aaa ggt tcg    1403
Gly Lys Gly Thr Leu His Val Gln Ala Lys Gly Glu Asn Lys Gly Ser
```

```
                 435                 440                 445
atc agc gta ggc gat ggt aaa gtc att ttg gag cag cag gca gac gat    1451
Ile Ser Val Gly Asp Gly Lys Val Ile Leu Glu Gln Gln Ala Asp Asp
    450                 455                 460 caa ggc aac aaa caa gcc ttt agt gaa att ggc ttg gtt agc ggc aga    1499
Gln Gly Asn Lys Gln Ala Phe Ser Glu Ile Gly Leu Val Ser Gly Arg
465                 470                 475                 480 ggg act gtt caa tta aac gat gat aaa caa ttt gat acc gat aaa ttt    1547
Gly Thr Val Gln Leu Asn Asp Asp Lys Gln Phe Asp Thr Asp Lys Phe
                485                 490                 495 tat ttc ggc ttt cgt ggt ggt cgc tta gat ctt aac ggg cat tca tta    1595
Tyr Phe Gly Phe Arg Gly Gly Arg Leu Asp Leu Asn Gly His Ser Leu
            500                 505                 510 acc ttt aaa cgt atc caa aat acg gac gag ggg gca atg att gtg aac    1643
Thr Phe Lys Arg Ile Gln Asn Thr Asp Glu Gly Ala Met Ile Val Asn
        515                 520                 525 cat aat aca act caa gcc gct aat gtc act att act ggg aac gaa agc    1691
His Asn Thr Thr Gln Ala Ala Asn Val Thr Ile Thr Gly Asn Glu Ser
    530                 535                 540 att gtt cta cct aat gga aat aat att aat aaa ctt gat tac aga aaa    1739
Ile Val Leu Pro Asn Gly Asn Asn Ile Asn Lys Leu Asp Tyr Arg Lys
545                 550                 555                 560 gaa att gcc tac aac ggt tgg ttt ggc gaa aca gat aaa aat aaa cac    1787
Glu Ile Ala Tyr Asn Gly Trp Phe Gly Glu Thr Asp Lys Asn Lys His
                565                 570                 575 aat ggg cga tta aac ctt att tat aaa cca acc aca gaa gat cgt act    1835
Asn Gly Arg Leu Asn Leu Ile Tyr Lys Pro Thr Thr Glu Asp Arg Thr
            580                 585                 590 ttg cta ctt tca ggt ggt aca aat tta aaa ggc gat att acc caa aca    1883
Leu Leu Leu Ser Gly Gly Thr Asn Leu Lys Gly Asp Ile Thr Gln Thr
        595                 600                 605 aaa ggt aaa cta ttt ttc agc ggt aga ccg aca ccg cac gcc tac aat    1931
Lys Gly Lys Leu Phe Phe Ser Gly Arg Pro Thr Pro His Ala Tyr Asn
    610                 615                 620 cat tta aat aaa cgt tgg tca gaa atg gaa ggt ata cca caa ggc gaa    1979
His Leu Asn Lys Arg Trp Ser Glu Met Glu Gly Ile Pro Gln Gly Glu
625                 630                 635                 640 att gtg tgg gat cac gat tgg atc aac cgt aca ttt aaa gct gaa aac    2027
Ile Val Trp Asp His Asp Trp Ile Asn Arg Thr Phe Lys Ala Glu Asn
                645                 650                 655 ttc caa att aaa ggc gga agt gcg gtg gtt tct cgc aat gtt tct tca    2075
Phe Gln Ile Lys Gly Gly Ser Ala Val Val Ser Arg Asn Val Ser Ser
            660                 665                 670 att gag gga aat tgg aca gtc agc aat aat gca aat gcc aca ttt ggt    2123
Ile Glu Gly Asn Trp Thr Val Ser Asn Asn Ala Asn Ala Thr Phe Gly
        675                 680                 685 gtt gtg cca aat caa caa aat acc att tgc acg cgt tca gat tgg aca    2171
Val Val Pro Asn Gln Gln Asn Thr Ile Cys Thr Arg Ser Asp Trp Thr
    690                 695                 700 gga tta acg act tgt caa aaa gtg gat tta acc gat aca aaa gtt att    2219
Gly Leu Thr Thr Cys Gln Lys Val Asp Leu Thr Asp Thr Lys Val Ile
705                 710                 715                 720 aat tct ata cca aaa aca caa atc aat ggc tct att aat tta act gat    2267
Asn Ser Ile Pro Lys Thr Gln Ile Asn Gly Ser Ile Asn Leu Thr Asp
                725                 730                 735 aat gca acg gcg aat gtt aaa ggt tta gca aaa ctt aat ggc aat gtc    2315
Asn Ala Thr Ala Asn Val Lys Gly Leu Ala Lys Leu Asn Gly Asn Val
            740                 745                 750 act tta aca aat cac agc caa ttt aca tta agc aac aat gcc acc caa    2363
```

```
        Thr Leu Thr Asn His Ser Gln Phe Thr Leu Ser Asn Asn Ala Thr Gln
                755                 760                 765 ata ggc aat att cga ctt tcc gac aat tca act gca acg gtg gat aat            2411
Ile Gly Asn Ile Arg Leu Ser Asp Asn Ser Thr Ala Thr Val Asp Asn
        770                 775                 780 gca aac ttg aac ggt aat gtg cat tta acg gat tca gct caa ttt tct            2459
Ala Asn Leu Asn Gly Asn Val His Leu Thr Asp Ser Ala Gln Phe Ser
785                 790                 795                 800 tta aaa aac agc cat ttt tcg cac caa att cag gga gac aaa ggc aca            2507
Leu Lys Asn Ser His Phe Ser His Gln Ile Gln Gly Asp Lys Gly Thr
                805                 810                 815 aca gtg acg ttg gaa aat gcg act tgg aca atg cct agc gat act aca            2555
Thr Val Thr Leu Glu Asn Ala Thr Trp Thr Met Pro Ser Asp Thr Thr
        820                 825                 830 ttg cag aat tta acg cta aat aac agt acg atc acg tta aat tca gct            2603
Leu Gln Asn Leu Thr Leu Asn Asn Ser Thr Ile Thr Leu Asn Ser Ala
                835                 840                 845 tat tca gct agc tca aac aat acg cca cgt cgc cgt tca tta gag acg            2651
Tyr Ser Ala Ser Ser Asn Asn Thr Pro Arg Arg Arg Ser Leu Glu Thr
850                 855                 860 gaa aca acg cca aca tcg gca gaa cat cgt ttc aac aca ttg aca gta            2699
Glu Thr Thr Pro Thr Ser Ala Glu His Arg Phe Asn Thr Leu Thr Val
865                 870                 875                 880 aat ggt aaa ttg agt ggg caa ggc aca ttc caa ttt act tca tct tta            2747
Asn Gly Lys Leu Ser Gly Gln Gly Thr Phe Gln Phe Thr Ser Ser Leu
                885                 890                 895 ttt ggc tat aaa agc gat aaa tta aaa tta tcc aat gac gct gag ggc            2795
Phe Gly Tyr Lys Ser Asp Lys Leu Lys Leu Ser Asn Asp Ala Glu Gly
        900                 905                 910 gat tac ata tta tct gtt cgc aac aca ggc aaa gaa ccc gaa acc ctt            2843
Asp Tyr Ile Leu Ser Val Arg Asn Thr Gly Lys Glu Pro Glu Thr Leu
        915                 920                 925 gag caa tta act ttg gtt gaa agc aaa gat aat caa ccg tta tca gat            2891
Glu Gln Leu Thr Leu Val Glu Ser Lys Asp Asn Gln Pro Leu Ser Asp
        930                 935                 940 aag ctc aaa ttt act tta gaa aat gac cac gtt gat gca ggt gca tta            2939
Lys Leu Lys Phe Thr Leu Glu Asn Asp His Val Asp Ala Gly Ala Leu
945                 950                 955                 960 cgt tat aaa tta gtg aag aat gat ggc gaa ttc cgc ttg cat aac cca            2987
Arg Tyr Lys Leu Val Lys Asn Asp Gly Glu Phe Arg Leu His Asn Pro
                965                 970                 975 ata aaa gag cag gaa ttg cac aat gat tta gta aga gca gag caa gca            3035
Ile Lys Glu Gln Glu Leu His Asn Asp Leu Val Arg Ala Glu Gln Ala
        980                 985                 990 gaa cga aca tta gaa gcc aaa caa  gtt gaa ccg act gct  aaa aca caa         3083
Glu Arg Thr Leu Glu Ala Lys Gln  Val Glu Pro Thr Ala  Lys Thr Gln
        995                 1000                 1005 aca ggt gag cca aaa gtg cgg  tca aga aga gca gcg  aga gca gcg              3128
Thr Gly Glu Pro Lys Val Arg  Ser Arg Arg Ala Ala  Arg Ala Ala
        1010                 1015                 1020 ttt cct gat acc ctg cct gat  caa agc ctg tta aac  gca tta gaa              3173
Phe Pro Asp Thr Leu Pro Asp  Gln Ser Leu Leu Asn  Ala Leu Glu
        1025                 1030                 1035 gcc aaa caa gct gaa ctg act  gct gaa aca caa aaa  agt aag gca              3218
Ala Lys Gln Ala Glu Leu Thr  Ala Glu Thr Gln Lys  Ser Lys Ala
        1040                 1045                 1050 aaa aca aaa aaa gtg cgg tca  aaa aga gca gtg ttt  tct gat ccc              3263
Lys Thr Lys Lys Val Arg Ser  Lys Arg Ala Val Phe  Ser Asp Pro
        1055                 1060                 1065
```

```
ctg ctt gat caa agc ctg ttc gca tta gaa gcc gca ctt gag gtt    3308
Leu Leu Asp Gln Ser Leu Phe Ala Leu Glu Ala Ala Leu Glu Val
        1070            1075            1080 att gat gcc cca cag caa tcg gaa aaa gat cgt cta gct caa gaa    3353
Ile Asp Ala Pro Gln Gln Ser Glu Lys Asp Arg Leu Ala Gln Glu
    1085            1090            1095 gaa gcg gaa aaa caa cgc aaa caa aaa gac ttg atc agc cgt tat    3398
Glu Ala Glu Lys Gln Arg Lys Gln Lys Asp Leu Ile Ser Arg Tyr
1100            1105            1110 tca aat agt gcg tta tca gaa tta tct gca aca gta aat agt atg    3443
Ser Asn Ser Ala Leu Ser Glu Leu Ser Ala Thr Val Asn Ser Met
        1115            1120            1125 ctt tct gtt caa gat gaa tta gat cgt ctt ttt gta gat caa gca    3488
Leu Ser Val Gln Asp Glu Leu Asp Arg Leu Phe Val Asp Gln Ala
    1130            1135            1140 caa tct gcc gtg tgg aca aat atc gca cag gat aaa aga cgc tat    3533
Gln Ser Ala Val Trp Thr Asn Ile Ala Gln Asp Lys Arg Arg Tyr
1145            1150            1155 gat tct gat gcg ttc cgt gct tat cag cag cag aaa acg aac tta    3578
Asp Ser Asp Ala Phe Arg Ala Tyr Gln Gln Gln Lys Thr Asn Leu
        1160            1165            1170 cgt caa att ggg gtg caa aaa gcc tta gct aat gga cga att ggg    3623
Arg Gln Ile Gly Val Gln Lys Ala Leu Ala Asn Gly Arg Ile Gly
    1175            1180            1185 gca gtt ttc tcg cat agc cgt tca gat aat acc ttt gat gaa cag    3668
Ala Val Phe Ser His Ser Arg Ser Asp Asn Thr Phe Asp Glu Gln
1190            1195            1200 gtt aaa aat cac gcg aca tta acg atg atg tcg ggt ttt gcc caa    3713
Val Lys Asn His Ala Thr Leu Thr Met Met Ser Gly Phe Ala Gln
        1205            1210            1215 tat caa tgg ggc gat tta caa ttt ggt gta aac gtg gga acg gga    3758
Tyr Gln Trp Gly Asp Leu Gln Phe Gly Val Asn Val Gly Thr Gly
    1220            1225            1230 atc agt gcg agt aaa atg gct gaa gaa caa agc cga aaa att cat    3803
Ile Ser Ala Ser Lys Met Ala Glu Glu Gln Ser Arg Lys Ile His
1235            1240            1245 cga aaa gcg ata aat tat ggc gtg aat gca agt tat cag ttc cgt    3848
Arg Lys Ala Ile Asn Tyr Gly Val Asn Ala Ser Tyr Gln Phe Arg
        1250            1255            1260 tta ggg caa ttg ggc att cag cct tat ttt gga gtt aat cgc tat    3893
Leu Gly Gln Leu Gly Ile Gln Pro Tyr Phe Gly Val Asn Arg Tyr
    1265            1270            1275 ttt att gaa cgt gaa aat tat caa tct gag gaa gtg aga gtg aaa    3938
Phe Ile Glu Arg Glu Asn Tyr Gln Ser Glu Glu Val Arg Val Lys
1280            1285            1290 acg cct agc ctt gca ttt aat cgc tat aat gct ggc att cga gtt    3983
Thr Pro Ser Leu Ala Phe Asn Arg Tyr Asn Ala Gly Ile Arg Val
        1295            1300            1305 gat tat aca ttt act ccg aca gat aat atc agc gtt aag cct tat    4028
Asp Tyr Thr Phe Thr Pro Thr Asp Asn Ile Ser Val Lys Pro Tyr
    1310            1315            1320 ttc ttc gtc aat tat gtt gat gtt tca aac gct aac gta caa acc    4073
Phe Phe Val Asn Tyr Val Asp Val Ser Asn Ala Asn Val Gln Thr
1325            1330            1335 acg gta aat ctc acg gtg ttg caa caa cca ttt gga cgt tat tgg    4118
Thr Val Asn Leu Thr Val Leu Gln Gln Pro Phe Gly Arg Tyr Trp
        1340            1345            1350 caa aaa gaa gtg gga tta aag gca gaa att tta cat ttc caa att    4163
Gln Lys Glu Val Gly Leu Lys Ala Glu Ile Leu His Phe Gln Ile
    1355            1360            1365
```

-continued

```
tcc gct ttt atc tca aaa tct caa ggt tca caa ctc ggc aaa cag    4208
Ser Ala Phe Ile Ser Lys Ser Gln Gly Ser Gln Leu Gly Lys Gln
    1370            1375                1380 caa aat gtg ggc gtg aaa ttg ggc tat cgt tgg taaaaatcaa          4251
Gln Asn Val Gly Val Lys Leu Gly Tyr Arg Trp
1385                1390 cataatttta tcgtttattg ataaacaagg tgggtcagat cagatcccac ctttttatt 4311 ccaataat                                                         4319

<210> SEQ ID NO 2
<211> LENGTH: 1394
<212> TYPE: PRT
<213> ORGANISM: Haemophilus influenzae

<400> SEQUENCE: 2
```

| Met | Lys | Lys | Thr | Val | Phe | Arg | Leu | Asn | Phe | Leu | Thr | Ala | Cys | Ile | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Gly Ile Val Ser Gln Ala Trp Ala Gly His Thr Tyr Phe Gly Ile
        20                  25                  30

Asp Tyr Gln Tyr Tyr Arg Asp Phe Ala Glu Asn Lys Gly Lys Phe Thr
            35                  40                  45

Val Gly Ala Gln Asn Ile Lys Val Tyr Asn Lys Gln Gly Gln Leu Val
    50                  55                  60

Gly Thr Ser Met Thr Lys Ala Pro Met Ile Asp Phe Ser Val Val Ser
65                  70                  75                  80

Arg Asn Gly Val Ala Ala Leu Val Glu Asn Gln Tyr Ile Val Ser Val
                85                  90                  95

Ala His Asn Val Gly Tyr Thr Asp Val Asp Phe Gly Ala Glu Gly Asn
            100                 105                 110

Asn Pro Asp Gln His Arg Phe Thr Tyr Lys Ile Val Lys Arg Asn Asn
        115                 120                 125

Tyr Lys Lys Asp Asn Leu His Pro Tyr Glu Asp Tyr His Asn Pro
    130                 135                 140

Arg Leu His Lys Phe Val Thr Glu Ala Ala Pro Ile Asp Met Thr Ser
145                 150                 155                 160

Asn Met Asn Gly Ser Thr Tyr Ser Asp Arg Thr Lys Tyr Pro Glu Arg
                165                 170                 175

Val Arg Ile Gly Ser Gly Arg Gln Phe Trp Arg Asn Asp Gln Asp Lys
            180                 185                 190

Gly Asp Gln Val Ala Gly Ala Tyr His Tyr Leu Thr Ala Gly Asn Thr
        195                 200                 205

His Asn Gln Arg Gly Ala Gly Asn Gly Tyr Ser Tyr Leu Gly Gly Asp
    210                 215                 220

Val Arg Lys Ala Gly Glu Tyr Gly Pro Leu Pro Ile Ala Gly Ser Lys
225                 230                 235                 240

Gly Asp Ser Gly Ser Pro Met Phe Ile Tyr Asp Ala Glu Lys Gln Lys
                245                 250                 255

Trp Leu Ile Asn Gly Ile Leu Arg Glu Gly Asn Pro Phe Glu Gly Lys
            260                 265                 270

Glu Asn Gly Phe Gln Leu Val Arg Lys Ser Tyr Phe Asp Glu Ile Phe
        275                 280                 285

Glu Arg Asp Leu His Thr Ser Leu Tyr Thr Arg Ala Gly Asn Gly Val
    290                 295                 300

Tyr Thr Ile Ser Gly Asn Asp Asn Gly Gln Gly Ser Ile Thr Gln Lys

```
                305                 310                 315                 320
Ser Gly Ile Pro Ser Glu Ile Lys Ile Thr Leu Ala Asn Met Ser Leu
                325                 330                 335
Pro Leu Lys Glu Lys Asp Lys Val His Asn Pro Arg Tyr Asp Gly Pro
                340                 345                 350
Asn Ile Tyr Ser Pro Arg Leu Asn Asn Gly Glu Thr Leu Tyr Phe Met
                355                 360                 365
Asp Gln Lys Gln Gly Ser Leu Ile Phe Ala Ser Asp Ile Asn Gln Gly
                370                 375                 380
Ala Gly Gly Leu Tyr Phe Glu Gly Asn Phe Thr Val Ser Pro Asn Ser
385                 390                 395                 400
Asn Gln Thr Trp Gln Gly Ala Gly Ile His Val Ser Glu Asn Ser Thr
                405                 410                 415
Val Thr Trp Lys Val Asn Gly Val Glu His Asp Arg Leu Ser Lys Ile
                420                 425                 430
Gly Lys Gly Thr Leu His Val Gln Ala Lys Gly Glu Asn Lys Gly Ser
                435                 440                 445
Ile Ser Val Gly Asp Gly Lys Val Ile Leu Glu Gln Gln Ala Asp Asp
450                 455                 460
Gln Gly Asn Lys Gln Ala Phe Ser Glu Ile Gly Leu Val Ser Gly Arg
465                 470                 475                 480
Gly Thr Val Gln Leu Asn Asp Asp Lys Gln Phe Asp Thr Asp Lys Phe
                485                 490                 495
Tyr Phe Gly Phe Arg Gly Gly Arg Leu Asp Leu Asn Gly His Ser Leu
                500                 505                 510
Thr Phe Lys Arg Ile Gln Asn Thr Asp Glu Gly Ala Met Ile Val Asn
                515                 520                 525
His Asn Thr Thr Gln Ala Ala Asn Val Thr Ile Thr Gly Asn Glu Ser
                530                 535                 540
Ile Val Leu Pro Asn Gly Asn Asn Ile Asn Lys Leu Asp Tyr Arg Lys
545                 550                 555                 560
Glu Ile Ala Tyr Asn Gly Trp Phe Gly Glu Thr Asp Lys Asn Lys His
                565                 570                 575
Asn Gly Arg Leu Asn Leu Ile Tyr Lys Pro Thr Thr Glu Asp Arg Thr
                580                 585                 590
Leu Leu Leu Ser Gly Gly Thr Asn Leu Lys Gly Asp Ile Thr Gln Thr
                595                 600                 605
Lys Gly Lys Leu Phe Phe Ser Gly Arg Pro Thr Pro His Ala Tyr Asn
                610                 615                 620
His Leu Asn Lys Arg Trp Ser Glu Met Glu Gly Ile Pro Gln Gly Glu
625                 630                 635                 640
Ile Val Trp Asp His Asp Trp Ile Asn Arg Thr Phe Lys Ala Glu Asn
                645                 650                 655
Phe Gln Ile Lys Gly Gly Ser Ala Val Val Ser Arg Asn Val Ser Ser
                660                 665                 670
Ile Glu Gly Asn Trp Thr Val Ser Asn Ala Asn Ala Thr Phe Gly
                675                 680                 685
Val Val Pro Asn Gln Gln Asn Thr Ile Cys Thr Arg Ser Asp Trp Thr
                690                 695                 700
Gly Leu Thr Thr Cys Gln Lys Val Asp Leu Thr Asp Thr Lys Val Ile
705                 710                 715                 720
Asn Ser Ile Pro Lys Thr Gln Ile Asn Gly Ser Ile Asn Leu Thr Asp
                725                 730                 735
```

```
Asn Ala Thr Ala Asn Val Lys Gly Leu Ala Lys Leu Asn Gly Asn Val
            740                 745                 750

Thr Leu Thr Asn His Ser Gln Phe Thr Leu Ser Asn Asn Ala Thr Gln
        755                 760                 765

Ile Gly Asn Ile Arg Leu Ser Asp Asn Ser Thr Ala Thr Val Asp Asn
    770                 775                 780

Ala Asn Leu Asn Gly Asn Val His Leu Thr Asp Ser Ala Gln Phe Ser
785                 790                 795                 800

Leu Lys Asn Ser His Phe Ser His Gln Ile Gln Gly Asp Lys Gly Thr
                805                 810                 815

Thr Val Thr Leu Glu Asn Ala Thr Trp Thr Met Pro Ser Asp Thr Thr
            820                 825                 830

Leu Gln Asn Leu Thr Leu Asn Asn Ser Thr Ile Thr Leu Asn Ser Ala
        835                 840                 845

Tyr Ser Ala Ser Ser Asn Asn Thr Pro Arg Arg Arg Ser Leu Glu Thr
    850                 855                 860

Glu Thr Thr Pro Thr Ser Ala Glu His Arg Phe Asn Thr Leu Thr Val
865                 870                 875                 880

Asn Gly Lys Leu Ser Gly Gln Gly Thr Phe Gln Phe Thr Ser Ser Leu
                885                 890                 895

Phe Gly Tyr Lys Ser Asp Lys Leu Lys Leu Ser Asn Asp Ala Glu Gly
            900                 905                 910

Asp Tyr Ile Leu Ser Val Arg Asn Thr Gly Lys Glu Pro Glu Thr Leu
        915                 920                 925

Glu Gln Leu Thr Leu Val Glu Ser Lys Asp Asn Gln Pro Leu Ser Asp
    930                 935                 940

Lys Leu Lys Phe Thr Leu Glu Asn Asp His Val Asp Ala Gly Ala Leu
945                 950                 955                 960

Arg Tyr Lys Leu Val Lys Asn Asp Gly Glu Phe Arg Leu His Asn Pro
                965                 970                 975

Ile Lys Glu Gln Glu Leu His Asn Asp Leu Val Arg Ala Glu Gln Ala
            980                 985                 990

Glu Arg Thr Leu Glu Ala Lys Gln  Val Glu Pro Thr Ala  Lys Thr Gln
        995                 1000                 1005

Thr Gly  Glu Pro Lys Val Arg  Ser Arg Arg Ala Ala  Arg Ala Ala
    1010                 1015                 1020

Phe Pro  Asp Thr Leu Pro Asp  Gln Ser Leu Leu Asn  Ala Leu Glu
    1025                 1030                 1035

Ala Lys  Gln Ala Glu Leu Thr  Ala Glu Thr Gln Lys  Ser Lys Ala
    1040                 1045                 1050

Lys Thr  Lys Lys Val Arg Ser  Lys Arg Ala Val Phe  Ser Asp Pro
    1055                 1060                 1065

Leu Leu  Asp Gln Ser Leu Phe  Ala Leu Glu Ala Ala  Leu Glu Val
    1070                 1075                 1080

Ile Asp  Ala Pro Gln Gln Ser  Glu Lys Asp Arg Leu  Ala Gln Glu
    1085                 1090                 1095

Glu Ala  Glu Lys Gln Arg Lys  Gln Lys Asp Leu Ile  Ser Arg Tyr
    1100                 1105                 1110

Ser Asn  Ser Ala Leu Ser Glu  Leu Ser Ala Thr Val  Asn Ser Met
    1115                 1120                 1125

Leu Ser  Val Gln Asp Glu Leu  Asp Arg Leu Phe Val  Asp Gln Ala
    1130                 1135                 1140
```

```
Gln Ser Ala Val Trp Thr Asn Ile Ala Gln Asp Lys Arg Arg Tyr
    1145                1150                1155

Asp Ser Asp Ala Phe Arg Ala Tyr Gln Gln Gln Lys Thr Asn Leu
    1160                1165                1170

Arg Gln Ile Gly Val Gln Lys Ala Leu Ala Asn Gly Arg Ile Gly
    1175                1180                1185

Ala Val Phe Ser His Ser Arg Ser Asp Asn Thr Phe Asp Glu Gln
    1190                1195                1200

Val Lys Asn His Ala Thr Leu Thr Met Met Ser Gly Phe Ala Gln
    1205                1210                1215

Tyr Gln Trp Gly Asp Leu Gln Phe Gly Val Asn Val Gly Thr Gly
    1220                1225                1230

Ile Ser Ala Ser Lys Met Ala Glu Glu Gln Ser Arg Lys Ile His
    1235                1240                1245

Arg Lys Ala Ile Asn Tyr Gly Val Asn Ala Ser Tyr Gln Phe Arg
    1250                1255                1260

Leu Gly Gln Leu Gly Ile Gln Pro Tyr Phe Gly Val Asn Arg Tyr
    1265                1270                1275

Phe Ile Glu Arg Glu Asn Tyr Gln Ser Glu Glu Val Arg Val Lys
    1280                1285                1290

Thr Pro Ser Leu Ala Phe Asn Arg Tyr Asn Ala Gly Ile Arg Val
    1295                1300                1305

Asp Tyr Thr Phe Thr Pro Asp Asn Ile Ser Val Lys Pro Tyr
    1310                1315                1320

Phe Phe Val Asn Tyr Val Asp Val Ser Asn Ala Asn Val Gln Thr
    1325                1330                1335

Thr Val Asn Leu Thr Val Leu Gln Gln Pro Phe Gly Arg Tyr Trp
    1340                1345                1350

Gln Lys Glu Val Gly Leu Lys Ala Glu Ile Leu His Phe Gln Ile
    1355                1360                1365

Ser Ala Phe Ile Ser Lys Ser Gln Gly Ser Gln Leu Gly Lys Gln
    1370                1375                1380

Gln Asn Val Gly Val Lys Leu Gly Tyr Arg Trp
    1385                1390

<210> SEQ ID NO 3
<211> LENGTH: 1541
<212> TYPE: PRT
<213> ORGANISM: Haemophilus influenzae

<400> SEQUENCE: 3

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Leu Val Lys Asp Lys Asn Asn Lys Asp Leu
        50                  55                  60

Gly Thr Ala Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110
```

-continued

```
Leu Asn Gly Asn Met Asn Asn Gly Asn Ala Lys Ala His Arg Asp Val
        115                 120                 125
Ser Ser Glu Asn Arg Tyr Phe Ser Val Glu Lys Asn Glu Tyr Pro
    130                 135                 140
Thr Lys Leu Asn Gly Lys Thr Val Thr Thr Glu Asp Gln Thr Gln Lys
145                 150                 155                 160
Arg Arg Glu Asp Tyr Tyr Met Pro Arg Leu Asp Lys Phe Val Thr Glu
                165                 170                 175
Val Ala Pro Ile Glu Ala Ser Thr Ala Ser Ser Asp Ala Gly Thr Tyr
            180                 185                 190
Asn Asp Gln Asn Lys Tyr Pro Ala Phe Val Arg Leu Gly Ser Gly Ser
        195                 200                 205
Gln Phe Ile Tyr Lys Lys Gly Asp Asn Tyr Ser Leu Ile Leu Asn Asn
    210                 215                 220
His Glu Val Gly Gly Asn Asn Leu Lys Leu Val Gly Asp Ala Tyr Thr
225                 230                 235                 240
Tyr Gly Ile Ala Gly Thr Pro Tyr Lys Val Asn His Glu Asn Asn Gly
                245                 250                 255
Leu Ile Gly Phe Gly Asn Ser Lys Glu Glu His Ser Asp Pro Lys Gly
            260                 265                 270
Ile Leu Ser Gln Asp Pro Leu Thr Asn Tyr Ala Val Leu Gly Asp Ser
        275                 280                 285
Gly Ser Pro Leu Phe Val Tyr Asp Arg Glu Lys Gly Lys Trp Leu Phe
    290                 295                 300
Leu Gly Ser Tyr Asp Phe Trp Ala Gly Tyr Asn Lys Lys Ser Trp Gln
305                 310                 315                 320
Glu Trp Asn Ile Tyr Lys Ser Gln Phe Thr Lys Asp Val Leu Asn Lys
                325                 330                 335
Asp Ser Ala Gly Ser Leu Ile Gly Ser Lys Thr Asp Tyr Ser Trp Ser
            340                 345                 350
Ser Asn Gly Lys Thr Ser Thr Ile Thr Gly Gly Glu Lys Ser Leu Asn
        355                 360                 365
Val Asp Leu Ala Asp Gly Lys Asp Lys Pro Asn His Gly Lys Ser Val
    370                 375                 380
Thr Phe Glu Gly Ser Gly Thr Leu Thr Leu Asn Asn Asn Ile Asp Gln
385                 390                 395                 400
Gly Ala Gly Gly Leu Phe Phe Glu Gly Asp Tyr Glu Val Lys Gly Thr
                405                 410                 415
Ser Asp Asn Thr Thr Trp Lys Gly Ala Gly Val Ser Val Ala Glu Gly
            420                 425                 430
Lys Thr Val Thr Trp Lys Val His Asn Pro Gln Tyr Asp Arg Leu Ala
        435                 440                 445
Lys Ile Gly Lys Gly Thr Leu Ile Val Glu Gly Thr Gly Asp Asn Lys
    450                 455                 460
Gly Ser Leu Lys Val Gly Asp Gly Thr Val Ile Leu Lys Gln Gln Thr
465                 470                 475                 480
Asn Gly Ser Gly Gln His Ala Phe Ala Ser Val Gly Ile Val Ser Gly
                485                 490                 495
Arg Ser Thr Leu Val Leu Asn Asp Asp Lys Gln Val Asp Pro Asn Ser
            500                 505                 510
Ile Tyr Phe Gly Phe Arg Gly Gly Arg Leu Asp Leu Asn Gly Asn Ser
        515                 520                 525
```

```
Leu Thr Phe Asp His Ile Arg Asn Ile Asp Asp Gly Ala Arg Leu Val
    530                 535                 540

Asn His Asn Met Thr Asn Ala Ser Asn Ile Thr Ile Thr Gly Glu Ser
545                 550                 555                 560

Leu Ile Thr Asp Pro Asn Thr Ile Thr Pro Tyr Asn Ile Asp Ala Pro
                565                 570                 575

Asp Glu Asp Asn Pro Tyr Ala Phe Arg Arg Ile Lys Asp Gly Gly Gln
            580                 585                 590

Leu Tyr Leu Asn Leu Glu Asn Tyr Thr Tyr Tyr Ala Leu Arg Lys Gly
        595                 600                 605

Ala Ser Thr Arg Ser Glu Leu Pro Lys Asn Ser Gly Glu Ser Asn Glu
    610                 615                 620

Asn Trp Leu Tyr Met Gly Lys Thr Ser Asp Glu Ala Lys Arg Asn Val
625                 630                 635                 640

Met Asn His Ile Asn Asn Glu Arg Met Asn Gly Phe Asn Gly Tyr Phe
                645                 650                 655

Gly Glu Glu Glu Gly Lys Asn Asn Gly Asn Leu Asn Val Thr Phe Lys
            660                 665                 670

Gly Lys Ser Glu Gln Asn Arg Phe Leu Leu Thr Gly Gly Thr Asn Leu
        675                 680                 685

Asn Gly Asp Leu Thr Val Glu Lys Gly Thr Leu Phe Leu Ser Gly Arg
    690                 695                 700

Pro Thr Pro His Ala Arg Asp Ile Ala Gly Ile Ser Ser Thr Lys Lys
705                 710                 715                 720

Asp Pro His Phe Ala Glu Asn Asn Glu Val Val Glu Asp Asp Trp
                725                 730                 735

Ile Asn Arg Asn Phe Lys Ala Thr Thr Met Asn Val Thr Gly Asn Ala
            740                 745                 750

Ser Leu Tyr Ser Gly Arg Asn Val Ala Asn Ile Thr Ser Asn Ile Thr
        755                 760                 765

Ala Ser Asn Lys Ala Gln Val His Ile Gly Tyr Lys Thr Gly Asp Thr
    770                 775                 780

Val Cys Val Arg Ser Asp Tyr Thr Gly Tyr Val Thr Cys Thr Thr Asp
785                 790                 795                 800

Lys Leu Ser Asp Lys Ala Leu Asn Ser Phe Asn Pro Thr Asn Leu Arg
                805                 810                 815

Gly Asn Val Asn Leu Thr Glu Ser Ala Asn Phe Val Leu Gly Lys Ala
            820                 825                 830

Asn Leu Phe Gly Thr Ile Gln Ser Arg Gly Asn Ser Gln Val Arg Leu
        835                 840                 845

Thr Glu Asn Ser His Trp His Leu Thr Gly Asn Ser Asp Val His Gln
    850                 855                 860

Leu Asp Leu Ala Asn Gly His Ile His Leu Asn Ser Ala Asp Asn Ser
865                 870                 875                 880

Asn Asn Val Thr Lys Tyr Asn Thr Leu Thr Val Asn Ser Leu Ser Gly
                885                 890                 895

Asn Gly Ser Phe Tyr Tyr Leu Thr Asp Leu Ser Asn Lys Gln Gly Asp
            900                 905                 910

Lys Val Val Thr Lys Ser Ala Thr Gly Asn Phe Thr Leu Gln Val
        915                 920                 925

Ala Asp Lys Thr Gly Glu Pro Asn His Asn Glu Leu Thr Leu Phe Asp
    930                 935                 940

Ala Ser Lys Ala Gln Arg Asp His Leu Asn Val Ser Leu Val Gly Asn
```

-continued

```
               945                 950                 955                 960
         Thr Val Asp Leu Gly Ala Trp Lys Tyr Lys Leu Arg Asn Val Asn Gly
                           965                 970                 975
         Arg Tyr Asp Leu Tyr Asn Pro Glu Val Glu Lys Arg Asn Gln Thr Val
                     980                 985                 990
         Asp Thr Thr Asn Ile Thr Thr Pro Asn Asn Ile Gln Ala Asp Val Pro
               995                 1000                1005
         Ser Val Pro Ser Asn Asn Glu Glu Ile Ala Arg Val Asp Glu Ala
             1010                1015                1020
         Pro Val Pro Pro Ala Pro Ala Thr Pro Ser Glu Thr Thr Glu
             1025                1030                1035
         Thr Val Ala Glu Asn Ser Lys Gln Glu Ser Lys Thr Val Glu Lys
             1040                1045                1050
         Asn Glu Gln Asp Ala Thr Glu Thr Thr Ala Gln Asn Arg Glu Val
             1055                1060                1065
         Ala Lys Glu Ala Lys Ser Asn Val Lys Ala Asn Thr Gln Thr Asn
             1070                1075                1080
         Glu Val Ala Gln Ser Gly Ser Glu Thr Lys Glu Thr Gln Thr Thr
             1085                1090                1095
         Glu Thr Lys Glu Thr Ala Thr Val Glu Lys Glu Glu Lys Ala Lys
             1100                1105                1110
         Val Glu Thr Glu Lys Thr Gln Glu Val Pro Lys Val Thr Ser Gln
             1115                1120                1125
         Val Ser Pro Lys Gln Glu Gln Ser Glu Thr Val Gln Pro Gln Ala
             1130                1135                1140
         Glu Pro Ala Arg Glu Asn Asp Pro Thr Val Asn Ile Lys Glu Pro
             1145                1150                1155
         Gln Ser Gln Thr Asn Thr Thr Ala Asp Thr Glu Gln Pro Ala Lys
             1160                1165                1170
         Glu Thr Ser Ser Asn Val Glu Gln Pro Val Thr Glu Ser Thr Thr
             1175                1180                1185
         Val Asn Thr Gly Asn Ser Val Val Glu Asn Pro Glu Asn Thr Thr
             1190                1195                1200
         Pro Ala Thr Thr Gln Pro Thr Val Asn Ser Glu Ser Ser Asn Lys
             1205                1210                1215
         Pro Lys Asn Arg His Arg Arg Ser Val Arg Ser Val Pro His Asn
             1220                1225                1230
         Val Glu Pro Ala Thr Thr Ser Ser Asn Asp Arg Ser Thr Val Ala
             1235                1240                1245
         Leu Cys Asp Leu Thr Ser Thr Asn Thr Asn Ala Val Leu Ser Asp
             1250                1255                1260
         Ala Arg Ala Lys Ala Gln Phe Val Ala Leu Asn Val Gly Lys Ala
             1265                1270                1275
         Val Ser Gln His Ile Ser Gln Leu Glu Met Asn Asn Glu Gly Gln
             1280                1285                1290
         Tyr Asn Val Trp Val Ser Asn Thr Ser Met Asn Lys Asn Tyr Ser
             1295                1300                1305
         Ser Ser Gln Tyr Arg Arg Phe Ser Ser Lys Ser Thr Gln Thr Gln
             1310                1315                1320
         Leu Gly Trp Asp Gln Thr Ile Ser Asn Asn Val Gln Leu Gly Gly
             1325                1330                1335
         Val Phe Thr Tyr Val Arg Asn Ser Asn Asn Phe Asp Lys Ala Thr
             1340                1345                1350
```

-continued

```
Ser Lys Asn Thr Leu Ala Gln Val Asn Phe Tyr Ser Lys Tyr Tyr
    1355                1360                1365

Ala Asp Asn His Trp Tyr Leu Gly Ile Asp Leu Gly Tyr Gly Lys
    1370                1375                1380

Phe Gln Ser Lys Leu Gln Thr Asn His Asn Ala Lys Phe Ala Arg
    1385                1390                1395

His Thr Ala Gln Phe Gly Leu Thr Ala Gly Lys Ala Phe Asn Leu
    1400                1405                1410

Gly Asn Phe Gly Ile Thr Pro Ile Val Gly Val Arg Tyr Ser Tyr
    1415                1420                1425

Leu Ser Asn Ala Asp Phe Ala Leu Asp Gln Ala Arg Ile Lys Val
    1430                1435                1440

Asn Pro Ile Ser Val Lys Thr Ala Phe Ala Gln Val Asp Leu Ser
    1445                1450                1455

Tyr Thr Tyr His Leu Gly Glu Phe Ser Val Thr Pro Ile Leu Ser
    1460                1465                1470

Ala Arg Tyr Asp Ala Asn Gln Gly Ser Gly Lys Ile Asn Val Asn
    1475                1480                1485

Gly Tyr Asp Phe Ala Tyr Asn Val Glu Asn Gln Gln Gln Tyr Asn
    1490                1495                1500

Ala Gly Leu Lys Leu Lys Tyr His Asn Val Lys Leu Ser Leu Ile
    1505                1510                1515

Gly Gly Leu Thr Lys Ala Lys Gln Ala Glu Lys Gln Lys Thr Ala
    1520                1525                1530

Glu Leu Lys Leu Ser Phe Ser Phe
    1535                1540

<210> SEQ ID NO 4
<211> LENGTH: 1545
<212> TYPE: PRT
<213> ORGANISM: Haemophilus influenzae

<400> SEQUENCE: 4

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Glu Val Arg Asp Lys Asn Asn Arg Pro Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95

Gly Val Lys His Val Ser Asn Gly Val Ser Glu Leu His Phe Gly Asn
                100                 105                 110

Leu Asn Gly Asn Met Asn Asn Gly Asn Ala Lys Ala His Arg Asp Val
            115                 120                 125

Ser Ser Glu Glu Asn Arg Tyr Tyr Thr Val Lys Asn Glu Tyr Pro
        130                 135                 140

Thr Lys Leu Asn Gly Lys Ala Val Thr Thr Asp Gln Ala Gln Lys
145                 150                 155                 160

Arg Arg Glu Asp Tyr Tyr Met Pro Arg Leu Asp Lys Phe Val Thr Glu
```

-continued

```
            165                 170                 175
Val Ala Pro Ile Glu Ala Ser Thr Asp Ser Ser Thr Ala Gly Thr Tyr
            180                 185                 190
Asn Asn Lys Asp Lys Tyr Pro Tyr Phe Val Arg Leu Gly Ser Gly Thr
            195                 200                 205
Gln Phe Ile Tyr Glu Asn Gly Thr Arg Tyr Glu Leu Trp Leu Gly Lys
            210                 215                 220
Glu Gly Gln Lys Ser Asp Ala Gly Gly Tyr Asn Leu Lys Leu Val Gly
225                 230                 235                 240
Asn Ala Tyr Thr Tyr Gly Ile Ala Gly Thr Pro Tyr Glu Val Asn His
            245                 250                 255
Glu Asn Asp Gly Leu Ile Gly Phe Gly Asn Ser Asn Asn Glu Tyr Ile
            260                 265                 270
Asn Pro Lys Glu Ile Leu Ser Lys Lys Pro Leu Thr Asn Tyr Ala Val
            275                 280                 285
Leu Gly Asp Ser Gly Ser Pro Leu Phe Val Tyr Asp Arg Glu Lys Gly
            290                 295                 300
Lys Trp Leu Phe Leu Gly Ser Tyr Asp Tyr Trp Ala Gly Tyr Asn Lys
305                 310                 315                 320
Lys Ser Trp Gln Glu Trp Asn Ile Tyr Lys Pro Glu Phe Ala Glu Lys
            325                 330                 335
Ile Tyr Glu Gln Tyr Ser Ala Gly Ser Leu Ile Gly Ser Lys Thr Asp
            340                 345                 350
Tyr Ser Trp Ser Ser Asn Gly Lys Thr Ser Thr Ile Thr Gly Gly Glu
            355                 360                 365
Lys Ser Leu Asn Val Asp Leu Ala Asp Gly Lys Asp Lys Pro Asn His
            370                 375                 380
Gly Lys Ser Val Thr Phe Glu Gly Ser Gly Thr Leu Thr Leu Asn Asn
385                 390                 395                 400
Asn Ile Asp Gln Gly Ala Gly Gly Leu Phe Phe Glu Gly Asp Tyr Glu
            405                 410                 415
Val Lys Gly Thr Ser Asp Asn Thr Thr Trp Lys Gly Ala Gly Val Ser
            420                 425                 430
Val Ala Glu Gly Lys Thr Val Thr Trp Lys Val His Asn Pro Gln Tyr
            435                 440                 445
Asp Arg Leu Ala Lys Ile Gly Lys Gly Thr Leu Ile Val Glu Gly Thr
            450                 455                 460
Gly Asp Asn Lys Gly Ser Leu Lys Val Gly Asp Gly Thr Val Ile Leu
465                 470                 475                 480
Lys Gln Gln Thr Asn Gly Ser Gly Gln His Ala Phe Ala Ser Val Gly
            485                 490                 495
Ile Val Ser Gly Arg Ser Thr Leu Val Leu Asn Asp Asp Lys Gln Val
            500                 505                 510
Asp Pro Asn Ser Ile Tyr Phe Gly Phe Arg Gly Gly Arg Leu Asp Leu
            515                 520                 525
Asn Gly Asn Ser Leu Thr Phe Asp His Ile Arg Asn Ile Asp Glu Gly
            530                 535                 540
Ala Arg Leu Val Asn His Ser Thr Ser Lys His Ser Thr Val Thr Ile
545                 550                 555                 560
Thr Gly Asp Asn Leu Ile Thr Asp Pro Asn Asn Val Ser Ile Tyr Tyr
            565                 570                 575
Val Lys Pro Leu Glu Asp Asp Asn Pro Tyr Ala Ile Arg Gln Ile Lys
            580                 585                 590
```

-continued

Tyr Gly Tyr Gln Leu Tyr Phe Asn Glu Glu Asn Arg Thr Tyr Tyr Ala
        595                 600                 605

Leu Lys Lys Asp Ala Ser Ile Arg Ser Glu Phe Pro Gln Asn Arg Gly
        610                 615                 620

Glu Ser Asn Asn Ser Trp Leu Tyr Met Gly Thr Glu Lys Ala Asp Ala
625                 630                 635                 640

Gln Lys Asn Ala Met Asn His Ile Asn Asn Glu Arg Met Asn Gly Phe
                645                 650                 655

Asn Gly Tyr Phe Gly Glu Glu Gly Lys Asn Asn Gly Asn Leu Asn
            660                 665                 670

Val Thr Phe Lys Gly Lys Ser Glu Gln Asn Arg Phe Leu Leu Thr Gly
        675                 680                 685

Gly Thr Asn Leu Asn Gly Asp Leu Asn Val Gln Gln Gly Thr Leu Phe
        690                 695                 700

Leu Ser Gly Arg Pro Thr Pro His Ala Arg Asp Ile Ala Gly Ile Ser
705                 710                 715                 720

Ser Thr Lys Lys Asp Ser His Phe Ser Glu Asn Asn Glu Val Val Val
                725                 730                 735

Glu Asp Asp Trp Ile Asn Arg Asn Phe Lys Ala Thr Asn Ile Asn Val
                740                 745                 750

Thr Asn Asn Ala Thr Leu Tyr Ser Gly Arg Asn Val Glu Ser Ile Thr
        755                 760                 765

Ser Asn Ile Thr Ala Ser Asn Ala Lys Val His Ile Gly Tyr Lys
        770                 775                 780

Ala Gly Asp Thr Val Cys Val Arg Ser Asp Tyr Thr Gly Tyr Val Thr
785                 790                 795                 800

Cys Thr Thr Asp Lys Leu Ser Asp Lys Ala Leu Asn Ser Phe Asn Pro
                805                 810                 815

Thr Asn Leu Arg Gly Asn Val Asn Leu Thr Glu Ser Ala Asn Phe Val
        820                 825                 830

Leu Gly Lys Ala Asn Leu Phe Gly Thr Ile Gln Ser Arg Gly Asn Ser
        835                 840                 845

Gln Val Arg Leu Thr Glu Asn Ser His Trp His Leu Thr Gly Asn Ser
850                 855                 860

Asp Val His Gln Leu Asp Leu Ala Asn Gly His Ile His Leu Asn Ser
865                 870                 875                 880

Ala Asp Asn Ser Asn Asn Val Thr Lys Tyr Asn Thr Leu Thr Val Asn
                885                 890                 895

Ser Leu Ser Gly Asn Gly Ser Phe Tyr Tyr Leu Thr Asp Leu Ser Asn
            900                 905                 910

Lys Gln Gly Asp Lys Val Val Thr Lys Ser Ala Thr Gly Asn Phe
        915                 920                 925

Thr Leu Gln Val Ala Asp Lys Thr Gly Glu Pro Asn His Asn Glu Leu
        930                 935                 940

Thr Leu Phe Asp Ala Ser Lys Ala Gln Arg Asp His Leu Asn Val Ser
945                 950                 955                 960

Leu Val Gly Asn Thr Val Asp Leu Gly Ala Trp Lys Tyr Lys Leu Arg
                965                 970                 975

Asn Val Asn Gly Arg Tyr Asp Leu Tyr Asn Pro Glu Val Glu Lys Arg
            980                 985                 990

Asn Gln Thr Val Asp Thr Thr Asn Ile Thr Thr Pro Asn Asn Ile Gln
        995                 1000                1005

-continued

| | | | | | | | | | | |
|---|---|---|---|---|---|---|---|---|---|---|
| Ala | Asp | Val | Pro | Ser | Val | Pro | Ser | Asn | Glu | Glu | Ile | Ala | Arg |
| | 1010 | | | | 1015 | | | | 1020 | |
| Val | Asp | Glu | Ala | Pro | Val | Pro | Pro | Ala | Pro | Ala | Thr | Pro | Ser |
| | 1025 | | | | 1030 | | | | 1035 | |
| Glu | Thr | Thr | Glu | Thr | Val | Ala | Glu | Asn | Ser | Lys | Gln | Glu | Ser | Lys |
| | 1040 | | | | 1045 | | | | 1050 | |
| Thr | Val | Glu | Lys | Asn | Glu | Gln | Asp | Ala | Thr | Glu | Thr | Thr | Ala | Gln |
| | 1055 | | | | 1060 | | | | 1065 | |
| Asn | Arg | Glu | Val | Ala | Lys | Glu | Ala | Lys | Ser | Asn | Val | Lys | Ala | Asn |
| | 1070 | | | | 1075 | | | | 1080 | |
| Thr | Gln | Thr | Asn | Glu | Val | Ala | Gln | Ser | Gly | Ser | Glu | Thr | Lys | Glu |
| | 1085 | | | | 1090 | | | | 1095 | |
| Thr | Gln | Thr | Thr | Glu | Thr | Lys | Glu | Thr | Ala | Thr | Val | Glu | Lys | Glu |
| | 1100 | | | | 1105 | | | | 1110 | |
| Glu | Lys | Ala | Lys | Val | Glu | Thr | Glu | Lys | Thr | Gln | Glu | Val | Pro | Lys |
| | 1115 | | | | 1120 | | | | 1125 | |
| Val | Thr | Ser | Gln | Val | Ser | Pro | Lys | Gln | Glu | Gln | Ser | Glu | Thr | Val |
| | 1130 | | | | 1135 | | | | 1140 | |
| Gln | Pro | Gln | Ala | Glu | Pro | Ala | Arg | Glu | Asn | Asp | Pro | Thr | Val | Asn |
| | 1145 | | | | 1150 | | | | 1155 | |
| Ile | Lys | Glu | Pro | Gln | Ser | Gln | Thr | Asn | Thr | Thr | Ala | Asp | Thr | Glu |
| | 1160 | | | | 1165 | | | | 1170 | |
| Gln | Pro | Ala | Lys | Glu | Thr | Ser | Ser | Asn | Val | Glu | Gln | Pro | Val | Thr |
| | 1175 | | | | 1180 | | | | 1185 | |
| Glu | Ser | Thr | Thr | Val | Asn | Thr | Gly | Asn | Ser | Val | Val | Glu | Asn | Pro |
| | 1190 | | | | 1195 | | | | 1200 | |
| Glu | Asn | Thr | Thr | Pro | Ala | Thr | Thr | Gln | Pro | Thr | Val | Asn | Ser | Glu |
| | 1205 | | | | 1210 | | | | 1215 | |
| Ser | Ser | Asn | Lys | Pro | Lys | Asn | Arg | His | Arg | Arg | Ser | Val | Arg | Ser |
| | 1220 | | | | 1225 | | | | 1230 | |
| Val | Pro | His | Asn | Val | Glu | Pro | Ala | Thr | Thr | Ser | Ser | Asn | Asp | Arg |
| | 1235 | | | | 1240 | | | | 1245 | |
| Ser | Thr | Val | Ala | Leu | Cys | Asp | Leu | Thr | Ser | Thr | Asn | Thr | Asn | Ala |
| | 1250 | | | | 1255 | | | | 1260 | |
| Val | Leu | Ser | Asp | Ala | Arg | Ala | Lys | Ala | Gln | Phe | Val | Ala | Leu | Asn |
| | 1265 | | | | 1270 | | | | 1275 | |
| Val | Gly | Lys | Ala | Val | Ser | Gln | His | Ile | Ser | Gln | Leu | Glu | Met | Asn |
| | 1280 | | | | 1285 | | | | 1290 | |
| Asn | Glu | Gly | Gln | Tyr | Asn | Val | Trp | Val | Ser | Asn | Thr | Ser | Met | Asn |
| | 1295 | | | | 1300 | | | | 1305 | |
| Lys | Asn | Tyr | Ser | Ser | Ser | Gln | Tyr | Arg | Arg | Phe | Ser | Ser | Lys | Ser |
| | 1310 | | | | 1315 | | | | 1320 | |
| Thr | Gln | Thr | Gln | Leu | Gly | Trp | Asp | Gln | Thr | Ile | Ser | Asn | Asn | Val |
| | 1325 | | | | 1330 | | | | 1335 | |
| Gln | Leu | Gly | Gly | Val | Phe | Thr | Tyr | Val | Arg | Asn | Ser | Asn | Asn | Phe |
| | 1340 | | | | 1345 | | | | 1350 | |
| Asp | Lys | Ala | Thr | Ser | Lys | Asn | Thr | Leu | Ala | Gln | Val | Asn | Phe | Tyr |
| | 1355 | | | | 1360 | | | | 1365 | |
| Ser | Lys | Tyr | Tyr | Ala | Asp | Asn | His | Trp | Tyr | Leu | Gly | Ile | Asp | Leu |
| | 1370 | | | | 1375 | | | | 1380 | |
| Gly | Tyr | Gly | Lys | Phe | Gln | Ser | Lys | Leu | Gln | Thr | Asn | His | Asn | Ala |
| | 1385 | | | | 1390 | | | | 1395 | |
| Lys | Phe | Ala | Arg | His | Thr | Ala | Gln | Phe | Gly | Leu | Thr | Ala | Gly | Lys |

```
                1400            1405            1410

Ala Phe Asn Leu Gly Asn Phe Gly Ile Thr Pro Ile Val Gly Val
    1415            1420            1425

Arg Tyr Ser Tyr Leu Ser Asn Ala Asp Phe Ala Leu Asp Gln Ala
    1430            1435            1440

Arg Ile Lys Val Asn Pro Ile Ser Val Lys Thr Ala Phe Ala Gln
    1445            1450            1455

Val Asp Leu Ser Tyr Thr Tyr His Leu Gly Glu Phe Ser Val Thr
    1460            1465            1470

Pro Ile Leu Ser Ala Arg Tyr Asp Ala Asn Gln Gly Ser Gly Lys
    1475            1480            1485

Ile Asn Val Asn Gly Tyr Asp Phe Ala Tyr Asn Val Glu Asn Gln
    1490            1495            1500

Gln Gln Tyr Asn Ala Gly Leu Lys Leu Lys Tyr His Asn Val Lys
    1505            1510            1515

Leu Ser Leu Ile Gly Gly Leu Thr Lys Ala Lys Gln Ala Glu Lys
    1520            1525            1530

Gln Lys Thr Ala Glu Leu Lys Leu Ser Phe Ser Phe
    1535            1540            1545

<210> SEQ ID NO 5
<211> LENGTH: 1702
<212> TYPE: PRT
<213> ORGANISM: Haemophilus influenzae

<400> SEQUENCE: 5

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Arg Phe Ser
            35                  40                  45

Val Gly Ala Thr Asn Val Glu Val Arg Asp Lys Asn Asn His Ser Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
                100                 105                 110

Leu Asn Gly Asn Met Asn Asn Gly Asn Asp Lys Ser His Arg Asp Val
            115                 120                 125

Ser Ser Glu Glu Asn Arg Tyr Phe Ser Val Glu Lys Asn Glu Tyr Pro
        130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Thr
        195                 200                 205

Gln Phe Ile Tyr Lys Lys Gly Asp Asn Tyr Ser Leu Ile Leu Asn Asn
    210                 215                 220
```

```
His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
            245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
        275                 280                 285

Gly Ser Pro Leu Phe Val Tyr Asp Arg Glu Lys Gly Lys Trp Leu Phe
        290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Ile Gly Ser Asn Thr Gln Tyr Asn Trp Asn
            340                 345                 350

Pro Thr Gly Lys Thr Ser Val Ile Ser Asn Gly Ser Glu Ser Leu Asn
        355                 360                 365

Val Asp Leu Phe Asp Ser Ser Gln Asp Thr Asp Ser Lys Lys Asn Asn
370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                405                 410                 415

Glu Val Lys Gly Thr Ser Asp Ser Thr Thr Trp Lys Gly Ala Gly Val
            420                 425                 430

Ser Val Ala Asp Gly Lys Thr Val Thr Trp Lys Val His Asn Pro Lys
        435                 440                 445

Ser Asp Arg Leu Ala Lys Ile Gly Lys Gly Thr Leu Ile Val Glu Gly
450                 455                 460

Lys Gly Glu Asn Lys Gly Ser Leu Lys Val Gly Asp Gly Thr Val Ile
465                 470                 475                 480

Leu Lys Gln Gln Ala Asp Ala Asn Asn Lys Val Lys Ala Phe Ser Gln
                485                 490                 495

Val Gly Ile Val Ser Gly Arg Ser Thr Val Val Leu Asn Asp Asp Lys
            500                 505                 510

Gln Val Asp Pro Asn Ser Ile Tyr Phe Gly Phe Arg Gly Gly Arg Leu
        515                 520                 525

Asp Ala Asn Gly Asn Asn Leu Thr Phe Glu His Ile Arg Asn Ile Asp
530                 535                 540

Asp Gly Ala Arg Leu Val Asn His Asn Thr Ser Lys Thr Ser Thr Val
545                 550                 555                 560

Thr Ile Thr Gly Glu Ser Leu Ile Thr Asp Pro Asn Thr Ile Thr Pro
            565                 570                 575

Tyr Asn Ile Asp Ala Pro Asp Glu Asp Asn Pro Tyr Ala Phe Arg Arg
        580                 585                 590

Ile Lys Asp Gly Gly Gln Leu Tyr Leu Asn Leu Glu Asn Tyr Thr Tyr
        595                 600                 605

Tyr Ala Leu Arg Lys Gly Ala Ser Thr Arg Ser Glu Leu Pro Lys Asn
        610                 615                 620

Ser Gly Glu Ser Asn Glu Asn Trp Leu Tyr Met Gly Lys Thr Ser Asp
625                 630                 635                 640

Ala Ala Lys Arg Asn Val Met Asn His Ile Asn Asn Glu Arg Met Asn
```

-continued

```
                645                 650                 655
Gly Phe Asn Gly Tyr Phe Gly Glu Glu Gly Lys Asn Asn Gly Asn
                660                 665                 670
Leu Asn Val Thr Phe Lys Gly Lys Ser Glu Gln Asn Arg Phe Leu Leu
                675                 680                 685
Thr Gly Gly Thr Asn Leu Asn Gly Asp Leu Lys Val Glu Lys Gly Thr
                690                 695                 700
Leu Phe Leu Ser Gly Arg Pro Thr Pro His Ala Arg Asp Ile Ala Gly
705                 710                 715                 720
Ile Ser Ser Thr Lys Lys Asp Gln His Phe Ala Glu Asn Asn Glu Val
                725                 730                 735
Val Val Glu Asp Asp Trp Ile Asn Arg Asn Phe Lys Ala Thr Asn Ile
                740                 745                 750
Asn Val Thr Asn Asn Ala Thr Leu Tyr Ser Gly Arg Asn Val Ala Asn
                755                 760                 765
Ile Thr Ser Asn Ile Thr Ala Ser Asp Asn Ala Lys Val His Ile Gly
                770                 775                 780
Tyr Lys Ala Gly Asp Thr Val Cys Val Arg Ser Asp Tyr Thr Gly Tyr
785                 790                 795                 800
Val Thr Cys Thr Thr Asp Lys Leu Ser Asp Lys Ala Leu Asn Ser Phe
                805                 810                 815
Asn Ala Thr Asn Val Ser Gly Asn Val Asn Leu Ser Gly Asn Ala Asn
                820                 825                 830
Phe Val Leu Gly Lys Ala Asn Leu Phe Gly Thr Ile Ser Gly Thr Gly
                835                 840                 845
Asn Ser Gln Val Arg Leu Thr Glu Asn Ser His Trp His Leu Thr Gly
                850                 855                 860
Asp Ser Asn Val Asn Gln Leu Asn Leu Asp Lys Gly His Ile His Leu
865                 870                 875                 880
Asn Ala Gln Asn Asp Ala Asn Lys Val Thr Thr Tyr Asn Thr Leu Thr
                885                 890                 895
Val Asn Ser Leu Ser Gly Asn Gly Ser Phe Tyr Tyr Leu Thr Asp Leu
                900                 905                 910
Ser Asn Lys Gln Gly Asp Lys Val Val Thr Lys Ser Ala Thr Gly
                915                 920                 925
Asn Phe Thr Leu Gln Val Ala Asp Lys Thr Gly Glu Pro Thr Lys Asn
                930                 935                 940
Glu Leu Thr Leu Phe Asp Ala Ser Asn Ala Thr Arg Asn Asn Leu Asn
945                 950                 955                 960
Val Ser Leu Val Gly Asn Thr Val Asp Leu Gly Ala Trp Lys Tyr Lys
                965                 970                 975
Leu Arg Asn Val Asn Gly Arg Tyr Asp Leu Tyr Asn Pro Glu Val Glu
                980                 985                 990
Lys Arg Asn Gln Thr Val Asp Thr  Thr Asn Ile Thr Thr  Pro Asn Asn
                995                 1000                1005
Ile Gln  Ala Asp Val Pro Ser  Val Pro Ser Asn Asn  Glu Glu Ile
       1010                 1015                1020
Ala Arg  Val Glu Thr Pro Val  Pro Pro Ala Pro  Ala Thr Pro
       1025                 1030                1035
Ser Glu  Thr Thr Glu Thr Val  Ala Glu Asn Ser Lys  Gln Glu Ser
       1040                 1045                1050
Lys Thr  Val Glu Lys Asn Glu  Gln Asp Ala Thr Glu  Thr Thr Ala
       1055                 1060                1065
```

-continued

```
Gln Asn Gly Glu Val Ala Glu Ala Lys Pro Ser Val Lys Ala
    1070                1075                1080

Asn Thr Gln Thr Asn Glu Val Ala Gln Ser Gly Ser Glu Thr Glu
    1085                1090                1095

Glu Thr Gln Thr Thr Glu Ile Lys Glu Thr Ala Lys Val Glu Lys
    1100                1105                1110

Glu Glu Lys Ala Lys Val Glu Lys Glu Glu Lys Ala Lys Val Glu
    1115                1120                1125

Lys Asp Glu Ile Gln Glu Ala Pro Gln Met Ala Ser Glu Thr Ser
    1130                1135                1140

Pro Lys Gln Ala Lys Pro Ala Pro Lys Glu Val Ser Thr Asp Thr
    1145                1150                1155

Lys Val Glu Glu Thr Gln Val Gln Ala Gln Pro Gln Thr Gln Ser
    1160                1165                1170

Thr Thr Val Ala Ala Ala Glu Ala Thr Ser Pro Asn Ser Lys Pro
    1175                1180                1185

Ala Glu Glu Thr Gln Pro Ser Glu Lys Thr Asn Ala Glu Pro Val
    1190                1195                1200

Thr Pro Val Val Ser Lys Asn Gln Thr Glu Asn Thr Thr Asp Gln
    1205                1210                1215

Pro Thr Glu Arg Glu Lys Thr Ala Lys Val Glu Thr Glu Lys Thr
    1220                1225                1230

Gln Glu Pro Pro Gln Val Ala Ser Gln Ala Ser Pro Lys Gln Glu
    1235                1240                1245

Gln Ser Glu Thr Val Gln Pro Gln Ala Val Leu Glu Ser Glu Asn
    1250                1255                1260

Val Pro Thr Val Asn Asn Ala Glu Glu Val Gln Ala Gln Leu Gln
    1265                1270                1275

Thr Gln Thr Ser Ala Thr Val Ser Thr Lys Gln Pro Ala Pro Glu
    1280                1285                1290

Asn Ser Ile Asn Thr Gly Ser Ala Thr Ala Ile Thr Glu Thr Ala
    1295                1300                1305

Glu Lys Ser Asp Lys Pro Gln Thr Glu Thr Ala Ala Ser Thr Glu
    1310                1315                1320

Asp Ala Ser Gln His Lys Ala Asn Thr Val Ala Asp Asn Ser Val
    1325                1330                1335

Ala Asn Asn Ser Glu Ser Ser Glu Pro Lys Ser Arg Arg Arg Arg
    1340                1345                1350

Ser Ile Ser Gln Pro Gln Glu Thr Ser Ala Glu Thr Thr Ala
    1355                1360                1365

Ala Ser Thr Asp Glu Thr Thr Ile Ala Asp Asn Ser Lys Arg Ser
    1370                1375                1380

Lys Pro Asn Arg Arg Ser Arg Arg Ser Val Arg Ser Glu Pro Thr
    1385                1390                1395

Val Thr Asn Gly Ser Asp Arg Ser Thr Val Ala Leu Arg Asp Leu
    1400                1405                1410

Thr Ser Thr Asn Thr Asn Ala Val Ile Ser Asp Ala Met Ala Lys
    1415                1420                1425

Ala Gln Phe Val Ala Leu Asn Val Gly Lys Ala Val Ser Gln His
    1430                1435                1440

Ile Ser Gln Leu Glu Met Asn Asn Glu Gly Gln Tyr Asn Val Trp
    1445                1450                1455
```

-continued

Val Ser Asn Thr Ser Met Asn Glu Asn Tyr Ser Ser Gln Tyr
1460            1465            1470

Arg Arg Phe Ser Ser Lys Ser Thr Gln Thr Gln Leu Gly Trp Asp
1475            1480            1485

Gln Thr Ile Ser Asn Asn Val Gln Leu Gly Gly Val Phe Thr Tyr
1490            1495            1500

Val Arg Asn Ser Asn Asn Phe Asp Lys Ala Ser Ser Lys Asn Thr
1505            1510            1515

Leu Ala Gln Val Asn Phe Tyr Ser Lys Tyr Tyr Ala Asp Asn His
1520            1525            1530

Trp Tyr Leu Gly Ile Asp Leu Gly Tyr Gly Lys Phe Gln Ser Asn
1535            1540            1545

Leu Lys Thr Asn His Asn Ala Lys Phe Ala Arg His Thr Ala Gln
1550            1555            1560

Phe Gly Leu Thr Ala Gly Lys Ala Phe Asn Leu Gly Asn Phe Gly
1565            1570            1575

Ile Thr Pro Ile Val Gly Val Arg Tyr Ser Tyr Leu Ser Asn Ala
1580            1585            1590

Asn Phe Ala Leu Ala Lys Asp Arg Ile Lys Val Asn Pro Ile Ser
1595            1600            1605

Val Lys Thr Ala Phe Ala Gln Val Asp Leu Ser Tyr Thr Tyr His
1610            1615            1620

Leu Gly Glu Phe Ser Val Thr Pro Ile Leu Ser Ala Arg Tyr Asp
1625            1630            1635

Thr Asn Gln Gly Ser Gly Lys Ile Asn Val Asn Gln Tyr Asp Phe
1640            1645            1650

Ala Tyr Asn Val Glu Asn Gln Gln Gln Tyr Asn Ala Gly Leu Lys
1655            1660            1665

Leu Lys Tyr His Asn Val Lys Leu Ser Leu Ile Gly Gly Leu Thr
1670            1675            1680

Lys Ala Lys Gln Ala Glu Lys Gln Lys Thr Ala Glu Leu Lys Leu
1685            1690            1695

Ser Phe Ser Phe
1700

<210> SEQ ID NO 6
<211> LENGTH: 1848
<212> TYPE: PRT
<213> ORGANISM: Haemophilus influenzae

<400> SEQUENCE: 6

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Glu Val Arg Asp Lys Lys Asn Gln Ser Leu
        50                  55                  60

Gly Ser Ala Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95

Gly Val Lys His Val Ser Asn Gly Val Ser Glu Leu His Phe Gly Asn
            100                 105                 110

-continued

```
Leu Asn Gly Asn Met Asn Asn Gly Asn Ala Lys Ser His Arg Asp Val
        115                 120                 125
Ser Ser Glu Glu Asn Arg Tyr Tyr Thr Val Glu Lys Asn Asn Phe Pro
130                 135                 140
Thr Glu Asn Val Thr Ser Phe Thr Lys Glu Glu Gln Asp Ala Gln Lys
145                 150                 155                 160
Arg Arg Glu Asp Tyr Tyr Met Pro Arg Leu Asp Lys Phe Val Thr Glu
                165                 170                 175
Val Ala Pro Ile Glu Ala Ser Thr Ala Asn Asn Asn Lys Gly Glu Tyr
                180                 185                 190
Asn Asn Ser Asp Lys Tyr Pro Ala Phe Val Arg Leu Gly Ser Gly Thr
                195                 200                 205
Gln Phe Ile Tyr Lys Lys Gly Ser Arg Tyr Gln Leu Ile Leu Thr Glu
            210                 215                 220
Lys Asp Lys Gln Gly Asn Leu Leu Arg Asn Trp Asp Val Gly Gly Asp
225                 230                 235                 240
Asn Leu Glu Leu Val Gly Asn Ala Tyr Thr Tyr Gly Ile Ala Gly Thr
                245                 250                 255
Pro Tyr Lys Val Asn His Glu Asn Asn Gly Leu Ile Gly Phe Gly Asn
                260                 265                 270
Ser Lys Glu Glu His Ser Asp Pro Lys Gly Ile Leu Ser Gln Asp Pro
            275                 280                 285
Leu Thr Asn Tyr Ala Val Leu Gly Asp Ser Gly Ser Pro Leu Phe Val
        290                 295                 300
Tyr Asp Arg Glu Lys Gly Lys Trp Leu Phe Leu Gly Ser Tyr Asp Phe
305                 310                 315                 320
Trp Ala Gly Tyr Asn Lys Lys Ser Trp Gln Glu Trp Asn Ile Tyr Lys
                325                 330                 335
His Glu Phe Ala Glu Lys Ile Tyr Gln Gln Tyr Ser Ala Gly Ser Leu
                340                 345                 350
Ile Gly Ser Asn Thr Gln Tyr Thr Trp Gln Ala Thr Gly Ser Thr Ser
            355                 360                 365
Thr Ile Thr Gly Gly Gly Glu Pro Leu Ser Val Asp Leu Thr Asp Gly
        370                 375                 380
Lys Asp Lys Pro Asn His Gly Lys Ser Ile Thr Leu Lys Gly Ser Gly
385                 390                 395                 400
Thr Leu Thr Leu Asn Asn His Ile Asp Gln Gly Ala Gly Gly Leu Phe
                405                 410                 415
Phe Glu Gly Asp Tyr Glu Val Lys Gly Thr Ser Asp Ser Thr Thr Trp
                420                 425                 430
Lys Gly Ala Gly Val Ser Val Ala Asp Gly Lys Thr Val Thr Trp Lys
            435                 440                 445
Val His Asn Pro Lys Tyr Asp Arg Leu Ala Lys Ile Gly Lys Gly Thr
        450                 455                 460
Leu Val Val Glu Gly Lys Gly Lys Asn Glu Gly Leu Leu Lys Val Gly
465                 470                 475                 480
Asp Gly Thr Val Ile Leu Lys Gln Lys Ala Asp Ala Asn Asn Lys Val
                485                 490                 495
Gln Ala Phe Ser Gln Val Gly Ile Val Ser Gly Arg Ser Thr Leu Val
            500                 505                 510
Leu Asn Asp Asp Lys Gln Val Asp Pro Asn Ser Ile Tyr Phe Gly Phe
        515                 520                 525
```

-continued

Arg Gly Gly Arg Leu Asp Leu Asn Gly Asn Ser Leu Thr Phe Asp His
    530                 535                 540

Ile Arg Asn Ile Asp Asp Gly Ala Arg Val Val Asn His Asn Met Thr
545                 550                 555                 560

Asn Thr Ser Asn Ile Thr Ile Thr Gly Glu Ser Leu Ile Thr Asn Pro
                565                 570                 575

Asn Thr Ile Thr Ser Tyr Asn Ile Glu Ala Gln Asp Asp His Pro
                580                 585                 590

Leu Arg Ile Arg Ser Ile Pro Tyr Arg Gln Leu Tyr Phe Asn Gln Asp
            595                 600                 605

Asn Arg Ser Tyr Tyr Thr Leu Lys Lys Gly Ala Ser Thr Arg Ser Glu
    610                 615                 620

Leu Pro Gln Asn Ser Gly Glu Ser Asn Glu Asn Trp Leu Tyr Met Gly
625                 630                 635                 640

Arg Thr Ser Asp Ala Ala Lys Arg Asn Val Met Asn His Ile Asn Asn
                645                 650                 655

Glu Arg Met Asn Gly Phe Asn Gly Tyr Phe Gly Glu Glu Thr Lys
                660                 665                 670

Ala Thr Gln Asn Gly Lys Leu Asn Val Thr Phe Asn Gly Lys Ser Asp
            675                 680                 685

Gln Asn Arg Phe Leu Leu Thr Gly Gly Thr Asn Leu Asn Gly Asp Leu
    690                 695                 700

Asn Val Glu Lys Gly Thr Leu Phe Leu Ser Gly Arg Pro Thr Pro His
705                 710                 715                 720

Ala Arg Asp Ile Ala Gly Ile Ser Ser Thr Lys Lys Asp Pro His Phe
                725                 730                 735

Thr Glu Asn Asn Glu Val Val Val Glu Asp Asp Trp Ile Asn Arg Asn
                740                 745                 750

Phe Lys Ala Thr Thr Met Asn Val Thr Gly Asn Ala Ser Leu Tyr Ser
            755                 760                 765

Gly Arg Asn Val Ala Asn Ile Thr Ser Asn Ile Thr Ala Ser Asn Asn
    770                 775                 780

Ala Gln Val His Ile Gly Tyr Lys Thr Gly Asp Thr Val Cys Val Arg
785                 790                 795                 800

Ser Asp Tyr Thr Gly Tyr Val Thr Cys His Asn Ser Asn Leu Ser Glu
                805                 810                 815

Lys Ala Leu Asn Ser Phe Asn Pro Thr Asn Leu Arg Gly Asn Val Asn
            820                 825                 830

Leu Thr Glu Asn Ala Ser Phe Thr Leu Gly Lys Ala Asn Leu Phe Gly
    835                 840                 845

Thr Ile Gln Ser Ile Gly Thr Ser Gln Val Asn Leu Lys Glu Asn Ser
850                 855                 860

His Trp His Leu Thr Gly Asn Ser Asn Val Asn Gln Leu Asn Leu Thr
865                 870                 875                 880

Asn Gly His Ile His Leu Asn Ala Gln Asn Asp Ala Asn Lys Val Thr
                885                 890                 895

Thr Tyr Asn Thr Leu Thr Val Asn Leu Ser Gly Asn Gly Ser Phe
                900                 905                 910

Tyr Tyr Trp Val Asp Phe Thr Asn Asn Lys Ser Asn Lys Val Val Val
            915                 920                 925

Asn Lys Ser Ala Thr Gly Asn Phe Thr Leu Gln Val Ala Asp Lys Thr
    930                 935                 940

Gly Glu Pro Asn His Asn Glu Leu Thr Leu Phe Asp Ala Ser Asn Ala

-continued

```
            945                 950                 955                 960
        Thr Arg Asn Asn Leu Glu Val Thr Leu Ala Asn Gly Ser Val Asp Arg
                        965                 970                 975
        Gly Ala Trp Lys Tyr Lys Leu Arg Asn Val Asn Gly Arg Tyr Asp Leu
                        980                 985                 990
        Tyr Asn Pro Glu Val Glu Lys Arg Asn Gln Thr Val Asp Thr Thr Asn
                        995                 1000                1005
        Ile Thr Thr Pro Asn Asp Ile Gln Ala Asp Ala Pro Ser Ala Gln
            1010                1015                1020
        Ser Asn Asn Glu Glu Ile Ala Arg Val Glu Thr Pro Val Pro Pro
            1025                1030                1035
        Pro Ala Pro Ala Thr Glu Ser Ala Ile Ala Ser Glu Gln Pro Glu
            1040                1045                1050
        Thr Arg Pro Ala Glu Thr Ala Gln Pro Ala Met Glu Glu Thr Asn
            1055                1060                1065
        Thr Ala Asn Ser Thr Glu Thr Ala Pro Lys Ser Asp Thr Ala Thr
            1070                1075                1080
        Gln Thr Glu Asn Pro Asn Ser Glu Ser Val Pro Ser Glu Thr Thr
            1085                1090                1095
        Glu Lys Val Ala Glu Asn Pro Pro Gln Glu Asn Glu Thr Val Ala
            1100                1105                1110
        Lys Asn Glu Gln Glu Ala Thr Glu Pro Thr Pro Gln Asn Gly Glu
            1115                1120                1125
        Val Ala Lys Glu Asp Gln Pro Thr Val Glu Ala Asn Thr Gln Thr
            1130                1135                1140
        Asn Glu Ala Thr Gln Ser Glu Gly Lys Thr Glu Glu Thr Gln Thr
            1145                1150                1155
        Ala Glu Thr Lys Ser Glu Pro Thr Glu Ser Val Thr Val Ser Glu
            1160                1165                1170
        Asn Gln Pro Glu Lys Thr Val Ser Gln Ser Thr Glu Asp Lys Val
            1175                1180                1185
        Val Val Glu Lys Glu Glu Lys Ala Lys Val Glu Thr Glu Glu Thr
            1190                1195                1200
        Gln Lys Ala Pro Gln Val Thr Ser Lys Glu Pro Lys Gln Ala
            1205                1210                1215
        Glu Pro Ala Pro Glu Glu Val Pro Thr Asp Thr Asn Ala Glu Glu
            1220                1225                1230
        Ala Gln Ala Leu Gln Gln Thr Gln Pro Thr Thr Val Ala Ala Ala
            1235                1240                1245
        Glu Thr Thr Ser Pro Asn Ser Lys Pro Ala Glu Thr Gln Gln
            1250                1255                1260
        Pro Ser Glu Lys Thr Asn Ala Glu Pro Val Thr Pro Val Val Ser
            1265                1270                1275
        Glu Asn Thr Ala Thr Gln Pro Thr Glu Thr Glu Glu Thr Ala Lys
            1280                1285                1290
        Val Glu Lys Glu Lys Thr Gln Glu Val Pro Gln Val Ala Ser Gln
            1295                1300                1305
        Glu Ser Pro Lys Gln Glu Gln Pro Ala Ala Lys Pro Gln Ala Gln
            1310                1315                1320
        Thr Lys Pro Gln Ala Glu Pro Ala Arg Glu Asn Val Leu Thr Thr
            1325                1330                1335
        Lys Asn Val Gly Glu Pro Gln Pro Gln Ala Gln Pro Gln Thr Gln
            1340                1345                1350
```

-continued

Ser Thr Ala Val Pro Thr Thr Gly Glu Thr Ala Ala Asn Ser Lys
    1355                1360            1365

Pro Ala Ala Lys Pro Gln Ala Gln Ala Lys Pro Gln Thr Glu Pro
    1370                1375            1380

Ala Arg Glu Asn Val Ser Thr Val Asn Thr Lys Glu Pro Gln Ser
    1385                1390            1395

Gln Thr Ser Ala Thr Val Ser Thr Glu Gln Pro Ala Lys Glu Thr
    1400                1405            1410

Ser Ser Asn Val Glu Gln Pro Ala Pro Glu Asn Ser Ile Asn Thr
    1415                1420            1425

Gly Ser Ala Thr Thr Met Thr Glu Thr Ala Glu Lys Ser Asp Lys
    1430                1435            1440

Pro Gln Met Glu Thr Val Thr Glu Asn Asp Arg Gln Pro Glu Ala
    1445                1450            1455

Asn Thr Val Ala Asp Asn Ser Val Ala Asn Asn Ser Glu Ser Ser
    1460                1465            1470

Glu Ser Lys Ser Arg Arg Arg Ser Val Ser Gln Pro Lys Glu
    1475                1480            1485

Thr Ser Ala Glu Glu Thr Thr Val Ala Ser Thr Gln Glu Thr Thr
    1490                1495            1500

Val Asp Asn Ser Val Ser Thr Pro Lys Pro Arg Ser Arg Arg Thr
    1505                1510            1515

Arg Arg Ser Val Gln Thr Asn Ser Tyr Glu Pro Val Glu Leu Pro
    1520                1525            1530

Thr Glu Asn Ala Glu Asn Ala Glu Asn Val Gln Ser Gly Asn Asn
    1535                1540            1545

Val Ala Asn Ser Gln Pro Ala Leu Arg Asn Leu Thr Ser Lys Asn
    1550                1555            1560

Thr Asn Ala Val Ile Ser Asn Ala Met Ala Lys Ala Gln Phe Val
    1565                1570            1575

Ala Leu Asn Val Gly Lys Ala Val Ser Gln His Ile Ser Gln Leu
    1580                1585            1590

Glu Met Asn Asn Glu Gly Gln Tyr Asn Val Trp Ile Ser Asn Thr
    1595                1600            1605

Ser Met Asn Lys Asn Tyr Ser Ser Glu Gln Tyr Arg Arg Phe Ser
    1610                1615            1620

Ser Lys Ser Thr Gln Thr Gln Leu Gly Trp Asp Gln Thr Ile Ser
    1625                1630            1635

Asn Asn Val Gln Leu Gly Gly Val Phe Thr Tyr Val Arg Asn Ser
    1640                1645            1650

Asn Asn Phe Asp Lys Ala Ser Ser Lys Asn Thr Leu Ala Gln Val
    1655                1660            1665

Asn Phe Tyr Ser Lys Tyr Tyr Ala Asp Asn His Trp Tyr Leu Gly
    1670                1675            1680

Ile Asp Leu Gly Tyr Gly Lys Phe Gln Ser Asn Leu Gln Thr Asn
    1685                1690            1695

Asn Asn Ala Lys Phe Ala Arg His Thr Ala Gln Ile Gly Leu Thr
    1700                1705            1710

Ala Gly Lys Ala Phe Asn Leu Gly Asn Phe Ala Val Lys Pro Thr
    1715                1720            1725

Val Gly Val Arg Tyr Ser Tyr Leu Ser Asn Ala Asp Phe Ala Leu
    1730                1735            1740

```
Ala Gln Asp Arg Ile Lys Val Asn Pro Ile Ser Val Lys Thr Ala
    1745                1750                1755

Phe Ala Gln Val Asp Leu Ser Tyr Thr Tyr His Leu Gly Glu Phe
    1760                1765                1770

Ser Ile Thr Pro Ile Leu Ser Ala Arg Tyr Asp Ala Asn Gln Gly
    1775                1780                1785

Asn Gly Lys Ile Asn Val Ser Val Tyr Asp Phe Ala Tyr Asn Val
    1790                1795                1800

Glu Asn Gln Gln Gln Tyr Asn Ala Gly Leu Lys Leu Lys Tyr His
    1805                1810                1815

Asn Val Lys Leu Ser Leu Ile Gly Gly Leu Thr Lys Ala Lys Gln
    1820                1825                1830

Ala Glu Lys Gln Lys Thr Ala Glu Val Lys Leu Ser Phe Ser Phe
    1835                1840                1845

<210> SEQ ID NO 7
<211> LENGTH: 1395
<212> TYPE: PRT
<213> ORGANISM: Haemophilus influenzae

<400> SEQUENCE: 7

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
                20                  25                  30

Asp Tyr Gln Tyr Tyr Arg Asp Phe Ala Glu Asn Lys Gly Lys Phe Thr
            35                  40                  45

Val Gly Ala Gln Asn Ile Lys Val Tyr Asn Lys Gln Gly Gln Leu Val
        50                  55                  60

Gly Thr Ser Met Thr Lys Ala Pro Met Ile Asp Phe Ser Val Val Ser
65                  70                  75                  80

Arg Asn Gly Val Ala Ala Leu Val Glu Asn Gln Tyr Ile Val Ser Val
                85                  90                  95

Ala His Asn Val Gly Tyr Thr Asp Val Asp Phe Gly Ala Glu Gly Asn
                100                 105                 110

Asn Pro Asp Gln His Arg Phe Thr Tyr Lys Ile Val Lys Arg Asn Asn
            115                 120                 125

Tyr Lys Lys Asp Asn Leu His Pro Tyr Glu Asp Tyr His Asn Pro
        130                 135                 140

Arg Leu His Lys Phe Val Thr Glu Ala Pro Ile Asp Met Thr Ser
145                 150                 155                 160

Asn Met Asn Gly Ser Thr Tyr Ser Asp Arg Thr Lys Tyr Pro Glu Arg
                165                 170                 175

Val Arg Ile Gly Ser Gly Arg Gln Phe Trp Arg Asn Asp Gln Asp Lys
            180                 185                 190

Gly Asp Gln Val Ala Gly Ala Tyr His Tyr Leu Thr Ala Gly Asn Thr
        195                 200                 205

His Asn Gln Arg Gly Ala Gly Asn Gly Tyr Ser Tyr Leu Gly Gly Asp
    210                 215                 220

Val Arg Lys Ala Gly Glu Tyr Gly Pro Leu Pro Ile Ala Gly Ser Lys
225                 230                 235                 240

Gly Asp Ser Gly Ser Pro Met Phe Ile Tyr Asp Ala Glu Lys Gln Lys
                245                 250                 255

Trp Leu Ile Asn Gly Ile Leu Arg Glu Gly Asn Pro Phe Glu Gly Lys
            260                 265                 270
```

-continued

```
Glu Asn Gly Phe Gln Leu Val Arg Lys Ser Tyr Phe Asp Glu Ile Phe
            275                 280                 285
Glu Arg Asp Leu His Thr Ser Leu Tyr Thr Arg Ala Gly Asn Gly Val
    290                 295                 300
Tyr Thr Ile Ser Gly Asn Asp Asn Gly Gln Gly Ser Ile Thr Gln Lys
305                 310                 315                 320
Ser Gly Ile Pro Ser Glu Ile Lys Ile Thr Leu Ala Asn Met Ser Leu
                325                 330                 335
Pro Leu Lys Glu Lys Asp Lys Val His Asn Pro Arg Tyr Asp Gly Pro
            340                 345                 350
Asn Ile Tyr Ser Pro Arg Leu Asn Asn Gly Glu Thr Leu Tyr Phe Met
        355                 360                 365
Asp Gln Lys Gln Gly Ser Leu Ile Phe Ala Ser Asp Ile Asn Gln Gly
    370                 375                 380
Ala Gly Gly Leu Tyr Phe Glu Gly Asn Phe Thr Val Ser Pro Asn Ser
385                 390                 395                 400
Asn Gln Thr Trp Gln Gly Ala Gly Ile His Val Ser Glu Asn Ser Thr
                405                 410                 415
Val Thr Trp Lys Val Asn Gly Val Glu His Asp Arg Leu Ser Lys Ile
            420                 425                 430
Gly Lys Gly Thr Leu His Val Gln Ala Lys Gly Glu Asn Lys Gly Ser
        435                 440                 445
Ile Ser Val Gly Asp Gly Lys Val Ile Leu Glu Gln Gln Ala Asp Asp
    450                 455                 460
Gln Gly Asn Lys Gln Ala Phe Ser Glu Ile Gly Leu Val Ser Gly Arg
465                 470                 475                 480
Gly Thr Val Gln Leu Asn Asp Asp Lys Gln Phe Asp Thr Asp Lys Phe
                485                 490                 495
Tyr Phe Gly Phe Arg Gly Gly Arg Leu Asp Leu Asn Gly His Ser Leu
            500                 505                 510
Thr Phe Lys Arg Ile Gln Asn Thr Asp Glu Gly Ala Met Ile Val Asn
        515                 520                 525
His Asn Thr Thr Gln Ala Ala Asn Val Thr Ile Thr Gly Asn Glu Ser
    530                 535                 540
Ile Val Leu Pro Asn Gly Asn Asn Ile Asn Lys Leu Asp Tyr Arg Lys
545                 550                 555                 560
Glu Ile Ala Tyr Asn Gly Trp Phe Gly Glu Thr Asp Lys Asn Lys His
                565                 570                 575
Asn Gly Arg Leu Asn Leu Ile Tyr Lys Pro Thr Thr Glu Asp Arg Thr
            580                 585                 590
Leu Leu Leu Ser Gly Gly Thr Asn Leu Lys Gly Asp Ile Thr Gln Thr
        595                 600                 605
Lys Gly Lys Leu Phe Phe Ser Gly Arg Pro Thr Pro His Ala Tyr Asn
    610                 615                 620
His Leu Asn Lys Arg Trp Ser Glu Met Glu Gly Ile Pro Gln Gly Glu
625                 630                 635                 640
Ile Val Trp Asp His Asp Trp Ile Asn Arg Thr Phe Lys Ala Glu Asn
                645                 650                 655
Phe Gln Ile Lys Gly Gly Ser Ala Val Val Ser Arg Asn Val Ser Ser
            660                 665                 670
Ile Glu Gly Asn Trp Thr Val Ser Asn Asn Ala Asn Ala Thr Phe Gly
        675                 680                 685
```

-continued

```
Val Val Pro Asn Gln Gln Asn Thr Ile Cys Thr Arg Ser Asp Trp Thr
    690                 695                 700
Gly Leu Thr Thr Cys Gln Lys Val Asp Leu Thr Asp Thr Lys Val Ile
705                 710                 715                 720
Asn Ser Ile Pro Lys Thr Gln Ile Asn Gly Ser Ile Asn Leu Thr Asp
                725                 730                 735
Asn Ala Thr Ala Asn Val Lys Gly Leu Ala Lys Leu Asn Gly Asn Val
                740                 745                 750
Thr Leu Thr Asn His Ser Gln Phe Thr Leu Ser Asn Asn Ala Thr Gln
                755                 760                 765
Ile Gly Asn Ile Arg Leu Ser Asp Asn Ser Thr Ala Thr Val Asp Asn
    770                 775                 780
Ala Asn Leu Asn Gly Asn Val His Leu Thr Asp Ser Ala Gln Phe Ser
785                 790                 795                 800
Leu Lys Asn Ser His Phe Ser His Gln Ile Gln Gly Asp Lys Gly Thr
                805                 810                 815
Thr Val Thr Leu Glu Asn Ala Thr Trp Thr Met Pro Ser Asp Thr Thr
                820                 825                 830
Leu Gln Asn Leu Thr Leu Asn Asn Ser Thr Ile Thr Leu Asn Ser Ala
                835                 840                 845
Tyr Ser Ala Ser Ser Asn Asn Thr Pro Arg Arg Arg Arg Ser Leu
850                 855                 860
Glu Thr Glu Thr Thr Pro Thr Ser Ala Glu His Arg Phe Asn Thr Leu
865                 870                 875                 880
Thr Val Asn Gly Lys Leu Ser Gly Gln Gly Thr Phe Gln Phe Thr Ser
                885                 890                 895
Ser Leu Phe Gly Tyr Lys Ser Asp Lys Leu Lys Leu Ser Asn Asp Ala
                900                 905                 910
Glu Gly Asp Tyr Ile Leu Ser Val Arg Asn Thr Gly Lys Glu Pro Glu
                915                 920                 925
Thr Leu Glu Gln Leu Thr Leu Val Glu Ser Lys Asp Asn Gln Pro Leu
930                 935                 940
Ser Asp Lys Leu Lys Phe Thr Leu Glu Asn Asp His Val Asp Ala Gly
945                 950                 955                 960
Ala Leu Arg Tyr Lys Leu Val Lys Asn Asp Gly Glu Phe Arg Leu His
                965                 970                 975
Asn Pro Ile Lys Glu Gln Glu Leu His Asn Asp Leu Val Arg Ala Glu
                980                 985                 990
Gln Ala Glu Arg Thr Leu Glu Ala Lys Gln Val Glu Pro Thr Ala Lys
                995                 1000                1005
Thr Gln Thr Gly Glu Pro Lys Val Arg Ser Arg Arg Ala Ala Arg
    1010                1015                1020
Ala Ala Phe Pro Asp Thr Leu Pro Asp Gln Ser Leu Leu Asn Ala
    1025                1030                1035
Leu Glu Ala Lys Gln Ala Glu Leu Thr Ala Glu Thr Gln Lys Ser
    1040                1045                1050
Lys Ala Lys Thr Lys Lys Val Arg Ser Lys Arg Ala Val Phe Ser
    1055                1060                1065
Asp Pro Leu Leu Asp Gln Ser Leu Phe Ala Leu Glu Ala Ala Leu
    1070                1075                1080
Glu Val Ile Asp Ala Pro Gln Ser Glu Lys Asp Arg Leu Ala
    1085                1090                1095
Gln Glu Glu Ala Glu Lys Gln Arg Lys Gln Lys Asp Leu Ile Ser
```

-continued

```
                    1100                1105                1110

Arg Tyr Ser Asn Ser Ala Leu Ser Glu Leu Ser Ala Thr Val Asn
    1115                1120                1125

Ser Met Leu Ser Val Gln Asp Glu Leu Asp Arg Leu Phe Val Asp
    1130                1135                1140

Gln Ala Gln Ser Ala Val Trp Thr Asn Ile Ala Gln Asp Lys Arg
    1145                1150                1155

Arg Tyr Asp Ser Asp Ala Phe Arg Ala Tyr Gln Gln Lys Thr Asn
    1160                1165                1170

Leu Arg Gln Ile Gly Val Gln Lys Ala Leu Ala Asn Gly Arg Ile
    1175                1180                1185

Gly Ala Val Phe Ser His Ser Arg Ser Asp Asn Thr Phe Asp Glu
    1190                1195                1200

Gln Val Lys Asn His Ala Thr Leu Thr Met Met Ser Gly Phe Ala
    1205                1210                1215

Gln Tyr Gln Trp Gly Asp Leu Gln Phe Gly Val Asn Val Gly Thr
    1220                1225                1230

Gly Ile Ser Ala Ser Lys Met Ala Glu Glu Gln Ser Arg Lys Ile
    1235                1240                1245

His Arg Lys Ala Ile Asn Tyr Gly Val Asn Ala Ser Tyr Gln Phe
    1250                1255                1260

Arg Leu Gly Gln Leu Gly Ile Gln Pro Tyr Phe Gly Val Asn Arg
    1265                1270                1275

Tyr Phe Ile Glu Arg Glu Asn Tyr Gln Ser Glu Val Arg Val
    1280                1285                1290

Lys Thr Pro Ser Leu Ala Phe Asn Arg Tyr Asn Ala Gly Ile Arg
    1295                1300                1305

Val Asp Tyr Thr Phe Thr Pro Thr Asp Asn Ile Ser Val Lys Pro
    1310                1315                1320

Tyr Phe Phe Val Asn Tyr Val Asp Val Ser Asn Ala Asn Val Gln
    1325                1330                1335

Thr Thr Val Asn Leu Thr Val Leu Gln Gln Pro Phe Gly Arg Tyr
    1340                1345                1350

Trp Gln Lys Glu Val Gly Leu Lys Ala Glu Ile Leu His Phe Gln
    1355                1360                1365

Ile Ser Ala Phe Ile Ser Lys Ser Gln Gly Ser Gln Leu Gly Lys
    1370                1375                1380

Gln Gln Asn Val Gly Val Lys Leu Gly Tyr Arg Trp
    1385                1390                1395
```

<210> SEQ ID NO 8
<211> LENGTH: 4305
<212> TYPE: DNA
<213> ORGANISM: Haemophilus influenzae
<220> FEATURE:
<221> NAME/KEY: misc_feature
<222> LOCATION: (1702)..(1702)
<223> OTHER INFORMATION: "n" at position 1702 can be any base.
<220> FEATURE:
<221> NAME/KEY: CDS
<222> LOCATION: (1)..(4305)
<223> OTHER INFORMATION:

<400> SEQUENCE: 8

```
atg aaa aaa act gta ttt cgt ctt aat ttt tta acc gct tgc att tca        48
Met Lys Lys Thr Val Phe Arg Leu Asn Phe Leu Thr Ala Cys Ile Ser
1               5                  10                  15
```

-continued

| | | |
|---|---|---|
| tta ggg ata gta tcg caa gcg tgg gca ggt cat act tat ttt ggg att<br>Leu Gly Ile Val Ser Gln Ala Trp Ala Gly His Thr Tyr Phe Gly Ile<br>           20                  25                 30 | 96 |
| gac tac caa tat tat cgt gat ttt gcc gag aat gaa ggc aag ttt gca<br>Asp Tyr Gln Tyr Tyr Arg Asp Phe Ala Glu Asn Glu Gly Lys Phe Ala<br>        35                  40                 45 | 144 |
| gtt ggg gct aaa aat att gat gtt tat aac aaa gaa ggg caa tta gtt<br>Val Gly Ala Lys Asn Ile Asp Val Tyr Asn Lys Glu Gly Gln Leu Val<br>50                  55                 60 | 192 |
| ggc aca tca atg aca aaa gcc ccg atg att gat ttc tca gtc gtt tcc<br>Gly Thr Ser Met Thr Lys Ala Pro Met Ile Asp Phe Ser Val Val Ser<br>65                  70                 75                 80 | 240 |
| aga aat gga gtt gct gcc tta gta ggc gat cag tat att gtg agt gtg<br>Arg Asn Gly Val Ala Ala Leu Val Gly Asp Gln Tyr Ile Val Ser Val<br>               85                  90                 95 | 288 |
| gca cat aat gta ggc tat acc aat gtg gat ttt ggt gct gaa gga caa<br>Ala His Asn Val Gly Tyr Thr Asn Val Asp Phe Gly Ala Glu Gly Gln<br>              100                 105              110 | 336 |
| aat cct gat caa cat cgt ttt act tat aaa att gtg aaa cgg aat aat<br>Asn Pro Asp Gln His Arg Phe Thr Tyr Lys Ile Val Lys Arg Asn Asn<br>             115                 120              125 | 384 |
| tat aat cac gat gcg aag cac cgc tat cta gat gac tac cat aat cca<br>Tyr Asn His Asp Ala Lys His Arg Tyr Leu Asp Asp Tyr His Asn Pro<br>130                   135                 140 | 432 |
| cgt tta cat aaa ttt gta acg gat gcg gca cca att gat atg act tca<br>Arg Leu His Lys Phe Val Thr Asp Ala Ala Pro Ile Asp Met Thr Ser<br>145                  150                 155                 160 | 480 |
| cat atg gat ggc aat aag tat gca aat aag gaa aaa tat cct gaa cga<br>His Met Asp Gly Asn Lys Tyr Ala Asn Lys Glu Lys Tyr Pro Glu Arg<br>                    165                 170              175 | 528 |
| gta cgc gtc gga tct gga gat cag tat tgg gat gac gat caa aac aac<br>Val Arg Val Gly Ser Gly Asp Gln Tyr Trp Asp Asp Asp Gln Asn Asn<br>             180                 185              190 | 576 |
| aga act tat tta tct gac gga tat aat tat tta aca ggt ggg aat aca<br>Arg Thr Tyr Leu Ser Asp Gly Tyr Asn Tyr Leu Thr Gly Gly Asn Thr<br>             195                 200              205 | 624 |
| tat aat caa agc ggt aga ggt gat gga tat tca tat gtg aga ggt gat<br>Tyr Asn Gln Ser Gly Arg Gly Asp Gly Tyr Ser Tyr Val Arg Gly Asp<br>210                  215                 220 | 672 |
| att cgc aaa gtt ggc gat tat ggt cca tta ccg att gca agt tca ttc<br>Ile Arg Lys Val Gly Asp Tyr Gly Pro Leu Pro Ile Ala Ser Ser Phe<br>225                  230                 235              240 | 720 |
| ggg gac agt gga tct cca atg ttt att tat gat gct gaa aca caa aaa<br>Gly Asp Ser Gly Ser Pro Met Phe Ile Tyr Asp Ala Glu Thr Gln Lys<br>                    245                 250              255 | 768 |
| tgg cta att aat gga gta ttg cgg gag ggg caa cct tat aca ggc gaa<br>Trp Leu Ile Asn Gly Val Leu Arg Glu Gly Gln Pro Tyr Thr Gly Glu<br>             260                 265              270 | 816 |
| ttc gat gga ttt caa tta gcc cgt aaa tct ttc ctt gat gaa att ata<br>Phe Asp Gly Phe Gln Leu Ala Arg Lys Ser Phe Leu Asp Glu Ile Ile<br>             275                 280              285 | 864 |
| cgc aaa gat caa cca aat ggt ttt tta acc cct aag ggg aat ggc gtt<br>Arg Lys Asp Gln Pro Asn Gly Phe Leu Thr Pro Lys Gly Asn Gly Val<br>290                  295                 300 | 912 |
| tat acc att tct aaa agt gac gat ggg ata gga gtt gtt act tcg aaa<br>Tyr Thr Ile Ser Lys Ser Asp Asp Gly Ile Gly Val Val Thr Ser Lys<br>305                  310                 315              320 | 960 |
| att gga aaa cct cgt gaa ata cct tta gcg aac aac aaa tta aaa ata<br>Ile Gly Lys Pro Arg Glu Ile Pro Leu Ala Asn Asn Lys Leu Lys Ile<br>                    325                 330              335 | 1008 |

```
gaa gat aaa gat act gtc tat aat aac aga tat aat ggt cct aat att    1056
Glu Asp Lys Asp Thr Val Tyr Asn Asn Arg Tyr Asn Gly Pro Asn Ile
            340                 345                 350 tat tct cct caa tta aac aat ggc aag aat att tat ttt gga gat gaa    1104
Tyr Ser Pro Gln Leu Asn Asn Gly Lys Asn Ile Tyr Phe Gly Asp Glu
            355                 360                 365 gaa tta gga tcc ata act tta acg act gat atc gat caa ggt gca ggc    1152
Glu Leu Gly Ser Ile Thr Leu Thr Thr Asp Ile Asp Gln Gly Ala Gly
            370                 375                 380 ggt ttg tat ttt gag ggg gat ttt ata gtt tcg cct acc aaa aat gaa    1200
Gly Leu Tyr Phe Glu Gly Asp Phe Ile Val Ser Pro Thr Lys Asn Glu
385                 390                 395                 400 acg tgg aaa ggt gcg ggc att cat gtc agt gaa att agt acc gtt act    1248
Thr Trp Lys Gly Ala Gly Ile His Val Ser Glu Ile Ser Thr Val Thr
                405                 410                 415 tgg aaa gta aac ggc gtg gaa aat gat cga ctt tct aaa atc ggt aaa    1296
Trp Lys Val Asn Gly Val Glu Asn Asp Arg Leu Ser Lys Ile Gly Lys
            420                 425                 430 gga aca tta cac gtt aaa gcc aaa ggg gaa aat aaa ggt tcg atc agc    1344
Gly Thr Leu His Val Lys Ala Lys Gly Glu Asn Lys Gly Ser Ile Ser
            435                 440                 445 gta ggc gat ggt aaa gtc att ttg gag cag cag gca gac gat caa ggc    1392
Val Gly Asp Gly Lys Val Ile Leu Glu Gln Gln Ala Asp Asp Gln Gly
450                 455                 460 aac aaa caa gcc ttt agt gaa att ggc ttg gtt agc ggc aga ggg act    1440
Asn Lys Gln Ala Phe Ser Glu Ile Gly Leu Val Ser Gly Arg Gly Thr
465                 470                 475                 480 gtt caa tta aac gat gat aaa caa ttt gat acc gat aaa ttt tat ttc    1488
Val Gln Leu Asn Asp Asp Lys Gln Phe Asp Thr Asp Lys Phe Tyr Phe
                485                 490                 495 ggc ttt cgt ggt ggt cgc tta gat ctt aac gga cat tca tta acc ttt    1536
Gly Phe Arg Gly Gly Arg Leu Asp Leu Asn Gly His Ser Leu Thr Phe
            500                 505                 510 aaa cgt atc caa aat acg gac gag ggg gcg atg att gtg aac cat aat    1584
Lys Arg Ile Gln Asn Thr Asp Glu Gly Ala Met Ile Val Asn His Asn
            515                 520                 525 aca act caa gtc gct aat att act att act ggg aac gaa agt att act    1632
Thr Thr Gln Val Ala Asn Ile Thr Ile Thr Gly Asn Glu Ser Ile Thr
            530                 535                 540 gct cca tct aat aaa aat aat att aat aaa ctt gat tac agc aaa gaa    1680
Ala Pro Ser Asn Lys Asn Asn Ile Asn Lys Leu Asp Tyr Ser Lys Glu
545                 550                 555                 560 att gcc tac aac ggc tgg ttt ngc gaa aca gat aaa aat aaa cat aat    1728
Ile Ala Tyr Asn Gly Trp Phe Xaa Glu Thr Asp Lys Asn Lys His Asn
                565                 570                 575 gga cga tta aac ctt att tat aaa cca acc aca gaa gat cgt act ttg    1776
Gly Arg Leu Asn Leu Ile Tyr Lys Pro Thr Thr Glu Asp Arg Thr Leu
            580                 585                 590 cta ctt tca ggc ggc aca aac tta aaa ggc gat att act caa aca aaa    1824
Leu Leu Ser Gly Gly Thr Asn Leu Lys Gly Asp Ile Thr Gln Thr Lys
            595                 600                 605 ggt aaa cta ttt ttc agc ggt aga ccg aca ccc cac gcc tac aat cat    1872
Gly Lys Leu Phe Phe Ser Gly Arg Pro Thr Pro His Ala Tyr Asn His
610                 615                 620 tta gac aaa cgt tgg tca gaa atg gaa ggt atc cca caa ggc gaa att    1920
Leu Asp Lys Arg Trp Ser Glu Met Glu Gly Ile Pro Gln Gly Glu Ile
625                 630                 635                 640 gtg tgg gat tac gat tgg att aac cgc aca ttt aaa gct gaa aac ttc    1968
Val Trp Asp Tyr Asp Trp Ile Asn Arg Thr Phe Lys Ala Glu Asn Phe
```

```
                 645                 650                 655
caa att aaa ggc gga agt gcg gtg gtt tct cgc aat gtt tct tca att      2016
Gln Ile Lys Gly Gly Ser Ala Val Val Ser Arg Asn Val Ser Ser Ile
            660                 665                 670 gag gga aat tgg aca gtc agc aat aat gca aat gcc aca ttt ggt gtt      2064
Glu Gly Asn Trp Thr Val Ser Asn Asn Ala Asn Ala Thr Phe Gly Val
        675                 680                 685 gtg cca aat cag caa aat acc att tgc acg cgt tca gat tgg aca gga      2112
Val Pro Asn Gln Gln Asn Thr Ile Cys Thr Arg Ser Asp Trp Thr Gly
    690                 695                 700 tta acg act tgt aaa aca gtt aat tta acc gat aaa aaa gtt att gat      2160
Leu Thr Thr Cys Lys Thr Val Asn Leu Thr Asp Lys Lys Val Ile Asp
705                 710                 715                 720 tcc ata ccg aca aca caa att aat ggt tct att aat tta act gat aat      2208
Ser Ile Pro Thr Thr Gln Ile Asn Gly Ser Ile Asn Leu Thr Asp Asn
                725                 730                 735 gca aca gtg aat att aat ggt tta gca aaa ctt aat ggt aat gtc act      2256
Ala Thr Val Asn Ile Asn Gly Leu Ala Lys Leu Asn Gly Asn Val Thr
            740                 745                 750 tta ata aat cat agc caa ttt aca ttg agc aac aat gcc acc caa ata      2304
Leu Ile Asn His Ser Gln Phe Thr Leu Ser Asn Asn Ala Thr Gln Ile
        755                 760                 765 ggc aat atc aaa ctt tca aat cac gca aat gca agg gta aat aat gcc      2352
Gly Asn Ile Lys Leu Ser Asn His Ala Asn Ala Arg Val Asn Asn Ala
    770                 775                 780 act tta atg ggc gat gtg aat tta gcg gat act agc cgt ttt aca tta      2400
Thr Leu Met Gly Asp Val Asn Leu Ala Asp Thr Ser Arg Phe Thr Leu
785                 790                 795                 800 agc aat caa gca aca cag att ggc aca atc agt ctt cat cag caa gct      2448
Ser Asn Gln Ala Thr Gln Ile Gly Thr Ile Ser Leu His Gln Gln Ala
                805                 810                 815 caa gca aca gtg gat aat gca aac ttg aac ggt aat gtg cat tta acg      2496
Gln Ala Thr Val Asp Asn Ala Asn Leu Asn Gly Asn Val His Leu Thr
            820                 825                 830 gat tct gcc aga ttt tct tta aaa aac agt cat ttt tcg cac caa att      2544
Asp Ser Ala Arg Phe Ser Leu Lys Asn Ser His Phe Ser His Gln Ile
        835                 840                 845 cag ggc gac aaa gac aca aca gtg acg ttg gaa aat gcg act tgg aca      2592
Gln Gly Asp Lys Asp Thr Thr Val Thr Leu Glu Asn Ala Thr Trp Thr
    850                 855                 860 atg cct agc gat act aca ttg cag aat tta acg cta aat aat agt act      2640
Met Pro Ser Asp Thr Thr Leu Gln Asn Leu Thr Leu Asn Asn Ser Thr
865                 870                 875                 880 gtt acg tta aat tca gct tat tca gct agc tca aat aat gcg cca cgt      2688
Val Thr Leu Asn Ser Ala Tyr Ser Ala Ser Ser Asn Asn Ala Pro Arg
                885                 890                 895 cgc cgc cgt tca tta gag acg gaa aca acg cca aca tcg gca gaa cat      2736
Arg Arg Arg Ser Leu Glu Thr Glu Thr Thr Pro Thr Ser Ala Glu His
            900                 905                 910 cgt ttc aac aca ttg aca gta aat ggt aaa ttg agc ggg caa ggc aca      2784
Arg Phe Asn Thr Leu Thr Val Asn Gly Lys Leu Ser Gly Gln Gly Thr
        915                 920                 925 ttc caa ttt act cca tct tta ttt ggc tat gaa agc gat aaa tta aaa      2832
Phe Gln Phe Thr Pro Ser Leu Phe Gly Tyr Glu Ser Asp Lys Leu Lys
    930                 935                 940 tta tcc aat gac gct gag ggc gat tac aca tta tct gtt cgc aac aca      2880
Leu Ser Asn Asp Ala Glu Gly Asp Tyr Thr Leu Ser Val Arg Asn Thr
945                 950                 955                 960 ggc aaa gaa ccc gtg acc ctt gag caa tta act ttg gtt gaa agc aaa      2928
```

```
                                                         -continued

Gly Lys Glu Pro Val Thr Leu Glu Gln Leu Thr Leu Val Glu Ser Lys
            965                 970                 975 gat aat aaa ccg tta tca gac aaa ctc aaa ttt act tta gaa aat gac      2976
Asp Asn Lys Pro Leu Ser Asp Lys Leu Lys Phe Thr Leu Glu Asn Asp
            980                 985                 990 cac gtt gat gca ggt gca tta cgt tat aaa tta gtg aag aat aag ggc      3024
His Val Asp Ala Gly Ala Leu Arg Tyr Lys Leu Val Lys Asn Lys Gly
        995                 1000                1005 gaa ttc cgc ttg cat aac cca ata aaa gag cag gaa ttg cgc tct          3069
Glu Phe Arg Leu His Asn Pro Ile Lys Glu Gln Glu Leu Arg Ser
    1010                1015                1020 gat tta gta aga gca gag caa gca gaa cga aca tta gaa gcc aaa          3114
Asp Leu Val Arg Ala Glu Gln Ala Glu Arg Thr Leu Glu Ala Lys
    1025                1030                1035 caa gtt gaa cag act gct gaa aca caa aca agt aat gca aga gtg          3159
Gln Val Glu Gln Thr Ala Glu Thr Gln Thr Ser Asn Ala Arg Val
    1040                1045                1050 cgg tca aga aga gcg gtg ttg tct gat acc ccg tct gct caa agc          3204
Arg Ser Arg Arg Ala Val Leu Ser Asp Thr Pro Ser Ala Gln Ser
    1055                1060                1065 ctg tta aac gca tta gaa gtc aaa caa gct gaa ccg aat gct aaa          3249
Leu Leu Asn Ala Leu Glu Val Lys Gln Ala Glu Pro Asn Ala Lys
    1070                1075                1080 aca caa aaa agt aag gca aaa aca aaa aaa gcg cgg tca aaa aga          3294
Thr Gln Lys Ser Lys Ala Lys Thr Lys Lys Ala Arg Ser Lys Arg
    1085                1090                1095 gca ttg aga gaa gcg ttt tct gat acc ccg cct gat cta agc cag          3339
Ala Leu Arg Glu Ala Phe Ser Asp Thr Pro Pro Asp Leu Ser Gln
    1100                1105                1110 tta aac gta tta gaa gcc gca ctt aag gtt att aat gcc caa ccg          3384
Leu Asn Val Leu Glu Ala Ala Leu Lys Val Ile Asn Ala Gln Pro
    1115                1120                1125 caa aca gaa aaa gaa cgt caa gct caa gag gaa gaa gcg aaa aga          3429
Gln Thr Glu Lys Glu Arg Gln Ala Gln Glu Glu Glu Ala Lys Arg
    1130                1135                1140 caa cgc aaa caa aaa gac ttg atc agc cgt tac tca aat agt gcg          3474
Gln Arg Lys Gln Lys Asp Leu Ile Ser Arg Tyr Ser Asn Ser Ala
    1145                1150                1155 tta tcg gag ttg tct gca aca gta aat agt atg ctt tcc gtt caa          3519
Leu Ser Glu Leu Ser Ala Thr Val Asn Ser Met Leu Ser Val Gln
    1160                1165                1170 gat gaa ttg gat cgt ctt ttt gta gat caa gca caa tct gcc ctg          3564
Asp Glu Leu Asp Arg Leu Phe Val Asp Gln Ala Gln Ser Ala Leu
    1175                1180                1185 tgg aca aat atc gca cag gat aaa aga cgc tat gat tct gat gcg          3609
Trp Thr Asn Ile Ala Gln Asp Lys Arg Arg Tyr Asp Ser Asp Ala
    1190                1195                1200 ttc cgt gct tat cag cag aaa acg aac ttg cgt caa att ggg gtg          3654
Phe Arg Ala Tyr Gln Gln Lys Thr Asn Leu Arg Gln Ile Gly Val
    1205                1210                1215 caa aaa gcc tta gat aat gga cga att ggg gcg gtt ttc tcg cat          3699
Gln Lys Ala Leu Asp Asn Gly Arg Ile Gly Ala Val Phe Ser His
    1220                1225                1230 agc cgt tca gat aat acc ttt gac gaa cag gtt aaa aat cac gcg          3744
Ser Arg Ser Asp Asn Thr Phe Asp Glu Gln Val Lys Asn His Ala
    1235                1240                1245 aca tta acg atg atg tcg ggt ttt gcc caa tat caa tgg ggc gat          3789
Thr Leu Thr Met Met Ser Gly Phe Ala Gln Tyr Gln Trp Gly Asp
    1250                1255                1260
```

```
tta caa ttt ggt gta aac gtg ggc gcg gga att agt gcg agt aaa    3834
Leu Gln Phe Gly Val Asn Val Gly Ala Gly Ile Ser Ala Ser Lys
    1265                1270                1275 atg gct gaa gaa caa agc cga aaa att cat cga aaa gcg ata aat    3879
Met Ala Glu Glu Gln Ser Arg Lys Ile His Arg Lys Ala Ile Asn
1280                1285                1290 tat ggt gtg aat gca agt tat cag ttc cgt tta ggg caa ttg ggt    3924
Tyr Gly Val Asn Ala Ser Tyr Gln Phe Arg Leu Gly Gln Leu Gly
    1295                1300                1305 att cag cct tat ttg ggt gtt aat cga tat ttt att gaa cgt gaa    3969
Ile Gln Pro Tyr Leu Gly Val Asn Arg Tyr Phe Ile Glu Arg Glu
1310                1315                1320 aat tat caa tct gaa gaa gtg aaa gtg caa aca ccg agc ctt gca    4014
Asn Tyr Gln Ser Glu Glu Val Lys Val Gln Thr Pro Ser Leu Ala
    1325                1330                1335 ttt aat cgc tat aat gct ggc att cga gtt gat tat aca ttt acc    4059
Phe Asn Arg Tyr Asn Ala Gly Ile Arg Val Asp Tyr Thr Phe Thr
1340                1345                1350 ccg aca gat aat atc agc gtt aag cct tat ttc ttt gtc aat tat    4104
Pro Thr Asp Asn Ile Ser Val Lys Pro Tyr Phe Phe Val Asn Tyr
    1355                1360                1365 gtt gat gtt tca aac gct aac gta caa acc act gta aat agc acg    4149
Val Asp Val Ser Asn Ala Asn Val Gln Thr Thr Val Asn Ser Thr
1370                1375                1380 atg ttg caa caa tca ttt ggg cgt tat tgg caa aaa gaa gtg gga    4194
Met Leu Gln Gln Ser Phe Gly Arg Tyr Trp Gln Lys Glu Val Gly
    1385                1390                1395 tta aag gca gaa att tta cat ttc caa ctt tcc gct ttt atc tca    4239
Leu Lys Ala Glu Ile Leu His Phe Gln Leu Ser Ala Phe Ile Ser
1400                1405                1410 aaa tct caa ggt tca caa ctc ggt aaa cag caa aat gtg ggc gtg    4284
Lys Ser Gln Gly Ser Gln Leu Gly Lys Gln Gln Asn Val Gly Val
    1415                1420                1425 aaa ttg ggc tat cgt tgg taa                                    4305
Lys Leu Gly Tyr Arg Trp
1430
```

<210> SEQ ID NO 9
<211> LENGTH: 1434
<212> TYPE: PRT
<213> ORGANISM: Haemophilus influenzae
<220> FEATURE:
<221> NAME/KEY: misc_feature
<222> LOCATION: (568)..(568)
<223> OTHER INFORMATION: The 'Xaa' at location 568 stands for Ser, Gly, Arg, or Cys.
<220> FEATURE:
<221> NAME/KEY: misc_feature
<222> LOCATION: (1702)..(1702)
<223> OTHER INFORMATION: "n" at position 1702 can be any base.

<400> SEQUENCE: 9

```
Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Glu Gly Lys Phe Ala
        35                  40                  45

Val Gly Ala Lys Asn Ile Asp Val Tyr Asn Lys Glu Gly Gln Leu Val
    50                  55                  60

Gly Thr Ser Met Thr Lys Ala Pro Met Ile Asp Phe Ser Val Val Ser
65                  70                  75                  80
```

```
Arg Asn Gly Val Ala Ala Leu Val Gly Asp Gln Tyr Ile Val Ser Val
                 85                  90                  95
Ala His Asn Val Gly Tyr Thr Asn Val Asp Phe Gly Ala Glu Gly Gln
                100                 105                 110
Asn Pro Asp Gln His Arg Phe Thr Tyr Lys Ile Val Lys Arg Asn Asn
                115                 120                 125
Tyr Asn His Asp Ala Lys His Arg Tyr Leu Asp Asp Tyr His Asn Pro
                130                 135                 140
Arg Leu His Lys Phe Val Thr Asp Ala Ala Pro Ile Asp Met Thr Ser
145                 150                 155                 160
His Met Asp Gly Asn Lys Tyr Ala Asn Lys Glu Lys Tyr Pro Glu Arg
                165                 170                 175
Val Arg Val Gly Ser Gly Asp Gln Tyr Trp Asp Asp Gln Asn Asn
                180                 185                 190
Arg Thr Tyr Leu Ser Asp Gly Tyr Asn Tyr Leu Thr Gly Gly Asn Thr
                195                 200                 205
Tyr Asn Gln Ser Gly Arg Gly Asp Gly Tyr Ser Tyr Val Arg Gly Asp
                210                 215                 220
Ile Arg Lys Val Gly Asp Tyr Gly Pro Leu Pro Ile Ala Ser Ser Phe
225                 230                 235                 240
Gly Asp Ser Gly Ser Pro Met Phe Ile Tyr Asp Ala Glu Thr Gln Lys
                245                 250                 255
Trp Leu Ile Asn Gly Val Leu Arg Glu Gly Gln Pro Tyr Thr Gly Glu
                260                 265                 270
Phe Asp Gly Phe Gln Leu Ala Arg Lys Ser Phe Leu Asp Glu Ile Ile
                275                 280                 285
Arg Lys Asp Gln Pro Asn Gly Phe Leu Thr Pro Lys Gly Asn Gly Val
290                 295                 300
Tyr Thr Ile Ser Lys Ser Asp Asp Gly Ile Gly Val Thr Ser Lys
305                 310                 315                 320
Ile Gly Lys Pro Arg Glu Ile Pro Leu Ala Asn Asn Lys Leu Lys Ile
                325                 330                 335
Glu Asp Lys Asp Thr Val Tyr Asn Asn Arg Tyr Asn Gly Pro Asn Ile
                340                 345                 350
Tyr Ser Pro Gln Leu Asn Asn Gly Lys Asn Ile Tyr Phe Gly Asp Glu
                355                 360                 365
Glu Leu Gly Ser Ile Thr Leu Thr Thr Asp Ile Asp Gln Gly Ala Gly
                370                 375                 380
Gly Leu Tyr Phe Glu Gly Asp Phe Ile Val Ser Pro Thr Lys Asn Glu
385                 390                 395                 400
Thr Trp Lys Gly Ala Gly Ile His Val Ser Glu Ile Ser Thr Val Thr
                405                 410                 415
Trp Lys Val Asn Gly Val Glu Asn Asp Arg Leu Ser Lys Ile Gly Lys
                420                 425                 430
Gly Thr Leu His Val Lys Ala Lys Gly Glu Asn Lys Gly Ser Ile Ser
                435                 440                 445
Val Gly Asp Gly Lys Val Ile Leu Glu Gln Gln Ala Asp Asp Gln Gly
                450                 455                 460
Asn Lys Gln Ala Phe Ser Glu Ile Gly Leu Val Ser Gly Arg Gly Thr
465                 470                 475                 480
Val Gln Leu Asn Asp Asp Lys Gln Phe Asp Thr Asp Lys Phe Tyr Phe
                485                 490                 495
```

-continued

```
Gly Phe Arg Gly Gly Arg Leu Asp Leu Asn Gly His Ser Leu Thr Phe
            500                 505                 510

Lys Arg Ile Gln Asn Thr Asp Glu Gly Ala Met Ile Val Asn His Asn
            515                 520                 525

Thr Thr Gln Val Ala Asn Ile Thr Ile Thr Gly Asn Glu Ser Ile Thr
            530                 535                 540

Ala Pro Ser Asn Lys Asn Asn Ile Asn Lys Leu Asp Tyr Ser Lys Glu
545                 550                 555                 560

Ile Ala Tyr Asn Gly Trp Phe Xaa Glu Thr Asp Lys Asn Lys His Asn
                565                 570                 575

Gly Arg Leu Asn Leu Ile Tyr Lys Pro Thr Thr Glu Asp Arg Thr Leu
            580                 585                 590

Leu Leu Ser Gly Gly Thr Asn Leu Lys Gly Asp Ile Thr Gln Thr Lys
            595                 600                 605

Gly Lys Leu Phe Phe Ser Gly Arg Pro Thr Pro His Ala Tyr Asn His
            610                 615                 620

Leu Asp Lys Arg Trp Ser Glu Met Glu Gly Ile Pro Gln Gly Glu Ile
625                 630                 635                 640

Val Trp Asp Tyr Asp Trp Ile Asn Arg Thr Phe Lys Ala Glu Asn Phe
                645                 650                 655

Gln Ile Lys Gly Gly Ser Ala Val Val Ser Arg Asn Val Ser Ser Ile
            660                 665                 670

Glu Gly Asn Trp Thr Val Ser Asn Asn Ala Asn Ala Thr Phe Gly Val
            675                 680                 685

Val Pro Asn Gln Gln Asn Thr Ile Cys Thr Arg Ser Asp Trp Thr Gly
            690                 695                 700

Leu Thr Thr Cys Lys Thr Val Asn Leu Thr Asp Lys Lys Val Ile Asp
705                 710                 715                 720

Ser Ile Pro Thr Thr Gln Ile Asn Gly Ser Ile Asn Leu Thr Asp Asn
                725                 730                 735

Ala Thr Val Asn Ile Asn Gly Leu Ala Lys Leu Asn Gly Asn Val Thr
            740                 745                 750

Leu Ile Asn His Ser Gln Phe Thr Leu Ser Asn Asn Ala Thr Gln Ile
            755                 760                 765

Gly Asn Ile Lys Leu Ser Asn His Ala Asn Ala Arg Val Asn Asn Ala
            770                 775                 780

Thr Leu Met Gly Asp Val Asn Leu Ala Asp Thr Ser Arg Phe Thr Leu
785                 790                 795                 800

Ser Asn Gln Ala Thr Gln Ile Gly Thr Ile Ser Leu His Gln Gln Ala
                805                 810                 815

Gln Ala Thr Val Asp Asn Ala Asn Leu Asn Gly Asn Val His Leu Thr
            820                 825                 830

Asp Ser Ala Arg Phe Ser Leu Lys Asn Ser His Phe Ser His Gln Ile
            835                 840                 845

Gln Gly Asp Lys Asp Thr Thr Val Thr Leu Glu Asn Ala Thr Trp Thr
            850                 855                 860

Met Pro Ser Asp Thr Thr Leu Gln Asn Leu Thr Leu Asn Asn Ser Thr
865                 870                 875                 880

Val Thr Leu Asn Ser Ala Tyr Ser Ala Ser Asn Asn Ala Pro Arg
                885                 890                 895

Arg Arg Arg Ser Leu Glu Thr Glu Thr Thr Pro Thr Ser Ala Glu His
            900                 905                 910

Arg Phe Asn Thr Leu Thr Val Asn Gly Lys Leu Ser Gly Gln Gly Thr
```

-continued

```
                915                 920                 925
Phe Gln Phe Thr Pro Ser Leu Phe Gly Tyr Glu Ser Asp Lys Leu Lys
    930                 935                 940

Leu Ser Asn Asp Ala Glu Gly Asp Tyr Thr Leu Ser Val Arg Asn Thr
945                 950                 955                 960

Gly Lys Glu Pro Val Thr Leu Glu Gln Leu Thr Leu Val Glu Ser Lys
                965                 970                 975

Asp Asn Lys Pro Leu Ser Asp Lys Leu Lys Phe Thr Leu Glu Asn Asp
            980                 985                 990

His Val Asp Ala Gly Ala Leu Arg Tyr Lys Leu Val Lys Asn Lys Gly
            995                 1000                1005

Glu Phe Arg Leu His Asn Pro Ile Lys Glu Gln Glu Leu Arg Ser
    1010                1015                1020

Asp Leu Val Arg Ala Glu Gln Ala Glu Arg Thr Leu Glu Ala Lys
    1025                1030                1035

Gln Val Glu Gln Thr Ala Glu Thr Gln Thr Ser Asn Ala Arg Val
    1040                1045                1050

Arg Ser Arg Arg Ala Val Leu Ser Asp Thr Pro Ser Ala Gln Ser
    1055                1060                1065

Leu Leu Asn Ala Leu Glu Val Lys Gln Ala Glu Pro Asn Ala Lys
    1070                1075                1080

Thr Gln Lys Ser Lys Ala Lys Thr Lys Lys Ala Arg Ser Lys Arg
    1085                1090                1095

Ala Leu Arg Glu Ala Phe Ser Asp Thr Pro Pro Asp Leu Ser Gln
    1100                1105                1110

Leu Asn Val Leu Glu Ala Ala Leu Lys Val Ile Asn Ala Gln Pro
    1115                1120                1125

Gln Thr Glu Lys Glu Arg Gln Ala Gln Glu Glu Ala Lys Arg
    1130                1135                1140

Gln Arg Lys Gln Lys Asp Leu Ile Ser Arg Tyr Ser Asn Ser Ala
    1145                1150                1155

Leu Ser Glu Leu Ser Ala Thr Val Asn Ser Met Leu Ser Val Gln
    1160                1165                1170

Asp Glu Leu Asp Arg Leu Phe Val Asp Gln Ala Gln Ser Ala Leu
    1175                1180                1185

Trp Thr Asn Ile Ala Gln Asp Lys Arg Arg Tyr Asp Ser Asp Ala
    1190                1195                1200

Phe Arg Ala Tyr Gln Gln Lys Thr Asn Leu Arg Gln Ile Gly Val
    1205                1210                1215

Gln Lys Ala Leu Asp Asn Gly Arg Ile Gly Ala Val Phe Ser His
    1220                1225                1230

Ser Arg Ser Asp Asn Thr Phe Asp Glu Gln Val Lys Asn His Ala
    1235                1240                1245

Thr Leu Thr Met Met Ser Gly Phe Ala Gln Tyr Gln Trp Gly Asp
    1250                1255                1260

Leu Gln Phe Gly Val Asn Val Gly Ala Gly Ile Ser Ala Ser Lys
    1265                1270                1275

Met Ala Glu Glu Gln Ser Arg Lys Ile His Arg Lys Ala Ile Asn
    1280                1285                1290

Tyr Gly Val Asn Ala Ser Tyr Gln Phe Arg Leu Gly Gln Leu Gly
    1295                1300                1305

Ile Gln Pro Tyr Leu Gly Val Asn Arg Tyr Phe Ile Glu Arg Glu
    1310                1315                1320
```

-continued

```
Asn Tyr Gln Ser Glu Glu Val Lys Val Gln Thr Pro Ser Leu Ala
    1325                1330                1335

Phe Asn Arg Tyr Asn Ala Gly Ile Arg Val Asp Tyr Thr Phe Thr
    1340                1345                1350

Pro Thr Asp Asn Ile Ser Val Lys Pro Tyr Phe Phe Val Asn Tyr
    1355                1360                1365

Val Asp Val Ser Asn Ala Asn Val Gln Thr Thr Val Asn Ser Thr
    1370                1375                1380

Met Leu Gln Gln Ser Phe Gly Arg Tyr Trp Gln Lys Glu Val Gly
    1385                1390                1395

Leu Lys Ala Glu Ile Leu His Phe Gln Leu Ser Ala Phe Ile Ser
    1400                1405                1410

Lys Ser Gln Gly Ser Gln Leu Gly Lys Gln Gln Asn Val Gly Val
    1415                1420                1425

Lys Leu Gly Tyr Arg Trp
    1430
```

<210> SEQ ID NO 10
<211> LENGTH: 4605
<212> TYPE: DNA
<213> ORGANISM: Haemophilus influenzae
<220> FEATURE:
<221> NAME/KEY: CDS
<222> LOCATION: (422)..(4597)
<223> OTHER INFORMATION:

<400> SEQUENCE: 10

```
tggcggcgga caaattattg cgacgggtac accagaacaa gttgctaaag taaaaagttc      60
ccacaccgct cgcttcctta aaccgatttt agaaaaacct tagaaaaaat gaccgcactt     120
tcagagaaaa ctcacataaa gtgcggttat tttattagtg atattgtttt aattttagtt     180
atctgtataa attacataca atattaatcc atcgcaagat tagattaccc actaagtatt     240
aagcaaaaac ctagaaattt tggcttaatt actatatagt tttactcatt tattttcttt     300
tgtgcctttt agttcatttt tttagctgaa atcccttaga aaatcaccgc acttttattg     360
ttcaatagtc gtttaaccac gtattttta atacgaaaaa ttacttaatt aaataaacat     420 t atg aaa aaa act gta ttt cgt ctg aat ttt tta acc gct tgc att tca      469
  Met Lys Lys Thr Val Phe Arg Leu Asn Phe Leu Thr Ala Cys Ile Ser
    1               5                  10                  15 tta ggg ata gta tcg caa gcg tgg gca ggt cat act tat ttt ggg att       517
Leu Gly Ile Val Ser Gln Ala Trp Ala Gly His Thr Tyr Phe Gly Ile
            20                  25                  30 gac tac caa tat tat cgt gat ttt gcc gag aat aaa ggg aag ttt aca       565
Asp Tyr Gln Tyr Tyr Arg Asp Phe Ala Glu Asn Lys Gly Lys Phe Thr
        35                  40                  45 gtt ggg gct caa gat att gat atc tac aat aaa aaa ggg gaa atg ata       613
Val Gly Ala Gln Asp Ile Asp Ile Tyr Asn Lys Lys Gly Glu Met Ile
    50                  55                  60 ggt acg atg atg aaa ggt gtg cct atg cct gat tta tct tcc atg gtt       661
Gly Thr Met Met Lys Gly Val Pro Met Pro Asp Leu Ser Ser Met Val
65                  70                  75                  80 cgt ggt ggt tat tca aca ttg ata agt gag cag cat tta att agc gtc       709
Arg Gly Gly Tyr Ser Thr Leu Ile Ser Glu Gln His Leu Ile Ser Val
                85                  90                  95 gca cat aat gta ggg tat gat gtc gtt gat ttt ggt atg gag ggg gaa       757
Ala His Asn Val Gly Tyr Asp Val Val Asp Phe Gly Met Glu Gly Glu
            100                 105                 110
```

-continued

| | |
|---|---:|
| aat cca gac caa cat cgt ttt aag tat aaa gtt gtt aaa cga tat aat<br>Asn Pro Asp Gln His Arg Phe Lys Tyr Lys Val Val Lys Arg Tyr Asn<br>115                      120                  125 | 805 |
| tat aag agc ggt gat aga caa tat aat gat tat caa cat cca aga tta<br>Tyr Lys Ser Gly Asp Arg Gln Tyr Asn Asp Tyr Gln His Pro Arg Leu<br>    130                  135                  140 | 853 |
| gag aaa ttt gta acg gaa act gca cct att gaa atg gtt tca tat atg<br>Glu Lys Phe Val Thr Glu Thr Ala Pro Ile Glu Met Val Ser Tyr Met<br>145                  150                  155                  160 | 901 |
| gat ggt aat cat tac aaa aat ttt aat caa tat cct ttg cga gtt aga<br>Asp Gly Asn His Tyr Lys Asn Phe Asn Gln Tyr Pro Leu Arg Val Arg<br>                  165                  170                  175 | 949 |
| gtt gga agt ggg cat caa tgg tgg aaa gac gat aat aat aaa acc att<br>Val Gly Ser Gly His Gln Trp Trp Lys Asp Asp Asn Asn Lys Thr Ile<br>                  180                  185                  190 | 997 |
| gga gac tta gcc tat gga ggt tca tgg tta ata ggt gga aat acc ttt<br>Gly Asp Leu Ala Tyr Gly Gly Ser Trp Leu Ile Gly Gly Asn Thr Phe<br>                  195                  200                  205 | 1045 |
| gaa gat gga cca gct ggt aac ggt aca tta gaa tta aat ggg cga gta<br>Glu Asp Gly Pro Ala Gly Asn Gly Thr Leu Glu Leu Asn Gly Arg Val<br>210                  215                  220 | 1093 |
| caa aat cct aat aaa tat ggt cca cta cct acg gca ggt tca ttc ggg<br>Gln Asn Pro Asn Lys Tyr Gly Pro Leu Pro Thr Ala Gly Ser Phe Gly<br>225                  230                  235                  240 | 1141 |
| gat agt ggt tct cca atg ttt att tat gat aag gaa gtt aag aaa tgg<br>Asp Ser Gly Ser Pro Met Phe Ile Tyr Asp Lys Glu Val Lys Lys Trp<br>                  245                  250                  255 | 1189 |
| tta tta aat ggc gtg tta cgt gaa gga aat cct tat gct gca gta gga<br>Leu Leu Asn Gly Val Leu Arg Glu Gly Asn Pro Tyr Ala Ala Val Gly<br>                  260                  265                  270 | 1237 |
| aac agc tat caa att aca cga aaa gat tat ttt caa ggt att ctt aat<br>Asn Ser Tyr Gln Ile Thr Arg Lys Asp Tyr Phe Gln Gly Ile Leu Asn<br>                  275                  280                  285 | 1285 |
| caa gac att aca gct aat ttt tgg gat act aat gct gaa tat aga ttt<br>Gln Asp Ile Thr Ala Asn Phe Trp Asp Thr Asn Ala Glu Tyr Arg Phe<br>290                  295                  300 | 1333 |
| aat ata ggg agt gac cac aat gga aga gtg gca aca atc aaa agt aca<br>Asn Ile Gly Ser Asp His Asn Gly Arg Val Ala Thr Ile Lys Ser Thr<br>305                  310                  315                  320 | 1381 |
| tta cct aaa aaa gct att cag cct gaa cga ata gtg ggt ctt tat gat<br>Leu Pro Lys Lys Ala Ile Gln Pro Glu Arg Ile Val Gly Leu Tyr Asp<br>                  325                  330                  335 | 1429 |
| aat agc caa ctt cat gat gct aga gat aaa aat ggc gat gaa tct ccc<br>Asn Ser Gln Leu His Asp Ala Arg Asp Lys Asn Gly Asp Glu Ser Pro<br>                  340                  345                  350 | 1477 |
| tct tat aaa ggt cct aat cca tgg tcg cca gca tta cat cat ggg aaa<br>Ser Tyr Lys Gly Pro Asn Pro Trp Ser Pro Ala Leu His His Gly Lys<br>                  355                  360                  365 | 1525 |
| agt att tac ttt ggc gat caa gga aca gga act tta aca att gaa aat<br>Ser Ile Tyr Phe Gly Asp Gln Gly Thr Gly Thr Leu Thr Ile Glu Asn<br>370                  375                  380 | 1573 |
| aat ata aat caa ggt gca ggt gga ttg tat ttt gaa ggt aat ttt gtt<br>Asn Ile Asn Gln Gly Ala Gly Gly Leu Tyr Phe Glu Gly Asn Phe Val<br>385                  390                  395                  400 | 1621 |
| gta aaa ggc aat caa aat aat ata act tgg caa ggt gca ggt gtt tct<br>Val Lys Gly Asn Gln Asn Asn Ile Thr Trp Gln Gly Ala Gly Val Ser<br>                  405                  410                  415 | 1669 |
| gtt gga gaa gaa agt act gtt gaa tgg cag gtg cat aat cca gaa ggc<br>Val Gly Glu Glu Ser Thr Val Glu Trp Gln Val His Asn Pro Glu Gly<br>                  420                  425                  430 | 1717 |

```
gat cgc tta tcc aaa att ggg ctg gga acc tta ctt gtt aat ggt aaa    1765
Asp Arg Leu Ser Lys Ile Gly Leu Gly Thr Leu Leu Val Asn Gly Lys
        435                 440                 445 ggg aaa aac tta gga agc ctg agt gtc ggt aac ggt ttg gtt gtg tta    1813
Gly Lys Asn Leu Gly Ser Leu Ser Val Gly Asn Gly Leu Val Val Leu
    450                 455                 460 gat caa caa gca gat gaa tca ggt caa aaa caa gcc ttt aaa gaa gtt    1861
Asp Gln Gln Ala Asp Glu Ser Gly Gln Lys Gln Ala Phe Lys Glu Val
465                 470                 475                 480 ggc att gta agt ggt aga gct acc gtt caa cta aat agt gca gat caa    1909
Gly Ile Val Ser Gly Arg Ala Thr Val Gln Leu Asn Ser Ala Asp Gln
            485                 490                 495 gtt gat cct aac aat att tat ttc ggc ttt cgt ggt ggt cgc tta gat    1957
Val Asp Pro Asn Asn Ile Tyr Phe Gly Phe Arg Gly Gly Arg Leu Asp
        500                 505                 510 ctt aat ggg cat tca tta acc ttt gaa cgt atc caa aat acg gat gaa    2005
Leu Asn Gly His Ser Leu Thr Phe Glu Arg Ile Gln Asn Thr Asp Glu
    515                 520                 525 ggc gcg atg att gtg aac cac aac gct tct caa acc gca aat att acg    2053
Gly Ala Met Ile Val Asn His Asn Ala Ser Gln Thr Ala Asn Ile Thr
530                 535                 540 att aca ggc aac gca act att aat tca gat agc aaa caa ctt act aat    2101
Ile Thr Gly Asn Ala Thr Ile Asn Ser Asp Ser Lys Gln Leu Thr Asn
545                 550                 555                 560 aaa aaa gat att gca ttt aac ggc tgg ttt ggt gag caa gat aaa gct    2149
Lys Lys Asp Ile Ala Phe Asn Gly Trp Phe Gly Glu Gln Asp Lys Ala
            565                 570                 575 aaa aca aat ggt cgt tta aat gtg aat tat caa cca gtt aat gca gaa    2197
Lys Thr Asn Gly Arg Leu Asn Val Asn Tyr Gln Pro Val Asn Ala Glu
        580                 585                 590 aat cat ttg ttg ctt tct ggg gga aca aat tta aac ggc aat atc acg    2245
Asn His Leu Leu Leu Ser Gly Gly Thr Asn Leu Asn Gly Asn Ile Thr
    595                 600                 605 caa aat ggt ggt acg tta gtt ttt agt ggt cgt cca acg cct cat gct    2293
Gln Asn Gly Gly Thr Leu Val Phe Ser Gly Arg Pro Thr Pro His Ala
610                 615                 620 tac aat cat tta aga aga gac ttg tct aac atg gaa ggt atc cca caa    2341
Tyr Asn His Leu Arg Arg Asp Leu Ser Asn Met Glu Gly Ile Pro Gln
625                 630                 635                 640 ggc gaa att gtg tgg gat cac gat tgg atc aac cgc aca ttt aaa gct    2389
Gly Glu Ile Val Trp Asp His Asp Trp Ile Asn Arg Thr Phe Lys Ala
            645                 650                 655 gaa aac ttc caa att aaa ggc gga agt gcg gtg gtt tct cgc aat gtt    2437
Glu Asn Phe Gln Ile Lys Gly Gly Ser Ala Val Val Ser Arg Asn Val
        660                 665                 670 tct tca att gag gga aat tgg aca gtc agc aat aat gca aat gcc aca    2485
Ser Ser Ile Glu Gly Asn Trp Thr Val Ser Asn Asn Ala Asn Ala Thr
    675                 680                 685 ttt ggt gtt gtg cca aat cag caa aat acc att tgc acg cgt tca gat    2533
Phe Gly Val Val Pro Asn Gln Gln Asn Thr Ile Cys Thr Arg Ser Asp
690                 695                 700 tgg aca gga tta acg act tgt aaa aca gtt gat tta acc gat aaa aaa    2581
Trp Thr Gly Leu Thr Thr Cys Lys Thr Val Asp Leu Thr Asp Lys Lys
705                 710                 715                 720 gtt att aat tcc ata ccg aca aca caa att aat ggt tct att aat tta    2629
Val Ile Asn Ser Ile Pro Thr Thr Gln Ile Asn Gly Ser Ile Asn Leu
            725                 730                 735 act gat aat gca aca gtg aat att cat ggt tta gca aaa ctt aat ggt    2677
Thr Asp Asn Ala Thr Val Asn Ile His Gly Leu Ala Lys Leu Asn Gly
```

-continued

|  |  |
|---|---|
| aat gtc act tta ata gat cac agc caa ttt aca ttg agc aac aat gcc<br>Asn Val Thr Leu Ile Asp His Ser Gln Phe Thr Leu Ser Asn Asn Ala<br>755                760              765 | 2725 |
| acc caa aca ggc aat atc aaa ctt tca aat cac gca aat gca acg gtg<br>Thr Gln Thr Gly Asn Ile Lys Leu Ser Asn His Ala Asn Ala Thr Val<br>    770              775              780 | 2773 |
| gac aat gca aat ttg aac ggt aat gtg aat tta atg gat tct gct caa<br>Asp Asn Ala Asn Leu Asn Gly Asn Val Asn Leu Met Asp Ser Ala Gln<br>785                790              795              800 | 2821 |
| ttt tct tta aaa aac agc cat ttt tcg cac caa atc caa ggt ggg gaa<br>Phe Ser Leu Lys Asn Ser His Phe Ser His Gln Ile Gln Gly Gly Glu<br>            805              810              815 | 2869 |
| gac aca aca gtg atg ttg gaa aat gcg act tgg aca atg cct agc gat<br>Asp Thr Thr Val Met Leu Glu Asn Ala Thr Trp Thr Met Pro Ser Asp<br>820                825              830 | 2917 |
| acc aca ttg cag aat tta acg cta aat aat agt act gtt acg tta aat<br>Thr Thr Leu Gln Asn Leu Thr Leu Asn Asn Ser Thr Val Thr Leu Asn<br>    835              840              845 | 2965 |
| tca gct tat tca gct atc tca aat aat gcg cca cgc cgt cgc cgc cgt<br>Ser Ala Tyr Ser Ala Ile Ser Asn Asn Ala Pro Arg Arg Arg Arg Arg<br>850                855              860 | 3013 |
| tca tta gag acg gaa aca acg cca aca tcg gca gaa cat cgt ttc aac<br>Ser Leu Glu Thr Glu Thr Thr Pro Thr Ser Ala Glu His Arg Phe Asn<br>865                870              875              880 | 3061 |
| aca ttg aca gta aat ggt aaa ttg agc ggg caa ggc aca ttc caa ttt<br>Thr Leu Thr Val Asn Gly Lys Leu Ser Gly Gln Gly Thr Phe Gln Phe<br>            885              890              895 | 3109 |
| act tca tct tta ttt ggc tat aaa agc gat aaa tta aaa tta tcc aat<br>Thr Ser Ser Leu Phe Gly Tyr Lys Ser Asp Lys Leu Lys Leu Ser Asn<br>            900              905              910 | 3157 |
| gac gct gag ggc gat tac aca tta tct gtt cgc aac aca ggc aaa gaa<br>Asp Ala Glu Gly Asp Tyr Thr Leu Ser Val Arg Asn Thr Gly Lys Glu<br>915                920              925 | 3205 |
| ccc gtg acc ttt ggg caa tta act ttg gtt gaa agc aaa gat aat aaa<br>Pro Val Thr Phe Gly Gln Leu Thr Leu Val Glu Ser Lys Asp Asn Lys<br>930                935              940 | 3253 |
| ccg tta tca gac aaa ctc aca ttc acg tta gaa aat gac cac gtt gat<br>Pro Leu Ser Asp Lys Leu Thr Phe Thr Leu Glu Asn Asp His Val Asp<br>945                950              955              960 | 3301 |
| gca ggt gca tta cgt tat aaa tta gtg aag aat gat ggc gaa ttc cgc<br>Ala Gly Ala Leu Arg Tyr Lys Leu Val Lys Asn Asp Gly Glu Phe Arg<br>            965              970              975 | 3349 |
| tta cat aac cca ata aaa gag cag gaa ttg cgc tct gat tta gta aga<br>Leu His Asn Pro Ile Lys Glu Gln Glu Leu Arg Ser Asp Leu Val Arg<br>            980              985              990 | 3397 |
| gca gag caa gca gaa cga aca tta gaa gcc aaa caa gtt gaa cag act<br>Ala Glu Gln Ala Glu Arg Thr Leu Glu Ala Lys Gln Val Glu Gln Thr<br>995                1000             1005 | 3445 |
| gct aaa aca caa aca agt aag gca aga gtg cgg tca aga aga gcg<br>Ala Lys Thr Gln Thr Ser Lys Ala Arg Val Arg Ser Arg Arg Ala<br>   1010              1015              1020 | 3490 |
| gtg ttt tct gat ccc ctg cct gct caa agc ctg tta aaa gca tta<br>Val Phe Ser Asp Pro Leu Pro Ala Gln Ser Leu Leu Lys Ala Leu<br>1025              1030              1035 | 3535 |
| gaa gcc aaa caa gct ctg act act gaa aca caa aca agt aag gca<br>Glu Ala Lys Gln Ala Leu Thr Thr Glu Thr Gln Thr Ser Lys Ala<br>1040              1045              1050 | 3580 |
| aaa aaa gtg cgg tca aaa aga gct gcg aga gag ttt tct gat acc | 3625 |

-continued

| | | | | | | | | | | | |
|---|---|---|---|---|---|---|---|---|---|---|---|
| Lys | Lys | Val | Arg | Ser | Lys | Arg | Ala | Ala | Arg | Glu | Phe | Ser | Asp | Thr |
| | 1055 | | | | 1060 | | | | 1065 | | |

| ctg | cct | gat | caa | ata | tta | caa | gcc | gca | ctt | gag | gtt | att | gat | gcc | 3670 |
| Leu | Pro | Asp | Gln | Ile | Leu | Gln | Ala | Ala | Leu | Glu | Val | Ile | Asp | Ala | |
| 1070 | | | | | 1075 | | | | | 1080 | | | | | |

| caa | cag | caa | gtg | aaa | aaa | gaa | cct | caa | act | caa | gag | gaa | gaa | gag | 3715 |
| Gln | Gln | Gln | Val | Lys | Lys | Glu | Pro | Gln | Thr | Gln | Glu | Glu | Glu | Glu | |
| 1085 | | | | | 1090 | | | | | 1095 | | | | | |

| aaa | aga | caa | cgc | aaa | caa | aaa | gaa | ttg | atc | agc | cgt | tac | tca | aat | 3760 |
| Lys | Arg | Gln | Arg | Lys | Gln | Lys | Glu | Leu | Ile | Ser | Arg | Tyr | Ser | Asn | |
| 1100 | | | | | 1105 | | | | | 1110 | | | | | |

| agt | gcg | tta | tcg | gag | ttg | tct | gcg | aca | gta | aat | agt | atg | ctt | tcc | 3805 |
| Ser | Ala | Leu | Ser | Glu | Leu | Ser | Ala | Thr | Val | Asn | Ser | Met | Leu | Ser | |
| 1115 | | | | | 1120 | | | | | 1125 | | | | | |

| gtt | caa | gat | gaa | ttg | gat | cgt | ctt | ttt | gta | gat | caa | gca | caa | tct | 3850 |
| Val | Gln | Asp | Glu | Leu | Asp | Arg | Leu | Phe | Val | Asp | Gln | Ala | Gln | Ser | |
| 1130 | | | | | 1135 | | | | | 1140 | | | | | |

| gcc | gtg | tgg | aca | aat | atc | gca | cag | gat | aaa | aga | cgc | tat | gat | tct | 3895 |
| Ala | Val | Trp | Thr | Asn | Ile | Ala | Gln | Asp | Lys | Arg | Arg | Tyr | Asp | Ser | |
| 1145 | | | | | 1150 | | | | | 1155 | | | | | |

| gat | gcg | ttc | cgt | gct | tat | cag | cag | aaa | acg | aac | ttg | cgt | caa | att | 3940 |
| Asp | Ala | Phe | Arg | Ala | Tyr | Gln | Gln | Lys | Thr | Asn | Leu | Arg | Gln | Ile | |
| 1160 | | | | | 1165 | | | | | 1170 | | | | | |

| ggg | gtg | caa | aaa | gcc | tta | gat | aat | gga | cga | att | ggg | gcg | gtt | ttc | 3985 |
| Gly | Val | Gln | Lys | Ala | Leu | Asp | Asn | Gly | Arg | Ile | Gly | Ala | Val | Phe | |
| 1175 | | | | | 1180 | | | | | 1185 | | | | | |

| tcg | cat | agc | cgt | tca | gat | aat | acc | ttt | gac | gaa | cag | gtt | aaa | aat | 4030 |
| Ser | His | Ser | Arg | Ser | Asp | Asn | Thr | Phe | Asp | Glu | Gln | Val | Lys | Asn | |
| 1190 | | | | | 1195 | | | | | 1200 | | | | | |

| cac | gcg | aca | tta | gcg | atg | atg | tcg | ggt | ttt | gcc | caa | tat | caa | tgg | 4075 |
| His | Ala | Thr | Leu | Ala | Met | Met | Ser | Gly | Phe | Ala | Gln | Tyr | Gln | Trp | |
| 1205 | | | | | 1210 | | | | | 1215 | | | | | |

| ggc | gat | tta | caa | ttt | ggt | gta | aac | gtg | ggt | gcg | gga | att | agt | gcg | 4120 |
| Gly | Asp | Leu | Gln | Phe | Gly | Val | Asn | Val | Gly | Ala | Gly | Ile | Ser | Ala | |
| 1220 | | | | | 1225 | | | | | 1230 | | | | | |

| agt | aaa | atg | gct | gaa | gaa | caa | agc | cga | aaa | att | cat | cga | aaa | gcg | 4165 |
| Ser | Lys | Met | Ala | Glu | Glu | Gln | Ser | Arg | Lys | Ile | His | Arg | Lys | Ala | |
| 1235 | | | | | 1240 | | | | | 1245 | | | | | |

| ata | aat | tat | ggt | gtg | aat | gca | agt | tat | cag | ttc | cgt | tta | ggg | caa | 4210 |
| Ile | Asn | Tyr | Gly | Val | Asn | Ala | Ser | Tyr | Gln | Phe | Arg | Leu | Gly | Gln | |
| 1250 | | | | | 1255 | | | | | 1260 | | | | | |

| ttg | ggt | att | cag | cct | tat | ttg | ggt | gtt | aat | cga | tat | ttt | att | gaa | 4255 |
| Leu | Gly | Ile | Gln | Pro | Tyr | Leu | Gly | Val | Asn | Arg | Tyr | Phe | Ile | Glu | |
| 1265 | | | | | 1270 | | | | | 1275 | | | | | |

| cgt | gaa | aat | tat | caa | tct | gaa | gaa | gtg | aaa | gtg | caa | aca | ccg | agc | 4300 |
| Arg | Glu | Asn | Tyr | Gln | Ser | Glu | Glu | Val | Lys | Val | Gln | Thr | Pro | Ser | |
| 1280 | | | | | 1285 | | | | | 1290 | | | | | |

| ctt | gta | ttt | aat | cgc | tat | aat | gct | ggc | att | cga | gtt | gat | tat | aca | 4345 |
| Leu | Val | Phe | Asn | Arg | Tyr | Asn | Ala | Gly | Ile | Arg | Val | Asp | Tyr | Thr | |
| 1295 | | | | | 1300 | | | | | 1305 | | | | | |

| ttt | acc | ccg | aca | gat | aat | atc | agc | att | aag | cct | tat | ttc | ttc | gtc | 4390 |
| Phe | Thr | Pro | Thr | Asp | Asn | Ile | Ser | Ile | Lys | Pro | Tyr | Phe | Phe | Val | |
| 1310 | | | | | 1315 | | | | | 1320 | | | | | |

| aat | tat | gtt | gat | gtt | tca | aac | gct | aac | gta | caa | acc | act | gta | aat | 4435 |
| Asn | Tyr | Val | Asp | Val | Ser | Asn | Ala | Asn | Val | Gln | Thr | Thr | Val | Asn | |
| 1325 | | | | | 1330 | | | | | 1335 | | | | | |

| cgc | acg | atg | ttg | caa | caa | tca | ttt | ggg | cgt | tat | tgg | caa | aaa | gaa | 4480 |
| Arg | Thr | Met | Leu | Gln | Gln | Ser | Phe | Gly | Arg | Tyr | Trp | Gln | Lys | Glu | |
| 1340 | | | | | 1345 | | | | | 1350 | | | | | |

-continued

```
gtg gga tta aag gca gaa att tta cat ttc caa ctt tcc gct ttt    4525
Val Gly Leu Lys Ala Glu Ile Leu His Phe Gln Leu Ser Ala Phe
1355             1360             1365 atc tca aaa tct caa ggt tca caa ctc ggc aaa cag caa aat gtg    4570
Ile Ser Lys Ser Gln Gly Ser Gln Leu Gly Lys Gln Gln Asn Val
1370             1375             1380 ggc gtg aaa ttg ggg tat cgt tgg taa aaatcaac                   4605
Gly Val Lys Leu Gly Tyr Arg Trp
1385             1390
```

<210> SEQ ID NO 11
<211> LENGTH: 1391
<212> TYPE: PRT
<213> ORGANISM: Haemophilus influenzae

<400> SEQUENCE: 11

```
Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
                20                  25                  30

Asp Tyr Gln Tyr Tyr Arg Asp Phe Ala Glu Asn Lys Gly Lys Phe Thr
            35                  40                  45

Val Gly Ala Gln Asp Ile Asp Ile Tyr Asn Lys Lys Gly Glu Met Ile
        50                  55                  60

Gly Thr Met Met Lys Gly Val Pro Met Pro Asp Leu Ser Ser Met Val
65                  70                  75                  80

Arg Gly Gly Tyr Ser Thr Leu Ile Ser Glu Gln His Leu Ile Ser Val
                85                  90                  95

Ala His Asn Val Gly Tyr Asp Val Val Asp Phe Gly Met Glu Gly Glu
            100                 105                 110

Asn Pro Asp Gln His Arg Phe Lys Tyr Lys Val Val Lys Arg Tyr Asn
        115                 120                 125

Tyr Lys Ser Gly Asp Arg Gln Tyr Asn Asp Tyr Gln His Pro Arg Leu
130                 135                 140

Glu Lys Phe Val Thr Glu Thr Ala Pro Ile Glu Met Val Ser Tyr Met
145                 150                 155                 160

Asp Gly Asn His Tyr Lys Asn Phe Asn Gln Tyr Pro Leu Arg Val Arg
                165                 170                 175

Val Gly Ser Gly His Gln Trp Trp Lys Asp Asn Asn Lys Thr Ile
            180                 185                 190

Gly Asp Leu Ala Tyr Gly Gly Ser Trp Leu Ile Gly Gly Asn Thr Phe
        195                 200                 205

Glu Asp Gly Pro Ala Gly Asn Gly Thr Leu Glu Leu Asn Gly Arg Val
    210                 215                 220

Gln Asn Pro Asn Lys Tyr Gly Pro Leu Pro Thr Ala Gly Ser Phe Gly
225                 230                 235                 240

Asp Ser Gly Ser Pro Met Phe Ile Tyr Asp Lys Glu Val Lys Lys Trp
                245                 250                 255

Leu Leu Asn Gly Val Leu Arg Glu Gly Asn Pro Tyr Ala Ala Val Gly
            260                 265                 270

Asn Ser Tyr Gln Ile Thr Arg Lys Asp Tyr Phe Gln Gly Ile Leu Asn
        275                 280                 285

Gln Asp Ile Thr Ala Asn Phe Trp Asp Thr Asn Ala Glu Tyr Arg Phe
    290                 295                 300

Asn Ile Gly Ser Asp His Asn Gly Arg Val Ala Thr Ile Lys Ser Thr
305                 310                 315                 320
```

```
Leu Pro Lys Lys Ala Ile Gln Pro Glu Arg Ile Val Gly Leu Tyr Asp
            325                 330                 335

Asn Ser Gln Leu His Asp Ala Arg Asp Lys Asn Gly Asp Glu Ser Pro
            340                 345                 350

Ser Tyr Lys Gly Pro Asn Pro Trp Ser Pro Ala Leu His His Gly Lys
            355                 360                 365

Ser Ile Tyr Phe Gly Asp Gln Gly Thr Gly Thr Leu Thr Ile Glu Asn
            370                 375                 380

Asn Ile Asn Gln Gly Ala Gly Gly Leu Tyr Phe Glu Gly Asn Phe Val
385                 390                 395                 400

Val Lys Gly Asn Gln Asn Asn Ile Thr Trp Gln Gly Ala Gly Val Ser
            405                 410                 415

Val Gly Glu Glu Ser Thr Val Glu Trp Gln Val His Asn Pro Glu Gly
            420                 425                 430

Asp Arg Leu Ser Lys Ile Gly Leu Gly Thr Leu Leu Val Asn Gly Lys
            435                 440                 445

Gly Lys Asn Leu Gly Ser Leu Ser Val Gly Asn Gly Leu Val Val Leu
            450                 455                 460

Asp Gln Gln Ala Asp Glu Ser Gly Gln Lys Gln Ala Phe Lys Glu Val
465                 470                 475                 480

Gly Ile Val Ser Gly Arg Ala Thr Val Gln Leu Asn Ser Ala Asp Gln
            485                 490                 495

Val Asp Pro Asn Asn Ile Tyr Phe Gly Phe Arg Gly Gly Arg Leu Asp
            500                 505                 510

Leu Asn Gly His Ser Leu Thr Phe Glu Arg Ile Gln Asn Thr Asp Glu
            515                 520                 525

Gly Ala Met Ile Val Asn His Asn Ala Ser Gln Thr Ala Asn Ile Thr
            530                 535                 540

Ile Thr Gly Asn Ala Thr Ile Asn Ser Asp Ser Lys Gln Leu Thr Asn
545                 550                 555                 560

Lys Lys Asp Ile Ala Phe Asn Gly Trp Phe Gly Glu Gln Asp Lys Ala
            565                 570                 575

Lys Thr Asn Gly Arg Leu Asn Val Asn Tyr Gln Pro Val Asn Ala Glu
            580                 585                 590

Asn His Leu Leu Leu Ser Gly Gly Thr Asn Leu Asn Gly Asn Ile Thr
            595                 600                 605

Gln Asn Gly Gly Thr Leu Val Phe Ser Gly Arg Pro Thr Pro His Ala
            610                 615                 620

Tyr Asn His Leu Arg Arg Asp Leu Ser Asn Met Glu Gly Ile Pro Gln
625                 630                 635                 640

Gly Glu Ile Val Trp Asp His Asp Trp Ile Asn Arg Thr Phe Lys Ala
            645                 650                 655

Glu Asn Phe Gln Ile Lys Gly Gly Ser Ala Val Val Ser Arg Asn Val
            660                 665                 670

Ser Ser Ile Glu Gly Asn Trp Thr Val Ser Asn Ala Asn Ala Thr
            675                 680                 685

Phe Gly Val Val Pro Asn Gln Gln Asn Thr Ile Cys Thr Arg Ser Asp
            690                 695                 700

Trp Thr Gly Leu Thr Thr Cys Lys Thr Val Asp Leu Thr Asp Lys Lys
705                 710                 715                 720

Val Ile Asn Ser Ile Pro Thr Thr Gln Ile Asn Gly Ser Ile Asn Leu
            725                 730                 735
```

```
Thr Asp Asn Ala Thr Val Asn Ile His Gly Leu Ala Lys Leu Asn Gly
            740                 745                 750

Asn Val Thr Leu Ile Asp His Ser Gln Phe Thr Leu Ser Asn Asn Ala
            755                 760                 765

Thr Gln Thr Gly Asn Ile Lys Leu Ser Asn His Ala Asn Ala Thr Val
        770                 775                 780

Asp Asn Ala Asn Leu Asn Gly Asn Val Asn Leu Met Asp Ser Ala Gln
785                 790                 795                 800

Phe Ser Leu Lys Asn Ser His Phe Ser His Gln Ile Gln Gly Gly Glu
                805                 810                 815

Asp Thr Thr Val Met Leu Glu Asn Ala Thr Trp Thr Met Pro Ser Asp
            820                 825                 830

Thr Thr Leu Gln Asn Leu Thr Leu Asn Asn Ser Thr Val Thr Leu Asn
            835                 840                 845

Ser Ala Tyr Ser Ala Ile Ser Asn Asn Ala Pro Arg Arg Arg Arg Arg
850                 855                 860

Ser Leu Glu Thr Glu Thr Thr Pro Thr Ser Ala Glu His Arg Phe Asn
865                 870                 875                 880

Thr Leu Thr Val Asn Gly Lys Leu Ser Gly Gln Gly Thr Phe Gln Phe
                885                 890                 895

Thr Ser Ser Leu Phe Gly Tyr Lys Ser Asp Lys Leu Lys Leu Ser Asn
            900                 905                 910

Asp Ala Glu Gly Asp Tyr Thr Leu Ser Val Arg Asn Thr Gly Lys Glu
        915                 920                 925

Pro Val Thr Phe Gly Gln Leu Thr Leu Val Glu Ser Lys Asp Asn Lys
        930                 935                 940

Pro Leu Ser Asp Lys Leu Thr Phe Thr Leu Glu Asn Asp His Val Asp
945                 950                 955                 960

Ala Gly Ala Leu Arg Tyr Lys Leu Val Lys Asn Asp Gly Glu Phe Arg
                965                 970                 975

Leu His Asn Pro Ile Lys Glu Gln Glu Leu Arg Ser Asp Leu Val Arg
            980                 985                 990

Ala Glu Gln Ala Glu Arg Thr Leu  Glu Ala Lys Gln Val  Glu Gln Thr
            995                 1000                1005

Ala Lys  Thr Gln Thr Ser Lys  Ala Arg Val Arg  Ser  Arg Arg Ala
    1010                1015                1020

Val Phe  Ser Asp Pro Leu Pro  Ala Gln Ser Leu Leu   Lys Ala Leu
1025                1030                1035

Glu Ala  Lys Gln Ala Leu Thr   Thr Glu Thr Gln Thr   Ser Lys Ala
    1040                1045                1050

Lys Lys  Val Arg Ser Lys Arg   Ala Ala Arg Glu Phe   Ser Asp Thr
    1055                1060                1065

Leu Pro  Asp Gln Ile Leu Gln   Ala Ala Leu Glu Val   Ile Asp Ala
    1070                1075                1080

Gln Gln  Gln Val Lys Lys Glu   Pro Gln Thr Gln Glu   Glu Glu Glu
    1085                1090                1095

Lys Arg  Gln Arg Lys Gln Lys   Glu Leu Ile Ser Arg    Tyr Ser Asn
    1100                1105                1110

Ser Ala  Leu Ser Glu Leu Ser   Ala Thr Val Asn Ser   Met Leu Ser
    1115                1120                1125

Val Gln  Asp Glu Leu Asp Arg   Leu Phe Val Asp Gln   Ala Gln Ser
    1130                1135                1140

Ala Val  Trp Thr Asn Ile Ala   Gln Asp Lys Arg Arg   Tyr Asp Ser
```

-continued

```
                1145                1150                1155

Asp Ala Phe Arg Ala Tyr Gln Gln Lys Thr Asn Leu Arg Gln Ile
    1160                1165                1170

Gly Val Gln Lys Ala Leu Asp Asn Gly Arg Ile Gly Ala Val Phe
    1175                1180                1185

Ser His Ser Arg Ser Asp Asn Thr Phe Asp Glu Gln Val Lys Asn
    1190                1195                1200

His Ala Thr Leu Ala Met Met Ser Gly Phe Ala Gln Tyr Gln Trp
    1205                1210                1215

Gly Asp Leu Gln Phe Gly Val Asn Val Gly Ala Gly Ile Ser Ala
    1220                1225                1230

Ser Lys Met Ala Glu Glu Gln Ser Arg Lys Ile His Arg Lys Ala
    1235                1240                1245

Ile Asn Tyr Gly Val Asn Ala Ser Tyr Gln Phe Arg Leu Gly Gln
    1250                1255                1260

Leu Gly Ile Gln Pro Tyr Leu Gly Val Asn Arg Tyr Phe Ile Glu
    1265                1270                1275

Arg Glu Asn Tyr Gln Ser Glu Glu Val Lys Val Gln Thr Pro Ser
    1280                1285                1290

Leu Val Phe Asn Arg Tyr Asn Ala Gly Ile Arg Val Asp Tyr Thr
    1295                1300                1305

Phe Thr Pro Thr Asp Asn Ile Ser Ile Lys Pro Tyr Phe Phe Val
    1310                1315                1320

Asn Tyr Val Asp Val Ser Asn Ala Asn Val Gln Thr Thr Val Asn
    1325                1330                1335

Arg Thr Met Leu Gln Gln Ser Phe Gly Arg Tyr Trp Gln Lys Glu
    1340                1345                1350

Val Gly Leu Lys Ala Glu Ile Leu His Phe Gln Leu Ser Ala Phe
    1355                1360                1365

Ile Ser Lys Ser Gln Gly Ser Gln Leu Gly Lys Gln Gln Asn Val
    1370                1375                1380

Gly Val Lys Leu Gly Tyr Arg Trp
    1385                1390

<210> SEQ ID NO 12
<211> LENGTH: 5245
<212> TYPE: DNA
<213> ORGANISM: Haemophilus influenzae
<220> FEATURE:
<221> NAME/KEY: CDS
<222> LOCATION: (430)..(4740)
<223> OTHER INFORMATION:

<400> SEQUENCE: 12
ggaggcagtg gtggcggaca aattattgcg acgggtacgc cagaacaagt tgccaaagta      60
gaaagttccc acaccgcccg cttccttaaa ccgattttag aaaaacctta gaaaaatga     120 ccgcactttc agagaaaact cacataaagt gcggttattt tattagtgat attgttttaa    180
ttttagttat ctgtataaat tacatataat attaatccat cgcaagataa gattacccac    240
taagtattaa gcaaaaacct agaaattttg gcttaattac tatatagttt tactgcttta    300
ttttcttttg tgcctttag ttcgtttttt tagctgaaat cccttagaaa atcaccgcac     360
ttttattgtt caatagtcgt ttaaccacgt atttttaat acgaaaaatt acttaattaa     420
```

-continued

```
ataaacatt atg aaa aaa act gta ttt cgt ctg aac ttt tta acc gct tgc      471
          Met Lys Lys Thr Val Phe Arg Leu Asn Phe Leu Thr Ala Cys
           1               5                  10 att tca tta ggg ata gta tcg caa gcg tgg gca ggt cac act tat ttt       519
Ile Ser Leu Gly Ile Val Ser Gln Ala Trp Ala Gly His Thr Tyr Phe
15              20                  25                  30 ggg att gac tac caa tat tat cgt gat ttt gct gag aat aaa ggg aag       567
Gly Ile Asp Tyr Gln Tyr Tyr Arg Asp Phe Ala Glu Asn Lys Gly Lys
                35                  40                  45 ttt tca gtt ggg gct aaa aat att gag gtt tat aac aaa gag ggg act       615
Phe Ser Val Gly Ala Lys Asn Ile Glu Val Tyr Asn Lys Glu Gly Thr
            50                  55                  60 tta gtt ggc aca tca atg aca aaa gcc ccg atg att gat ttt tct gtg       663
Leu Val Gly Thr Ser Met Thr Lys Ala Pro Met Ile Asp Phe Ser Val
        65                  70                  75 gtg tcg cga aat ggg gtg gcg gca tta gta ggc gat cag tat att gtg       711
Val Ser Arg Asn Gly Val Ala Ala Leu Val Gly Asp Gln Tyr Ile Val
    80                  85                  90 agt gtg gca cat aac ggt gga tat aat agc gtt gat ttt gga gca gaa       759
Ser Val Ala His Asn Gly Gly Tyr Asn Ser Val Asp Phe Gly Ala Glu
95                  100                 105                 110 ggt cca aat ccc gat cag cat cgt ttt act tat caa att gta aaa aga       807
Gly Pro Asn Pro Asp Gln His Arg Phe Thr Tyr Gln Ile Val Lys Arg
                115                 120                 125 aat aat tat aag cca ggc aaa gat aac cct tat cat ggt gac tat cac       855
Asn Asn Tyr Lys Pro Gly Lys Asp Asn Pro Tyr His Gly Asp Tyr His
            130                 135                 140 atg cct cgt ttg cac aaa ttt gtc act gac gct gaa cca gca aag atg       903
Met Pro Arg Leu His Lys Phe Val Thr Asp Ala Glu Pro Ala Lys Met
        145                 150                 155 aca gac aat atg aat gga aag aac tac gct gat tta agt aaa tat cct       951
Thr Asp Asn Met Asn Gly Lys Asn Tyr Ala Asp Leu Ser Lys Tyr Pro
    160                 165                 170 gat cgt gtg cgt att ggt aca ggt gaa caa tgg tgg agg act gat gaa       999
Asp Arg Val Arg Ile Gly Thr Gly Glu Gln Trp Trp Arg Thr Asp Glu
175                 180                 185                 190 gaa caa aag caa gga agt aag agt tca tgg ctt gct gat gct tat ctg      1047
Glu Gln Lys Gln Gly Ser Lys Ser Ser Trp Leu Ala Asp Ala Tyr Leu
                195                 200                 205 tgg aga ata gca ggt aac aca cat tca caa agt gga gcg ggc aac ggc      1095
Trp Arg Ile Ala Gly Asn Thr His Ser Gln Ser Gly Ala Gly Asn Gly
            210                 215                 220 acg gta aac tta agt gga gat atc aca aaa cca aat aac tat gga cct      1143
Thr Val Asn Leu Ser Gly Asp Ile Thr Lys Pro Asn Asn Tyr Gly Pro
        225                 230                 235 ctt cct acg ggt gtt tcg ttt gga gat agt ggt tct cca atg ttt att      1191
Leu Pro Thr Gly Val Ser Phe Gly Asp Ser Gly Ser Pro Met Phe Ile
    240                 245                 250 tat gat gca ata aaa caa aaa tgg ctt att aat ggc gta ttg caa act      1239
Tyr Asp Ala Ile Lys Gln Lys Trp Leu Ile Asn Gly Val Leu Gln Thr
255                 260                 265                 270 ggt aac cct ttc tcg gga gct gga aat gga ttc caa tta att aga aaa      1287
Gly Asn Pro Phe Ser Gly Ala Gly Asn Gly Phe Gln Leu Ile Arg Lys
                275                 280                 285 aat tgg ttt tat gat aat gtc ttt gta gaa gat ttg cct ata aca ttt      1335
Asn Trp Phe Tyr Asp Asn Val Phe Val Glu Asp Leu Pro Ile Thr Phe
            290                 295                 300 tta gag cca aga agt aac ggt cat tat tca ttt act tca aat aat aat      1383
Leu Glu Pro Arg Ser Asn Gly His Tyr Ser Phe Thr Ser Asn Asn Asn
        305                 310                 315
```

-continued

```
gga act ggt acg gtt act caa acg aat gaa aaa gtg agt atg cct caa         1431
Gly Thr Gly Thr Val Thr Gln Thr Asn Glu Lys Val Ser Met Pro Gln
320                 325                 330 ttt aaa gtc aga acg gtt cag tta ttt aat gaa gca tta aaa gaa aaa         1479
Phe Lys Val Arg Thr Val Gln Leu Phe Asn Glu Ala Leu Lys Glu Lys
335                 340                 345                 350 gat aaa gaa cct gtt tat gct gca ggt ggt gta aat gct tat aaa cca         1527
Asp Lys Glu Pro Val Tyr Ala Ala Gly Gly Val Asn Ala Tyr Lys Pro
        355                 360                 365 aga cta aat aat ggt aaa aat att tac ttt ggc gat cga gga aca gga         1575
Arg Leu Asn Asn Gly Lys Asn Ile Tyr Phe Gly Asp Arg Gly Thr Gly
370                 375                 380 act tta aca att gaa aat aat ata aat caa ggt gct ggt ggt ttg tat         1623
Thr Leu Thr Ile Glu Asn Asn Ile Asn Gln Gly Ala Gly Gly Leu Tyr
        385                 390                 395 ttt gag ggt aac ttt acg gta tct tca gaa aat aat gca act tgg caa         1671
Phe Glu Gly Asn Phe Thr Val Ser Ser Glu Asn Asn Ala Thr Trp Gln
400                 405                 410 ggt gct gga gtg cat gta ggt gaa gac agt act gtt act tgg aaa gta         1719
Gly Ala Gly Val His Val Gly Glu Asp Ser Thr Val Thr Trp Lys Val
415                 420                 425                 430 aac ggc gtg gaa cat gat cgc ctt tct aaa att ggt aaa gga acg ttg         1767
Asn Gly Val Glu His Asp Arg Leu Ser Lys Ile Gly Lys Gly Thr Leu
        435                 440                 445 cat att caa gca aaa ggt gaa aac tta ggc tca att agc gta ggt gac         1815
His Ile Gln Ala Lys Gly Glu Asn Leu Gly Ser Ile Ser Val Gly Asp
        450                 455                 460 ggc aaa gtc att tta gat caa caa gcc gat gag aac aac caa aaa caa         1863
Gly Lys Val Ile Leu Asp Gln Gln Ala Asp Glu Asn Asn Gln Lys Gln
465                 470                 475 gcc ttt aaa gaa gtt ggc att gta agt ggt aga gct acc gtt caa cta         1911
Ala Phe Lys Glu Val Gly Ile Val Ser Gly Arg Ala Thr Val Gln Leu
480                 485                 490 aat agt gca gat caa gtt gat cct aac aat att tat ttc gga ttt cgt         1959
Asn Ser Ala Asp Gln Val Asp Pro Asn Asn Ile Tyr Phe Gly Phe Arg
495                 500                 505                 510 ggt ggt cgc tta gat ctt aac gga cat tca tta acc ttt aaa cgt atc         2007
Gly Gly Arg Leu Asp Leu Asn Gly His Ser Leu Thr Phe Lys Arg Ile
        515                 520                 525 caa aat acg gac gag ggc gcg atg att gtg aac cat aat aca act caa         2055
Gln Asn Thr Asp Glu Gly Ala Met Ile Val Asn His Asn Thr Thr Gln
        530                 535                 540 gtc gct aat att act att act ggg aac gaa agt att act gct cca tct         2103
Val Ala Asn Ile Thr Ile Thr Gly Asn Glu Ser Ile Thr Ala Pro Ser
        545                 550                 555 aat aaa aat aat att aat aaa ctt gat tac agc aaa gaa att gct tac         2151
Asn Lys Asn Asn Ile Asn Lys Leu Asp Tyr Ser Lys Glu Ile Ala Tyr
560                 565                 570 aac ggt tgg ttt ggc gaa aca gat gaa aat aaa cac aat gga aga tta         2199
Asn Gly Trp Phe Gly Glu Thr Asp Glu Asn Lys His Asn Gly Arg Leu
575                 580                 585                 590 aac ctt att tat aaa cca acc aca gaa gat cgt act ttg cta ctt tca         2247
Asn Leu Ile Tyr Lys Pro Thr Thr Glu Asp Arg Thr Leu Leu Leu Ser
        595                 600                 605 ggt gga aca aat tta aaa ggc aat att act cag gaa ggc ggc act tta         2295
Gly Gly Thr Asn Leu Lys Gly Asn Ile Thr Gln Glu Gly Gly Thr Leu
        610                 615                 620 gtg ttt agt ggt cgc cca act cca cac gct tac aat cat tta aat cgc         2343
Val Phe Ser Gly Arg Pro Thr Pro His Ala Tyr Asn His Leu Asn Arg
```

```
                      -continued
         625              630              635
cca aac gag ctt ggg cga cct caa ggc gaa gtg gtt att gat gac gat    2391
Pro Asn Glu Leu Gly Arg Pro Gln Gly Glu Val Val Ile Asp Asp Asp
        640              645              650 tgg atc acc cgc aca ttt aaa gct gaa aac ttc caa att aaa ggc gga    2439
Trp Ile Thr Arg Thr Phe Lys Ala Glu Asn Phe Gln Ile Lys Gly Gly
655              660              665              670 agt gcg gtg gtt tct cgc aat gtt tct tca att gag gga aat tgg aca    2487
Ser Ala Val Val Ser Arg Asn Val Ser Ser Ile Glu Gly Asn Trp Thr
                675              680              685 gtc agc aat aat gca aat gcc gca ttt ggt gtt gtg cca aat cag caa    2535
Val Ser Asn Asn Ala Asn Ala Ala Phe Gly Val Val Pro Asn Gln Gln
            690              695              700 aat acc att tgc acg cgt tca gat tgg aca gga tta acg act tgt aaa    2583
Asn Thr Ile Cys Thr Arg Ser Asp Trp Thr Gly Leu Thr Thr Cys Lys
        705              710              715 act gtg gat tta acc gat aca aaa gtt att aat tcc ata ccg aca aca    2631
Thr Val Asp Leu Thr Asp Thr Lys Val Ile Asn Ser Ile Pro Thr Thr
720              725              730 caa att aat ggc tct att aat tta act gat aat gca aca gtg aat att    2679
Gln Ile Asn Gly Ser Ile Asn Leu Thr Asp Asn Ala Thr Val Asn Ile
735              740              745              750 cat ggt tta gca aaa ctt aat ggt aat gtc act tta ata aat cat agc    2727
His Gly Leu Ala Lys Leu Asn Gly Asn Val Thr Leu Ile Asn His Ser
                755              760              765 caa ttt aca ttg agc aac aat gcc acc caa aca ggc aat atc caa ctt    2775
Gln Phe Thr Leu Ser Asn Asn Ala Thr Gln Thr Gly Asn Ile Gln Leu
            770              775              780 tca aat cac gca aat gca acg gtg gac aat gca aat ttg aac ggt aat    2823
Ser Asn His Ala Asn Ala Thr Val Asp Asn Ala Asn Leu Asn Gly Asn
        785              790              795 gtg cat tta acg gat tct gct caa ttt tct tta aaa aac agc cat ttt    2871
Val His Leu Thr Asp Ser Ala Gln Phe Ser Leu Lys Asn Ser His Phe
800              805              810 tcg cac caa att cag ggc gac aaa gac aca aca gtg acg ttg gaa aat    2919
Ser His Gln Ile Gln Gly Asp Lys Asp Thr Thr Val Thr Leu Glu Asn
815              820              825              830 gcg act tgg aca atg cct agc gat gcc aca ttg cag aat tta acg cta    2967
Ala Thr Trp Thr Met Pro Ser Asp Ala Thr Leu Gln Asn Leu Thr Leu
                835              840              845 aat aat agt act gtt acg tta aat tca gct tat tca gct agc tca aat    3015
Asn Asn Ser Thr Val Thr Leu Asn Ser Ala Tyr Ser Ala Ser Ser Asn
            850              855              860 aat gcg cca cgt cac cgc cgt tca tta gag acg gaa aca acg cca aca    3063
Asn Ala Pro Arg His Arg Arg Ser Leu Glu Thr Glu Thr Thr Pro Thr
        865              870              875 tcg gca gaa cat cgt ttc aac aca ttg aca gta aat ggt aaa ttg agc    3111
Ser Ala Glu His Arg Phe Asn Thr Leu Thr Val Asn Gly Lys Leu Ser
880              885              890 ggg caa ggc aca ttc caa ttt act tca tct tta ttt ggc tat aaa agc    3159
Gly Gln Gly Thr Phe Gln Phe Thr Ser Ser Leu Phe Gly Tyr Lys Ser
895              900              905              910 gat aaa tta aaa tta tcc aat gac gct gag ggc gat tac aca tta tct    3207
Asp Lys Leu Lys Leu Ser Asn Asp Ala Glu Gly Asp Tyr Thr Leu Ser
                915              920              925 gtt cgc aac aca ggc aaa gaa ccc gaa gcc ctt gag caa tta act ttg    3255
Val Arg Asn Thr Gly Lys Glu Pro Glu Ala Leu Glu Gln Leu Thr Leu
            930              935              940 gtt gaa agc aaa gat aat aaa ccg tta tca gac aaa ctc aaa ttt act    3303
```

```
                Val Glu Ser Lys Asp Asn Lys Pro Leu Ser Asp Lys Leu Lys Phe Thr
                            945                 950                 955 tta gaa aat gac cac gtt gat gca ggt gca tta cgt tat aaa tta gtg        3351
Leu Glu Asn Asp His Val Asp Ala Gly Ala Leu Arg Tyr Lys Leu Val
            960                 965                 970 aag aat aat ggc gaa ttc cgc ttg cat aac cca ata aaa gag cag gaa        3399
Lys Asn Asn Gly Glu Phe Arg Leu His Asn Pro Ile Lys Glu Gln Glu
975                 980                 985                 990 ttg cgc aat gat tta gta aga gca gag caa gca gaa cga aca tta gaa        3447
Leu Arg Asn Asp Leu Val Arg Ala Glu Gln Ala Glu Arg Thr Leu Glu
                995                 1000                1005 gcc aaa caa gtt gaa cag act gct gaa aca caa aca agt aat gca            3492
Ala Lys Gln Val Glu Gln Thr Ala Glu Thr Gln Thr Ser Asn Ala
            1010                1015                1020 aga gtg cgg tca aaa aga gcg gtg ttt tct gat acc ctg cct gat            3537
Arg Val Arg Ser Lys Arg Ala Val Phe Ser Asp Thr Leu Pro Asp
            1025                1030                1035 caa agc cag tta gac gta tta caa gcc gaa caa gtt gaa ccg act            3582
Gln Ser Gln Leu Asp Val Leu Gln Ala Glu Gln Val Glu Pro Thr
            1040                1045                1050 gct gaa aaa caa aaa aat aag gca aaa aaa gtg cgg tca aaa aga            3627
Ala Glu Lys Gln Lys Asn Lys Ala Lys Lys Val Arg Ser Lys Arg
            1055                1060                1065 gcg gtg ttt tct gat acc ctg cct gat caa agc cag tta gac gta            3672
Ala Val Phe Ser Asp Thr Leu Pro Asp Gln Ser Gln Leu Asp Val
            1070                1075                1080 tta caa gcc gaa caa gtt gaa ccg act gct gaa aaa caa aaa aat            3717
Leu Gln Ala Glu Gln Val Glu Pro Thr Ala Glu Lys Gln Lys Asn
            1085                1090                1095 aag gca aaa aaa gtg cgg tca aaa aga gcc gcg aga gag ttt tct            3762
Lys Ala Lys Lys Val Arg Ser Lys Arg Ala Ala Arg Glu Phe Ser
            1100                1105                1110 gat acc ccg ctt gat cta agc cgg tta aag gta tta gaa gtc aaa            3807
Asp Thr Pro Leu Asp Leu Ser Arg Leu Lys Val Leu Glu Val Lys
            1115                1120                1125 ctt gag gtt att aat gcc caa cag caa gtg aaa aaa gaa cct caa            3852
Leu Glu Val Ile Asn Ala Gln Gln Gln Val Lys Lys Glu Pro Gln
            1130                1135                1140 gat caa gag aaa caa cgc aaa caa aaa gac ttg atc agc cgt tat            3897
Asp Gln Glu Lys Gln Arg Lys Gln Lys Asp Leu Ile Ser Arg Tyr
            1145                1150                1155 tca aat agt gcg tta tca gaa tta tct gca aca gta aat agt atg            3942
Ser Asn Ser Ala Leu Ser Glu Leu Ser Ala Thr Val Asn Ser Met
            1160                1165                1170 ctt tct gtt caa gat gaa tta gat cgt ctt ttt gta gat caa gca            3987
Leu Ser Val Gln Asp Glu Leu Asp Arg Leu Phe Val Asp Gln Ala
            1175                1180                1185 caa tct gcc gtg tgg aca aat atc gca cag gat aaa aga cgc tat            4032
Gln Ser Ala Val Trp Thr Asn Ile Ala Gln Asp Lys Arg Arg Tyr
            1190                1195                1200 gat tct gat gcg ttc cgt gct tat cag cag aaa acg aac tta cgt            4077
Asp Ser Asp Ala Phe Arg Ala Tyr Gln Gln Lys Thr Asn Leu Arg
            1205                1210                1215 caa att ggg gtg caa aaa gcc tta gct aat gga cga att ggg gca            4122
Gln Ile Gly Val Gln Lys Ala Leu Ala Asn Gly Arg Ile Gly Ala
            1220                1225                1230 gtt ttc tcg cat agc cgt tca gat aat act ttt gat gaa cag gtt            4167
Val Phe Ser His Ser Arg Ser Asp Asn Thr Phe Asp Glu Gln Val
            1235                1240                1245
```

| | | | | | | | | | | | | | | |
|---|---|---|---|---|---|---|---|---|---|---|---|---|---|---|
| aaa | aat | cac | gcg | aca | tta | acg | atg | atg | tcg | ggt | ttt | gcc | caa | tat | 4212 |
| Lys | Asn | His | Ala | Thr | Leu | Thr | Met | Met | Ser | Gly | Phe | Ala | Gln | Tyr | |
| | | | 1250 | | | | 1255 | | | | | 1260 | | | |

| caa | tgg | ggc | gat | tta | caa | ttt | ggt | gta | aac | gtg | gga | acg | gga | atc | 4257 |
| Gln | Trp | Gly | Asp | Leu | Gln | Phe | Gly | Val | Asn | Val | Gly | Thr | Gly | Ile | |
| 1265 | | | | | 1270 | | | | | 1275 | | | | | |

| agt | gcg | agt | aaa | atg | gct | gaa | gaa | caa | agc | cga | aaa | att | cat | cga | 4302 |
| Ser | Ala | Ser | Lys | Met | Ala | Glu | Glu | Gln | Ser | Arg | Lys | Ile | His | Arg | |
| | 1280 | | | | | 1285 | | | | | 1290 | | | | |

| aaa | gcg | ata | aat | tat | ggc | gtg | aat | gca | agt | tat | cag | ttc | cgt | tta | 4347 |
| Lys | Ala | Ile | Asn | Tyr | Gly | Val | Asn | Ala | Ser | Tyr | Gln | Phe | Arg | Leu | |
| | | 1295 | | | | | 1300 | | | | | 1305 | | | |

| ggg | caa | ttg | ggc | att | cag | cct | tat | ttt | gga | gtt | aat | cgc | tat | ttt | 4392 |
| Gly | Gln | Leu | Gly | Ile | Gln | Pro | Tyr | Phe | Gly | Val | Asn | Arg | Tyr | Phe | |
| 1310 | | | | | 1315 | | | | | 1320 | | | | | |

| att | gaa | cgt | gaa | aat | tat | caa | tct | gag | gaa | gtg | aaa | gtg | aaa | acg | 4437 |
| Ile | Glu | Arg | Glu | Asn | Tyr | Gln | Ser | Glu | Glu | Val | Lys | Val | Lys | Thr | |
| | 1325 | | | | | 1330 | | | | | 1335 | | | | |

| cct | agc | ctt | gca | ttt | aat | cgc | tat | aat | gct | ggc | att | cga | gtt | gat | 4482 |
| Pro | Ser | Leu | Ala | Phe | Asn | Arg | Tyr | Asn | Ala | Gly | Ile | Arg | Val | Asp | |
| | | 1340 | | | | | 1345 | | | | | 1350 | | | |

| tat | aca | ttt | act | ccg | aca | gat | aat | atc | agc | gtt | aag | cct | tat | ttc | 4527 |
| Tyr | Thr | Phe | Thr | Pro | Thr | Asp | Asn | Ile | Ser | Val | Lys | Pro | Tyr | Phe | |
| Tyr | | 1355 | | | | | 1360 | | | | | 1365 | | | |

| ttc | gtc | aat | tat | gtt | gat | gtt | tca | aac | gct | aac | gta | caa | acc | acg | 4572 |
| Phe | Val | Asn | Tyr | Val | Asp | Val | Ser | Asn | Ala | Asn | Val | Gln | Thr | Thr | |
| | | | 1370 | | | | | 1375 | | | | | 1380 | | |

| gta | aat | agc | acg | gtg | ttg | caa | caa | cca | ttt | gga | cgt | tat | tgg | caa | 4617 |
| Val | Asn | Ser | Thr | Val | Leu | Gln | Gln | Pro | Phe | Gly | Arg | Tyr | Trp | Gln | |
| | | 1385 | | | | | 1390 | | | | | 1395 | | | |

| aaa | gaa | gtg | gga | tta | aaa | gcg | gaa | att | tta | cat | ttc | caa | ctt | tct | 4662 |
| Lys | Glu | Val | Gly | Leu | Lys | Ala | Glu | Ile | Leu | His | Phe | Gln | Leu | Ser | |
| | | | 1400 | | | | | 1405 | | | | | 1410 | | |

| gct | ttt | att | tct | aaa | tct | caa | ggt | tcg | caa | ctc | ggc | aaa | cag | caa | 4707 |
| Ala | Phe | Ile | Ser | Lys | Ser | Gln | Gly | Ser | Gln | Leu | Gly | Lys | Gln | Gln | |
| | | 1415 | | | | | 1420 | | | | | 1425 | | | |

| aat | gtg | ggc | gtg | aaa | ttg | ggg | tat | cgt | tgg | taa | aaatcaacat | | | | 4750 |
| Asn | Val | Gly | Val | Lys | Leu | Gly | Tyr | Arg | Trp | | | | | | |
| | 1430 | | | | | 1435 | | | | | | | | | |

| aattgtatcg | tttattgata | acaaggtgg | ggcagatccc | accttttta | tttcaataat | 4810 |
|---|---|---|---|---|---|---|
| ggaactttat | ttaattaaga | gcatctaagt | agcaccccat | ataggggatt | aattaagagg | 4870 |
| atttaataat | gaatttaact | aaacttttac | cagcatttgc | tgctgcagtc | gtattatctg | 4930 |
| cttgtgcaaa | ggatgcacct | gaaatgacaa | atcatctgc | gcaaatagct | gaaatgcaaa | 4990 |
| cacttccaac | aatcactgat | aaaacagttg | tatattcctg | caataaacaa | actgtaactg | 5050 |
| ccgtgtatca | atttgaaaac | caagaaccag | ttgctgcaat | ggtaagtgtg | ggcgatggca | 5110 |
| ttattgcgaa | agatttttact | cgtgataaat | cacaaaatga | ctttacaagt | ttcgtttctg | 5170 |
| gggattatgt | ttggaatgta | gatagtggct | taacgttaga | taaatttgat | tctgttgtgc | 5230 |
| ctgtcaattt | aattc | | | | | 5245 |

<210> SEQ ID NO 13
<211> LENGTH: 1436
<212> TYPE: PRT
<213> ORGANISM: Haemophilus influenzae

<400> SEQUENCE: 13

Met Lys Lys Thr Val Phe Arg Leu Asn Phe Leu Thr Ala Cys Ile Ser

```
            1               5              10              15
Leu Gly Ile Val Ser Gln Ala Trp Ala Gly His Thr Tyr Phe Gly Ile
                 20                  25                  30

Asp Tyr Gln Tyr Arg Asp Phe Ala Glu Asn Lys Gly Lys Phe Ser
                 35                  40                  45

Val Gly Ala Lys Asn Ile Glu Val Tyr Asn Lys Glu Gly Thr Leu Val
                 50                  55                  60

Gly Thr Ser Met Thr Lys Ala Pro Met Ile Asp Phe Ser Val Val Ser
 65                  70                  75                  80

Arg Asn Gly Val Ala Ala Leu Val Gly Asp Gln Tyr Ile Val Ser Val
                 85                  90                  95

Ala His Asn Gly Gly Tyr Asn Ser Val Asp Phe Gly Ala Glu Gly Pro
                100                 105                 110

Asn Pro Asp Gln His Arg Phe Thr Tyr Gln Ile Val Lys Arg Asn Asn
                115                 120                 125

Tyr Lys Pro Gly Lys Asp Asn Pro Tyr His Gly Asp Tyr His Met Pro
                130                 135                 140

Arg Leu His Lys Phe Val Thr Asp Ala Glu Pro Ala Lys Met Thr Asp
145                 150                 155                 160

Asn Met Asn Gly Lys Asn Tyr Ala Asp Leu Ser Lys Tyr Pro Asp Arg
                165                 170                 175

Val Arg Ile Gly Thr Gly Glu Gln Trp Trp Arg Thr Asp Glu Glu Gln
                180                 185                 190

Lys Gln Gly Ser Lys Ser Ser Trp Leu Ala Asp Ala Tyr Leu Trp Arg
                195                 200                 205

Ile Ala Gly Asn Thr His Ser Gln Ser Gly Ala Gly Asn Gly Thr Val
                210                 215                 220

Asn Leu Ser Gly Asp Ile Thr Lys Pro Asn Asn Tyr Gly Pro Leu Pro
225                 230                 235                 240

Thr Gly Val Ser Phe Gly Asp Ser Gly Ser Pro Met Phe Ile Tyr Asp
                245                 250                 255

Ala Ile Lys Gln Lys Trp Leu Ile Asn Gly Val Leu Gln Thr Gly Asn
                260                 265                 270

Pro Phe Ser Gly Ala Gly Asn Gly Phe Gln Leu Ile Arg Lys Asn Trp
                275                 280                 285

Phe Tyr Asp Asn Val Phe Val Glu Asp Leu Pro Ile Thr Phe Leu Glu
                290                 295                 300

Pro Arg Ser Asn Gly His Tyr Ser Phe Thr Ser Asn Asn Gly Thr
305                 310                 315                 320

Gly Thr Val Thr Gln Thr Asn Glu Lys Val Ser Met Pro Gln Phe Lys
                325                 330                 335

Val Arg Thr Val Gln Leu Phe Asn Glu Ala Leu Lys Glu Lys Asp Lys
                340                 345                 350

Glu Pro Val Tyr Ala Ala Gly Val Asn Ala Tyr Lys Pro Arg Leu
                355                 360                 365

Asn Asn Gly Lys Asn Ile Tyr Phe Gly Asp Arg Gly Thr Gly Thr Leu
                370                 375                 380

Thr Ile Glu Asn Asn Ile Asn Gln Gly Ala Gly Gly Leu Tyr Phe Glu
385                 390                 395                 400

Gly Asn Phe Thr Val Ser Ser Glu Asn Asn Ala Thr Trp Gln Gly Ala
                405                 410                 415

Gly Val His Val Gly Glu Asp Ser Thr Val Thr Trp Lys Val Asn Gly
                420                 425                 430
```

```
Val Glu His Asp Arg Leu Ser Lys Ile Gly Lys Gly Thr Leu His Ile
    435                 440                 445

Gln Ala Lys Gly Glu Asn Leu Gly Ser Ile Ser Val Gly Asp Gly Lys
    450                 455                 460

Val Ile Leu Asp Gln Gln Ala Asp Glu Asn Asn Gln Lys Gln Ala Phe
465                 470                 475                 480

Lys Glu Val Gly Ile Val Ser Gly Arg Ala Thr Val Gln Leu Asn Ser
                485                 490                 495

Ala Asp Gln Val Asp Pro Asn Asn Ile Tyr Phe Gly Phe Arg Gly Gly
                500                 505                 510

Arg Leu Asp Leu Asn Gly His Ser Leu Thr Phe Lys Arg Ile Gln Asn
    515                 520                 525

Thr Asp Glu Gly Ala Met Ile Val Asn His Asn Thr Thr Gln Val Ala
    530                 535                 540

Asn Ile Thr Ile Thr Gly Asn Glu Ser Ile Thr Ala Pro Ser Asn Lys
545                 550                 555                 560

Asn Asn Ile Asn Lys Leu Asp Tyr Ser Lys Glu Ile Ala Tyr Asn Gly
                565                 570                 575

Trp Phe Gly Glu Thr Asp Glu Asn Lys His Asn Gly Arg Leu Asn Leu
                580                 585                 590

Ile Tyr Lys Pro Thr Thr Glu Asp Arg Thr Leu Leu Ser Gly Gly
    595                 600                 605

Thr Asn Leu Lys Gly Asn Ile Thr Gln Glu Gly Gly Thr Leu Val Phe
    610                 615                 620

Ser Gly Arg Pro Thr Pro His Ala Tyr Asn His Leu Asn Arg Pro Asn
625                 630                 635                 640

Glu Leu Gly Arg Pro Gln Gly Glu Val Val Ile Asp Asp Trp Ile
                645                 650                 655

Thr Arg Thr Phe Lys Ala Glu Asn Phe Gln Ile Lys Gly Gly Ser Ala
                660                 665                 670

Val Val Ser Arg Asn Val Ser Ser Ile Glu Gly Asn Trp Thr Val Ser
                675                 680                 685

Asn Asn Ala Asn Ala Ala Phe Gly Val Val Pro Asn Gln Gln Asn Thr
    690                 695                 700

Ile Cys Thr Arg Ser Asp Trp Thr Gly Leu Thr Thr Cys Lys Thr Val
705                 710                 715                 720

Asp Leu Thr Asp Thr Lys Val Ile Asn Ser Ile Pro Thr Thr Gln Ile
                725                 730                 735

Asn Gly Ser Ile Asn Leu Thr Asp Asn Ala Thr Val Asn Ile His Gly
                740                 745                 750

Leu Ala Lys Leu Asn Gly Asn Val Thr Leu Ile Asn His Ser Gln Phe
    755                 760                 765

Thr Leu Ser Asn Asn Ala Thr Gln Thr Gly Asn Ile Gln Leu Ser Asn
    770                 775                 780

His Ala Asn Ala Thr Val Asp Asn Ala Asn Leu Asn Gly Asn Val His
785                 790                 795                 800

Leu Thr Asp Ser Ala Gln Phe Ser Leu Lys Asn Ser His Phe Ser His
                805                 810                 815

Gln Ile Gln Gly Asp Lys Asp Thr Thr Val Thr Leu Glu Asn Ala Thr
                820                 825                 830

Trp Thr Met Pro Ser Asp Ala Thr Leu Gln Asn Leu Thr Leu Asn Asn
                835                 840                 845
```

-continued

Ser Thr Val Thr Leu Asn Ser Ala Tyr Ser Ala Ser Ser Asn Asn Ala
    850                 855                 860

Pro Arg His Arg Arg Ser Leu Glu Thr Glu Thr Thr Pro Thr Ser Ala
865                 870                 875                 880

Glu His Arg Phe Asn Thr Leu Thr Val Asn Gly Lys Leu Ser Gly Gln
                885                 890                 895

Gly Thr Phe Gln Phe Thr Ser Ser Leu Phe Gly Tyr Lys Ser Asp Lys
                900                 905                 910

Leu Lys Leu Ser Asn Asp Ala Glu Gly Asp Tyr Thr Leu Ser Val Arg
            915                 920                 925

Asn Thr Gly Lys Glu Pro Glu Ala Leu Glu Gln Leu Thr Leu Val Glu
    930                 935                 940

Ser Lys Asp Asn Lys Pro Leu Ser Asp Lys Leu Lys Phe Thr Leu Glu
945                 950                 955                 960

Asn Asp His Val Asp Ala Gly Ala Leu Arg Tyr Lys Leu Val Lys Asn
            965                 970                 975

Asn Gly Glu Phe Arg Leu His Asn Pro Ile Lys Glu Gln Glu Leu Arg
                980                 985                 990

Asn Asp Leu Val Arg Ala Glu Gln Ala Glu Arg Thr Leu Glu Ala Lys
            995                 1000                1005

Gln Val Glu Gln Thr Ala Glu Thr Gln Thr Ser Asn Ala Arg Val
    1010                1015                1020

Arg Ser Lys Arg Ala Val Phe Ser Asp Thr Leu Pro Asp Gln Ser
    1025                1030                1035

Gln Leu Asp Val Leu Gln Ala Glu Gln Val Glu Pro Thr Ala Glu
    1040                1045                1050

Lys Gln Lys Asn Lys Ala Lys Lys Val Arg Ser Lys Arg Ala Val
    1055                1060                1065

Phe Ser Asp Thr Leu Pro Asp Gln Ser Gln Leu Asp Val Leu Gln
    1070                1075                1080

Ala Glu Gln Val Glu Pro Thr Ala Glu Lys Gln Lys Asn Lys Ala
    1085                1090                1095

Lys Lys Val Arg Ser Lys Arg Ala Ala Arg Glu Phe Ser Asp Thr
    1100                1105                1110

Pro Leu Asp Leu Ser Arg Leu Lys Val Leu Glu Val Lys Leu Glu
    1115                1120                1125

Val Ile Asn Ala Gln Gln Gln Val Lys Lys Glu Pro Gln Asp Gln
    1130                1135                1140

Glu Lys Gln Arg Lys Gln Lys Asp Leu Ile Ser Arg Tyr Ser Asn
    1145                1150                1155

Ser Ala Leu Ser Glu Leu Ser Ala Thr Val Asn Ser Met Leu Ser
    1160                1165                1170

Val Gln Asp Glu Leu Asp Arg Leu Phe Val Asp Gln Ala Gln Ser
    1175                1180                1185

Ala Val Trp Thr Asn Ile Ala Gln Asp Lys Arg Arg Tyr Asp Ser
    1190                1195                1200

Asp Ala Phe Arg Ala Tyr Gln Gln Lys Thr Asn Leu Arg Gln Ile
    1205                1210                1215

Gly Val Gln Lys Ala Leu Ala Asn Gly Arg Ile Gly Ala Val Phe
    1220                1225                1230

Ser His Ser Arg Ser Asp Asn Thr Phe Asp Glu Gln Val Lys Asn
    1235                1240                1245

His Ala Thr Leu Thr Met Met Ser Gly Phe Ala Gln Tyr Gln Trp

-continued

|  |  |  |  |  |  |  |  |  |  |  |  |
|---|---|---|---|---|---|---|---|---|---|---|---|
|  |  | 1250 |  |  |  | 1255 |  |  |  | 1260 |  |
| Gly | Asp | Leu | Gln | Phe | Gly | Val | Asn | Val | Gly | Thr | Gly | Ile | Ser | Ala |
|  |  | 1265 |  |  |  | 1270 |  |  |  | 1275 |  |
| Ser | Lys | Met | Ala | Glu | Glu | Gln | Ser | Arg | Lys | Ile | His | Arg | Lys | Ala |
|  |  | 1280 |  |  |  | 1285 |  |  |  | 1290 |  |
| Ile | Asn | Tyr | Gly | Val | Asn | Ala | Ser | Tyr | Gln | Phe | Arg | Leu | Gly | Gln |
|  |  | 1295 |  |  |  | 1300 |  |  |  | 1305 |  |
| Leu | Gly | Ile | Gln | Pro | Tyr | Phe | Gly | Val | Asn | Arg | Tyr | Phe | Ile | Glu |
|  |  | 1310 |  |  |  | 1315 |  |  |  | 1320 |  |
| Arg | Glu | Asn | Tyr | Gln | Ser | Glu | Glu | Val | Lys | Val | Lys | Thr | Pro | Ser |
|  |  | 1325 |  |  |  | 1330 |  |  |  | 1335 |  |
| Leu | Ala | Phe | Asn | Arg | Tyr | Asn | Ala | Gly | Ile | Arg | Val | Asp | Tyr | Thr |
|  |  | 1340 |  |  |  | 1345 |  |  |  | 1350 |  |
| Phe | Thr | Pro | Thr | Asp | Asn | Ile | Ser | Val | Lys | Pro | Tyr | Phe | Phe | Val |
|  |  | 1355 |  |  |  | 1360 |  |  |  | 1365 |  |
| Asn | Tyr | Val | Asp | Val | Ser | Asn | Ala | Asn | Val | Gln | Thr | Thr | Val | Asn |
|  |  | 1370 |  |  |  | 1375 |  |  |  | 1380 |  |
| Ser | Thr | Val | Leu | Gln | Gln | Pro | Phe | Gly | Arg | Tyr | Trp | Gln | Lys | Glu |
|  |  | 1385 |  |  |  | 1390 |  |  |  | 1395 |  |
| Val | Gly | Leu | Lys | Ala | Glu | Ile | Leu | His | Phe | Gln | Leu | Ser | Ala | Phe |
|  |  | 1400 |  |  |  | 1405 |  |  |  | 1410 |  |
| Ile | Ser | Lys | Ser | Gln | Gly | Ser | Gln | Leu | Gly | Lys | Gln | Gln | Asn | Val |
|  |  | 1415 |  |  |  | 1420 |  |  |  | 1425 |  |
| Gly | Val | Lys | Leu | Gly | Tyr | Arg | Trp |
|  |  | 1430 |  |  |  | 1435 |

<210> SEQ ID NO 14
<211> LENGTH: 4822
<212> TYPE: DNA
<213> ORGANISM: Haemophilus influenzae
<220> FEATURE:
<221> NAME/KEY: CDS
<222> LOCATION: (388)..(4563)
<223> OTHER INFORMATION:

<400> SEQUENCE: 14
cctgaagacg ttgctcaagt taaaggctct cacacagccc gattccttaa accgatttta     60
gaaaaccttt agaaaaaatg accgcacttt cagagaaaac tcacataaag tgcggttatt    120
ttattagtga tattgtttta attatttgta taaattacat acaatattaa tccatcgaaa    180
aataagatta cccactaagt attaagccaa aacctagaaa ttttggctta attactatat    240
aattttactc ctttattttc ttttgtgcct tttagttagt tcgttttttta gctgaaatcc    300 ctcagaaaat caccgcactt ttattgttca atagtcgttt aaccacgtat ttttttaatac    360 gaaaaattac ttaattaaat aaacatt atg aaa aaa act gta ttt cgt ctt aat   414
                                Met Lys Lys Thr Val Phe Arg Leu Asn
                                  1               5 ttt cta acc gct tgt att tca tta ggg ata gta tcg caa gcg tgg gca    462
Phe Leu Thr Ala Cys Ile Ser Leu Gly Ile Val Ser Gln Ala Trp Ala
 10              15                  20                  25 ggt cac act tat ttt ggg att gac tac caa tat tat cgt gat ttt gcc    510
Gly His Thr Tyr Phe Gly Ile Asp Tyr Gln Tyr Tyr Arg Asp Phe Ala
                 30                  35                  40 gag aat aaa ggg aag ttt aca gtt ggg gct caa gat att gat atc tac    558
Glu Asn Lys Gly Lys Phe Thr Val Gly Ala Gln Asp Ile Asp Ile Tyr
             45                  50                  55 aat aaa aaa ggg gaa atg ata ggt acg atg atg aaa ggt gtg cct atg    606

-continued

|  |  |
|---|---|
| Asn Lys Lys Gly Glu Met Ile Gly Thr Met Met Lys Gly Val Pro Met<br>60              65                  70 |  |
| cct gat tta tct tcc atg gtt cgt ggt ggt tat tca aca ttg ata agt<br>Pro Asp Leu Ser Ser Met Val Arg Gly Gly Tyr Ser Thr Leu Ile Ser<br>75              80                  85 | 654 |
| gag cag cat tta att agc gtc gca cat aat gta ggg tat gat gtc gtt<br>Glu Gln His Leu Ile Ser Val Ala His Asn Val Gly Tyr Asp Val Val<br>90              95                  100                 105 | 702 |
| gat ttt ggt atg gag ggg gaa aat cca gac caa cat cgt ttt aag tat<br>Asp Phe Gly Met Glu Gly Glu Asn Pro Asp Gln His Arg Phe Lys Tyr<br>110                 115                 120 | 750 |
| aaa gtt gtt aaa cga tat aat tat aag agc ggt gat aga caa tat aat<br>Lys Val Val Lys Arg Tyr Asn Tyr Lys Ser Gly Asp Arg Gln Tyr Asn<br>125                 130                 135 | 798 |
| gat tat caa cat cca aga tta gag aaa ttt gta acg gaa act gca cct<br>Asp Tyr Gln His Pro Arg Leu Glu Lys Phe Val Thr Glu Thr Ala Pro<br>140                 145                 150 | 846 |
| att gaa atg gtt tca tat atg gat ggt aat cat tac aaa aat ttt aat<br>Ile Glu Met Val Ser Tyr Met Asp Gly Asn His Tyr Lys Asn Phe Asn<br>155                 160                 165 | 894 |
| caa tat cct ttg cga gtt aga gtt gga agt ggg cat caa tgg tgg aaa<br>Gln Tyr Pro Leu Arg Val Arg Val Gly Ser Gly His Gln Trp Trp Lys<br>170                 175                 180                 185 | 942 |
| gac gat aat aat aaa acc att gga gac tta gcc tat gga ggt tca tgg<br>Asp Asp Asn Asn Lys Thr Ile Gly Asp Leu Ala Tyr Gly Gly Ser Trp<br>190                 195                 200 | 990 |
| tta ata ggt gga aat acc ttt gaa gat gga cca gct ggt aac ggt aca<br>Leu Ile Gly Gly Asn Thr Phe Glu Asp Gly Pro Ala Gly Asn Gly Thr<br>205                 210                 215 | 1038 |
| tta gaa tta aat ggg cga gta caa aat cct aat aaa tat ggt cca cta<br>Leu Glu Leu Asn Gly Arg Val Gln Asn Pro Asn Lys Tyr Gly Pro Leu<br>220                 225                 230 | 1086 |
| cct acg gca ggt tca ttc ggg gat agt ggt tct cca atg ttt att tat<br>Pro Thr Ala Gly Ser Phe Gly Asp Ser Gly Ser Pro Met Phe Ile Tyr<br>235                 240                 245 | 1134 |
| gat aag gaa gtt aag aaa tgg tta tta aat ggc gtg tta cgt gaa gga<br>Asp Lys Glu Val Lys Lys Trp Leu Leu Asn Gly Val Leu Arg Glu Gly<br>250                 255                 260                 265 | 1182 |
| aat cct tat gct gca gta gga aac agc tat caa att aca cga aaa gat<br>Asn Pro Tyr Ala Ala Val Gly Asn Ser Tyr Gln Ile Thr Arg Lys Asp<br>270                 275                 280 | 1230 |
| tat ttt caa ggt att ctt aat caa gac att aca gct aat ttt tgg gat<br>Tyr Phe Gln Gly Ile Leu Asn Gln Asp Ile Thr Ala Asn Phe Trp Asp<br>285                 290                 295 | 1278 |
| act aat gct gaa tat aga ttt aat ata ggg agt gac cac aat gga aga<br>Thr Asn Ala Glu Tyr Arg Phe Asn Ile Gly Ser Asp His Asn Gly Arg<br>300                 305                 310 | 1326 |
| gtg gca aca atc aaa agt aca tta cct aaa aaa gct att cag cct gaa<br>Val Ala Thr Ile Lys Ser Thr Leu Pro Lys Lys Ala Ile Gln Pro Glu<br>315                 320                 325 | 1374 |
| cga ata gtg ggt ctt tat gat aat agc caa ctt cat gat gct aga gat<br>Arg Ile Val Gly Leu Tyr Asp Asn Ser Gln Leu His Asp Ala Arg Asp<br>330                 335                 340                 345 | 1422 |
| aaa aat ggc gat gaa tct ccc tct tat aaa ggt cct aat cca tgg tcg<br>Lys Asn Gly Asp Glu Ser Pro Ser Tyr Lys Gly Pro Asn Pro Trp Ser<br>350                 355                 360 | 1470 |
| cca gca tta cat cat ggg aaa agt att tac ttt ggc gat caa gga aca<br>Pro Ala Leu His His Gly Lys Ser Ile Tyr Phe Gly Asp Gln Gly Thr<br>365                 370                 375 | 1518 |

-continued

| | | |
|---|---|---|
| gga act tta aca att gaa aat aat ata aat caa ggt gca ggt gga ttg<br>Gly Thr Leu Thr Ile Glu Asn Asn Ile Asn Gln Gly Ala Gly Gly Leu<br>380 385 390 | | 1566 |
| tat ttt gaa ggt aat ttt gtt gta aaa ggc aat caa aat aat ata act<br>Tyr Phe Glu Gly Asn Phe Val Val Lys Gly Asn Gln Asn Asn Ile Thr<br>395 400 405 | | 1614 |
| tgg caa ggt gca ggc gtt tct gtt gga gaa gaa agt act gtt gaa tgg<br>Trp Gln Gly Ala Gly Val Ser Val Gly Glu Glu Ser Thr Val Glu Trp<br>410 415 420 425 | | 1662 |
| cag gtg cat aat cca gaa ggc gat cgc tta tcc aaa att ggg ctg gga<br>Gln Val His Asn Pro Glu Gly Asp Arg Leu Ser Lys Ile Gly Leu Gly<br>430 435 440 | | 1710 |
| acc tta ctt gtt aat ggt aaa ggg aaa aac tta gga agc ctg agt gtc<br>Thr Leu Leu Val Asn Gly Lys Gly Lys Asn Leu Gly Ser Leu Ser Val<br>445 450 455 | | 1758 |
| ggt aac ggt ttg gtt gtg tta gat caa caa gca gat gaa tca ggt caa<br>Gly Asn Gly Leu Val Val Leu Asp Gln Gln Ala Asp Glu Ser Gly Gln<br>460 465 470 | | 1806 |
| aaa caa gcc ttt aaa gaa gtt ggc att gta agt ggt aga gct acc gtt<br>Lys Gln Ala Phe Lys Glu Val Gly Ile Val Ser Gly Arg Ala Thr Val<br>475 480 485 | | 1854 |
| caa cta aat agt gca gat caa gtt gat cct aac aat att tat ttc ggc<br>Gln Leu Asn Ser Ala Asp Gln Val Asp Pro Asn Asn Ile Tyr Phe Gly<br>490 495 500 505 | | 1902 |
| ttt cgt ggt ggt cgc tta gat ctt aat ggg cat tca tta acc ttt gaa<br>Phe Arg Gly Gly Arg Leu Asp Leu Asn Gly His Ser Leu Thr Phe Glu<br>510 515 520 | | 1950 |
| cgt atc caa aat acg gat gaa ggc gcg atg att gtg aac cac aac gct<br>Arg Ile Gln Asn Thr Asp Glu Gly Ala Met Ile Val Asn His Asn Ala<br>525 530 535 | | 1998 |
| tct caa acc gca aat att acg att aca ggc aac gca act att aat tca<br>Ser Gln Thr Ala Asn Ile Thr Ile Thr Gly Asn Ala Thr Ile Asn Ser<br>540 545 550 | | 2046 |
| gat agc aaa caa ctt act aat aaa aaa gat att gca ttt aac ggc tgg<br>Asp Ser Lys Gln Leu Thr Asn Lys Lys Asp Ile Ala Phe Asn Gly Trp<br>555 560 565 | | 2094 |
| ttt ggt gag caa gat aaa gct aaa aca aat ggt cgt tta aat gtg aat<br>Phe Gly Glu Gln Asp Lys Ala Lys Thr Asn Gly Arg Leu Asn Val Asn<br>570 575 580 585 | | 2142 |
| tat caa cca gtt aat gca gaa aat cat ttg ttg ctt tct ggg ggg aca<br>Tyr Gln Pro Val Asn Ala Glu Asn His Leu Leu Leu Ser Gly Gly Thr<br>590 595 600 | | 2190 |
| aat tta aac ggc aat atc acg caa aat ggt ggt acg tta gtt ttt agt<br>Asn Leu Asn Gly Asn Ile Thr Gln Asn Gly Gly Thr Leu Val Phe Ser<br>605 610 615 | | 2238 |
| ggt cgt cca acg cct cat gct tac aat cat tta aga aga gac ttg tct<br>Gly Arg Pro Thr Pro His Ala Tyr Asn His Leu Arg Arg Asp Leu Ser<br>620 625 630 | | 2286 |
| aac atg gaa ggt atc cca caa ggc gaa att gtg tgg gat cac gat tgg<br>Asn Met Glu Gly Ile Pro Gln Gly Glu Ile Val Trp Asp His Asp Trp<br>635 640 645 | | 2334 |
| atc aac cgc aca ttt aaa gct gaa aac ttc caa att aaa ggc gga agt<br>Ile Asn Arg Thr Phe Lys Ala Glu Asn Phe Gln Ile Lys Gly Gly Ser<br>650 655 660 665 | | 2382 |
| gcg gtg gtt tct cgc aat gtt tct tca att gag gga aat tgg aca gtc<br>Ala Val Val Ser Arg Asn Val Ser Ser Ile Glu Gly Asn Trp Thr Val<br>670 675 680 | | 2430 |
| agc aat aat gca aat gcc aca ttt ggt gtt gtg cca aat cag caa aat<br>Ser Asn Asn Ala Asn Ala Thr Phe Gly Val Val Pro Asn Gln Gln Asn<br>685 690 695 | | 2478 |

-continued

```
acc att tgc acg cgt tca gat tgg aca gga tta acg act tgt aaa aca     2526
Thr Ile Cys Thr Arg Ser Asp Trp Thr Gly Leu Thr Thr Cys Lys Thr
        700                 705                 710 gtt gat tta acc gat aaa aaa gtt att aat tcc ata ccg aca aca caa     2574
Val Asp Leu Thr Asp Lys Lys Val Ile Asn Ser Ile Pro Thr Thr Gln
715                 720                 725 att aat ggt tct att aat tta act gat aat gca aca gtg aat att cat     2622
Ile Asn Gly Ser Ile Asn Leu Thr Asp Asn Ala Thr Val Asn Ile His
730                 735                 740                 745 ggt tta gca aaa ctt aat ggt aat gtc act tta ata gat cac agc caa     2670
Gly Leu Ala Lys Leu Asn Gly Asn Val Thr Leu Ile Asp His Ser Gln
            750                 755                 760 ttt aca ttg agc aac aat gcc acc caa gca ggc aat atc aaa ctt tca     2718
Phe Thr Leu Ser Asn Asn Ala Thr Gln Ala Gly Asn Ile Lys Leu Ser
                765                 770                 775 aat cac gca aat gca acg gtg gac aat gca aat ttg aac ggt aat gtg     2766
Asn His Ala Asn Ala Thr Val Asp Asn Ala Asn Leu Asn Gly Asn Val
780                 785                 790 aat tta atg gat tct gct caa ttt tct tta aaa aac agc cat ttt tcg     2814
Asn Leu Met Asp Ser Ala Gln Phe Ser Leu Lys Asn Ser His Phe Ser
795                 800                 805 cac caa atc caa ggt ggg gaa gac aca aca gtg atg ttg gaa aat gcg     2862
His Gln Ile Gln Gly Gly Glu Asp Thr Thr Val Met Leu Glu Asn Ala
810                 815                 820                 825 act tgg aca atg cct agc gat acc aca ttg cag aat tta acg cta aat     2910
Thr Trp Thr Met Pro Ser Asp Thr Thr Leu Gln Asn Leu Thr Leu Asn
                830                 835                 840 aat agt act gtt acg tta aat tca gct tat tca gct atc tca aat aat     2958
Asn Ser Thr Val Thr Leu Asn Ser Ala Tyr Ser Ala Ile Ser Asn Asn
                845                 850                 855 gcg cca cgc cgt cgc cgc cgt tca tta gag acg gaa aca acg cca aca     3006
Ala Pro Arg Arg Arg Arg Arg Ser Leu Glu Thr Glu Thr Thr Pro Thr
            860                 865                 870 tcg gca gaa cat cgt ttc aac aca ttg aca gta aat ggt aaa ttg agc     3054
Ser Ala Glu His Arg Phe Asn Thr Leu Thr Val Asn Gly Lys Leu Ser
875                 880                 885 ggg caa ggc aca ttc caa ttt act tca tct tta ttt ggc tat aaa agc     3102
Gly Gln Gly Thr Phe Gln Phe Thr Ser Ser Leu Phe Gly Tyr Lys Ser
890                 895                 900                 905 gat aaa tta aaa tta tcc aat gac gct gag ggc gat tac aca tta tct     3150
Asp Lys Leu Lys Leu Ser Asn Asp Ala Glu Gly Asp Tyr Thr Leu Ser
                910                 915                 920 gtt cgc aac aca ggc aaa gaa ccc gtg acc ttt ggg caa tta act ttg     3198
Val Arg Asn Thr Gly Lys Glu Pro Val Thr Phe Gly Gln Leu Thr Leu
                925                 930                 935 gtt gaa agc aaa gat aat aaa ccg tta tca gac aaa ctc aca ttc acg     3246
Val Glu Ser Lys Asp Asn Lys Pro Leu Ser Asp Lys Leu Thr Phe Thr
            940                 945                 950 tta gaa aat gac cac gtt gat gca ggt gca tta cgt tat aaa tta gtg     3294
Leu Glu Asn Asp His Val Asp Ala Gly Ala Leu Arg Tyr Lys Leu Val
955                 960                 965 aag aat gat ggc gaa ttc cgc tta cat aac cca ata aaa gag cag gaa     3342
Lys Asn Asp Gly Glu Phe Arg Leu His Asn Pro Ile Lys Glu Gln Glu
970                 975                 980                 985 ttg cgc tct gat tta gta aga gca gag caa gca gaa cga aca tta  gaa   3390
Leu Arg Ser Asp Leu Val Arg Ala Glu Gln Ala Glu Arg Thr Leu  Glu
                990                 995                 1000 gcc aaa caa gtt  gaa cag act gct aaa  aca caa aca agt aag  gca     3435
Ala Lys Gln Val  Glu Gln Thr Ala Lys  Thr Gln Thr Ser Lys  Ala
```

-continued

|  |  |  | 1005 |  |  |  | 1010 |  |  |  | 1015 |  |  |  |
|---|---|---|---|---|---|---|---|---|---|---|---|---|---|---|

```
aga gtg cgg tca aga aga gcg gtg ttt tct gat ccc ctg cct gct      3480
Arg Val Arg Ser Arg Arg Ala Val Phe Ser Asp Pro Leu Pro Ala
        1020            1025                1030 caa agc ctg tta aac gca tta gaa gcc aaa caa gct ctg act act      3525
Gln Ser Leu Leu Asn Ala Leu Glu Ala Lys Gln Ala Leu Thr Thr
        1035            1040                1045 gaa aca caa aca agt aag gca aaa aaa gtg cgg tca aaa aga gct      3570
Glu Thr Gln Thr Ser Lys Ala Lys Lys Val Arg Ser Lys Arg Ala
        1050            1055                1060 gcg aga gag ttt tct gat acc ctg cct gat caa ata tta caa gcc      3615
Ala Arg Glu Phe Ser Asp Thr Leu Pro Asp Gln Ile Leu Gln Ala
        1065            1070                1075 gca ctt gag gtt att gat gcc caa cag caa gtg aaa aaa gaa cct      3660
Ala Leu Glu Val Ile Asp Ala Gln Gln Gln Val Lys Lys Glu Pro
        1080            1085                1090 caa act caa gag gaa gaa gag aaa aga caa cgc aaa caa aaa gaa      3705
Gln Thr Gln Glu Glu Glu Glu Lys Arg Gln Arg Lys Gln Lys Glu
        1095            1100                1105 ttg atc agc cgt tac tca aat agt gcg tta tcg gag ttg tct gcg      3750
Leu Ile Ser Arg Tyr Ser Asn Ser Ala Leu Ser Glu Leu Ser Ala
        1110            1115                1120 aca gta aat agt atg ctt tcc gtt caa gat gaa ttg gat cgt ctt      3795
Thr Val Asn Ser Met Leu Ser Val Gln Asp Glu Leu Asp Arg Leu
        1125            1130                1135 ttt gta gat caa gca caa tct gcc gtg tgg aca aat atc gca cag      3840
Phe Val Asp Gln Ala Gln Ser Ala Val Trp Thr Asn Ile Ala Gln
        1140            1145                1150 gat aaa aga cgc tat gat tct gat gcg ttc cgt gct tat cag cag      3885
Asp Lys Arg Arg Tyr Asp Ser Asp Ala Phe Arg Ala Tyr Gln Gln
        1155            1160                1165 aaa acg aac ttg cgt caa att ggg gtg caa aaa gcc tta gat aat      3930
Lys Thr Asn Leu Arg Gln Ile Gly Val Gln Lys Ala Leu Asp Asn
        1170            1175                1180 gga cga att ggg gcg gtt ttc tcg cat agc cgt tca gat aat acc      3975
Gly Arg Ile Gly Ala Val Phe Ser His Ser Arg Ser Asp Asn Thr
        1185            1190                1195 ttt gac gaa cag gtt aaa aat cac gcg aca tta gcg atg atg tct      4020
Phe Asp Glu Gln Val Lys Asn His Ala Thr Leu Ala Met Met Ser
        1200            1205                1210 ggt ttt gcc caa tat caa tgg ggc gat tta caa ttt ggt gta aac      4065
Gly Phe Ala Gln Tyr Gln Trp Gly Asp Leu Gln Phe Gly Val Asn
        1215            1220                1225 gtg ggt gcg gga att agt gcg agt aaa atg gct gaa gaa caa agc      4110
Val Gly Ala Gly Ile Ser Ala Ser Lys Met Ala Glu Glu Gln Ser
        1230            1235                1240 cga aaa att cat cga aaa gcg ata aat tat ggt gtg aat gca agt      4155
Arg Lys Ile His Arg Lys Ala Ile Asn Tyr Gly Val Asn Ala Ser
        1245            1250                1255 tat cag ttc cgt tta ggg caa ttg ggt att cag cct tat ttg ggt      4200
Tyr Gln Phe Arg Leu Gly Gln Leu Gly Ile Gln Pro Tyr Leu Gly
        1260            1265                1270 gtt aat cga tat ttt att gaa cgt gaa aat tat caa tct gaa gaa      4245
Val Asn Arg Tyr Phe Ile Glu Arg Glu Asn Tyr Gln Ser Glu Glu
        1275            1280                1285 gtg aaa gtg caa aca ccg agc ctt gta ttt aat cgc tat aat gct      4290
Val Lys Val Gln Thr Pro Ser Leu Val Phe Asn Arg Tyr Asn Ala
        1290            1295                1300 ggc att cga gtt gat tat aca ttt acc ccg aca gat aat atc agc      4335
Gly Ile Arg Val Asp Tyr Thr Phe Thr Pro Thr Asp Asn Ile Ser
```

-continued

| | | | | | | | | | | | | |
|---|---|---|---|---|---|---|---|---|---|---|---|---|
| Gly | Ile | Arg | Val<br>1305 | Asp | Tyr | Thr | Phe<br>1310 | Thr | Pro | Thr | Asp | Asn | Ile | Ser<br>1315 |

```
att aag cct tat ttc ttc gtc aat tat gtt gat gtt tca aac gct      4380
Ile Lys Pro Tyr Phe Phe Val Asn Tyr Val Asp Val Ser Asn Ala
        1320                1325                1330 aac gta caa acc act gta aat cgc acg atg ttg caa caa tca ttt      4425
Asn Val Gln Thr Thr Val Asn Arg Thr Met Leu Gln Gln Ser Phe
            1335                1340                1345 ggg cgt tat tgg caa aaa gaa gtg gga tta aag gca gaa att tta      4470
Gly Arg Tyr Trp Gln Lys Glu Val Gly Leu Lys Ala Glu Ile Leu
        1350                1355                1360 cat ttc caa ctt tcc gct ttt atc tca aaa tct caa ggt tca caa      4515
His Phe Gln Leu Ser Ala Phe Ile Ser Lys Ser Gln Gly Ser Gln
        1365                1370                1375 ctc ggc aaa cag caa aat gtg ggc gtg aaa ttg ggg tat cgt tgg      4560
Leu Gly Lys Gln Gln Asn Val Gly Val Lys Leu Gly Tyr Arg Trp
        1380                1385                1390 taa aaatcaacat aattttatcg tttattgata aacaaggtgg ggcagatcaa       4613
atcctacctt ttttattcca ataatggaac tttattttat taaaggtatc taagtagcac 4673 cctatatagg gattaattaa gaggatttaa taatgaattt aactaaaatt ttacccacat 4733 ttgctgctgt agtcgtatta tctgcttgtg caaaggatgc acctgaaatg acaaaatcat 4793 ctgcgcaaat agctgaaatg caaacactt                                   4822

<210> SEQ ID NO 15
<211> LENGTH: 1391
<212> TYPE: PRT
<213> ORGANISM: Haemophilus influenzae

<400> SEQUENCE: 15

Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Lys Gly Lys Phe Thr
        35                  40                  45

Val Gly Ala Gln Asp Ile Asp Ile Tyr Asn Lys Lys Gly Glu Met Ile
    50                  55                  60

Gly Thr Met Met Lys Gly Val Pro Met Pro Asp Leu Ser Ser Met Val
65                  70                  75                  80

Arg Gly Gly Tyr Ser Thr Leu Ile Ser Glu Gln His Leu Ile Ser Val
                85                  90                  95

Ala His Asn Val Gly Tyr Asp Val Val Asp Phe Gly Met Glu Gly Glu
            100                 105                 110

Asn Pro Asp Gln His Arg Phe Lys Tyr Lys Val Val Lys Arg Tyr Asn
        115                 120                 125

Tyr Lys Ser Gly Asp Arg Gln Tyr Asn Asp Tyr Gln His Pro Arg Leu
    130                 135                 140

Glu Lys Phe Val Thr Glu Thr Ala Pro Ile Glu Met Val Ser Tyr Met
145                 150                 155                 160

Asp Gly Asn His Tyr Lys Asn Phe Asn Gln Tyr Pro Leu Arg Val Arg
                165                 170                 175

Val Gly Ser Gly His Gln Trp Trp Lys Asp Asn Asn Lys Thr Ile
            180                 185                 190

Gly Asp Leu Ala Tyr Gly Gly Ser Trp Leu Ile Gly Gly Asn Thr Phe
        195                 200                 205
```

-continued

```
Glu Asp Gly Pro Ala Gly Asn Gly Thr Leu Glu Leu Asn Gly Arg Val
    210                 215                 220

Gln Asn Pro Asn Lys Tyr Gly Pro Leu Pro Thr Ala Gly Ser Phe Gly
225                 230                 235                 240

Asp Ser Gly Ser Pro Met Phe Ile Tyr Asp Lys Glu Val Lys Lys Trp
                245                 250                 255

Leu Leu Asn Gly Val Leu Arg Glu Gly Asn Pro Tyr Ala Ala Val Gly
            260                 265                 270

Asn Ser Tyr Gln Ile Thr Arg Lys Asp Tyr Phe Gln Gly Ile Leu Asn
        275                 280                 285

Gln Asp Ile Thr Ala Asn Phe Trp Asp Thr Asn Ala Glu Tyr Arg Phe
    290                 295                 300

Asn Ile Gly Ser Asp His Asn Gly Arg Val Ala Thr Ile Lys Ser Thr
305                 310                 315                 320

Leu Pro Lys Lys Ala Ile Gln Pro Glu Arg Ile Val Gly Leu Tyr Asp
                325                 330                 335

Asn Ser Gln Leu His Asp Ala Arg Asp Lys Asn Gly Asp Glu Ser Pro
            340                 345                 350

Ser Tyr Lys Gly Pro Asn Pro Trp Ser Pro Ala Leu His His Gly Lys
        355                 360                 365

Ser Ile Tyr Phe Gly Asp Gln Gly Thr Gly Thr Leu Thr Ile Glu Asn
    370                 375                 380

Asn Ile Asn Gln Gly Ala Gly Gly Leu Tyr Phe Glu Gly Asn Phe Val
385                 390                 395                 400

Val Lys Gly Asn Gln Asn Asn Ile Thr Trp Gln Gly Ala Gly Val Ser
                405                 410                 415

Val Gly Glu Glu Ser Thr Val Glu Trp Gln Val His Asn Pro Glu Gly
            420                 425                 430

Asp Arg Leu Ser Lys Ile Gly Leu Gly Thr Leu Leu Val Asn Gly Lys
        435                 440                 445

Gly Lys Asn Leu Gly Ser Leu Ser Val Gly Asn Gly Leu Val Val Leu
    450                 455                 460

Asp Gln Gln Ala Asp Glu Ser Gly Gln Lys Gln Ala Phe Lys Glu Val
465                 470                 475                 480

Gly Ile Val Ser Gly Arg Ala Thr Val Gln Leu Asn Ser Ala Asp Gln
                485                 490                 495

Val Asp Pro Asn Asn Ile Tyr Phe Gly Phe Arg Gly Gly Arg Leu Asp
            500                 505                 510

Leu Asn Gly His Ser Leu Thr Phe Glu Arg Ile Gln Asn Thr Asp Glu
        515                 520                 525

Gly Ala Met Ile Val Asn His Asn Ala Ser Gln Thr Ala Asn Ile Thr
    530                 535                 540

Ile Thr Gly Asn Ala Thr Ile Asn Ser Asp Ser Lys Gln Leu Thr Asn
545                 550                 555                 560

Lys Lys Asp Ile Ala Phe Asn Gly Trp Phe Gly Glu Gln Asp Lys Ala
                565                 570                 575

Lys Thr Asn Gly Arg Leu Asn Val Asn Tyr Gln Pro Val Asn Ala Glu
            580                 585                 590

Asn His Leu Leu Leu Ser Gly Gly Thr Asn Leu Asn Gly Asn Ile Thr
        595                 600                 605

Gln Asn Gly Gly Thr Leu Val Phe Ser Gly Arg Pro Thr Pro His Ala
    610                 615                 620
```

```
Tyr Asn His Leu Arg Arg Asp Leu Ser Asn Met Glu Gly Ile Pro Gln
625                 630                 635                 640

Gly Glu Ile Val Trp Asp His Asp Trp Ile Asn Arg Thr Phe Lys Ala
                    645                 650                 655

Glu Asn Phe Gln Ile Lys Gly Gly Ser Ala Val Val Ser Arg Asn Val
                660                 665                 670

Ser Ser Ile Glu Gly Asn Trp Thr Val Ser Asn Asn Ala Asn Ala Thr
            675                 680                 685

Phe Gly Val Val Pro Asn Gln Gln Asn Thr Ile Cys Thr Arg Ser Asp
        690                 695                 700

Trp Thr Gly Leu Thr Thr Cys Lys Thr Val Asp Leu Thr Asp Lys Lys
705                 710                 715                 720

Val Ile Asn Ser Ile Pro Thr Thr Gln Ile Asn Gly Ser Ile Asn Leu
                725                 730                 735

Thr Asp Asn Ala Thr Val Asn Ile His Gly Leu Ala Lys Leu Asn Gly
                740                 745                 750

Asn Val Thr Leu Ile Asp His Ser Gln Phe Thr Leu Ser Asn Asn Ala
            755                 760                 765

Thr Gln Ala Gly Asn Ile Lys Leu Ser Asn His Ala Asn Ala Thr Val
        770                 775                 780

Asp Asn Ala Asn Leu Asn Gly Asn Val Asn Leu Met Asp Ser Ala Gln
785                 790                 795                 800

Phe Ser Leu Lys Asn Ser His Phe Ser His Gln Ile Gln Gly Gly Glu
                805                 810                 815

Asp Thr Thr Val Met Leu Glu Asn Ala Thr Trp Thr Met Pro Ser Asp
                820                 825                 830

Thr Thr Leu Gln Asn Leu Thr Leu Asn Asn Ser Thr Val Thr Leu Asn
            835                 840                 845

Ser Ala Tyr Ser Ala Ile Ser Asn Asn Ala Pro Arg Arg Arg Arg Arg
        850                 855                 860

Ser Leu Glu Thr Glu Thr Thr Pro Thr Ser Ala Glu His Arg Phe Asn
865                 870                 875                 880

Thr Leu Thr Val Asn Gly Lys Leu Ser Gly Gln Gly Thr Phe Gln Phe
                885                 890                 895

Thr Ser Ser Leu Phe Gly Tyr Lys Ser Asp Lys Leu Lys Leu Ser Asn
            900                 905                 910

Asp Ala Glu Gly Asp Tyr Thr Leu Ser Val Arg Asn Thr Gly Lys Glu
        915                 920                 925

Pro Val Thr Phe Gly Gln Leu Thr Leu Val Glu Ser Lys Asp Asn Lys
930                 935                 940

Pro Leu Ser Asp Lys Leu Thr Phe Thr Leu Glu Asn Asp His Val Asp
945                 950                 955                 960

Ala Gly Ala Leu Arg Tyr Lys Leu Val Lys Asn Asp Gly Glu Phe Arg
                965                 970                 975

Leu His Asn Pro Ile Lys Glu Gln Glu Leu Arg Ser Asp Leu Val Arg
                980                 985                 990

Ala Glu Gln Ala Glu Arg Thr Leu  Glu Ala Lys Gln Val  Glu Gln Thr
            995                 1000                1005

Ala Lys  Thr Gln Thr Ser Lys  Ala Arg Val Arg Ser  Arg Arg Ala
    1010                1015                1020

Val Phe  Ser Asp Pro Leu Pro  Ala Gln Ser Leu Leu  Asn Ala Leu
    1025                1030                1035

Glu Ala  Lys Gln Ala Leu Thr  Thr Glu Thr Gln Thr  Ser Lys Ala
```

|      |      |      |      |      |      |      |      |      |      |
|------|------|------|------|------|------|------|------|------|------|
|      |      |      | 1040 |      |      | 1045 |      |      | 1050 |

Lys Lys Val Arg Ser Lys Arg Ala Ala Arg Glu Phe Ser Asp Thr
1055                     1060                    1065

Leu Pro Asp Gln Ile Leu Gln Ala Ala Leu Glu Val Ile Asp Ala
1070                     1075                    1080

Gln Gln Gln Val Lys Lys Glu Pro Gln Thr Gln Glu Glu Glu Glu
1085                     1090                    1095

Lys Arg Gln Arg Lys Gln Lys Glu Leu Ile Ser Arg Tyr Ser Asn
1100                     1105                    1110

Ser Ala Leu Ser Glu Leu Ser Ala Thr Val Asn Ser Met Leu Ser
1115                     1120                    1125

Val Gln Asp Glu Leu Asp Arg Leu Phe Val Asp Gln Ala Gln Ser
1130                     1135                    1140

Ala Val Trp Thr Asn Ile Ala Gln Asp Lys Arg Arg Tyr Asp Ser
1145                     1150                    1155

Asp Ala Phe Arg Ala Tyr Gln Lys Thr Asn Leu Arg Gln Ile
1160                     1165                    1170

Gly Val Gln Lys Ala Leu Asp Asn Gly Arg Ile Gly Ala Val Phe
1175                     1180                    1185

Ser His Ser Arg Ser Asp Asn Thr Phe Asp Glu Gln Val Lys Asn
1190                     1195                    1200

His Ala Thr Leu Ala Met Met Ser Gly Phe Ala Gln Tyr Gln Trp
1205                     1210                    1215

Gly Asp Leu Gln Phe Gly Val Asn Val Gly Ala Gly Ile Ser Ala
1220                     1225                    1230

Ser Lys Met Ala Glu Glu Gln Ser Arg Lys Ile His Arg Lys Ala
1235                     1240                    1245

Ile Asn Tyr Gly Val Asn Ala Ser Tyr Gln Phe Arg Leu Gly Gln
1250                     1255                    1260

Leu Gly Ile Gln Pro Tyr Leu Gly Val Asn Arg Tyr Phe Ile Glu
1265                     1270                    1275

Arg Glu Asn Tyr Gln Ser Glu Glu Val Lys Val Gln Thr Pro Ser
1280                     1285                    1290

Leu Val Phe Asn Arg Tyr Asn Ala Gly Ile Arg Val Asp Tyr Thr
1295                     1300                    1305

Phe Thr Pro Thr Asp Asn Ile Ser Ile Lys Pro Tyr Phe Phe Val
1310                     1315                    1320

Asn Tyr Val Asp Val Ser Asn Ala Asn Val Gln Thr Thr Val Asn
1325                     1330                    1335

Arg Thr Met Leu Gln Gln Ser Phe Gly Arg Tyr Trp Gln Lys Glu
1340                     1345                    1350

Val Gly Leu Lys Ala Glu Ile Leu His Phe Gln Leu Ser Ala Phe
1355                     1360                    1365

Ile Ser Lys Ser Gln Gly Ser Gln Leu Gly Lys Gln Gln Asn Val
1370                     1375                    1380

Gly Val Lys Leu Gly Tyr Arg Trp
1385                     1390

<210> SEQ ID NO 16
<211> LENGTH: 4828
<212> TYPE: DNA
<213> ORGANISM: Haemophilus influenzae
<220> FEATURE:
<221> NAME/KEY: CDS
<222> LOCATION: (313)..(4548)

<223> OTHER INFORMATION:

<400> SEQUENCE: 16

```
tgaccgcact ttcagagaaa actcacataa agtgcggtta ttttattagt gatattgttt      60
taattttagt tatctgtata aattacatac aatattaatc catcgcaaga taagattacc     120
cactaagtat taagcaaaaa cctagaaatt ttggcttaat tactatatag ttttactcat     180
ttattttctt ttgtgccttt tagttcgttt ttttagctga aatcccttag aaaatcaccg     240
cacttttatt gttcaatagt cgtttaacca cgtattttt aatacgaaaa attacttaat      300
taaataaaca tt atg aaa aaa act gta ttt cgt ctg aat ttt tta acc gct    351
              Met Lys Lys Thr Val Phe Arg Leu Asn Phe Leu Thr Ala
                1               5                  10 tgc att tca tta ggg ata gta tcg caa gcg tgg gca ggt cat act tat    399
Cys Ile Ser Leu Gly Ile Val Ser Gln Ala Trp Ala Gly His Thr Tyr
    15                  20                  25 ttt ggg att gac tac caa tat tat cgt gat ttt gcc gag aat aaa ggg    447
Phe Gly Ile Asp Tyr Gln Tyr Tyr Arg Asp Phe Ala Glu Asn Lys Gly
30                  35                  40                  45 aag ttc aca gtt ggg gct aaa aat att gag gtt tac aat aaa aat gga    495
Lys Phe Thr Val Gly Ala Lys Asn Ile Glu Val Tyr Asn Lys Asn Gly
                50                  55                  60 aat tta gtt ggc aca tca atg aca aaa gcc cca atg att gat ttt tcc    543
Asn Leu Val Gly Thr Ser Met Thr Lys Ala Pro Met Ile Asp Phe Ser
            65                  70                  75 gtg gtg tcg cga aat ggg gtg gcg gca ttg gtg ggc gat cag tat att    591
Val Val Ser Arg Asn Gly Val Ala Ala Leu Val Gly Asp Gln Tyr Ile
        80                  85                  90 gtg agt gtg gca cat aat gta ggc tat acc aat gtg gat ttt ggt gct    639
Val Ser Val Ala His Asn Val Gly Tyr Thr Asn Val Asp Phe Gly Ala
    95                  100                 105 gaa gga caa aat cct gat caa cat cgt ttt act tat aaa att gtg aaa    687
Glu Gly Gln Asn Pro Asp Gln His Arg Phe Thr Tyr Lys Ile Val Lys
110                 115                 120                 125 cgg aat aat tat aaa aac gat caa acg cat cct tat gag aaa gac tac    735
Arg Asn Asn Tyr Lys Asn Asp Gln Thr His Pro Tyr Glu Lys Asp Tyr
                130                 135                 140 cac aac cca cgc tta cat aaa ttt gtt acg gaa gcc acc cca atc gat    783
His Asn Pro Arg Leu His Lys Phe Val Thr Glu Ala Thr Pro Ile Asp
            145                 150                 155 atg act tct gat atg aac ggc aac aaa tat aca gat agg acg aaa tat    831
Met Thr Ser Asp Met Asn Gly Asn Lys Tyr Thr Asp Arg Thr Lys Tyr
        160                 165                 170 ccc gaa cgc gtg cgt atc ggc tcc ggg tgg cag ttt tgg cga aac gat    879
Pro Glu Arg Val Arg Ile Gly Ser Gly Trp Gln Phe Trp Arg Asn Asp
    175                 180                 185 caa aac aac ggc gac caa gtt gcc ggc gca tat cat tac ctg aca gca    927
Gln Asn Asn Gly Asp Gln Val Ala Gly Ala Tyr His Tyr Leu Thr Ala
190                 195                 200                 205 ggc aat aca cac aac caa ggc gga gca ggg ggc ggc tgg tca agt ctg    975
Gly Asn Thr His Asn Gln Gly Gly Ala Gly Gly Gly Trp Ser Ser Leu
                210                 215                 220 agc ggc gat gtg cgc caa gcg ggc aat tac ggc ccc att cct att gca   1023
Ser Gly Asp Val Arg Gln Ala Gly Asn Tyr Gly Pro Ile Pro Ile Ala
            225                 230                 235 ggc tca agc ggc gac agc ggt tcg cct atg ttt att tat gat gcg gaa   1071
Gly Ser Ser Gly Asp Ser Gly Ser Pro Met Phe Ile Tyr Asp Ala Glu
        240                 245                 250 aaa caa aaa tgg ttg att aac ggc gta ttg agg acc ggc aac cct tgg   1119
```

```
                        -continued

Lys Gln Lys Trp Leu Ile Asn Gly Val Leu Arg Thr Gly Asn Pro Trp
    255                 260                 265 gcg ggg aca gag aat aca ttc caa ctg gta cgc aag tct ttt ttt gat      1167
Ala Gly Thr Glu Asn Thr Phe Gln Leu Val Arg Lys Ser Phe Phe Asp
270                 275                 280                 285 gaa atc ctt gaa aaa gat ttg cgt aca tcg ttt tat agc cca tcg ggc      1215
Glu Ile Leu Glu Lys Asp Leu Arg Thr Ser Phe Tyr Ser Pro Ser Gly
                    290                 295                 300 aat ggt gca tac acc att aca gac aaa ggc gac ggc agc ggc att gtc      1263
Asn Gly Ala Tyr Thr Ile Thr Asp Lys Gly Asp Gly Ser Gly Ile Val
                305                 310                 315 aaa caa caa aca gga aga cca tct gaa gtc cgc atc ggt tta aaa gac      1311
Lys Gln Gln Thr Gly Arg Pro Ser Glu Val Arg Ile Gly Leu Lys Asp
            320                 325                 330 gac aaa tta cct gcc gaa ggt aaa gac gat gtt tac caa tac caa ggt      1359
Asp Lys Leu Pro Ala Glu Gly Lys Asp Asp Val Tyr Gln Tyr Gln Gly
        335                 340                 345 cca aat ata tac ctg cct cgt ttg aat aac ggt gga aac ctg tat ttc      1407
Pro Asn Ile Tyr Leu Pro Arg Leu Asn Asn Gly Gly Asn Leu Tyr Phe
350                 355                 360                 365 gga gat caa aaa aac ggc act gtt acc tta tca acc aac atc aac caa      1455
Gly Asp Gln Lys Asn Gly Thr Val Thr Leu Ser Thr Asn Ile Asn Gln
                    370                 375                 380 ggt gcg ggc ggt ttg tat ttt gag ggt aac ttt acg gta tct tca gaa      1503
Gly Ala Gly Gly Leu Tyr Phe Glu Gly Asn Phe Thr Val Ser Ser Glu
                385                 390                 395 aat aat gca act tgg caa ggt gct gga gtg cat gta ggt gaa gac agt      1551
Asn Asn Ala Thr Trp Gln Gly Ala Gly Val His Val Gly Glu Asp Ser
            400                 405                 410 act gtt act tgg aaa gta aat ggt gtt gaa aat gat cgc ctt tct aaa      1599
Thr Val Thr Trp Lys Val Asn Gly Val Glu Asn Asp Arg Leu Ser Lys
        415                 420                 425 atc ggc aaa ggc aca ttg cac gtt aaa gcc aaa ggg gaa aat aaa ggt      1647
Ile Gly Lys Gly Thr Leu His Val Lys Ala Lys Gly Glu Asn Lys Gly
430                 435                 440                 445 tcg atc agc gta ggc gat ggt aaa gtc att ttg gag cag cag gca gac      1695
Ser Ile Ser Val Gly Asp Gly Lys Val Ile Leu Glu Gln Gln Ala Asp
                    450                 455                 460 gat caa ggc aac aaa caa gcc ttt agt gaa att ggc ttg gtt agt ggc      1743
Asp Gln Gly Asn Lys Gln Ala Phe Ser Glu Ile Gly Leu Val Ser Gly
                465                 470                 475 aga ggt acg gtt cag tta aac gat gac aag caa ttt aat act gat aaa      1791
Arg Gly Thr Val Gln Leu Asn Asp Asp Lys Gln Phe Asn Thr Asp Lys
            480                 485                 490 ttt tat ttc ggc ttc cgt ggt ggt cgc tta gat ctt aat ggg cat tca      1839
Phe Tyr Phe Gly Phe Arg Gly Gly Arg Leu Asp Leu Asn Gly His Ser
        495                 500                 505 tta acc ttt aaa cgt atc caa aat acg gat gag gga gca acg att gtt      1887
Leu Thr Phe Lys Arg Ile Gln Asn Thr Asp Glu Gly Ala Thr Ile Val
510                 515                 520                 525 aat cac aat gcc aca aca gaa tct aca gtg acc att act ggc agc gat      1935
Asn His Asn Ala Thr Thr Glu Ser Thr Val Thr Ile Thr Gly Ser Asp
                    530                 535                 540 acc att aat gac aac act ggc gat tta acc aat aaa cgt gat att gct      1983
Thr Ile Asn Asp Asn Thr Gly Asp Leu Thr Asn Lys Arg Asp Ile Ala
                545                 550                 555 ttt aat ggt tgg ttt ggt gat aaa gat gat act aaa aat act gga cgt      2031
Phe Asn Gly Trp Phe Gly Asp Lys Asp Asp Thr Lys Asn Thr Gly Arg
            560                 565                 570
```

-continued

```
ttg aat gtt act tac aat ccg ctt aac aaa gat aat cac ttc ctt cta    2079
Leu Asn Val Thr Tyr Asn Pro Leu Asn Lys Asp Asn His Phe Leu Leu
575                 580                 585 tca ggt gga aca aat tta aaa ggc aat att act caa gac ggt ggc act    2127
Ser Gly Gly Thr Asn Leu Lys Gly Asn Ile Thr Gln Asp Gly Gly Thr
590                 595                 600                 605 tta gtt ttt agt ggt cgc cca aca cca cac gca tac aat cat tta aat    2175
Leu Val Phe Ser Gly Arg Pro Thr Pro His Ala Tyr Asn His Leu Asn
            610                 615                 620 cgc cta aac gag ctt ggg cga cct aag ggc gaa gtg gtt att gat gac    2223
Arg Leu Asn Glu Leu Gly Arg Pro Lys Gly Glu Val Val Ile Asp Asp
            625                 630                 635 gat tgg atc aac cgt aca ttt aaa gct gaa aac ttc caa att aaa ggc    2271
Asp Trp Ile Asn Arg Thr Phe Lys Ala Glu Asn Phe Gln Ile Lys Gly
            640                 645                 650 gga agt acg gtg gtt tct cgc aat gtt tct tca att gaa gga aat tgg    2319
Gly Ser Thr Val Val Ser Arg Asn Val Ser Ser Ile Glu Gly Asn Trp
655                 660                 665 aca atc agc aat aac gcc aac gcg aca ttt ggt gtt gtg cca aat caa    2367
Thr Ile Ser Asn Asn Ala Asn Ala Thr Phe Gly Val Val Pro Asn Gln
670                 675                 680                 685 caa aat acc att tgc acg cgt tca gat tgg aca gga tta acg act tgt    2415
Gln Asn Thr Ile Cys Thr Arg Ser Asp Trp Thr Gly Leu Thr Thr Cys
            690                 695                 700 aaa aca gtt aat tta acc gat aaa aaa gtt att gat tcc ata ccg aca    2463
Lys Thr Val Asn Leu Thr Asp Lys Lys Val Ile Asp Ser Ile Pro Thr
            705                 710                 715 aca caa att aat ggc tct att aat tta act aat aat gca aca gtg aat    2511
Thr Gln Ile Asn Gly Ser Ile Asn Leu Thr Asn Asn Ala Thr Val Asn
            720                 725                 730 att cat ggt tta gca aaa ctt aat ggt aat gtc act tta ata aat cat    2559
Ile His Gly Leu Ala Lys Leu Asn Gly Asn Val Thr Leu Ile Asn His
735                 740                 745 agc caa ttt aca ttg agc aac aat gcc acc caa aca ggc aat atc caa    2607
Ser Gln Phe Thr Leu Ser Asn Asn Ala Thr Gln Thr Gly Asn Ile Gln
750                 755                 760                 765 ctt tca aat cac gca aat gca acg gtg gat aat gca aac ttg aac ggt    2655
Leu Ser Asn His Ala Asn Ala Thr Val Asp Asn Ala Asn Leu Asn Gly
            770                 775                 780 aat gtg cat tta acg gat tct gct caa ttt tct tta aaa aac agc cat    2703
Asn Val His Leu Thr Asp Ser Ala Gln Phe Ser Leu Lys Asn Ser His
            785                 790                 795 ttt tcg cac caa att cag ggc gac aaa gac aca aca gtg acg ttg gaa    2751
Phe Ser His Gln Ile Gln Gly Asp Lys Asp Thr Thr Val Thr Leu Glu
            800                 805                 810 aat gcg act tgg aca atg cct agc gat act aca ttg cag aat tta acg    2799
Asn Ala Thr Trp Thr Met Pro Ser Asp Thr Thr Leu Gln Asn Leu Thr
815                 820                 825 cta aat aat agt act gtt acg tta aat tca gct tat tca gct agc tca    2847
Leu Asn Asn Ser Thr Val Thr Leu Asn Ser Ala Tyr Ser Ala Ser Ser
830                 835                 840                 845 aat aat gcg cca cgt cac cgc cgt tca tta gag acg gaa aca acg cca    2895
Asn Asn Ala Pro Arg His Arg Arg Ser Leu Glu Thr Glu Thr Thr Pro
            850                 855                 860 aca tcg gaa gaa cat cgt ttc aac aca ttg aca gta aat ggt aaa ttg    2943
Thr Ser Glu Glu His Arg Phe Asn Thr Leu Thr Val Asn Gly Lys Leu
            865                 870                 875 agc ggg caa ggc aca ttc caa ttt act tca tct tta ttt ggc tat aaa    2991
Ser Gly Gln Gly Thr Phe Gln Phe Thr Ser Ser Leu Phe Gly Tyr Lys
880                 885                 890
```

```
agc gat aaa ata aaa tta tct aat gac gct gaa ggc gat tac aca tta      3039
Ser Asp Lys Ile Lys Leu Ser Asn Asp Ala Glu Gly Asp Tyr Thr Leu
895                 900                 905 gct gtt cgc gac aca ggc aaa gaa cct gtg acc ctt gag caa tta act      3087
Ala Val Arg Asp Thr Gly Lys Glu Pro Val Thr Leu Glu Gln Leu Thr
910                 915                 920                 925 tta att gaa ggc ttg gat aat caa ccc ttg cca gat aag cta aaa att      3135
Leu Ile Glu Gly Leu Asp Asn Gln Pro Leu Pro Asp Lys Leu Lys Ile
            930                 935                 940 act tta aaa aat aaa cac gtt gat gcg ggt gca tgg cgt tat gaa tta      3183
Thr Leu Lys Asn Lys His Val Asp Ala Gly Ala Trp Arg Tyr Glu Leu
        945                 950                 955 gtg aag aaa aac ggc gaa ttc cgc ttg cat aat cca ata aaa gag cag      3231
Val Lys Lys Asn Gly Glu Phe Arg Leu His Asn Pro Ile Lys Glu Gln
    960                 965                 970 gaa ttg cgc aat gat tta gta aaa gca gag caa gta gaa cga gca tta      3279
Glu Leu Arg Asn Asp Leu Val Lys Ala Glu Gln Val Glu Arg Ala Leu
975                 980                 985 gaa gca aaa caa gct gaa ctg act act aaa aaa caa aaa act gag gct      3327
Glu Ala Lys Gln Ala Glu Leu Thr Thr Lys Lys Gln Lys Thr Glu Ala
990                 995                 1000                1005 aaa gtg cgg tca aaa aga gcg gcg ttt tct gat acc ccg cct gat           3372
Lys Val Arg Ser Lys Arg Ala Ala Phe Ser Asp Thr Pro Pro Asp
                  1010                1015                1020 caa agc cag tta aac gca tta caa gcc gaa ctc gag acg att aat           3417
Gln Ser Gln Leu Asn Ala Leu Gln Ala Glu Leu Glu Thr Ile Asn
                  1025                1030                1035 gcc caa cag caa gtg gca caa gcg gtg caa aat cag aaa gta act           3462
Ala Gln Gln Gln Val Ala Gln Ala Val Gln Asn Gln Lys Val Thr
                  1040                1045                1050 gca ctt aac caa aag aac gag caa gtt aaa acc act caa gat aaa           3507
Ala Leu Asn Gln Lys Asn Glu Gln Val Lys Thr Thr Gln Asp Lys
                  1055                1060                1065 gca aat tta gtc ttg gca act gca ttg gtg gaa aaa gaa acc gct           3552
Ala Asn Leu Val Leu Ala Thr Ala Leu Val Glu Lys Glu Thr Ala
                  1070                1075                1080 cag att gat ttt gct aat gca aaa tta gct cag ttg aat tta aca           3597
Gln Ile Asp Phe Ala Asn Ala Lys Leu Ala Gln Leu Asn Leu Thr
                  1085                1090                1095 caa caa cta gaa aaa gcc tta gca gtg gct gag caa gca gaa aaa           3642
Gln Gln Leu Glu Lys Ala Leu Ala Val Ala Glu Gln Ala Glu Lys
                  1100                1105                1110 gag cgt aaa gct caa gag caa gcg aaa aga caa cgc aaa caa aaa           3687
Glu Arg Lys Ala Gln Glu Gln Ala Lys Arg Gln Arg Lys Gln Lys
                  1115                1120                1125 gac ttg atc agc cgt tat tca aat agt gcg tta tca gaa tta tct           3732
Asp Leu Ile Ser Arg Tyr Ser Asn Ser Ala Leu Ser Glu Leu Ser
                  1130                1135                1140 gca aca gta aat agt atg ctt tcc gtt caa gat gaa tta gat cgt           3777
Ala Thr Val Asn Ser Met Leu Ser Val Gln Asp Glu Leu Asp Arg
                  1145                1150                1155 ctt ttt gta gat caa gct caa tct gcg gtg tgg aca aat atc tca           3822
Leu Phe Val Asp Gln Ala Gln Ser Ala Val Trp Thr Asn Ile Ser
                  1160                1165                1170 cag gat aaa aga cgt tat gat tct gat gcg ttc cgt gct tat cag           3867
Gln Asp Lys Arg Arg Tyr Asp Ser Asp Ala Phe Arg Ala Tyr Gln
                  1175                1180                1185 cag aaa acg aac ttg cgt caa att ggg gtg caa aaa gcc tta gct           3912
Gln Lys Thr Asn Leu Arg Gln Ile Gly Val Gln Lys Ala Leu Ala
```

```
                    1190                    1195                    1200
aac gga cga att ggg  gca gtt ttc tcg cat  agc cgt tca gat aat        3957
Asn Gly Arg Ile Gly  Ala Val Phe Ser His  Ser Arg Ser Asp Asn
                1205                    1210                    1215 act ttt gat gaa cag  gtt aaa aat cac gca  aca tta acg atg atg        4002
Thr Phe Asp Glu Gln  Val Lys Asn His Ala  Thr Leu Thr Met Met
                1220                    1225                    1230 tcg ggt ttt gcc caa  tat caa tgg ggt gat  tta caa ttt ggt gta        4047
Ser Gly Phe Ala Gln  Tyr Gln Trp Gly Asp  Leu Gln Phe Gly Val
                1235                    1240                    1245 aac gtg gga acg gga  att agt gcg agt aaa  atg gct gaa gaa caa        4092
Asn Val Gly Thr Gly  Ile Ser Ala Ser Lys  Met Ala Glu Glu Gln
                1250                    1255                    1260 agc cga aaa att cat  cga aaa gcg ata aat  tat ggc gtg aat gca        4137
Ser Arg Lys Ile His  Arg Lys Ala Ile Asn  Tyr Gly Val Asn Ala
                1265                    1270                    1275 agt tat tcg ttc cat  tta ggg caa ttg ggt  att cag cct tat ttt        4182
Ser Tyr Ser Phe His  Leu Gly Gln Leu Gly  Ile Gln Pro Tyr Phe
                1280                    1285                    1290 gga gtt aat cgc tat  ttt att gaa cgt aaa  aat tat caa tct gag        4227
Gly Val Asn Arg Tyr  Phe Ile Glu Arg Lys  Asn Tyr Gln Ser Glu
                1295                    1300                    1305 gaa gtg aaa gtg caa  aca ccg agc ctt gca  ttt aat cgc tat aat        4272
Glu Val Lys Val Gln  Thr Pro Ser Leu Ala  Phe Asn Arg Tyr Asn
                1310                    1315                    1320 gct gga gta cgg gtc  gat tat acg ttt acc  ccg aca gag aat atc        4317
Ala Gly Val Arg Val  Asp Tyr Thr Phe Thr  Pro Thr Glu Asn Ile
                1325                    1330                    1335 agc gtt aag cct tat  ttc ttc gtc aat tat  gtt gat gtt tca aac        4362
Ser Val Lys Pro Tyr  Phe Phe Val Asn Tyr  Val Asp Val Ser Asn
                1340                    1345                    1350 gct aac gta caa acc  act gta aat cgc gcg  gtg ttg caa caa cca        4407
Ala Asn Val Gln Thr  Thr Val Asn Arg Ala  Val Leu Gln Gln Pro
                1355                    1360                    1365 ttt gga cgt tat tgg  caa aaa gaa gtg gga  tta aaa gcg gaa att        4452
Phe Gly Arg Tyr Trp  Gln Lys Glu Val Gly  Leu Lys Ala Glu Ile
                1370                    1375                    1380 tta cat ttc caa ctt  tct gct ttt att tct  aaa tct caa ggt tcg        4497
Leu His Phe Gln Leu  Ser Ala Phe Ile Ser  Lys Ser Gln Gly Ser
                1385                    1390                    1395 caa ctc ggt aaa cag  cga aat atg ggc gtg  aaa tta gga tat cgt        4542
Gln Leu Gly Lys Gln  Arg Asn Met Gly Val  Lys Leu Gly Tyr Arg
                1400                    1405                    1410 tgg taa aaatcaacat aattttattc taataatgga actttattta attaaaagta       4598
Trp tctaagtagc accctatagg ggattaatta agaggattta ataatgaatt taactaaaat    4658
tttacccgca tttgctgctg cagtcgtatt atctgcttgt gcaaaggatg cacctgaaat    4718
gacaaaatca tctgcgcaaa tagctgaaat gcaaacactt ccaacaatca ctgataaaac    4778
agttgtatat tcttgcaata aacaaactgt gactgcagtg tatcaatttg                4828

<210> SEQ ID NO 17
<211> LENGTH: 1411
<212> TYPE: PRT
<213> ORGANISM: Haemophilus influenzae

<400> SEQUENCE: 17

Met Lys Lys Thr Val Phe Arg Leu Asn Phe Leu Thr Ala Cys Ile Ser
1               5                   10                  15
```

-continued

```
Leu Gly Ile Val Ser Gln Ala Trp Ala Gly His Thr Tyr Phe Gly Ile
             20                  25                  30
Asp Tyr Gln Tyr Tyr Arg Asp Phe Ala Glu Asn Lys Gly Lys Phe Thr
         35                  40                  45
Val Gly Ala Lys Asn Ile Glu Val Tyr Asn Lys Asn Gly Asn Leu Val
 50                  55                  60
Gly Thr Ser Met Thr Lys Ala Pro Met Ile Asp Phe Ser Val Val Ser
 65                  70                  75                  80
Arg Asn Gly Val Ala Ala Leu Val Gly Asp Gln Tyr Ile Val Ser Val
                 85                  90                  95
Ala His Asn Val Gly Tyr Thr Asn Val Asp Phe Gly Ala Glu Gly Gln
            100                 105                 110
Asn Pro Asp Gln His Arg Phe Thr Tyr Lys Ile Val Lys Arg Asn Asn
            115                 120                 125
Tyr Lys Asn Asp Gln Thr His Pro Tyr Glu Lys Asp Tyr His Asn Pro
130                 135                 140
Arg Leu His Lys Phe Val Thr Glu Ala Thr Pro Ile Asp Met Thr Ser
145                 150                 155                 160
Asp Met Asn Gly Asn Lys Tyr Thr Asp Arg Thr Lys Tyr Pro Glu Arg
                165                 170                 175
Val Arg Ile Gly Ser Gly Trp Gln Phe Trp Arg Asn Asp Gln Asn Asn
            180                 185                 190
Gly Asp Gln Val Ala Gly Ala Tyr His Tyr Leu Thr Ala Gly Asn Thr
            195                 200                 205
His Asn Gln Gly Gly Ala Gly Gly Trp Ser Ser Leu Ser Gly Asp
            210                 215                 220
Val Arg Gln Ala Gly Asn Tyr Gly Pro Ile Pro Ile Ala Gly Ser Ser
225                 230                 235                 240
Gly Asp Ser Gly Ser Pro Met Phe Ile Tyr Asp Ala Glu Lys Gln Lys
                245                 250                 255
Trp Leu Ile Asn Gly Val Leu Arg Thr Gly Asn Pro Trp Ala Gly Thr
            260                 265                 270
Glu Asn Thr Phe Gln Leu Val Arg Lys Ser Phe Phe Asp Glu Ile Leu
            275                 280                 285
Glu Lys Asp Leu Arg Thr Ser Phe Tyr Ser Pro Ser Gly Asn Gly Ala
            290                 295                 300
Tyr Thr Ile Thr Asp Lys Gly Asp Gly Ser Gly Ile Val Lys Gln Gln
305                 310                 315                 320
Thr Gly Arg Pro Ser Glu Val Arg Ile Gly Leu Lys Asp Asp Lys Leu
                325                 330                 335
Pro Ala Glu Gly Lys Asp Asp Val Tyr Gln Tyr Gln Gly Pro Asn Ile
            340                 345                 350
Tyr Leu Pro Arg Leu Asn Asn Gly Gly Asn Leu Tyr Phe Gly Asp Gln
            355                 360                 365
Lys Asn Gly Thr Val Thr Leu Ser Thr Asn Ile Asn Gln Gly Ala Gly
            370                 375                 380
Gly Leu Tyr Phe Glu Gly Asn Phe Thr Val Ser Ser Glu Asn Asn Ala
385                 390                 395                 400
Thr Trp Gln Gly Ala Gly Val His Val Gly Glu Asp Ser Thr Val Thr
                405                 410                 415
Trp Lys Val Asn Gly Val Glu Asn Asp Arg Leu Ser Lys Ile Gly Lys
            420                 425                 430
```

-continued

```
Gly Thr Leu His Val Lys Ala Lys Gly Glu Asn Lys Gly Ser Ile Ser
        435                 440                 445

Val Gly Asp Gly Lys Val Ile Leu Glu Gln Gln Ala Asp Asp Gln Gly
        450                 455                 460

Asn Lys Gln Ala Phe Ser Glu Ile Gly Leu Val Ser Gly Arg Gly Thr
465                 470                 475                 480

Val Gln Leu Asn Asp Asp Lys Gln Phe Asn Thr Asp Lys Phe Tyr Phe
                485                 490                 495

Gly Phe Arg Gly Gly Arg Leu Asp Leu Asn Gly His Ser Leu Thr Phe
            500                 505                 510

Lys Arg Ile Gln Asn Thr Asp Glu Gly Ala Thr Ile Val Asn His Asn
        515                 520                 525

Ala Thr Thr Glu Ser Thr Val Thr Ile Thr Gly Ser Asp Thr Ile Asn
        530                 535                 540

Asp Asn Thr Gly Asp Leu Thr Asn Lys Arg Asp Ile Ala Phe Asn Gly
545                 550                 555                 560

Trp Phe Gly Asp Lys Asp Thr Lys Asn Thr Gly Arg Leu Asn Val
                565                 570                 575

Thr Tyr Asn Pro Leu Asn Lys Asp Asn His Phe Leu Leu Ser Gly Gly
                580                 585                 590

Thr Asn Leu Lys Gly Asn Ile Thr Gln Asp Gly Gly Thr Leu Val Phe
        595                 600                 605

Ser Gly Arg Pro Thr Pro His Ala Tyr Asn His Leu Asn Arg Leu Asn
        610                 615                 620

Glu Leu Gly Arg Pro Lys Gly Glu Val Val Ile Asp Asp Trp Ile
625                 630                 635                 640

Asn Arg Thr Phe Lys Ala Glu Asn Phe Gln Ile Lys Gly Gly Ser Thr
                645                 650                 655

Val Val Ser Arg Asn Val Ser Ser Ile Glu Gly Asn Trp Thr Ile Ser
            660                 665                 670

Asn Asn Ala Asn Ala Thr Phe Gly Val Val Pro Asn Gln Gln Asn Thr
        675                 680                 685

Ile Cys Thr Arg Ser Asp Trp Thr Gly Leu Thr Thr Cys Lys Thr Val
        690                 695                 700

Asn Leu Thr Asp Lys Lys Val Ile Asp Ser Ile Pro Thr Thr Gln Ile
705                 710                 715                 720

Asn Gly Ser Ile Asn Leu Thr Asn Asn Ala Thr Val Asn Ile His Gly
                725                 730                 735

Leu Ala Lys Leu Asn Gly Asn Val Thr Leu Ile Asn His Ser Gln Phe
            740                 745                 750

Thr Leu Ser Asn Asn Ala Thr Gln Thr Gly Asn Ile Gln Leu Ser Asn
        755                 760                 765

His Ala Asn Ala Thr Val Asp Asn Ala Asn Leu Asn Gly Asn Val His
        770                 775                 780

Leu Thr Asp Ser Ala Gln Phe Ser Leu Lys Asn Ser His Phe Ser His
785                 790                 795                 800

Gln Ile Gln Gly Asp Lys Asp Thr Thr Val Thr Leu Glu Asn Ala Thr
            805                 810                 815

Trp Thr Met Pro Ser Asp Thr Thr Leu Gln Asn Leu Thr Leu Asn Asn
        820                 825                 830

Ser Thr Val Thr Leu Asn Ser Ala Tyr Ser Ala Ser Ser Asn Asn Ala
        835                 840                 845

Pro Arg His Arg Arg Ser Leu Glu Thr Glu Thr Thr Pro Thr Ser Glu
```

-continued

```
                      850             855             860
Glu His Arg Phe Asn Thr Leu Thr Val Asn Gly Lys Leu Ser Gly Gln
865                 870             875                 880
Gly Thr Phe Gln Phe Thr Ser Ser Leu Phe Gly Tyr Lys Ser Asp Lys
                885             890             895
Ile Lys Leu Ser Asn Asp Ala Glu Gly Asp Tyr Thr Leu Ala Val Arg
            900             905             910
Asp Thr Gly Lys Glu Pro Val Thr Leu Glu Gln Leu Thr Leu Ile Glu
        915             920             925
Gly Leu Asp Asn Gln Pro Leu Pro Asp Lys Leu Lys Ile Thr Leu Lys
930             935             940
Asn Lys His Val Asp Ala Gly Ala Trp Arg Tyr Glu Leu Val Lys Lys
945             950             955             960
Asn Gly Glu Phe Arg Leu His Asn Pro Ile Lys Glu Gln Glu Leu Arg
            965             970             975
Asn Asp Leu Val Lys Ala Glu Gln Val Glu Arg Ala Leu Glu Ala Lys
            980             985             990
Gln Ala Glu Leu Thr Thr Lys Lys Gln Lys Thr Glu Ala Lys Val Arg
            995             1000            1005
Ser Lys Arg Ala Ala Phe Ser Asp Thr Pro Pro Asp Gln Ser Gln
    1010            1015            1020
Leu Asn Ala Leu Gln Ala Glu Leu Glu Thr Ile Asn Ala Gln Gln
    1025            1030            1035
Gln Val Ala Gln Ala Val Gln Asn Gln Lys Val Thr Ala Leu Asn
    1040            1045            1050
Gln Lys Asn Glu Gln Val Lys Thr Thr Gln Asp Lys Ala Asn Leu
    1055            1060            1065
Val Leu Ala Thr Ala Leu Val Glu Lys Glu Thr Ala Gln Ile Asp
    1070            1075            1080
Phe Ala Asn Ala Lys Leu Ala Gln Leu Asn Leu Thr Gln Gln Leu
    1085            1090            1095
Glu Lys Ala Leu Ala Val Ala Glu Gln Ala Glu Lys Glu Arg Lys
    1100            1105            1110
Ala Gln Glu Gln Ala Lys Arg Gln Arg Lys Gln Lys Asp Leu Ile
    1115            1120            1125
Ser Arg Tyr Ser Asn Ser Ala Leu Ser Glu Leu Ser Ala Thr Val
    1130            1135            1140
Asn Ser Met Leu Ser Val Gln Asp Glu Leu Asp Arg Leu Phe Val
    1145            1150            1155
Asp Gln Ala Gln Ser Ala Val Trp Thr Asn Ile Ser Gln Asp Lys
    1160            1165            1170
Arg Arg Tyr Asp Ser Asp Ala Phe Arg Ala Tyr Gln Gln Lys Thr
    1175            1180            1185
Asn Leu Arg Gln Ile Gly Val Gln Lys Ala Leu Ala Asn Gly Arg
    1190            1195            1200
Ile Gly Ala Val Phe Ser His Ser Arg Ser Asp Asn Thr Phe Asp
    1205            1210            1215
Glu Gln Val Lys Asn His Ala Thr Leu Thr Met Met Ser Gly Phe
    1220            1225            1230
Ala Gln Tyr Gln Trp Gly Asp Leu Gln Phe Gly Val Asn Val Gly
    1235            1240            1245
Thr Gly Ile Ser Ala Ser Lys Met Ala Glu Glu Gln Ser Arg Lys
    1250            1255            1260
```

```
Ile His Arg Lys Ala Ile Asn Tyr Gly Val Asn Ala Ser Tyr Ser
1265                1270                1275

Phe His Leu Gly Gln Leu Gly Ile Gln Pro Tyr Phe Gly Val Asn
1280                1285                1290

Arg Tyr Phe Ile Glu Arg Lys Asn Tyr Gln Ser Glu Glu Val Lys
1295                1300                1305

Val Gln Thr Pro Ser Leu Ala Phe Asn Arg Tyr Asn Ala Gly Val
1310                1315                1320

Arg Val Asp Tyr Thr Phe Thr Pro Thr Glu Asn Ile Ser Val Lys
1325                1330                1335

Pro Tyr Phe Phe Val Asn Tyr Val Asp Val Ser Asn Ala Asn Val
1340                1345                1350

Gln Thr Thr Val Asn Arg Ala Val Leu Gln Gln Pro Phe Gly Arg
1355                1360                1365

Tyr Trp Gln Lys Glu Val Gly Leu Lys Ala Glu Ile Leu His Phe
1370                1375                1380

Gln Leu Ser Ala Phe Ile Ser Lys Ser Gln Gly Ser Gln Leu Gly
1385                1390                1395

Lys Gln Arg Asn Met Gly Val Lys Leu Gly Tyr Arg Trp
1400                1405                1410
```

<210> SEQ ID NO 18
<211> LENGTH: 47
<212> TYPE: PRT
<213> ORGANISM: Haemophilus influenzae

<400> SEQUENCE: 18

```
Met Lys Lys Thr Val Phe Arg Leu Asn Phe Leu Thr Ala Cys Ile Ser
1               5                   10                  15

Leu Gly Ile Val Ser Gln Ala Trp Ala Gly His Thr Tyr Phe Gly Ile
            20                  25                  30

Asp Tyr Gln Tyr Tyr Arg Asp Phe Ala Glu Asn Lys Gly Lys Phe
        35                  40                  45
```

<210> SEQ ID NO 19
<211> LENGTH: 7
<212> TYPE: PRT
<213> ORGANISM: Haemophilus influenzae

<400> SEQUENCE: 19

```
Asn Pro Asp Gln His Arg Phe
1               5
```

<210> SEQ ID NO 20
<211> LENGTH: 11
<212> TYPE: PRT
<213> ORGANISM: Haemophilus influenzae

<400> SEQUENCE: 20

```
Gly Asp Ser Gly Ser Pro Met Phe Ile Tyr Asp
1               5                   10
```

<210> SEQ ID NO 21
<211> LENGTH: 14
<212> TYPE: PRT
<213> ORGANISM: Haemophilus influenzae

<400> SEQUENCE: 21

```
Ile Asn Gln Gly Ala Gly Gly Leu Tyr Phe Glu Gly Asn Gly
```

```
<210> SEQ ID NO 22
<211> LENGTH: 7
<212> TYPE: PRT
<213> ORGANISM: Haemophilus influenzae

<400> SEQUENCE: 22

Asp Arg Leu Ser Lys Ile Gly
1               5

<210> SEQ ID NO 23
<211> LENGTH: 18
<212> TYPE: PRT
<213> ORGANISM: Haemophilus influenzae

<400> SEQUENCE: 23

Tyr Phe Gly Phe Arg Gly Gly Arg Leu Asp Leu Asn Gly His Ser Leu
1               5                   10                  15

Thr Phe

<210> SEQ ID NO 24
<211> LENGTH: 15
<212> TYPE: PRT
<213> ORGANISM: Haemophilus influenzae

<400> SEQUENCE: 24

Arg Ile Gln Asn Thr Asp Glu Gly Ala Met Ile Val Asn His Asn
1               5                   10                  15

<210> SEQ ID NO 25
<211> LENGTH: 9
<212> TYPE: PRT
<213> ORGANISM: Haemophilus influenzae

<400> SEQUENCE: 25

Leu Leu Leu Ser Gly Gly Thr Asn Leu
1               5

<210> SEQ ID NO 26
<211> LENGTH: 13
<212> TYPE: PRT
<213> ORGANISM: Haemophilus influenzae

<400> SEQUENCE: 26

Phe Ser Gly Arg Pro Thr Pro His Ala Tyr Asn His Leu
1               5                   10

<210> SEQ ID NO 27
<211> LENGTH: 36
<212> TYPE: PRT
<213> ORGANISM: Haemophilus influenzae

<400> SEQUENCE: 27

Arg Thr Phe Lys Ala Glu Asn Phe Gln Ile Lys Gly Gly Ser Ala Val
1               5                   10                  15

Val Ser Arg Asn Val Ser Ser Ile Glu Gly Asn Trp Thr Val Ser Asn
                20                  25                  30

Asn Ala Asn Ala
            35

<210> SEQ ID NO 28
<211> LENGTH: 23
```

-continued

```
<212> TYPE: PRT
<213> ORGANISM: Haemophilus influenzae

<400> SEQUENCE: 28

Phe Gly Val Val Pro Asn Gln Gln Asn Thr Ile Cys Thr Arg Ser Asp
1               5                   10                  15

Trp Thr Gly Leu Thr Thr Cys
            20

<210> SEQ ID NO 29
<211> LENGTH: 7
<212> TYPE: PRT
<213> ORGANISM: Haemophilus influenzae

<400> SEQUENCE: 29

Lys Val Ile Asn Ser Ile Pro
1               5

<210> SEQ ID NO 30
<211> LENGTH: 14
<212> TYPE: PRT
<213> ORGANISM: Haemophilus influenzae

<400> SEQUENCE: 30

Thr Gln Ile Asn Gly Ser Ile Asn Leu Thr Asp Asn Ala Thr
1               5                   10

<210> SEQ ID NO 31
<211> LENGTH: 11
<212> TYPE: PRT
<213> ORGANISM: Haemophilus influenzae

<400> SEQUENCE: 31

Gly Leu Ala Lys Leu Asn Gly Asn Val Thr Leu
1               5                   10

<210> SEQ ID NO 32
<211> LENGTH: 12
<212> TYPE: PRT
<213> ORGANISM: Haemophilus influenzae

<400> SEQUENCE: 32

His Ser Gln Phe Thr Leu Ser Asn Asn Ala Thr Gln
1               5                   10

<210> SEQ ID NO 33
<211> LENGTH: 12
<212> TYPE: PRT
<213> ORGANISM: Haemophilus influenzae

<400> SEQUENCE: 33

Ala Thr Val Asp Asn Ala Asn Leu Asn Gly Asn Val
1               5                   10

<210> SEQ ID NO 34
<211> LENGTH: 18
<212> TYPE: PRT
<213> ORGANISM: Haemophilus influenzae

<400> SEQUENCE: 34

Asp Ser Ala Gln Phe Ser Leu Lys Asn Ser His Phe Ser His Gln Ile
1               5                   10                  15

Gln Gly
```

```
<210> SEQ ID NO 35
<211> LENGTH: 11
<212> TYPE: PRT
<213> ORGANISM: Haemophilus influenzae

<400> SEQUENCE: 35

Leu Glu Asn Ala Thr Trp Thr Met Pro Ser Asp
1               5                   10

<210> SEQ ID NO 36
<211> LENGTH: 11
<212> TYPE: PRT
<213> ORGANISM: Haemophilus influenzae

<400> SEQUENCE: 36

Thr Leu Gln Asn Leu Thr Leu Asn Asn Ser Thr
1               5                   10

<210> SEQ ID NO 37
<211> LENGTH: 8
<212> TYPE: PRT
<213> ORGANISM: Haemophilus influenzae

<400> SEQUENCE: 37

Thr Leu Asn Ser Ala Tyr Ser Ala
1               5

<210> SEQ ID NO 38
<211> LENGTH: 54
<212> TYPE: PRT
<213> ORGANISM: Haemophilus influenzae

<400> SEQUENCE: 38

Arg Arg Ser Leu Glu Thr Glu Thr Thr Pro Thr Ser Ala Glu His Arg
1               5                   10                  15

Phe Asn Thr Leu Thr Val Asn Gly Lys Leu Ser Gly Gln Gly Thr Phe
            20                  25                  30

Gln Phe Thr Ser Ser Leu Phe Gly Tyr Lys Ser Asp Lys Leu Ser Asn
        35                  40                  45

Asp Ala Glu Gly Asp Tyr
    50

<210> SEQ ID NO 39
<211> LENGTH: 10
<212> TYPE: PRT
<213> ORGANISM: Haemophilus influenzae

<400> SEQUENCE: 39

Leu Ser Val Arg Asn Thr Gly Lys Glu Pro
1               5                   10

<210> SEQ ID NO 40
<211> LENGTH: 10
<212> TYPE: PRT
<213> ORGANISM: Haemophilus influenzae

<400> SEQUENCE: 40

Gln Leu Thr Leu Val Glu Ser Lys Asp Asn
1               5                   10

<210> SEQ ID NO 41
<211> LENGTH: 20
<212> TYPE: PRT
```

```
<213> ORGANISM: Haemophilus influenzae

<400> SEQUENCE: 41

Phe Thr Leu Glu Asn Asp His Val Asp Ala Gly Ala Leu Arg Tyr Lys
1               5                   10                  15

Leu Val Lys Asn
            20

<210> SEQ ID NO 42
<211> LENGTH: 14
<212> TYPE: PRT
<213> ORGANISM: Haemophilus influenzae

<400> SEQUENCE: 42

Gly Glu Phe Arg Leu His Asn Pro Ile Lys Glu Gln Glu Leu
1               5                   10

<210> SEQ ID NO 43
<211> LENGTH: 18
<212> TYPE: PRT
<213> ORGANISM: Haemophilus influenzae

<400> SEQUENCE: 43

Asp Leu Val Arg Ala Glu Gln Ala Glu Arg Thr Leu Glu Ala Lys Gln
1               5                   10                  15

Val Glu

<210> SEQ ID NO 44
<211> LENGTH: 73
<212> TYPE: PRT
<213> ORGANISM: Haemophilus influenzae

<400> SEQUENCE: 44

Leu Ile Ser Arg Tyr Ser Asn Ser Ala Leu Ser Glu Leu Ser Ala Thr
1               5                   10                  15

Val Asn Ser Met Leu Ser Val Gln Asp Glu Leu Asp Arg Leu Phe Val
            20                  25                  30

Asp Gln Ala Gln Ser Ala Val Trp Thr Asn Ile Ala Gln Asp Lys Arg
        35                  40                  45

Arg Tyr Asp Ser Asp Ala Phe Arg Ala Tyr Gln Gln Lys Thr Asn Leu
    50                  55                  60

Arg Gln Ile Gly Val Gln Lys Ala Leu
65                  70

<210> SEQ ID NO 45
<211> LENGTH: 27
<212> TYPE: PRT
<213> ORGANISM: Haemophilus influenzae

<400> SEQUENCE: 45

Asn Gly Arg Ile Gly Ala Val Phe Ser His Ser Arg Ser Asp Asn Thr
1               5                   10                  15

Phe Asp Glu Gln Val Lys Asn His Ala Thr Leu
            20                  25

<210> SEQ ID NO 46
<211> LENGTH: 20
<212> TYPE: PRT
<213> ORGANISM: Haemophilus influenzae

<400> SEQUENCE: 46
```

Met Met Ser Gly Phe Ala Gln Tyr Gln Trp Gly Asp Leu Gln Phe Gly
1               5                   10                  15

Val Asn Val Gly
            20

<210> SEQ ID NO 47
<211> LENGTH: 40
<212> TYPE: PRT
<213> ORGANISM: Haemophilus influenzae

<400> SEQUENCE: 47

Gly Ile Ser Ala Ser Lys Met Ala Glu Gln Ser Arg Lys Ile His
1               5                   10                  15

Arg Lys Ala Ile Asn Tyr Gly Val Asn Ala Ser Tyr Gln Phe Arg Lys
            20                  25                  30

Gly Gln Leu Gly Ile Gln Pro Tyr
            35                  40

<210> SEQ ID NO 48
<211> LENGTH: 17
<212> TYPE: PRT
<213> ORGANISM: Haemophilus influenzae

<400> SEQUENCE: 48

Gly Val Asn Arg Tyr Phe Ile Glu Arg Glu Asn Tyr Gln Ser Glu Glu
1               5                   10                  15

Val

<210> SEQ ID NO 49
<211> LENGTH: 20
<212> TYPE: PRT
<213> ORGANISM: Haemophilus influenzae

<400> SEQUENCE: 49

Phe Asn Arg Asn Ala Gly Ile Arg Val Asp Tyr Thr Phe Thr Pro Thr
1               5                   10                  15

Asp Asn Ile Ser
            20

<210> SEQ ID NO 50
<211> LENGTH: 21
<212> TYPE: PRT
<213> ORGANISM: Haemophilus influenzae

<400> SEQUENCE: 50

Lys Pro Tyr Phe Phe Val Asn Tyr Val Asp Val Ser Asn Ala Asn Val
1               5                   10                  15

Gln Thr Thr Val Asn
            20

<210> SEQ ID NO 51
<211> LENGTH: 19
<212> TYPE: PRT
<213> ORGANISM: Haemophilus influenzae

<400> SEQUENCE: 51

Phe Gly Arg Tyr Trp Gln Lys Glu Val Gly Leu Lys Ala Glu Ile Leu
1               5                   10                  15

His Phe Gln

<210> SEQ ID NO 52

```
<211> LENGTH: 26
<212> TYPE: PRT
<213> ORGANISM: Haemophilus influenzae

<400> SEQUENCE: 52

Ser Ala Phe Ile Ser Lys Ser Gln Gly Ser Gln Leu Gly Lys Gln Gln
1               5                   10                  15
Asn Val Gly Val Lys Leu Gly Tyr Arg Trp
            20                  25

<210> SEQ ID NO 53
<211> LENGTH: 8
<212> TYPE: PRT
<213> ORGANISM: Haemophilus influenzae

<400> SEQUENCE: 53

Gly Asp Ser Gly Ser Pro Met Phe
1               5

<210> SEQ ID NO 54
<211> LENGTH: 8
<212> TYPE: PRT
<213> ORGANISM: Neisseria gonorrhoeae

<400> SEQUENCE: 54

Gly Asp Ser Gly Ser Pro Leu Phe
1               5

<210> SEQ ID NO 55
<211> LENGTH: 7
<212> TYPE: PRT
<213> ORGANISM: Haemophilus influenzae

<400> SEQUENCE: 55

His Thr Tyr Phe Gly Ile Asp
1               5

<210> SEQ ID NO 56
<211> LENGTH: 28
<212> TYPE: DNA
<213> ORGANISM: Haemophilus influenzae

<400> SEQUENCE: 56
tgcaggatcc ccgcagactg gattgttg                                28

<210> SEQ ID NO 57
<211> LENGTH: 28
<212> TYPE: DNA
<213> ORGANISM: Haemophilus influenzae

<400> SEQUENCE: 57
tgcaggatcc gatctgcccc accttgtt                                28

<210> SEQ ID NO 58
<211> LENGTH: 7
<212> TYPE: PRT
<213> ORGANISM: Haemophilus influenzae

<400> SEQUENCE: 58

Gly Asp Ser Gly Ser Pro Met
1               5
```

HAEMOPHILUS ADHERENCE AND PENETRATION PROTEINS

This is a divisional of application Ser. NO. 10/080,505, filed Feb. 22, 2002, now U.S. Pat. No. 6,676,948, which is a continuation-part of application Ser. No. 08/296,791, filed Aug. 25, 1994, now U.S. Pat. No. 6,245,337 and Ser. No. 09/839,996, filed Apr. 20, 2001, now U.S. Pat. No. 6,642,371, which is a divisional of application Ser. No. 08,296,791 filed Aug. 25, 1994 now U.S. Pat. No. 6,245,337.

FIELD OF THE INVENTION

The invention relates to *Haemophilus* adhesion and penetration proteins, nucleic acids, and vaccines.

BACKGROUND OF THE INVENTION

Most bacterial diseases begin with colonization of a particular mucosal surface (Beachey et al., 1981, J. Infect. Dis. 143:325–345). Successful colonization requires that an organism overcome mechanical cleansing of the mucosal surface and evade the local immune response. The process of colonization is dependent upon specialized microbial factors that promote binding to host cells (Hultgren et al., 1993 Cell, 73:887–901). In some cases the colonizing organism will subsequently enter (invade) these cells and survive intracellularly (Falkow, 1991, Cell 65:1099–1102).

*Haemophilus influenzae* is a common commensal organism of the human respiratory tract (Kuklinska and Kilian, 1984, Eur. J. Clin. Microbiol. 3:249–252). It is a human-specific organism that normally resides in the human nasopharynx and must colonize this site in order to avoid extinction. This microbe has a number of surface structures capable of promoting attachment to host cells (Guerina et al., 1982, J. Infect. Dis. 146:564; Pichichero et al., 1982, Lancet ii:960–962; St. Geme et al., 1993, Proc. Natl. Acad. Sci. U.S.A. 90:2875–2879). In addition, *H. influenzae* has acquired the capacity to enter and survive within these cells (Forsgren et al., 1994, Infect. Immun. 62:673–679; St. Geme and Falkow, 1990, Infect. Immun. 58:4036–4044; St. Geme and Falkow, 1991, Infect. Immun. 59:1325–1333, Infect. Immun. 59:3366–3371). As a result, this bacterium is an important cause of both localized respiratory tract and systemic disease (Turk, 1984, J. Med. Microbiol. 18:1–16). Nonencapsulated, non-typable (NT) strains account for the majority of local disease (Turk, 1984, supra); in contrast, serotype b strains, which express a capsule composed of a polymer of ribose and ribitol-5-phosphate (PRP), are responsible for over 95% of cases of *H. influenzae* systemic disease (Turk, 1982, Clinical importance of *Haemophilus influenzae*, p. 3–9. In S. H. Sell and P. F. Wright (ed.), *Haemophilus influenzae* epidemiology, immunology, and prevention of disease. Elsevier/North-Holland Publishing Co., New York).

The initial step in the pathogenesis of disease due to *H. influenzae* involves colonization of the upper respiratory mucosa (Murphy et al., 1987, J. Infect. Dis. 5:723–731). Colonization with a particular strain may persist for weeks to months, and most individuals remain asymptomatic throughout this period (Spinosa et al., 1986, I. Infect. Dis. 154:100–109). However, in certain circumstances colonization will be followed by contiguous spread within the respiratory tract, resulting in local disease in the middle ear, the sinuses, the conjunctiva, or the lungs. Alternatively, on occasion bacteria will penetrate the nasopharyngeal epithelial barrier and enter the bloodstream.

In vitro observations and animal studies suggest that bacterial surface appendages called pili (or fimbriae) play an important role in *H. influenzae* colonization. In 1982 two groups reported a correlation between piliation and increased attachment to human oropharyngeal epithelial cells and erythrocytes (Guerina et al., supra; Pichichero et al., supra). Other investigators have demonstrated that anti-pilus antibodies block in vitro attachment by piliated *H. influenzae* (Forney et al., 1992, J. Infect. Dis. 165:464–470; van Alphen et al., 1988, Infect. Immun. 56:1800–1806). Recently Weber et al. insertionally inactivated the pilus structural gene in an *H. influenzae* type b strain and thereby eliminated expression of pili; the resulting mutant exhibited a reduced capacity for colonization of year-old monkeys (Weber et al., 1991, Infect. Immun. 59:4724–4728).

A number of reports suggest that nonpilus factors also facilitate *Haemophilus* colonization. Using the human nasopharyngeal organ culture model, Farley et al. (1986, J. Infect. Dis. 15 161:274–280) and Loeb et al. (1988, Infect. Immun. 49:484–489) noted that nonpiliated type b strains were capable of mucosal attachment. Read and coworkers made similar observations upon examining nontypable strains in a model that employs nasal turbinate tissue in organ culture (1991, J. Infect. Dis. 163:549–558). In the monkey colonization study by Weber et al. (1991, supra), nonpiliated organisms retained a capacity for colonization, though at reduced densities; moreover, among monkeys originally infected with the piliated strain, virtually all organisms recovered from the nasopharynx were nonpiliated. All of these observations are consistent with the finding that nasopharyngeal isolates from children colonized with *H. influenzae* are frequently nonpiliated (Mason et al., 1985, Infect. Immun. 49:98–103; Brinton et al., 1989, Pediatr. Infect. Dis. J. 8:554–561).

Previous studies have shown that *H. influenzae* are capable of entering (invading) cultured human epithelial cells via a pili-independent mechanism (St. Geme and Falkow, 1990, supra; St. Geme and Falkow, 1991, supra). Although *H. influenzae* is not generally considered an intracellular parasite, a recent report suggests that these in vitro findings may have an in vivo correlate (Forsgren et al., 1994, supra). Forsgren and coworkers examined adenoids from 10 children who had their adenoids removed because of long-standing secretory otitis media or adenoidal hypertrophy. In all 10 cases there were viable intracellular *H. influenzae*. Electron microscopy demonstrated that these organisms were concentrated in the reticular crypt epithelium and in macrophage-like cells in the subepithelial layer of tissue. One possibility is that bacterial entry into host cells provides a mechanism for evasion of the local immune response, thereby allowing persistence in the respiratory tract.

Thus, a vaccine for the therapeutic and prophylactic treatment of *Haemophilus* infection is desirable. Accordingly, it is an object of the present invention to provide for recombinant Haemophilus Adherence and Penetration (HAP) proteins and variants thereof, and to produce useful quantities of these HAP proteins using recombinant DNA techniques.

It is a further object of the invention to provide recombinant nucleic acids encoding HAP proteins, and expression vectors and host cells containing the nucleic acid encoding the HAP protein.

An additional object of the invention is to provide monoclonal antibodies for the diagnosis of *Haemophilus* infection.

A further object of the invention is to provide methods for producing the HAP proteins, and a vaccine comprising the HAP proteins of the present invention. Methods for the therapeutic and prophylactic treatment of *Haemophilus* infection are also provided.

SUMMARY OF THE INVENTION

In accordance with the foregoing objects, the present invention provides recombinant HAP proteins, and isolated or recombinant nucleic acids which encode the HAP proteins of the present invention. Also provided are expression vectors which comprise DNA encoding a HAP protein operably linked to transcriptional and translational regulatory DNA, and host cells which contain the expression vectors.

The invention also provides methods for producing HAP proteins which comprises culturing a host cell transformed with an expression vector and causing expression of the nucleic acid encoding the HAP protein to produce a recombinant HAP protein.

The invention also includes vaccines for *Haemophilus influenzae* infection comprising an HAP protein for prophylactic or therapeutic use in generating an immune response in a patient. Methods of treating or preventing *Haemophilus influenzae* infection comprise administering a vaccine.

BRIEF DESCRIPTION OF THE DRAWINGS

FIGS. 1A and 1B depict light micrographs of *H. influenzae* strains DB117(pGJB103) and DB117(pN187) incubated with Chang epithelial cells. Bacteria were incubated with an epithelial monolayer for 30 minutes before rinsing and straining with Giemsa stain. FIG. 1A: *H. influenzae* strain DB117 carrying cloning vector alone (pGJB103); FIG. 1B: *H. influenzae* strain DB117 harboring recombinant plasmid pN187. Bar represents 3.5 μm.

FIGS. 2A, 2B, 2C and 2D depict thin section transmission electron micrographs demonstrating interaction between *H. influenzae* strains N187 and DB117(pN187) with Chang epithelial cells. Bacteria were incubated with epithelial monolayers for four hours before rinsing and processing for examination by transmission electron microscopy. FIG. 2A: strain N187 associated with the epithelial cell surface and present in an intracellular location; FIG. 2B: *H. influenzae* DB117 (pN187) in intimate contact with the epithelial cell surface; FIG. 2C: strain DB117(pN187) in the process of entering an epithelial cell; FIG. 2D: strain DB117(pN187) present in an intracellular location. Bar represents 1 μm.

FIG. 3 depicts outer membrane protein profiles of various strains. Outer membrane proteins were isolated on the basis of sarcosyl insolubility and resolved on a 10% SDS-polyacrylamide gel. Proteins were visualized by staining with Coomassie blue. Lane 1, *H. influenzae* strain DB117 (pGJB103); lane 2, strain DB117(pN187); lane 3, strain DB117(pJS106); lane 4, *E. coli* HB101(pGJB103); lane 5, HB101(pN187). Note novel proteins at ~160 kD and 45 kD marked by asterisks in lanes 2 and 3.

FIG. 5 depicts the identification of plasmid-encoded proteins using the bacteriophage T7 expression system. Bacteria were radiolabeled with [$^{35}$S] methionine, and whole cell lysates were resolved on a 10% SDS-polyacrylamide gel. Proteins were visualized by autoradiography. Lane 1, *E. coli* XL-1 Blue(pT7-7) uninduced; lane 2, XL-1 Blue(pT7-7) induced with IPTG; lane 3, XL-1 Blue(pJS103) uninduced; lane 4, XL-1 Blue(pJS103) induced with IPTG; lane 5, XL-1 Blue(pJS104) uninduced; lane 6, XL-1 Blue(pJS104) induced with IPTG. The plasmids pJS103 and pJS104 are derivatives of pT7-7 that contain the 6.7-kb PstI fragment from pN187 in opposite orientations. Asterisk indicates overexpressed protein in XL-1 Blue(pJS104).

FIGS. 6A–F depict the nucleotide sequence (SEQ ID NO: 1) and predicted amino acid sequence (SEQ ID NO: 2) of hap gene. Putative −10 and −35 sequences 5' to the hap coding sequence are underlined; a putative rho-independent terminator 3' to the hap stop codon is indicated with inverted arrows. The first 25 amino acids of the protein, which are boxed, represent the signal sequence.

FIGS. 7A–J depict a sequence comparison of the hap product (SEQ ID NO: 2) and the cloned *H. influenzae* IgA1 proteases (SEQ ID NO: 3–6). Amino acid homologies between the deduced hap gene product and the iga gene products from *H influenzae* HK368 (SEQ ID NO: 3), HK61 (SEQ ID NO: 6), HK393 (SEQ ID NO: 4), and HK715 (SEQ ID NO: 5) are shown. Dashes indicate gaps introduced in the sequences in order to obtain maximal homology. A consensus sequence for the five proteins is shown on the lower line. The conserved serine-type protease catalytic domain is underlined, and the common active site serine is denoted by an asterisk. The conserved cysteines are also indicated by asterisks.

FIG. 8 depicts the IgA1 protease activity assay. Culture supernatants were assayed for the ability to cleave IgA1. Reaction mixtures were resolved on a 10% SDS-polyacrylamide gel and then transferred to a nitrocellulose membrane. The membrane was probed with antibody against human IgA1 heavy chain. Lane 1, *H. influenzae* strain N187; lane 2, strain DB117(pGJB103); lane 3, strain DB117 (pN187). The cleavage product patterns suggest that strain N187 contains a type 2 IgA1 protease while strains DB117 (pGJB103) and DB117(pN187) contain a type 1 enzyme. The upper band of ~70-kD seen with the DB117 derivatives represents intact IgA1 heavy chain.

FIGS. 9A and 9B depict southern analysis of chromosomal DNA from strain *H. influenzae* N187, probing with hap versus iga. DNA fragments were separated on a 0.7% agarose gel and transferred bidirectionally to nitrocellulose membranes prior to probing with either hap or iga. Lane 1, N187 chromosomal DNA digested with EcoRI; lane 2, N187 chromosomal DNA digested with Bg/II; lane 3, N187 chromosomal DNA digested with BamHI; lane 4, the 4.8-kb ClaI-PstI fragment from pN187 that contains the intact hap gene. FIG. 9A: Hybridization with the 4.8-kb ClaI-PstI fragment containing the hap gene; FIG. 9B: hybridization with the iga gene from *H. influenzae* strain Rd, carried as a 4.8-kb ClaI-EcoRI fragment in pVD116.

FIG. 10 depicts a SDS-polyacrylamide gel of secreted proteins. Bacteria were grown to late log phase, and culture supernatants were precipitated with trichloroacetic acid and then resolved on a 10% SDS-polyacrylamide gel. Proteins were visualized by staining with Coomassie blue. Lane 1, *H. influenzae* strain DB117(pGJB103); lane 2, DB117(pN187); lane 3, DB117(pJS106); lane 4, DB117(pJS102); lane 5, DB117(pJS105); lane 6, DB117(Tn10-18); lane 7, DB117 (Tn10-4'); lane 8, DB117(Tn10-30); lane 9, DB117(Tn10-16); lane 10, DB117(Tn10-10); lane 11, DB117(Tn10-8); lane 12, N187. Asterisk indicates 110-kd secreted protein encoded by hap.

FIGS. 11A–D depict an alignment of the deduced amino acid sequence of HAP proteins obtained from various *H. influenzae* strains. The strains include N187 (SEQ ID NO: 7), TN106 (SEQ ID NO: 11) and 860295 (SEQ ID NO: 13).

FIGS. 12A–B depict Western blot of Hap proteins. Panel A shows outer membrane proteins, and panel B shows culture supernatants after precipitation with trichloroacetic acid. In each panel, lane 1 contains DB117/pGJB103 (vector), lane 2 contains DB117/pJS106 (encoding HapN187), lane 3 contains DB117/pHapP860295, and lane 4 contains DB117/pHapTN106. Inmunoblotting was performed with guinea pig antiserum GP74, which was raised against purified Hap$_s$ from strain N187 and recognizes full-length Hap in outer membranes and Hap$_s$ in culture supernatants. Without being bound by theory, it is thought that the lower band in lane 3 of panel B presumably reflects autoproteolysis of multiple sites in Hap from strain P860925 (Fink et al; 2001).

FIG. 13 Adherence to Chang epithelial cells by *H. influenzae* strain DB117 expressing HapN187, HapTN106, or HapP860295 and the inhibitory effect of preincubation with anti-Haps antiserum. Adherence was determined in 30 minute assays and was calculated by dividing the number of adherent bacteria by the number of inoculated bacteria. For all strains, inocula were approximately 2×10$^7$ CFU/ml. Bars represent the mean+standard error of the mean.

FIG. 14 depicts SDS-PAGE of purified HAPs proteins from both strain P860295 and strain N187. Amino terminal amino acid sequencing confirmed that purified protein was Haps.

FIG. 15 depicts clearance of NTHi TN106.P2 in Balb/c mice vaccinated with Hap$_s$ P860295 with and without CT-E29H. Six week old female Balb/c mice were vaccinated intranasally with Hap$_s$ from P860295, HAP+CT-E29H, or Formalin Fixed TN106.P2 in a 40 μl volume at weeks 0, 1, 3, & 5. Five animals from each group were IN challenged with ~1×10$^6$ CFU/; mouse in 10 μl, 2 and 3 weeks post vaccination. Nasal tissue were harvested 3 days after challenge. (*=Statistically different from 0.1 μg E29H control/Student's T test; @=Statistically different from PBS control/Student's T test.

FIGS. 16A–B depict the nucleotide sequence for NTHi strain 11 hap gene (SEQ ID NO: 8) (start codon to stop codon).

FIG. 17 depicts the amino acid sequence for NTHi strain 11 Hap protein (SEQ ID NO: 9) (first amino acid to last amino acid).

FIGS. 18A–C depict the nucleotide sequence for NTHi strain TN106 hap gene (SEQ ID NO: 10) (start codon begins at position 422, stop codon begins at position 4595).

FIG. 19 depicts the amino acid sequence for NTHi strain TN106 Hap protein (SEQ ID NO: 11) (first amino acid to last amino acid).

FIGS. 20A–C depict the nucleotide sequence for NTHi strain 860295 hap gene (SEQ ID NO: 12) (start codon begins at position 430, stop codon begins at position 4738).

FIG. 21 depicts the amino acid sequence for NTHi strain 860295 Hap protein (SEQ ID NO: 13) (first amino acid to last amino acid).

FIGS. 22A–C depict the nucleotide sequence for NTHi strain 3219B hap gene (SEQ ID NO: 14) (start codon begins at position 388, stop codon begins at position 4561).

FIG. 23 depicts the amino acid sequence for NTHi strain 3219B Hap protein (SEQ ID NO: 15) (first amino acid to last amino acid).

FIGS. 24A–C depict the nucleotide sequence for NTHi strain 1396B hap gene (SEQ ID NO: 16)(start codon begins at position 313, stop codon begins at position 4546).

FIG. 25 depicts the amino acid sequence for NTHi strain 1396B Hap protein (SEQ ID NO: 17) (first amino acid to last amino acid).

DETAILED DESCRIPTION OF THE INVENTION

Figure 4:
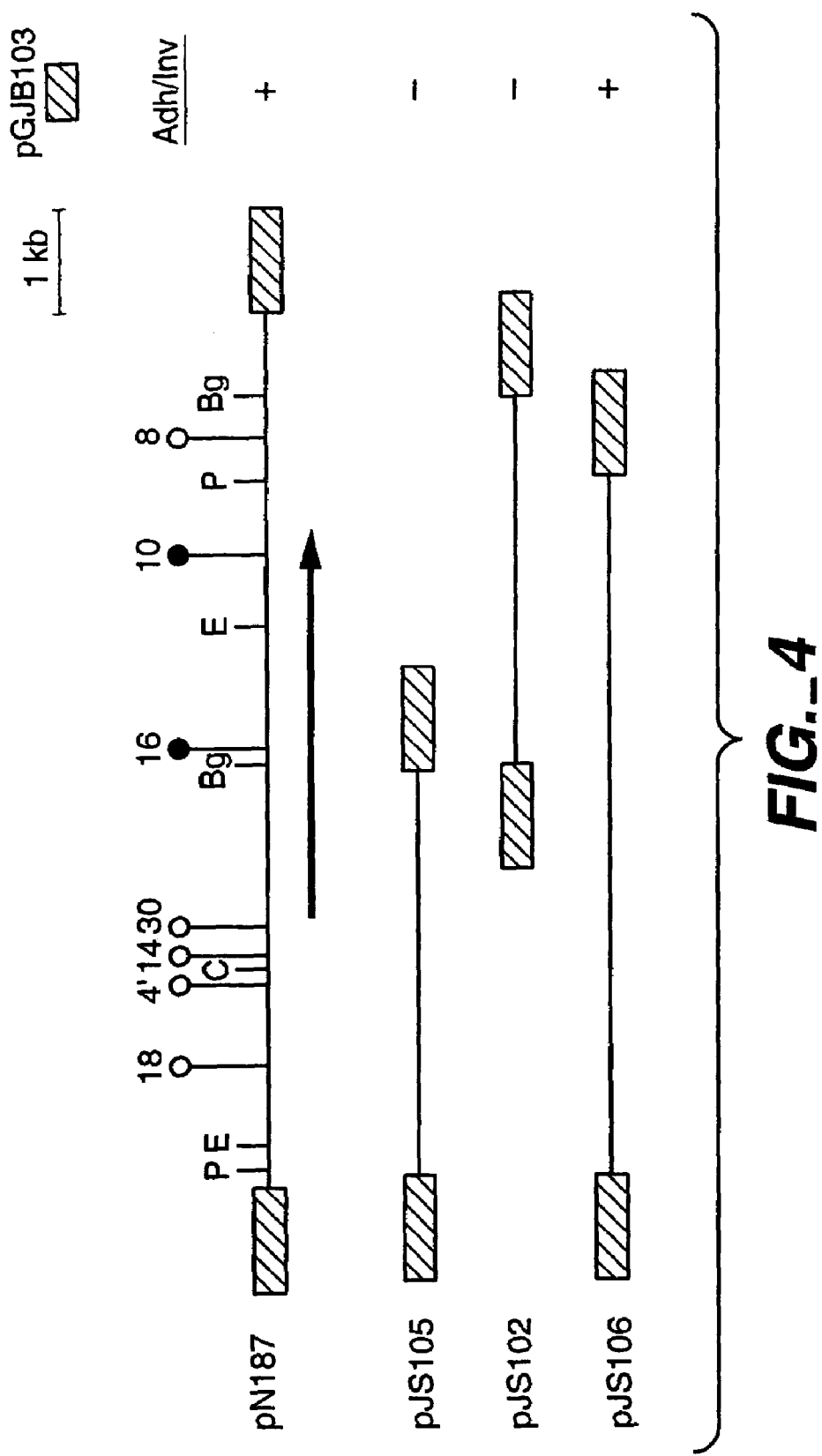
FIG. 4 depicts a restriction map of pN187 and derivatives and locations of mini-Tn10 kan insertions. pN187 is a derivative of pGJB103 that contains an 8.5-kb Sau3AI fragment of chromosomal DNA from *H. influenzae* strain N187. Vector sequences are represented by hatched boxes. Letters above top horizontal line indicate restriction enzyme sites: Bg, Bg/II; C, ClaI; E, EcoRI; P, PstI. Numbers and lollipops above top horizontal line show positions of mini-Tn 10 kan insertions; open lollipops represent insertions that have no effect on adherence and invasion, while closed lollipops indicate insertions that eliminate the capacity of pN187 to promote association with epithelial monolayers. Heavy horizontal line with arrow represents location of hap locus within pN187 and direction of transcription. (+): recombinant plasmids that promote adherence and invasion; (−): recombinant plasmids that fail to promote adherence and invasion.

The present invention provides novel *Haemophilus* Adhesion and Penetration (HAP) proteins. In a preferred embodiment, the HAP proteins are from *Haemophilus* strains, and in the preferred embodiment, from *Haemophilus influenzae*. However, using the techniques outlined below, HAP proteins from other *Haemophilus influenzae* strains, including but not limited to NTHI TN 106, TN106.P2, N187, P860295, 11, 3219B, 1396B or from other bacterial species such as *Neisseria* spp. or *Bordetella* spp. may also be obtained.

A HAP protein may be identified in several ways. A HAP nucleic acid or HAP protein is initially identified by substantial nucleic acid and/or amino acid sequence homology to the sequences shown in FIG. 6. Such homology can be based upon the overall nucleic acid or amino acid sequence. In addition a HAP protein is identifiable by substantial amino acid sequence homology or identity to the sequences shown in FIG. 11 (SEQ ID NOS 7, 11, 13), 17 (SEQ ID NO 9), 19 (SEQ ID NO 11), 21 (SEQ ID NO 13), 23 (SEQ ID NO 15) or 25 (SEQ ID NO 17). In addition a HAP nucleic acid is identified by substantial nucleic acid sequence indentity to the sequences set forth in FIGS. 16 (SEQ ID NO 8), 18 (SEQ ID NO 10), 20 (SEQ ID NO 12), 22 (SEQ ID NO 14), or 24 (SEQ ID NO 16).

The HAP proteins of the present invention have limited homology to *Haemophilus influenzae* and *N. gonorrhoeae* serine-type IgA1 proteases. This homology, shown in FIG. 7, is approximately 30–35% at the amino acid level, with several stretches showing 55–60% identity, including amino acids 457–549, 399–466, 572–622, and 233–261. However, the homology between the HAP protein and the IgA1 protease is considerably lower than the similarity among the IgA1 proteases themselves.

In addition, the full length HAP protein has homology to Tsh, a hemagglutinin expressed by an avian *E. coli* strain (Provence and Curtiss 1994, Infect. Immun. 62:1369–1380). The homology is greatest in the N-terminal half of the proteins, and the overall homology is 30.5% homologous. The full length HAP protein also has homology with pertactin, a 69 kD outer membrane protein expressed by *B. pertussis*, with the middle portion of the proteins showing 39% homology. HAP also has 34–52% homology with six regions of HpmA, a calcium-independent hemolysin expressed by *Proteus mirabilis* (Uphoff and Welch, 1990, J. Bacteriol. 172:1206–1216).

As used herein, a protein is a "HAP protein" if the overall homology of the protein sequence to one of the amino acid sequences shown in FIG. 6, 11, 17, 19, 21, 23, or 25, is preferably greater than about 40–50%, more preferably greater than about 60% and most preferably greater than 80%. In some embodiments the homology will be as high as about 90 to 95 or 98%. This homology will be determined using standard techniques known in the art, such as the Best Fit sequence program described by Devereux et al., *Nucl. Acid Res.* 12:387–395 (1984). The alignment may include the introduction of gaps in the sequences to be aligned. In addition, for sequences which contain either more or fewer amino acids than the proteins shown in FIG. 6 or FIG. 11, it is understood that the percentage of homology will be determined based on the number of homologous amino acids in relation to the total number of amino acids. Thus, for example, homology of sequences shorter than that shown in FIG. 6 or 11, as discussed below, will be determined using the number of amino acids in the shorter sequence.

HAP proteins of the present invention may be shorter than the amino acid sequence shown in FIG. 6 or 11. As shown in the Examples, the HAP protein may undergo post-translational processing similar to that seen for the serine-type IgA1 proteases expressed by *Haemophilus influenzae* and *N. gonorrhoeae*. These proteases are synthesized as preproteins with three functional domains: the N-terminal signal peptide, the protease, and a C-terminal helper domain. Following movement of these proteins into the periplasmic space, the carboxy terminal β-domain of the proenzyme is inserted into the outer membrane, possibly forming a pore (Poulsen et al., 1989, Infect. Immun. 57:3097–3105; Pohlner et al., 1987, Nature (London). 325:458–462; Klauser et al., 1992, EMBO J. 11:2327–2335; Klauser et al., 1993, J. Mol. Biol. 234:579–593). Subsequently the amino end of the protein is exported through the outer membrane, and autoproteolytic cleavage occurs to result in secretion of the mature 100 to 106-kD protease. The 45 to 56-kD C-terminal β-domain remains associated with the outer membrane following the cleavage event. As shown in the Examples, the HAP nucleic acid is associated with expression of a 155 kD outer membrane protein. The secreted gene product is an approximately 110 kD protein, with the simultaneous appearance of a 45 kD outer membrane protein. The 45 kD protein corresponds to amino acids from about 1037 to about 1395 of FIG. 6. Any one of these proteins is considered a HAP protein for the purposes of this invention.

Thus, in a preferred embodiment, included within the defintion of HAP proteins are portions or fragments of the sequence shown in FIG. 6 or 11. The fragments may be fragments of the entire sequence, the 110 kD sequence, or the 45 kD sequence. Generally, the HAP protein fragments may range in size from about 10 amino acids to about 1900 amino acids, with from about 50 to about 1000 amino acids being preferred, and from about 100 to about 500 amino acids also preferred. Particularly preferred fragments are sequences unique to HAP; these sequences have particular use in cloning HAP proteins from other organisms or to generate antibodies specific to HAP proteins. Unique sequences are easily identified by those skilled in the art after examination of the HAP protein sequence and comparison to other proteins; for example, by examination of the sequence alignment shown in FIG. 7. For instance, as compared to the IgA proteases, unique sequences include, but are not limited to, amino acids 11–14, 16–22, 108–120, 155–164, 257–265, 281–288, 318–336, 345–353, 398–416, 684–693, 712–718, 753–761, 871–913, 935–953, 985–1008, 1023–1034, 1067–1076, 1440–1048, 1585–1592, 1631–1639, 1637–1648, 1735–1743, 1863–1871, 1882–1891, 1929–1941, and 1958–1966 (using the numbering of FIG. 7). HAP protein fragments which are included within the definition of a HAP protein include N- or C-terminal truncations and deletions which still allow the protein to be biologically active; for example, which still exhibit proteolytic activity in the case of the 110 kD putative protease sequence. In addition, when the HAP protein is to be used to generate antibodies, for example as a vaccine, the HAP protein must share at least one epitope or determinant with either the full length protein, the 110 kD protein or the 45 kD protein, shown in FIG. 6. In a preferred embodiment, the epitope is unique to the HAP protein; that is, antibodies generated to a unique epitope exhibit little or no cross-reactivity with other proteins. By "epitope" or "determinant" herein is meant a portion of a protein which will generate and/or bind an antibody. Thus, in most instances, antibodies made to a smaller HAP protein will be able to bind to the full length protein.

In a preferred embodiment the HAP protein contains sequences conserved among HAP proteins from different species or strains. As shown in FIG. 11, alignment of the amino acid sequences of Hap TN106, HapP860295, and HapN187 revealed absolute identity through the first 47 amino acids, divergence over the next 350 amino acids, and then marked similarity over the final 1000–1050 amino acids. Accordingly, in a preferred embodiment the HAP protein of the invention includes amino acids 1–47 of the proteins shown in FIG. 11. In another embodiment the HAP protein of the invention includes amino acids that are invariant among the sequences set forth in FIG. 11 and contiguous for at least about 3, preferably at least about 5 and most preferably at least about 8 amino acids in length. Preferred peptides are included in the following Table 1.

TABLE 1

| SEQ. ID NO. | PEPTIDE SEQUENCE |
|---|---|
| 18 | MKKTVFRLNFLTACISLGIVSQAWAGHTYFGIDYQYYRDFAENKGKF |
| 19 | NPDQHRF |
| 20 | GDSGSPMFIYD |
| 21 | INQGAGGLYFEGNG |
| 22 | DRLSKIG |
| 23 | YFGFRGGRLDLNGHSLTF |
| 24 | RIQNTDEGAMIVNHN |
| 25 | LLLSGGTNL |

TABLE 1-continued

| SEQ. ID NO. | PEPTIDE SEQUENCE |
|---|---|
| 26 | FSGRPTPHAYNHL |
| 27 | RTFKAENFQIKGGSAVVSRNVSSIEGNWTVSNNANA |
| 28 | FGVVPNQQNTICTRSDWTGLTTC |
| 29 | KVINSIP |
| 30 | TQINGSINLTDNAT |
| 31 | GLAKLNGNVTL |
| 32 | HSQFTLSNNATQ |
| 33 | ATVDNANLNGNV |
| 34 | DSAQFSLKNSHFSHQIQG |
| 35 | LENATWTMPSD |
| 36 | TLQNLTLNNST |
| 37 | TLNSAYSA |
| 38 | RRSLETETTPTSAEHRFNTLTVNGKLSGQGTFQFTSSLFGYKSDKLSNDAEGDY |
| 39 | LSVRNTGKEP |
| 40 | QLTLVESKDN |
| 41 | FTLENDHVDAGALRYKLVKN |
| 42 | GEFRLHNPIKEQEL |
| 43 | DLVRAEQAERTLEAKQVE |
| 44 | LISRYSNSALSELSATVNSMLSVQDELDRLFVDQAQSAVWTNIAQDKRRYDSDAFRAYQQKTNLRQIGVQKAL |
| 45 | NGRIGAVFSHSRSDNTFDEQVKNHATL |
| 46 | MMSGFAQYQWGDLQFGVNVG |
| 47 | GISASKMAEEQSRKIHRKAINYGVNASYQFRKGQLGIQPY |
| 48 | GVNRYFIERENYQSEEV |
| 49 | FNRNAGIRVDYTFTPTDNIS |
| 50 | KPYFFVNYVDVSNANVQTTVN |
| 51 | FGRYWQKEVGLKAEILHFQ |
| 52 | SAFISKSQGSQLGKQQNVGVKLGYRW |

In some embodiments, the fragment of the HAP protein used to generate antibodies are small; thus, they may be used as haptens and coupled to protein carriers to generate antibodies, as is known in the art. In one embodiment the fragment of the HAP protein is a fragment of one of the peptides listed above. In this embodiment the fragment need only comprise a single epitope.

Accordingly in one embodiment the invention provides a composition comprising at least one of the peptides as shown in Table I. In addition the invention provides a polypeptide comprising at least one of the peptides as shown in Table I.

Preferably, the antibodies are generated to a portion of the HAP protein which remains attached to the *Haemophilus influenzae* organism. For example, the HAP protein can be used to vaccinate a patient to produce antibodies which upon exposure to the *Haemophilus influenzae* organism (e.g. during a subsequent infection) bind to the organism and allow an immune response. Thus, in one embodiment, the antibodies are generated to the roughly 45 kD fragment of the full length HAP protein. Preferably, the antibodies are generated to the portion of the 45 kD fragment which is exposed at the outer membrane.

In an alternative embodiment, the antibodies bind to the mature secreted 110 kD fragment. For example, as explained in detail below, the HAP proteins of the present invention may be administered therapeutically to generate neutralizing antibodies to the 110 kD putative protease, to decrease the undesirable effects and/or binding activity of the 100 kD fragment.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 6, 16, 18, 20, 22 or 24, is preferably greater than 40%, more preferably greater than about 60% and most preferably greater than 80%. In some embodiments the homology will be as high as about 90 to 95 or 98%.

In one embodiment, the nucleic acid homology is determined through hybridization studies. Thus, for example, nucleic acids which hybridize under high stringency to all or part of the nucleic acid sequence shown in FIG. 6 are considered HAP protein genes. High stringency conditions include washes with 0.1×SSC at 65° C. for 2 hours.

In one embodiment the nucleic acid of the invention are preferably greater than 40%, more preferably greater than about 60% and most preferably greater than 80% identical to the nucleic acids as set forth in FIG. 6, 16, 18, 20, 22 or 24. In some embodiments the identity will be as high as about 90 to 95 or 98% up to 100%.

The HAP proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequence shown in FIG. 6, but may contain ribonucleotides as well as deoxyribonucleotides. Generally, anti-sense nucleic acids function to prevent expression of mRNA, such that a HAP protein is not made, or made at reduced levels. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated HAP protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host, or found in the absence of the host cells themselves. Thus, the protein may be partially or substantially purified. The definition includes the production of a HAP protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of HAP protein are HAP proteins from other organisms, including, but not limited to various *H. influenza* strains, which are cloned and expressed as outlined below.

In the case of anti-sense nucleic acids, an anti-sense nucleic acid is defined as one which will hybridize to all or part of the corresponding non-coding sequence of the sequence shown in FIG. 6. Generally, the hybridization conditions used for the determination of anti-sense hybridization will be high stringency conditions, such as 0.1×SSC at 65° C.

Once the HAP protein nucleic acid is identified, it can be cloned and, if necessary, its constituent parts recombined to form the entire HAP protein nucleic acid. Once isolated from its natural source, e.g., contained within a plasmid or other vector or excised therefrom as a linear nucleic acid segment, the recombinant HAP protein nucleic acid can be further used as a probe to identify and isolate other HAP protein nucleic acids. It can also be used as a "precursor" nucleic acid to make modified or variant HAP protein nucleic acids and proteins.

Using the nucleic acids of the present invention which encode HAP protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the HAP protein. "Operably linked" in this context means that the transcriptional and translational regulatory DNA is positioned relative to the coding sequence of the HAP protein in such a manner that transcription is initiated. Generally, this will mean that the promoter and transcriptional initiation or start sequences are positioned 5' to the HAP protein coding region. The transcriptional and translational regulatory nucleic acid will generally be appropriate to the host cell used to express the HAP protein; for example, transcriptional and translational regulatory nucleic acid sequences from Bacillus will be used to express the HAP protein in *Bacillus*. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The HAP proteins of the present invention are produced by culturing a host cell transformed with an expression vector containing nucleic acid encoding a HAP protein, under the appropriate conditions to induce or cause expression of the HAP protein. The conditions appropriate for HAP protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, immortalized mammalian myeloid and lymphoid cell lines.

In a preferred embodiment, HAP proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of HAP protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the HAP protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, HAP proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the HAP protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for HAP protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide(s) in liposomes, and direct microinjection of the DNA into nuclei.

In a preferred embodiment, HAP protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guilerimondii* and *P. pastoris, Schizosaccharomyces pombe*, and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant HAP protein may be expressed intracellularly or secreted. The HAP protein may also be made as a fusion protein, using techniques well known in the art. Thus, for example, if the desired epitope is small, the HAP protein may be fused to a carrier protein to form an immunogen. Alternatively, the HAP protein may be made as a fusion protein to increase expression.

Also included within the definition of HAP proteins of the present invention are amino acid sequence variants. These variants fall into one or more of three classes: substitutional, insertional or deletional variants. These variants ordinarily are prepared by site specific mutagenesis of nucleotides in the DNA encoding the HAP protein, using cassette mutagenesis or other techniques well known in the art, to produce DNA encoding the variant, and thereafter expressing the DNA in recombinant cell culture as outlined above. However, variant HAP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the HAP protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed HAP protein variants screened for the optimal combination of desired activity. Techniques for making substitution mutations at predetermined sites in DNA having a known sequence are well known, for example, PCR primer mutagenesis. Screening of the mutants is done using assays of HAP protein activities; for example, mutated HAP genes are placed in HAP deletion strains and tested for HAP activity, as disclosed herein. The creation of deletion strains, given a gene sequence, is known in the art. For example, nucleic acid encoding the variants may be expressed in a *Haemophilus influenzae* strain deficient in the HAP protein, and the adhesion and infectivity of the variant *Haemophilus influenzae* evaluated. Alternatively, the variant HAP protein may be expressed and its biological characteristics evaluated, for example its proteolytic activity.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when one of the domains of the HAP protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the HAP protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the HAP protein is altered. For example, the proteolytic activity of the larger 110 kD domain of the HAP protein may be altered, through the substitution of the amino acids of the active site. The putative catalytic domain of this protein was considered to be GDSGSPMF (SEQ ID NO: 53). The residues of the active site may be individually or simultaneously altered to decrease or eliminate proteolytic activity. This may be done to decrease the toxicity or side effects of the vaccine. Similarly, the cleavage site between the 45 kD domain and the 100 kD domain may be altered, for example to eliminate proteolytic processing to form the two domains. Indeed, the catalytic triad has been defined as His98, Asp 140 and Ser 243. Each of these amino acids has been mutated; the mutations eliminated proteolytic activity. In addition, four sites have been identified at which autoproteolytic cleavage occurs (Hendrixson et al., 1997; Hendrixson and St. Geme, 1998; Fink et al., 2001).

In a preferred embodiment, the HAP protein is purified or isolated after expression. HAP proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the HAP protein may be purified using a standard anti-HAP antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the HAP protein. In some instances no purification will be necessary.

Once expressed and purified if necessary, the HAP proteins are useful in a number of applications.

For example, the HAP proteins can be coupled, using standard technology, to affinity chromatography columns. These columns may then be used to purify antibodies from samples obtained from animals or patients exposed to the *Haemophilus influenzae* organism. The purified antibodies may then be used as outlined below.

Additionally, the HAP proteins are useful to make antibodies to HAP proteins. These antibodies find use in a number of applications. In a preferred embodiment, the antibodies are used to diagnose the presence of an *Haemophilus influenzae* infection in a sample or patient. This will be done using techniques well known in the art; for example, samples such as blood or tissue samples may be obtained from a patient and tested for reactivity with the antibodies, for example using standard techniques such as ELISA. In a preferred embodiment, monoclonal antibodies are generated to the HAP protein, using techniques well known in the art. As outlined above, the antibodies may be generated to the full length HAP protein, or a portion of the HAP protein.

Antibodies generated to HAP proteins may also be used in passive immunization treatments, as is known in the art.

Antibodies generated to unique sequences of HAP proteins may also be used to screen expression libraries from other organisms to find, and subsequently clone, HAP nucleic acids from other organisms.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the HAP protein antibody may be labelled for detection, or a secondary antibody to the HAP protein antibody may be created and labelled.

In one embodiment, the antibodies generated to the HAP proteins of the present invention are used to purify or separate HAP proteins or the *Haemophilus influenzae* organism from a sample. Thus for example, antibodies generated to HAP proteins which will bind to the *Haemophilus influenzae* organism may be coupled, using standard technology, to affinity chromatography columns. These columns can be used to pull out the *Haemophilus* organism from environmental or tissue samples. Alternatively, antibodies generated to the soluble 110 kD portion of the full-length portion of the protein shown in FIG. 7 may be used to purify the 110 kD protein from samples.

In a preferred embodiment, the HAP proteins of the present invention are used as vaccines for the prophylactic or therapeutic treatment of a *Haemophilus influenzae* infection in a patient. By "vaccine" herein is meant an antigen or compound which elicits an immune response in an animal or patient. The vaccine may be administered prophylactically, for example to a patient never previously exposed to the antigen, such that subsequent infection by the *Haemophilus influenzae* organism is prevented. Alternatively, the vaccine may be administered therapeutically to a patient previously exposed or infected by the *Haemophilus influenzae* organism. While infection cannot be prevented, in this case an immune response is generated which allows the patient's immune system to more effectively combat the infection. Thus, for example, there may be a decrease or lessening of the symptoms associated with infection.

In a preferred embodiment the HAP proteins of the invention protect against infection by *H. influenza*. That is, administration of at least one of the HAP proteins of the invention to a patient results in protection against *H. influenza* infection. In another embodiment administration of at least one HAP protein of the invention results in reduced colonization by *H. influenza*. In a particularly preferred embodiment administration of at least one of the HAP proteins of the invention results in protection against infection or colonization by a heterologous strain of *Haemophilus influenzae*. By "heterologous" is meant a strain that is not the same strain from which the HAP protein is obtained. Accordingly, the present invention provides a method of vaccinating against infection by a heterologous strain of *H. influenza*.

A "patient" for the purposes of the present invention includes both humans and other animals and organisms. Thus the methods are applicable to both human therapy and veterinary applications.

The administration of the HAP protein as a vaccine is done in a variety of ways, including but not limited to intramuscular or subcutaneous injection, intranasal delivery, oral delivery, intravenous delivery and intradermal delivery as is known in the art. Generally, the HAP proteins can be formulated according to known methods to prepare pharmaceutically useful compositions, whereby therapeutically effective amounts of the HAP protein are combined in admixture with a pharmaceutically acceptable carrier vehicle. Suitable vehicles and their formulation are well known in the art. Such compositions will contain an effective amount of the HAP protein together with a suitable amount of vehicle in order to prepare pharmaceutically acceptable compositions for effective administration to the host. The composition may include salts, buffers, carrier proteins such as serum albumin, targeting molecules to localize the HAP protein at the appropriate site or tissue within the organism, and other molecules. The composition may include adjuvants as well. In a preferred embodiment the HAP protein is administered combined with an adjuvant as is known in the art, such as aluminum hydroxide. In a preferred embodiment the adjuvant is a modified cholera toxin adjuvant.

Cholera toxin (CT) is well known as a potent mucosal adjuvant but is highly toxic to humans (Snider, D. P., 1995, Crit. Rev. Immunol 15:317–48). CT-E29H is a mutant form of CT that contains a histidine in place of a glutamic acid at residue 29 in the enzymatic A subunit. This mutant lacks enzymatic activity and has <1% of the cellular toxicity of native cholera toxin but remains fully active as an adjuvant, suggesting considerable utility in humans (Tebbey et al. 2000, Vaccine 18:2723–34). Accordingly, in a preferred embodiment the invention provides a composition comprising a HAP protein of the invention and cholera toxin CT-E29H. In addition the invention provides a method of improving immunization by administering an immunogenic protein of the invention and an adjuvant. In a preferred embodiment the adjuvant is CT-E29H.

In one embodiment, the vaccine is administered as a single dose; that is, one dose is adequate to induce a sufficient immune response to prophylactically or therapeutically treat a *Haemophilus influenzae* infection. In alternate embodiments, the vaccine is administered as several doses over a period of time, as a primary vaccination and "booster" vaccinations.

By "therapeutically effective amounts" herein is meant an amount of the HAP protein which is sufficient to induce an immune response. This amount may be different depending on whether prophylactic or therapeutic treatment is desired. Generally, this ranges from about 0.001 mg to about 1 gm, with a preferred range of about 0.05 mg to about 0.5 g, and the preferred dose being 0.1 mg to about 0.1 g These amounts may be adjusted if adjuvants are used.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Cloning of the HAP Protein

Bacterial Strains, plasmids, and phage. *H. influenzae* strain N187 is a clinical isolate that was originally cultivated from the middle ear fluid of a child with acute otitis media. This strain was classified as nontypable based on the absence of agglutination with typing antisera for *H. influenzae* types a-f (Burroughs Wellcome) and the failure to hybridize with pU038, a plasmid that contains the entire cap b locus (Kroll and Moxon, 1988, J. Bacteriol. 170:859–864).

*H. influenzae* strain DB117 is a rec-1 mutant of Rd, a capsule-deficient serotype d strain that has been in the laboratory for over 40 years (Alexander and Leidy, 1951, J. Exp. Med. 83:345–359); DB117 was obtained from G. Barcak (University of Maryland, Baltimore, Md.) (Sellow et al., 1968). DB117 is deficient for in vitro adherence and invasion, as assayed below.

*H. influenzae* strain 12 is the nontypable strain from which the genes encoding the HMW1 and HMW2 proteins were cloned (Barenkamp and Leininger, 1992, Infect. Immun. 60:1302–1313); HMW1 and HMW2 are the prototypic members of a family of nontypable *Haemophilus* antigenically-related high-molecular-weight adhesive proteins (St. Geme et al., 1993).

*E. coli* HB101, which is nonadherent and noninvasive, has been previously described (Sambrook et al., 1989, Molecular cloning: a laboratory manual, 2nd ed. Cold Spring Harbor Laboratory, Cold Spring Harbor, N.Y. ). *E. coli* DH5α was obtained from Bethesda Research Laboratories. *E. coli* MC1061 was obtained from H. Kimsey (Tufts University, Boston, Mass.). *E. coli* XL-1 Blue and the plasmid pBluescript KS—were obtained from Stratagene. Plasmid pT7-7 and phage mGP1-2 were provided by S. Tabor (Harvard Medical School, Boston, Mass.) (Tabor and Richardson, 1985, Proc. Natl. Acad. Sci. USA. 82:1074–1078). The *E. coli-Haemophilus* shuttle vector pGJB103 (Tomb et al., 1989, Rd. J. Bacteriol. 171:3796–3802) and phage λ1105 (Way et al., 1984, Gene. 32:3 69–379) were provided by G. Barcak (University of Maryland, Baltimore, Md.). Plasmid pVD116 harbors the IgA1 protease gene from *H. influenzae* strain Rd (Koomey and Falkow, 1984, Infect. Immun. 43:101–107) and was obtained from M. Koomey (University of Michigan, Ann Arbor, Mich.).

Growth conditions. *H. influenzae* strains were grown as described (Anderson et al., 1972, J. Clin. Invest. 51:31–38). They were stored at −80° C. in brain heart infusion broth with 25% glycerol. *E. coli* strains were grown on LB agar or in LB broth. They were stored at −80° C. in LB broth with 50% glycerol.

For *H. influenzae*, tetracycline was used in a concentration of 5 μg/ml and kanamycin was used in a concentration of 25 μg/ml. For *E. coli*, antibiotics were used in the following concentrations: tetracycline, 12.5 μg/ml; kanamycin, 50 μg/ml; ampicillin, 100 μg/ml.

Recombinant DNA methods. DNA ligations, restriction endonuclease digestions, and gel electrophoresis were performed according to standard techniques (Sambrook et a., 1989, supra). Plasmids were introduced into *E. coli* strains by either chemical transformation or electroporation, as described (Sambrook et al, 1989, supra; Dower et a., 1988, Nucleic Acids Res. 16:6127–6145). In *H. influenzae* transformation was performed using the MIV method of Herriott et al. (1970, J. Bacteriol. 101:517–524), and electroporation was carried out using the protocol developed for *E. coli* (Dower et al., 1988, supra).

Construction of genomic library from *H. influenzae* strain N187. High-molecular-weight chromosomal DNA was prepared from 3 ml of an overnight broth culture of *H. influenzae* N 187 as previously described (Mekalanos, 1983, Cell. 35:253–263). Following partial digestion with Sau3AI, 8 to 12 kb fragments were eluted into DEAE paper (Schleicher & Schuell, Keene, H. H.) and then ligated to Bg/II-digested calf intestine phosphatase-treated pGJB103. The ligation mixture was electroporated into *H. influenzae* DB117, and transformants were selected on media containing tetracycline.

Transposon mutagenesis. Mutagenesis of plasmid DNA was performed using the mini-Tn10 kan element described by Way et al. (1984, supra). Initially, the appropriate plasmid was introduced into *E. coli* MC1061. The resulting strain was infected with λ1105, which carries the mini-Tn10 kan transposon. Transductants were grown overnight in the presence of kanamycin and an antibiotic to select for the plasmid, and plasmid DNA was isolated using the alkaline lysis method. In order to recover plasmids containing a transposon insertion, plasmid DNA was electroporated into *E. coli* DH5α, plating on media containing kanamycin and the appropriate second antibiotic.

In order to establish more precisely the region of pN187 involved in promoting interaction with host cells, initially this plasmid was subjected to restriction endonuclease analysis. Subsequently, several subclones were constructed in the vector pGJB103 and were reintroduced into *H. influenzae* strain DB117. The resulting strains were then examined for adherence and invasion. As summarized in FIG. 4, subclones containing either a 3.9-kb PstI-Bg/II fragment (pJS105) or the adjoining 4.2-kb Bg/II fragment (pJS102) failed to confer the capacity to associate with Chang cells. In contrast, a subclone containing an insert that included portions of both of these fragments (pJS106) did promote interaction with epithelial monolayers. Transposon mutagenesis performed on pN187 confirmed that the flanking portions of the insert in this plasmid were not required for the adherent/invasive phenotype. On the other hand, a transposon insertion located adjacent to the Bg/II site in pJS106 eliminated adherence and invasion. An insertion between the second EcoRI and PstI sites in this plasmid had a similar effect (FIG. 4).

Examination of plasmid-encoded proteins. In order to examine plasmid encoded proteins, relevant DNA was ligated into the bacteriophage T7 expression vector pT7-7, and the resulting construct was transformed into *E. coli* XL-1 Blue. Plasmid pT7-7 contains the T7 phage φ10 promoter and ribosomal binding site upstream of a multiple cloning site (Tabor and Richardson, 1985, supra). The T7 promoter was induced by infection with the recombinant M13 phage mGP1-2 and addition of isopropyl-β-D-thiogalactopyranoside (final concentration, 1 mM). Phage mGP1-2 contains the gene encoding T7 RNA polymerase, which activates the φ10 promoter in pT7-7 (Tabor and Richardson, 1985, supra).

Like DB117(pN187), strain DB117 carrying pJS106 expressed new outer membrane proteins 160-kD and 45-kD in size (FIG. 3, lane 3). In order to examine whether the 6.5-kb insert in pJS106 actually encodes these proteins, this fragment of DNA was ligated into the bacteriophage T7 expression vector pT7-7. The resulting plasmid containing the insert in the same orientation as in pN187 was designated pJS104, and the plasmid with the insert in the opposite orientation was designated pJS103. Both pJS104, and pJS103 were introduced into *E. coli* XL-1 Blue, producing XL-1 Blue(pJS104) and XL-1 Blue(pJS103), respectively. As a negative control, pT7-7 was also transformed into XL-1 Blue. The T7 promoter was induced in these three strains by infection with the recombinant M13 phage mGP1-2 and addition of isopropyl-β-D-thiogalactopyranoside (final concentration, 1 mM), and induced proteins were detected using [$^{35}$S] methionine. As shown in FIG. 5, induction of XL-1 Blue(pJS104) resulted in expression of a 160-kD protein and several smaller proteins which presumably represent degradation products. In contrast, when XL-1 Blue(pJS103) and XL-1 Blue(pT7-7) were induced, there was no expression of these proteins. There was no 45-kD protein induced in any of the three strains. This experiment suggested that the 6.5-kb insert present in pJS106 contains the structural gene for the 160-kD outer membrane protein identified in DB117 (pJS106). On the other hand, this analysis failed to establish the origin of the 45-kD membrane protein expressed by DB117(pJS106).

Adherence and invasion assays. Adherence and invasion assays were performed with Chang epithelial cells [Wong-Kilbourne derivative, clone 1-5c-4 (human conjunctiva)], which were seeded into wells of 24-well tissue culture plates as previously described (St. Geme and Falkow, 1990). Adherence was measured after incubating bacteria with epithelial monolayers for 30 minutes as described (St. Geme et al., 1993). Invasion assays were carried out according to our original protocol and involved incubating bacteria with epithelial cells for four hours followed by treatment with gentamicin for two hours (100 μg/ml) (St. Geme and Falkow, 1990).

Nucleotide sequence determination and analysis. Nucleotide sequence was determined using a Sequenase kit and double stranded plasmid template. DNA fragments were subcloned into pBluescript KS⁻ and sequenced along both strands by primer walking. DNA sequence analysis was performed using the Genetics Computer Group (GCG) software package from the University of Wisconsin (Devereux et al., 1984). Sequence similarity searches were carried out using the BLAST program of the National Center for Biotechnology Information (Altschul et al., 1990, J. Mol. Biol. 215:403–410). The DNA sequence described here will be deposited in the EMBL/GenBank/DDBJ Nucleotide Sequence Data Libraries.

Based on the our subcloning results, we reasoned that the central Bg/II site in pN187 was positioned within an open reading frame. Examination of a series of mini-Tn10 kan mutants supported this conclusion (FIG. 4). Consequently, we sequenced DHA on either side of this Bg/II site and identified a 4182 bp gene, which we have designated hap for *Haemophilus* adherence and penetration (FIG. 6). This gene encodes a 1394 amino acid polypeptide, which we have called Hap, with a calculated molecular mass of 155.4-kD, in good agreement with the molecular mass of the larger of the two novel outer membrane proteins expressed by DB117 (pN187) and the protein expressed after induction of XL-1 Blue/pJS104. The hap gene has a G+C content of 39.1%, similar to the published estimate of 38.7% for the whole genome (Kilian, 1976, J. Gen. Microbiol. 93:9–62). Putative –10 and –35 promoter sequences are present upstream of the initiation codon. A consensus ribosomal binding site is lacking. A sequence similar to a rho-independent transcription terminator is present beginning 39 nucleotides beyond the stop codon and contains interrupted inverted repeats with the potential for forming a hairpin structure containing a loop of three bases and a stem of eight bases. Similar to the situation with typical *E. coli* terminators, this structure is followed by a stretch rich in T residues. Analysis of the predicted amino acid sequence suggested the presence of a 25 amino acid signal peptide at the amino terminus. This region has characteristics typical of procaryotic signal peptides, with three positive H-terminal charges, a central hydrophobic region, and alanine residues at positions 23 and 25 (–3 and –1 relative to the putative cleavage site) (von Heijne, 1984, J. Mol. Biol. 173:243–251).

Comparison of the deduced amino acid sequence of Hap with other proteins. A protein sequence similarity search was performed with the predicted amino acid sequence using the BLAST network service of the National Center for Biotechnology Information (Altschul et al., 1990, supra). This search revealed homology with the IgA1 proteases of *H. influenzae* and *Neisseria gonorrhoeae*. Alignment of the derived amino acid sequences for the hap gene product and the IgA1 proteases from four different *H. influenzae* strains revealed homology across the extent of the proteins (FIG. 7), with several stretches showing 55–60% identity and 70–80% similarity. Similar levels of homology were noted between the hap product and the IgA1 protease from *N. gonorrhoeae* strain MS11. This homology includes the region identified as the catalytic site of the IgA1 proteases, which is comprised of the sequence GDSGSPLF (SEQ ID NO: 54), where 2 is the active site serine characteristic of serine proteases (Brenner, 1988, Nature (London). 334: 528–530; Poulsen et al., 1992, J. Bacteriol. 174:2913–2921). In the case of Hap, the corresponding sequence is GDSG-SPMF (SEQ ID NO: 53). The hap product also contains two cysteines corresponding to the cysteines proposed to be important in forming the catalytic domain of the IgA proteases (Pohlner et al., 1987, supra). Overall there is 30–35% identity and 51–55% similarity between the hap gene product and the *H. influenzae* and *N. gonorrhoeae* IgA proteases.

The deduced amino acid sequence encoded by hap was also found to contain significant homology to Tsh, a hemagglutinin expressed by an avian *E. coli* strain (Provence and Curtiss, 1994, supra). This homology extends throughout both proteins but is greatest in the H-terminal half of each. Overall the two proteins are 30.5% identical and 51.6% similar. Tsh is also synthesized as a preprotein and is secreted as a smaller form; like the IgA1 proteases and perhaps Hap, a carboxy terminal peptide remains associated with the outer membrane (D. Provence, personal communication). While this protein is presumed to have proteolytic activity, its substrate has not yet been determined. Interestingly, Tsh was first identified on the basis of its capacity to promote agglutination of erythrocytes. Thus Hap and Tsh are possibly the first members of a novel class of adhesive proteins that are processed analogously to the IgA1 proteases.

Homology was also noted with pertactin, a 69-kD outer membrane protein expressed by *B. pertussis* (Charles et al., 1989, Proc. Natl. Acad. Sci. USA. 86:3554–3558). The middle portions of these two molecules are 39% identical and nearly 60% similar. This protein contains the amino acid triplet arginine-glycine-aspartic acid (RGD) and has been shown to promote attachment to cultured mammalian cells via this sequence (Leininger et al., 1991, Proc. Natl. Acad. Sci. USA. 88:345–349). Although Bordetella species are not generally considered intracellular parasites, work by Ewanowich and coworkers indicates that these respiratory pathogens are capable of in vitro entry into human epithelial cells (Ewanowich et al., 1989, Infect. Immun. 57:2698–2704; Ewanowich et al., 1989, Infect. Immun. 57:1240–1247). Recently Leininger et al. reported that pre-incubation of epithelial monolayers with an RGD-containing peptide derived from the pertactin sequence specifically inhibited *B. pertussis* entry (Leininger et al., 1992, Infect. Immun. 60:2380–2385). In addition, these investigators found that coating of *Staphylococcus aureus* with purified pertactin resulted in more efficient *S. aureus* entry; the RGD-containing peptide from pertactin inhibited this pertactin-enhanced entry by 75%. Although the hap product lacks an RGD motif, it is possible that Hap and pertactin serve similar biologic functions for *H. influenzae* and *Bordetella* species, respectively.

Additional analysis revealed significant homology (34 to 52% identity, 42 to 70% similarity) with six regions of HpmA, a calcium-independent hemolysin expressed by *Proteus mirabilis* (Uphoff and Welch, 1990, supra).

The hap locus is distinct from the *H. influenzae* IgA1 protease gene. Given the degree of similarity between the hap gene product and *H. influenzae* IgA1 protease, we wondered whether we had isolated the IgA1 protease gene of strain N187. To examine this possibility, we performed IgA1 protease activity assays. Among *H. influenzae* strains, two enzymatically distinct types of IgA1 protease have been found (Mulks et al., 1982, J. Infect. Dis. 146:266–274). Type 1 enzymes cleave the Pro-Ser peptide bond between residues 231 and 232 in the hinge region of human IgA1 heavy chain and generate fragments of roughly 28-kD and 31-kD; type 2 enzymes cleave the Pro-Thr bond between residues 235 and 236 in the hinge region and generate 26.5-kD and 32.5-kD fragments. Previous studies of the parent strain from which DB117 was derived have demonstrated that this strain produces a type 1 IgA1 protease (Koomey and Falkow, 1984, supra). As shown in FIG. 8, comparison of the proteolytic activities of strain DB117 and strain N187 suggested that N187 produces a type 2 IgA1 protease. We reasoned that DB117(pN187) might generate a total of four fragments from IgA1 protease, consistent with two distinct cleavage specificities. Examination of DB117(pN187) revealed instead that this transformant produces the same two fragments of the IgA1 heavy chain as does DB117, arguing that this strain produces only a type 1 enzyme.

In an effort to obtain additional evidence against the possibility that plasmid pN187 contains the N187 IgA1 protease gene, we performed a series of Southern blots. As shown in FIG. 9, when genomic DNA from strain N187 was digested with EcoRI, Bg/II, or BamHI and then probed with the hap gene, one set of hybridizing fragments was detected. Probing of the same DNA with the iga gene from *H. influenzae* strain Rd resulted in a different set of hybridizing bands. Moreover, the iga gene failed to hybridize with a purified 4.8-kb fragment that contained the intact hap gene.

The recombinant plasmid associated with adherence and invasion encodes a secreted protein. The striking homology between the hap gene product and the *Haemophilus* and *Neisseria* IgA1 proteases suggested the possibility that these proteins might be processed in a similar manner. The IgA1 proteases are synthesized as preproteins with three functional domains: the N-terminal signal peptide, the protease, and a C-terminal helper domain, which is postulated to form a pore in the outer membrane for secretion of the protease (Poulsen et al., 1989, supra; Pohlner et al., 1987, supra). The C-terminal peptide remains associated with the outer membrane following an autoproteolytic cleavage event that results in release of the mature enzyme. Consistent with the possibility that the hap gene product follows a similar fate, we found that DB117(pN187) produced a secreted protein approximately 110-kD in size that was absent from DB117 (pGJB103) (FIG. 10). This protein was also produced by DB117(pJS106), but not by DB117(pJ5102) or DB117 (pJS105). Furthermore, the two mutants with transposon insertions within the hap coding region were deficient in this protein. In order to determine the relationship between hap and the secreted protein, this protein was transferred to a PVDF membrane and N-terminal amino acid sequencing was performed. Excessive background on the first cycle precluded identification of the first amino acid residue of the free amino terminus. The sequence of the subsequent seven residues was found to be HTYFGID (SEQ ID NO: 55), which corresponds to amino acids 27 through 33 of the hap product.

The introduction of hap into laboratory strains of *E. coli* strains was unable to endow these organisms with the capacity for adherence or invasion. In considering these results, it is noteworthy that the *E. coli* transformants failed to express either the 160-kD or the 45-kD outer membrane protein. Accordingly, they also failed to express the 110-kD secreted protein. The explanation for this lack of expression is unclear. One possibility is that the *H. influenzae* promoter or ribosomal binding site was poorly recognized in *E. coli*. Indeed the putative −35 sequence upstream of the hap initiation codon is fairly divergent from the σ70 consensus sequence, and the ribosomal binding site is unrecognizable. Alternatively, an accessory gene may be required for proper export of the Hap protein, although the striking homology with the IgA proteases, which are normally expressed and secreted in *E. coli*, argues against this hypothesis.

In considering the possibility that the hap gene product promotes adherence and invasion by directly binding to a host cell surface structure, it seems curious that the mature protein is secreted from the organism. However, there are examples of other adherence factors that are also secreted. Filamentous hemagglutinin is a 220-kD protein expressed by *B. pertussis* that mediates in vitro adherence and facilitates natural colonization (Relman et al., 1989, Proc. Natl. Acad. Sci. U.S.A. 86:2637–2641; Kimura et al., 1990, Infect. Immun. 58:7–16). This protein remains surface-associated to some extent but is also released from the cell. The process of Filamentous hemagglutinin secretion involves an accessory protein designated FhaC, which appears to be localized to the outer membrane (Willems et al., 1994, Molec. Microbiol. 11:337–347). Similarly, the Ipa proteins implicated in Shigella invasion are also secreted. Secretion of these proteins requires the products of multiple genes within the mxi and spa loci (Allaoui et al., 1993, Molec. Microbiol. 7:59–68; Andrews et al., 1991, Infect. Immun. 59:1997–2005; Venkatsan et al., 1992, J. Bacteriol. 174:1990–2001).

It is conceivable that secretion is simply a consequence of the mechanism for export of the hap gene product to the surface of the organism. However, it is noteworthy that the secreted protein contains a serine-type protease catalytic domain and shows homology with the *P. mirobilis* hemolysin. These findings suggest that the mature Hap protein may possess proteolytic activity and raise the possibility that Hap promotes interaction with the host cell at a distance by modifying the host cell surface. Alternatively, Hap may modify the bacterial surface in order to facilitate interaction with a host cell receptor. It is possible that hap encodes a molecule with dual functions, serving as both adhesin and protease.

Analysis of outer membrane and secreted proteins. Outer membrane proteins were isolated on the basis of sarcosyl insolubility according to the method of Carlone et al. (1986, J. Clin. Microbiol. 24:330–332). Secreted proteins were isolated by centrifuging bacterial cultures at 16,000 g for 10 minutes, recovering the supernatant, and precipitating with trichloroacetic acid in a final concentration of 10%. SDS-polyacrylamide gel electrophoresis was performed as previously described (Laemmli, 1970, Nature (London). 227: 680–685).

To identify proteins that might be involved in the interaction with the host cell surface, outer membrane protein profiles for DB117(pN187) and DB117(pGJB103) were compared. As shown in FIG. 3, DB117(pN187) expressed two new outer membrane proteins: a high-molecular-weight protein approximately 160-kD in size and a 45-kD protein. *E. coli* HB101 harboring pN187 failed to express these proteins, suggesting an explanation for the observation that HB101(pN187) is incapable of adherence or invasion.

Previous studies have demonstrated that a family of antigenically-related high-molecular-weight proteins with similarity to filamentous hemagglutinin of *Bordetella pertussis* mediate attachment by nontypable *H. influenzae* to cultured epithelial cells (St. Geme et al., 1993). To explore the possibility that the gene encoding the strain H187 member of this family was cloned, whole cell lysates of N187, DB117(pN187), and DB117(pGJB103) were examined by Western immunoblot. Our control strain for this experiment was *H. influenzae* strain 12. Using a polyclonal antiserum directed against HMW1 and HMW2, the prototypic proteins in this family, we identified a 140-kD protein in strain H187 (not shown). In contrast, this antiserum failed to react with either DB117(pN187) or DB117(pGJB103) (not shown), indicating that pN187 has no relationship to HMW protein expression.

Determination of amino terminal sequence. Secreted proteins were precipitated with trichloroacetic acid, separated on a 10% SDS-polyacrylamide gel, and electrotransferred to a polyvinylidene difluoride (PVDF) membrane (Matsudaira, 1987, J. Biol. Chem. 262:10035–10038). Following staining with Coomassie Brilliant Blue R-250, the 110-kD protein was cut from the PVDF membrane and submitted to the Protein Chemistry Laboratory at Washington University School of Medicine for amino terminal sequence determination. Sequence analysis was performed by automated Edman degradation using an Applied Biosystems Model 470A protein sequencer.

Examination of IgA1 protease activity. In order to assess IgA1 protease activity, bacteria were inoculated into broth and grown aerobically overnight. Samples were then centrifuged in a microphage for two minutes, and supernatants were collected. A 10 μl volume of supernatant was mixed with 16 μl of 0.5 μg/ml human IgA1 (Calbiochem), and chloramphenicol was added to a final concentration of 2 μg/ml. After overnight incubation at 37° C., reaction mixtures were electrophoresed on a 10% SDS-polyacrylamide gel, transferred to a nitrocellulose membrane, and probed with goat anti-human IgA1 heavy chain conjugated to alkaline phosphatase (Kirkegaard & Perry). The membrane was developed by immersion in phosphatase substrate solution (5-bromo4-chloro-3-indolylphosphate toluidinium-nitro blue tetrazolium substrate system; Kirkegaard & Perry).

Immunoblot analysis. Immunoblot analysis of bacterial whole cell lysates was carried out as described (St. Geme et al., 1991).

Southern hybridization. Southern blotting was performed using high stringency conditions as previously described (St. Geme and Falkow, 1991).

Microscopy.

i. Light microscopy. Samples of epithelial cells with associated bacteria were stained with Giemsa stain and examined by light microscopy as described (St. Geme and Falkow, 1990).

ii. Transmission electron microscopy. For transmission electron microscopy, bacteria were incubated with epithelial cell monolayers for four hours and were then rinsed four times with PBS, fixed with 2% glutaraldehyde/1% osmium tetroxide in 0.1 M sodium phosphate buffer pH 6.4 for two hours on ice, and stained with 0.25% aqueous uranyl acetate overnight. Samples were then dehydrated in graded ethanol solutions and embedded in polybed. Ultrathin sections (0.4 μm) were examined in a Phillips 201c electron microscope.

As shown in FIG. 2, DB117(pN187) incubated with monolayers for four hours demonstrated intimate interaction with the epithelial cell surface and was occasionally found to be intracellular. In a given thin section, invaded cells generally contained one or two intracellular organisms. Of note, intracellular bacteria were more common in sections prepared with strain N187, an observation consistent with results using the gentamicin assay. In contrast, examination of samples prepared with strain DB117 carrying cloning vector alone (pGJB103) failed to reveal internalized bacteria (not shown).

Example 2

HAP Immunization

Bacterial Strains. NTHi strains N187 and P860295 were isolated from middle ear fluid of children with acute otitis media, while NTHi strain TN106 was isolated from a patient with pneumonia. Strain N187 is the strain from which the hap gene was originally cloned (Sanders et al., 1993, Infect. Immun. 61:3966–3975; St. Geme et al., 1994, Mol. Microbiol. 14:217–233). Strain P860295 was obtained from Dr. Charles Brinton (University of Pittsburgh), and strain TN106 was obtained from Dr. Eric Hansen (University of Texas, Southwestern School of Medicine). Strain TN106.P2 is a derivative of TN106 that was recovered after plating on medium containing 100 µg/ml of streptomycin, then inoculating into the nasopharynx of a Balb/c mouse. Strains TN106.P2 and TN106 are indistinguishable in terms of morphology and growth characteristics. *H. influenzae* strain DB117 is a rec1 mutant of Rd, a capsule-deficient serotype d strain (Setlow et al., 1968, J. Bacteriol. 95:546–558). DB117 contains a nonfunctional hap gene because of a spontaneous nonsense mutation at codon 710 and is nonadherent in assays with cultured epithelial cells (Fleischmann et al., 1995. Rd. Science 269:496–512).

*H. influenzae* strains were grown on chocolate agar supplemented with 1% IsoVitaleX, on brain heart infusion agar supplemented with hemin and NAD (BHI-XV agar), or in brain-heart infusion broth supplemented with hemin and NAD (BHIs), as described previously (St. Geme and Falkow, 1990, supra). These strains were stored at −80° C. in BHI broth with 20% glycerol. *E. coli* strains were grown on Luria-Bertani (LB) agar or in LB broth and were stored at −80° C. in LB broth with 50% glycerol. Antibiotic concentrations used to select for plasmids included 5 µg/ml tetracycline in *H. influenzae* and 100 µg/ml ampicillin and 12.5 µg/ml tetracycline in *E. coli*. DNA ligations, restriction endonuclease digestions and gel electrophoresis were performed according to standard techniques (Sambrook et al., 1989, supra). Plasmids were introduced into *E. coli* by electroporation (Dower et al., 1988, supra). In *H. influenzae*, transformation was performed using the MIV method of Herriott et al. (Herriott et al., 1970, supra).

Cloning and sequencing of hap from strains P860295 and TN106

The hap gene was cloned from strains P860295 and TN106 using the polymerase chain reaction (PCR) and primers corresponding to sequence flanking hap in strain N187. Reactions were performed with Expand polymerase (Roche Molecular Biochemicals) to enhance long range amplification and to minimize PCR-related errors. The 5' primer was based on sequence beginning approximately 500 base pairs upstream of hap (5'-TGCAGGATCCCCGCA-GACTGGATTGTTG-3') (SEQ ID NO: 56), and the 3' primer corresponded to sequence beginning roughly 50 base pairs downstream of hap (5'-TGCAGGATCCGATCTGC-CCCACCTTGTT-3') (SEQ ID NO: 57). To facilitate initial cloning, both the 5' and the 3' primers included a BamHI site. The amplified genes were cloned into BamHI-digested pUC19 and Bg/II-digested pGJB103.

Nucleotide sequencing was performed using an Applied Biosystems automated sequencer and the Big Dye Terminator Premix-20 kit (Applied Biosystems/Perkins Elmer). Double-stranded plasmid DNA was used as template, and sequencing was carried out along both strands. With strain TN106, clones from two separate PCR assays were sequenced, and the two sequences were identical. With strain P860295, a single clone was sequenced.

The sequences for hapTN106 and hapP860295 have been submitted to GeneBank and are awaiting accession numbers.

The hapTN106 gene encodes a protein with 1392 amino acids, and the hapP860295 gene encodes a slightly larger protein with a total of 1436 amino acids. HapTN106 is 80% similar and 77% identical to HapN187, while HapP860295 is 85% similar and 83% identical to HapN187. Overall, the predicted amino acid sequences of Hap TN106 and Hap P860295 are 82% similar and 79% identical to each other.

As shown in FIG. 11, alignment of the amino acid sequences of Hap TN106, HapP860295, and HapN187 revealed absolute identity through the first 47 amino acids, then significant divergence over the next 350 amino acids, and then marked similarity over the final 1000–1050 amino acids. Of note, the signal peptide and the sequence containing the active site serine residue (GDSGSPM) (SEQ ID NO: 58) are completely conserved in all three proteins. Similarly, the amino acids in the P1 (leucine), P3 (serine), and P4 (glutamine) positions of the primary autoproteolytic cleavage site between Haps and HapB are invariant.

Protein Analysis and Western Immunoblotting

Outer membrane proteins were isolated from *H. influenzae* on the basis of sarcosyl insolubility, as described previously (Carlone et al., 1986, supra). Proteins released into the culture supernatant were precipitated using trichloroacetic acid, as described previously (St. Geme et al., 1994, Mol. Microbiol. 14:217–233). Proteins were resolved by sodium dodecyl sulfate-polyacrylamide gel electrophoresis (SDS-PAGE) on 7–10% polyacrylamide gels, and Western blots were performed as detailed elsewhere (Laemmli, 1970, supra; Towbin, et al., 1979, Proc. Natl. Acad. Sci. USA 76:4350–4354). Hap was detected using guinea pig antiserum GP74, which was raised against purified Haps and reacts with full-length Hap and Hap$_s$.

As shown in FIG. 12, Western analysis of outer membrane proteins and secreted proteins from strain DB117/pHap (TN106) revealed full-length protein at ~155 kDa and Hap$_s$ at ~110 kDa, virtually identical to control samples from strain DB117/pJS106 (HapN187). Examination of protein samples from strain DB117/pHap(P860295) revealed that full-length Hap migrated at ~160 kDa and that Haps migrated at ~115 kDa.

Adherence Assays

Adherence assays were performed with Chang conjunctival epithelial cells (Wong-Kilbourne derivative, clone 1-5c-4 [human conjunctiva], as previously described (St. Geme, et al., 1993, supra). Percent adherence was calculated by dividing the number of adherent colony-forming units per monolayer by the number of inoculated colony-forming units.

To assess adhesive activity, DB117/pHap(TN106) and DB117/pHap(P860295) were compared with DB117/pJS106 in adherence assays with Chang conjunctival epithelial cells. As shown in FIG. 13, both Hap TN106 and HapP860295 promoted appreciable levels of adherence to these cells, similar to levels associated with HapN187. To extend this result, we examined whether antiserum raised against Haps purified from strain N187 could block adherence mediated by either HapP860295 or Hap TN106. As shown in FIG. 13, in experiments with DB117/pHap (TN106), preincubation with a 1:500 dilution of guinea pig antiserum GP74 resulted in a nearly 50% decrease in adherence, and preincubation with a 1:100 dilution of GP74 resulted in a 70% decrease in adherence. Similarly, with DB117/pHap(P860295), a 1:500 dilution of GP74 blocked adherence by 40%, and a 1:100 dilution of GP74 blocked adherence by almost 80%.

Purification of NTHi P860295 $Hap_s$ protein. To purify Haps from strain P860295, bacteria were grown in BHIs broth for 18 hours at 35° C. with aeration, i.e. to stationary phase. The bacterial cells were pelleted by centrifuging at 10,000×g at 4° C. and were discarded. Without being bound by theory, it is thought that the autoproteolysis of HAP results in secretion of $Hap_s$. As such, the supernatant was collected and concentrated 20-fold using an Amicon stirred cell, then adjusted to 60% saturation with ammonium sulfate powder, incubated overnight at 4° C., and centrifuged at 17,000×g for 1 hour at 4° C. The resulting precipitate was dissolved in 50 mM sodium phosphate buffer, pH 5.8, 1 mM EDTA, 50 mM NaCl and was dialyzed at 4° C. against the same buffer (Buffer 1), then centrifuged at 100,000×g for 1 hour at 4° C. to remove insoluble material. A 10 ml bed volume CM sepharose (Pharmacia) column was equilibrated with Buffer 1, and 70 ml of the above soluble material was loaded onto the column at a flow rate of 5 ml/min. The column was washed with Buffer 1 until the OD280 reached baseline, and the flow through material was discarded. Next the column was washed with 3 column volumes of 50 mM sodium phosphate buffer, pH7.0, 1 mM EDTA, 50 mM NaCl. $Hap_s$ was eluted with 50 mM sodium phosphate buffer, pH 8.0, 1 mM EDTA, 0.5 M NaCl. Fractions were examined by SDS-PAGE analysis, and fractions containing Haps were pooled. $Hap_s$ from NTHi strain N187 was purified as previously described (Hendrixson, et al., 1997, Mol. Microbiol. 26:505–518; Hendrixson and St. Geme, 1998, Mol. Cell 2:841–850). Strain P860295 $Hap_s$ was purified from the native strain, while strain N187 $Hap_s$ was purified from DB117 harboring pJS106 (encoding HapN187). Using this purification scheme, highly pure protein from both strain P860295 and strain N187 (FIG. 14) was recovered. Amino terminal amino acid sequencing (described below) confirmed that purified protein was $Hap_s$.

Determination of N-terminal amino acid sequence To confirm the identity of purified $Hap_s$, protein was resolved by SDS-PAGE, then electrotransferred to a polyvinylidene membrane. After staining with Coomassie brilliant blue R-250, protein was excised from the membrane and submitted to Midwest Analytical, Inc. (St. Louis, Mo.). Amino-terminal sequence determination was performed by automated Edman degradation using a Perkin-Elmer Biosystems model 477A sequencing system.

Intranasal immunization of mice. Groups of ten, 6-week old, female Balb/c mice were immunized intranasally with $Hap_s$ purified from either strain P860295 or strain N187. $Hap_s$ was diluted in Dulbecco's PBS (D-PBS) to a final concentration of 5 or 15 µg/40 µl, with or without 0.1 µg CT-E29H (a mutant cholera toxin used as an adjuvant) (Tebbey, et al., 2000, Vaccine 18:2723–34). Control mice received D-PBS alone or D-PBS with 0.1 µg CT-E29H, again in 40 µl volumes.

Prior to intranasal immunization, mice were anesthetized with an injectable mixture of ketamine (0.008 mis×body weight)/xylazene (0.007 mis×body weight), a mixture that maintains a state of anesthesia for 15–20 minutes. Immunizing preparations were delivered by pipette in a volume of 20 µl/nostril. The pipette was positioned so that the tip touched the opening of the nostril and liquid was drawn into the nasopharynx during breathing. Immediately following immunization, mice were placed in a supine position for a 3 to 5 minutes. Mice were immunized at weeks 0, 1, 3, and 5.

Intranasal challenge of mice. Either two or three weeks after the final immunization, animals were challenged intranasally with approximately $1 \times 10^6$ CFU of strain TN106.P2. The TN106.P2 challenge strain was prepared for challenge by first inoculating three BBL Chocolate II agar plates from frozen stocks. Plates were incubated overnight at 37° C. in 5% $CO_2$. Five ml of D-PBS was added to each plate and bacteria were resuspended with a curved glass rod. Bacteria from all three plates were combined with an additional 10 ml of D-PBS and the suspension was poured over a D-PBS pre-wetted nylon wool column to remove clumps of bacteria and debris. The suspension was diluted with D-PBS to an OD490=0.33, which was shown to equal ~$1.0 \times 10^8$ CFU/ml. This suspension was used for challenge. Mice were anesthetized as described for immunization, and 5 µl of bacteria were administered in each nostril. Twenty minutes after the challenge began, an aliquot of the bacterial suspension was diluted in D-PBS and plated onto BHI-XV agar to determine the actual inoculum. Three days after challenge, nasal tissue was harvested, weighed, homogenized and plated on BHI-XV plates containing 100 µg/ml streptomycin. Following incubation of plates overnight, colonies were counted, and CFU/g of nasal tissue were determined. Statistical differences among groups were analyzed using the Student t-test (JMP Software v3.2.1)

Measurement of serum antibody responses by ELISA To quantitate serum antibody responses against $Hap_s$, purified $Hap_s$ was diluted and then blocked with 1% bovine serum albumin (BSA)/PBS at 37° C. for 2 hours. Mouse sera were diluted in 1 % BSA/PBS/0.05% Tween 20 (diluent buffer) and were transferred to coated and blocked plates. After incubation at 37° C. overnight, plates were washed and then incubated with a 1:15,000 dilution of biotinylated rabbit anti-mouse IgG at 37° C. for 2 hours. Next plates were washed again and then incubated with a 1:10,000 dilution of streptavidin-HRP (Zymed) at room temperature for 30 minutes. Finally, plates were washed and incubated with ABTS peroxidase substrate (Kirkegaard and Perry Laboratories) at room temperature for 20 minutes. Reactions were stopped with 1% SDS, and absorbance of ABTS was measured at 405 nm. ELISA endpoints were defined as the highest dilution of sera giving an OD405 of >0.1. Control wells containing all reagents except for mouse sera had baseline OD405 values of <0.05.

Serum antibody responses. Animals immunized IN will primarily produce a secretory immune response. Addition of CT-E29H increases the secretory immune response and also helps induce a serum antibody response. The volumes of the immunogens used in this experiment (40 µl) probably resulted in some of the material being aspirated into the mice's lungs, further increasing the immune response in the serum. The anti-$Hap_s$ ELISA titers of the sera obtained from immunized mice are shown in Table 2. The titers are somewhat lower than those usually seen with parenteral immunization since animals were immunized via the IN route. Significant increases in anti-$Hap_s$ titers were seen in the sera. The responses increase in a dose dependent manner and are augmented approximately 3-fold by addition of 0.1 µg of CT-E29H. This augmentation occurs at both dosage levels. No anti-$Hap_s$ titers are seen in any of the control groups. Secretory IgA titers were not obtained from nasopharyngeal secretions.

TABLE 2

Systemic hmoral immune response in Balb/c mice after intranasal vaccination with Hap$_s$ admixed with or without CT-E29H

| Vaccine | Route (40 µl) | Dose (µg) | Adjuvant | Anti-Hap$_s$ ELISA (IgG) |
|---|---|---|---|---|
| HAP | IN | 5 | — | 1,604 |
| HAP | IN | 15 | — | 5,204 |
| HAP | IN | 5 | CT-E29H | 4,653 |
| HAP | IN | 15 | CT-E29H | 15,111 |
| — | IN | — | CT-E29H | <500 |
| 1xPBS | IN | — | — | <500 |
| Formalin Fixed TN106.P2 | IN | — | — | <500 |

6-week old female Balb/c mice were vaccinated week 0, 1, 3, & 5.
Week 7 Sera - no antibody titers were detected in earlier bleeds.

Effect of Hap$_s$ immunization on nasopharyngeal colonization. IN immunization with purified native Hap$_s$ protein from NTHi strain P860295 significantly reduced the nasal colonization of NGHi strain TN106.P2 as shown in FIG. 15. The reductions in recovered NTHi per gram of nasal tissue ranged from 1.5 to 2.5 logs when animals were challenged 2 weeks after the last immunization to approximately 1.5 logs when the animals were challenged 3 weeks after the last immunization all of the differences observed in groups immunized with Hap$_s$, whether with or without CT-E29H, were significant as measured by the Student's T-test. The lowest level of colonization for all groups was in the 5 µg Hap$_s$ dose mixed with 0.1 µg CT-E29H. These results indicate that IN immunization with Hap$_s$ mixed CT-E29H given enhanced immune responses as comapred to IN immunization with Hap$_s$ alone, and that the antibodies elicited by Hap$_s$ are biologically active against a heterologous NTHi challenge.

Having described the preferred embodiments of the present invention it will appear to those of ordinary skill in the art that various modifications may be made to the disclosed embodiments, and that such modifications are intended to be within the scope of the present invention.

What is claimed is:

1. A recombinant nucleic acid comprising a nucleic acid that hybridizes to a nucleic acid having a sequence selected from the group consisting of the sequences or full-length complement of the sequences, shown in SEQ ID NOs: 8, 10, 12, 14 and 16, under the high stringency conditions of washes at 0.1×SSC at 65° C. for 2 hours
wherein said recombinant nucleic acid is capable of detecting by hybridization a nucleic acid sequence selected from the group of SEQ ID Nos: 8, 10, 12, 14 or 16 from *Haemophilus influenzae.*

2. A recombinant nucleic acid comprising DNA having a sequence identical to a nucleic acid having the sequence selected from the group consisting of SEQ ID NOs: 8, 10, 12, 14, and 16.

3. An expression vector comprising transcriptional and translational regulatory nucleic acid operably linked to the nucleic acid of claim 1 or 2 encoding an *Haemophilus* adhesion and penetration protein.

4. A host cell transformed with an expression vector of claim 3.

5. A method of producing an *Haemophilus* adhesion and penetration protein comprising:
   a) culturing a host cell transformed with the expression vector of claim 3; and
   b) expressing said nucleic acid to produce an *Haemophilus* adhesion and penetration protein.

6. A recombinant nucleic acid encoding an *Haemophilus* adhesion and penetration protein comprising DNA having a nucleic acid sequence at least 95% identical to a nucleic acid sequence selected from the group consisting of SEQ ID NOs: 8, 10, 12, 14, and 16, wherein said nucleic acid encodes an amino acid sequence selected from the group consisting of SEQ ID NOs: 9, 11, 13, 15, and 17, respectively.

7. The recombinant nucleic acid of claim 6, wherein said nucleic acid comprises DNA having a nucleic acid sequence at least 98% identical to a nucleic acid sequence selected from the group consisting of SEQ ID NOs: 8, 10, 12, 14, and 16.

* * * * *